US010689692B2

(12) United States Patent
Koehler et al.

(10) Patent No.: US 10,689,692 B2
(45) Date of Patent: *Jun. 23, 2020

(54) METHODS FOR PLACING, ACCEPTING, AND FILLING ORDERS FOR PRODUCTS AND SERVICES

(71) Applicant: APPLIED BIOSYSTEMS, LLC, Carlsbad, CA (US)

(72) Inventors: Ryan T. Koehler, Happy Valley, OR (US); Kenneth J. Livak, Arlington, MA (US); Junko Stevens, Menlo Park, CA (US); Francisco M. De La Vega, San Mateo, CA (US); Michael Rhodes, San Mateo, CA (US); Laurent R. Bellon, San Mateo, CA (US); Dawn Madden, Half Moon Bay, CA (US); Dennis A. Gilbert, San Francisco, CA (US); Yu N. Wang, Sharon, MA (US); Eugene G. Spier, Los Altos, CA (US); Xiaoqing You, San Mateo, CA (US); Lily Xu, Chicago, IL (US); Jeremy Heil, Middleton, WI (US); Emily S. Winn-Deen, San Diego, CA (US); Ivy McMullen, Towson, MD (US); Susan Eddins, Redwood City, CA (US); Leila G. Smith, Echenevex (FR)

(73) Assignee: APPLIED BIOSYSTEMS, LLC, Carlsbad, CA (US)

( * ) Notice: Subject to any disclaimer, the term of this patent is extended or adjusted under 35 U.S.C. 154(b) by 263 days.

This patent is subject to a terminal disclaimer.

(21) Appl. No.: 15/256,827

(22) Filed: Sep. 6, 2016

(65) Prior Publication Data

US 2017/0268051 A1    Sep. 21, 2017

Related U.S. Application Data

(63) Continuation of application No. 13/458,879, filed on Apr. 27, 2012, now Pat. No. 9,464,320, which is a continuation of application No. 12/015,143, filed on Jan. 16, 2008, now abandoned, which is a continuation of application No. 10/334,793, filed on Jan. 2, 2003, now abandoned.

(60) Provisional application No. 60/399,860, filed on Jul. 31, 2002, provisional application No. 60/394,115, filed on Jul. 5, 2002, provisional application No. 60/390,708, filed on Jun. 21, 2002, provisional application No. 60/383,954, filed on May 29, 2002, provisional application No. 60/383,627, filed on May 28, 2002, provisional application No. 60/380,057, filed on May 6, 2002, provisional application No. 60/376,171, filed on Apr. 26, 2002, provisional (Continued)

(51) Int. Cl.
| | | |
|---|---|---|
| C12Q 1/6858 | (2018.01) | |
| G16B 30/00 | (2019.01) | |
| G16B 35/00 | (2019.01) | |
| G16B 50/00 | (2019.01) | |
| G16C 20/60 | (2019.01) | |
| G06Q 30/06 | (2012.01) | |
| G06Q 50/22 | (2018.01) | |
| B01L 3/00 | (2006.01) | |
| G01N 35/00 | (2006.01) | |
| G16B 25/00 | (2019.01) | |
| G16B 45/00 | (2019.01) | |

(52) U.S. Cl.
CPC ........... *C12Q 1/6858* (2013.01); *B01L 3/545* (2013.01); *G01N 35/00663* (2013.01); *G06Q 30/0621* (2013.01); *G06Q 30/0633* (2013.01); *G06Q 30/0641* (2013.01); *G06Q 50/22* (2013.01); *G16B 30/00* (2019.02); *G16B 35/00* (2019.02); *G16B 50/00* (2019.02); *G16C 20/60* (2019.02); *B01L 3/5453* (2013.01); *B01L 2300/021* (2013.01); *C12Q 2600/156* (2013.01); *G16B 25/00* (2019.02); *G16B 45/00* (2019.02)

(58) Field of Classification Search
None
See application file for complete search history.

(56) References Cited

U.S. PATENT DOCUMENTS

| | | |
|---|---|---|
| 5,081,584 A | 1/1992 | Omichinski et al. |
| 5,374,395 A | 12/1994 | Robinson et al. |
| (Continued) | | |

FOREIGN PATENT DOCUMENTS

| | | |
|---|---|---|
| JP | H08-503091 A | 4/1996 |
| JP | 2001258568 | 9/2001 |
| (Continued) | | |

OTHER PUBLICATIONS

Burt et al. E-commerce and the retail process: a review Journal of Retailing and Consumer Services vol. 10 pp. 275-286 (Year: 2003).*

(Continued)

*Primary Examiner* — John S Brusca
(74) *Attorney, Agent, or Firm* — Jones Robb, PLLC

(57) ABSTRACT

Methods and systems for ordering assays which detect SNPs or gene expression are provided. The methods use PCR and RT-PCR procedures. Collections of stock assays are assembled using pre- and post-manufacturing quality control procedures and made available to consumers via the Internet. In addition, custom assays are prepared upon order from the consumer and these assays are also prepared using pre- and post-manufacturing quality control procedures. The assays are then delivered to the consumer.

19 Claims, 81 Drawing Sheets

Specification includes a Sequence Listing.

Related U.S. Application Data application No. 60/370,921, filed on Apr. 9, 2002, provisional application No. 60/369,657, filed on Apr. 3, 2002, provisional application No. 60/369,127, filed on Apr. 1, 2002, provisional application No. 60/352,356, filed on Jan. 28, 2002, provisional application No. 60/352,039, filed on Jan. 25, 2002.

(56) References Cited

U.S. PATENT DOCUMENTS

| | | |
|---|---|---|
| 5,446,139 A | 8/1995 | Seela et al. |
| 5,512,438 A | 4/1996 | Ecker |
| 5,537,528 A | 7/1996 | Takahashi et al. |
| 5,556,749 A | 9/1996 | Mitsuhashi et al. |
| 5,582,986 A | 12/1996 | Monia et al. |
| 5,593,834 A | 1/1997 | Lane et al. |
| 5,670,633 A | 9/1997 | Cook et al. |
| 5,727,163 A | 3/1998 | Bezos |
| 5,753,186 A | 5/1998 | Hanley et al. |
| 5,825,881 A | 10/1998 | Colvin, Sr. |
| 5,960,411 A | 9/1999 | Hartman et al. |
| 5,990,303 A | 11/1999 | Seela |
| 6,058,373 A * | 5/2000 | Blinn .............. G06Q 10/087 705/22 |
| 6,127,121 A | 10/2000 | Meyer, Jr. et al. |
| 6,143,877 A | 11/2000 | Meyer et al. |
| 6,147,199 A | 11/2000 | Seela et al. |
| 6,172,214 B1 | 1/2001 | Brenner |
| 6,174,670 B1 | 1/2001 | Wittwer et al. |
| 6,189,013 B1 | 2/2001 | Maslyn et al. |
| 6,235,475 B1 | 5/2001 | Brenner et al. |
| 6,239,139 B1 | 5/2001 | Kim et al. |
| 6,251,588 B1 | 6/2001 | Shannon et al. |
| 6,282,550 B1 | 8/2001 | Venkatesan et al. |
| 6,300,058 B1 | 10/2001 | Akitaya et al. |
| 6,316,230 B1 | 11/2001 | Egholm et al. |
| 6,329,139 B1 | 12/2001 | Nova et al. |
| 7,013,221 B1 | 3/2006 | Friend et al. |
| 7,117,095 B2 | 10/2006 | Hubbell |
| 7,430,496 B2 | 9/2008 | Yue et al. |
| 7,844,495 B2 | 11/2010 | Verchere |
| 9,464,320 B2 * | 10/2016 | Koehler .............. C12Q 1/6858 |
| 2001/0039014 A1 | 11/2001 | Bass et al. |
| 2001/0047312 A1 | 11/2001 | Verchere |
| 2002/0178079 A1 | 11/2002 | Russell et al. |
| 2003/0175774 A1 | 9/2003 | Hunkapiller et al. |
| 2003/0190652 A1 | 10/2003 | De La Vega et al. |
| 2004/0014067 A1 | 1/2004 | Lyamichev et al. |
| 2004/0175733 A1 | 9/2004 | Andersen et al. |
| 2005/0066276 A1 | 3/2005 | Moore et al. |

FOREIGN PATENT DOCUMENTS

| | | |
|---|---|---|
| JP | 2005516296 | 6/2005 |
| JP | 2005516300 | 6/2005 |
| WO | WO/1992/020702 | 11/1992 |
| WO | WO/1994/011837 | 5/1994 |
| WO | WO/1996/001693 | 1/1996 |
| WO | WO/1997/020197 | 6/1997 |
| WO | WO/2001/016149 | 3/2001 |
| WO | WO/2001/038584 | 5/2001 |
| WO | WO/2001/056216 | 8/2001 |
| WO | WO/2001/069415 | 9/2001 |
| WO | WO/2002/044994 | 6/2002 |
| WO | WO/2003/064670 | 8/2003 |
| WO | WO/2003/064694 | 8/2003 |
| WO | WO/2003/065146 | 8/2003 |
| WO | WO/2004/055709 | 7/2004 |

OTHER PUBLICATIONS

Wikipedia-Graphical User Interface [retrieved Apr. 17, 2019] Retrieved from the Internet https://en.wikipedia.org/wiki/Graphical_user-inteface (Year: 2019).*

Ivory et al. Empirically Validated Web Page Design Metrics (CHI 2001 Proceedings of the SIGCHE Conference on Human Factors in Computing Systems ACM Digital Library Seattle WA (Year: 2001).*
McCann Web PCR Nature Biotechnology vol. 17 p. 304 (Year: 1999).*
Gibco BRL Produces and Reference Guide (Life Technologies Catalog (Year: 1997).*
Varotto et al. GST-PRIME: a genome-wide primer design software for the generation of gene sequence tags Nucleic Acids Research vol. 29 pp. 4373-4377 (Year: 2001).*
Medhurst et al. The use of TaqMan RT-PCR assays for semiquantitative analysis of gene expression in CNS tissues and disease models Journal of Neuroscience Methods vol. 98 pp. 9-20 (Year: 2000).*
International Human Genome Sequencing Consortium Initial sequencing and analysis of the human genome Nature vol. 409 pp. 860-921 (Year: 2001).*
ABI 3900 High Throughput DNA Synthesizer User's Manual Applied Biosystems (Year: 2001).*
Non-Final Office Action in U.S. Appl. No. 10/334,793, dated Jul. 16, 2007.
Final Office Action in U.S. Appl. No. 12/015,143, dated Dec. 27, 2011.
Final Office Action in U.S. Appl. No. 12/015,143, dated Oct. 13, 2010.
Non-Final Office Action in U.S. Appl. No. 12/015,143, dated Mar. 5, 2010.
Non-Final Office Action in U.S. Appl. No. 12/015,143, dated Jun. 23, 2011.
Affymetrix, "NetAffx™ User's Guide—The Lab," 2001.
Affymetrix, Press Release, Jul. 25, 2001.
Affymetrix, Press Release, Aug. 28, 1997.
Afonina et al., "Efficient priming of PCR with short oligonucleotides conjugated to a minor groove binder," *Nucleic Acids Research*, 25(13):2657-2660 (1997).
Altschul et al., "Basic Local Alignment Search Tool," *J. Mol. Biol.*, 215:403-410 (1990).
Altschul et al., "Issues in searching molecular sequence databases," *Nature Genetics*, 6:119-129 (1994).
Applied Biosystems, "Applied Biosystems Launches 'Assays-By-Design' Genomic Assays," Press Release, Oct. 25, 2001.
Applied Biosystems, "Oligo Factory Price List," Aug. 2002, pp. 1-13, including Assays-by-Design$^{SM}$ and Assays-on-Demand™ products, pp. 6-8.
Baner et al., "More keys to padlock probes: mechanisms for high-throughput nucleic acid analysis," *Current Opinion in Biotechnology*, 12:11-15 (2001).
Beacon Designer 2.0 Manual, *PREMIER Biosoft International*, 2001.
Bergstrom et al., "Synthesis, Structure, and Deoxyribonucleic Acid Sequencing with a Universal Nucleoside: I-(2'-Deoxy-β-D-ribofuranosyl)-3-nitropyrrole," *J. Am. Chem. Soc.*, 117:1201-1209 (1995).
Breen et al., "Determining SNP Allele Frequencies in DNA Pools," *Biotechniques*, 28(3):464-470.
Brown et al., "Modern machine-aided methods of oligodeoxyribonudeotide synthesis," *Oligonucleotides and Analogues: a Practical Approach*, Oxford University Press, 1991.
CFAR (Center for Aids Research), "Proposed Stategy for Using the TaqMan," University of California San Diego (2003).
Egholm et al., "PNA hybridizes to complementary oligonucleotides obeying the Watson-Crick hydrogen-bonding rules," *Nature*, 365:566-568 (1993).
Estruch, "OLIGO Primer Selection," *Methods in Molecular Biology*, vol. 70: Sequence Data Analysis Guidebook, pp. 279-285, including especially Fig. 3 and p. 285 (1997).
Fasman, "Practical Handbook of Biochemistry and Molecular Biology," *CRC Press*, pp. 385-394 (1989).
Furtado et al., "Persistence of HIV-1 Transcription in Peripheral-Blood Mononuclear Cells in Patients Receiving Potent Antiretroviral Therapy," *N. Engl. J. Med.*, 340:1614-1622 (1999).
Helt et al., "BioViews: Java-Based tools for Genomic Data Visualization," *Genome Research*, 8:291-305 (1998).

(56) References Cited

OTHER PUBLICATIONS

Judson et al., "How Many SNPs does a genome-wide haplotype map require?," *Pharmacogenomics*, 3:379-391 (2002).
Kanehisa et al., "KEGG: Kyoto Encyclopedia of Genes and Genomes," *Nucleic Acids Research*, 28:27-30 (2000).
Karlin et al., "Applications and statistics for multiple high-scoring segments in molecular sequences," *Proc. Natl. Acad. Sci.*, 90:5873-5877 (1993).
Karlin et al., "Methods for assessing the statistical significance of molecular sequence features by using general scoring schemes," *Proc. Natl. Acad. Sci.*, 87:2264-2268 (1990).
Korf et al., "MPBLAST: improved BLAST performance with multiplexed queries," *Bioinformatics*, 16(11):1052-1053 (2000).
Kricka, "Stains, labels and detection strategies for nucleic acids assays" *Ann. Clin. Biochem.*, 39:114-129 (2002).
Kutyavin et al., "3'-Minor groove binder-DNA probes increase sequence specificity at PCR extension temperatures," *Nucleic Acids Research*, 28(2):655-661 (2000).
Life Technologies, "GIBCO BRL Products & Reference Guide 1997-1998."
Life Technologies, "Catalogue and Reference Guide 2001," including Custom Primers products at pp. 20-2 and 20-3.
Lowe et al., "A computer program for selection of oligonucleotide primers for polymerase chain reactions," *Nucleic Acids Research*, 18(7):1757-1761 (1990).
McCann, "Web PCR," *Nature Biotechnology*, vol. 17, p. 304 (1999).
McCarthy et al., "The use of single-nucleotide polymorphism maps in pharmacogenomics," *Nature Biotechnology*, 18:505-508 (2000).
Mein et al., "Evaluation of Single Nucleotide Polymorphism Typing with Invader on PCR Amplicons and its Automation," *Genome Research*, 10:330-343 (2000).
Miller et al., "The birth and death of human single-nucleotide polymorphisms: new experimental evidence and implications for human history and medicine," *Hum. Mol. Genet.*, 10(20):2195-2198.
Mulder et al., "Rapid and Simple PCR Assay for Quantitation of Human Immunodeficiency Virus Type 1 RNA in Plasma: Application to Acute Retroviral Infection," *Journal of Clinical Microbiology*, 32(2):292-300 (1994).
Nielsen et al., "Sequence-Selective Recognition of DNA by Strand Displacement with a Thymine-Substituted Polyamide," *Science*, 254:1497-1500 (1991).
Oliver et al., "Use of Single Nucleotide Polymorphisms (SNP) and Real-Time Polymerase Chain Reaction for Bone Marrow Engraftment Analysis," *Journal of Molecular Diagnostics*, 2(4):202-208 (2000).
International Search Report in International Appl. No. PCT/US02/34599, dated Apr. 29, 2003.
International Search Report in International Appl. No. PCT/US03/02238, dated Jun. 27, 2003.
International Search Report in International Appl. No. PCT/US03/00128, dated Jun. 30, 2004.
Rozen et al., "Primer3 on the WWW for General Users and for Biologist Programmers," *Methods in Molecular Biology*, vol. 132: Bioinformatics Methods and Protocols, pp. 365-386 (2000).
Schmittgen et al., "Quantitative Reverse Transcription-Polymerase Chain Reaction to Study mRNA Decay: Comparison of Endpoint and Real-Time Methods," *Anal. Biochem.*, 285:194-204 (2000).
Shi et al., "Enabling Large-Scale Pharmacogenetic Studies by High-Throughput Mutation Detection and Genotyping Tehnologies," *Clin. Chem.*, 47(2):164-172 (2001).
Favis, R., Day, J.P., Gerty, N.P., Phelan, C.. Narod, S., and Barany, F. 2000. Universal DNA array detection of small insertions and deletions in BRCA I and BRCA2. Nat. Biotech. 18:561-564.
Sachidanandam, R., D. Weissman, S.C. Schmidt, J.M. Kakol, L.D. Stein, G. Marth, S. Sherry, J.C. Mullikin, et al. 2001. A map of human genome sequence variation containing 1.42 million single nucleotide Polymorphisms. Nature 409:928-933.

Livak, K.J. 1999. Allelic discrimination using fluorogenic probes and the 5' nuclease assay. Genet Anal 14:143-149.
Venter, J.C., M.D. Adams, E.W. Myers, P.W. Li, R.J. Mural, G.G. Sutton, H.O. Smith, M. Yandell, et al. 2001. The sequence of the human genome. Science 291:1304-1351.
E Masood, As Consortium Plans Free SNP Map of Human Genome, Nature, vol. 398, pp. 545-546, (1999).
Kwok, S. and Higuchi, R. 1989. Avoiding false positives with PCR. Nature 339:237-238.
Lakowicz, J.R. 1983. Energy Transfer. In Principles of Fluorescence Spectroscopy, New York: Plenum Press 303-339.
Livak, K.J., Marmaro, J., and Todd, J.A. 1995. Towards fully automated genome-wide polymorphism screening [letter]. Nat. Genet. 9:341-342.
Longo, M.C., Berninger, M.S., and Hartley, J.L. 1990. Use of uracil DNA glycosylase to control carry-over contamination in polymerase chain reactions. Gene 93:125-128.
Mullis, K.B. and Faloona, F.A. 1987. Specific synthesis of DNA in vitro via a polymerase-catalyzed chain reaction. Methods Enzymol. 155:335-350.
Saiki, R.K., Scharf, S., Faloona, F., et al. 1985. Enzymatic amplification of β-globin genomic sequences and restriction site analysis for diagnosis of sickle cell anemia. Science 230: 1350-1354.
D Wang et al., Large Scale identification, Mapping, and Genotyping of Single Nucleotide Polymorphisms in the Human Genome, Science, vol. 280, pp. 1077-1082, (1998).
D Meldrum, Automation for Genomics, Part One, Genome Research, vol. 10, pp. 1081-1092, (2000).
J Hampe et al, An Integrated System for High Throughput Taqman Based SNP Genotyping, Bioinformatics, vol. 17, pp. 654-655, (2001).
Kutyavin, I.V., Lukhtanov, E.A., Gamper, H.B., and Meyer, R.B. 1997. Oligonucleotides with conjugated dihydropyrroloindole tripeptides: base composition and backbone effects on hybridization. Nucleic Acids Res. 25:3718-3723.
E Lai, Application of SNP Technologies in Medicine, Genome Research, vol. 11, pp. 927-929, (2001).
Kerlavage, A. V. Bonazzi, M. di Tommaso, C. Lawrence, P. Li, F. Mayberry, R. Mural, M. Nodell, et al. 2002. The Celera Discovery System. Nucleic Acids Res 30: 129-136.
Levy, S., S. Hannenhalli and C. Workman. 2001. Enrichment of regulatory signals in conserved non-coding genomic sequence. Bioinformatics 17:871-877.
H. Avi-Itzhak, X. Su and F. De Le Vega, Selection of Minimum Subsets of Single Nucleotide Polymorphisms to Capture Haplotype Block Diversity, 2003.
Altshuler, D. V.J. Pollara, C.R. Cowles, W.J. Van Etten, J. Baldwin, L. Linton and E.S. Lander. 2000. An SNP map of the human genome generated by reduced representation shotgun sequencing. Nature 407:513-516.
Daly, M.J. J.D. Rioux, S.F. Schaffner, T.J. Hudson and E.S. Lander. 2001. High-resolution haplotype structure in the human genome. Nat Genet 29:229-232.
Kruglyak, L. 1999. Prospects for whole-genome linkage disequilibrium mapping of common disease genes. Nat Genet 22: 139-144.
Marth, G. R. Yeh, M. Minton, R. Donaldson, Q. Li, S. Duan, R. Davenport, R.D. Miller and P.Y. Kwok. 2001. Single-nucleotide polymorphisms in the public domain: how useful are they? Nat Genet 27:371-372.
Nordborg, M. and S. Tavare. 2002. Linkage disequilibrium: what history has to tell us. Trends Genet 18:83-90.
Reich, D.E. M. Cargill, S. Bolk, J. Ireland, P.C. Sabeti, D.J. Richter, T. Lavery, R. Kouyoumjian, et al. 2001. Linkage disequilibrium in the human genome. Nature 411:199-204.
Reich, D.E. and E.S. Lander. 2001. On the allelic spectrum of human disease. Trends Genet 17:502-510.
Remm, M. and A. Metspalu. 2002. High-density genotyping and linkage disequilibrium in the human genome using chromosome 22 as a model. Curr Opin Chem Biol 6:24-30.
M Perlin, G Lancia, S Ng, Toward Fully Automated Genotyping: Genotyping Microsatellite Markers by Deconvolution, Am. J. Hum. Gen, vol. 57, pp. 1199-1210, (1995).

(56) References Cited

OTHER PUBLICATIONS

A Clark, Inference of haplotypes from PCR-amplified samples of diploid populations, Mol Biol Evol., Mar. 7, pp. 111-122, (1990).
Abecasis, G.R., E. Noguchi, A. Heinzmann, J.A. Traheme, S. Bhattacharyya, N.I. Leaves, G.G. Anderson, Y. Zhang, et al. 2001. Extent and distribution of linkage disequilibrium in three genomic regions. Am J Hum Gen et 68: 191-197.
Collins, A., S. Ennis, P. Taillon-Miller, P.Y. Kwok and N.E. Morton. 2001. Allelic association with SNPs: metrics, populations, and the linkage disequilibrium map. Hum Mutat 17:255-262.
J Weber, J Cbe, D David, J Heil, J Opolka, C Volkmann, M Doktycz, K Beattie, Identification and Analysis of Human Short Insertion/ Deletion Polymorphisms, Am. Society of Ilum. Gen. (Oct. 1998).
C Zhoa, J Heil, W Dickenson, L Ott, J Weber et al., A Computer System for Large Scale STRP Genotyping, Am. J. of Hum. Genetics, vol. 61, p. A302, (1997).
Lander, E.S., L.M. Linton, B. Birren, C. Nusbaum, M.C. Zody, J. Baldwin, K. Devon, K. Dewar, et al. 2001. Initial sequencing and analysis of the human genome. Nature 409:860-885.
Lander, E.S., L.M. Linton, B. Birren, C. Nusbaum, M.C. Zody, J. Baldwin, K. Devon, K. Dewar, et al. 2001. Initial sequencing and analysis of the human genome. Nature 409:886-921.
Förster, V. T. 1948. Zwischenmolekulare Energiewanderung and Fluoreszenz. Ann. of Phys. (Leipzig) 2:55-75. English Summary.
MGB Eclipsetm Design Software Users Manual, from Epoch Biosciences dated Feb. 1, 2002.
Koustubh et al., High Throughput Genotyping with Single Nucleotide Polymorphisms, Genome Research, vol. 11, pp. 1262-1268, (2001).
Heil et al., "An Automated Computer System to Support Ultra High Throughput SNP Genotyping," *Pacific Symposium on Biocomputing*, pp. 30-40 (Jan. 3-7, 2002).
Ball et al., Matrix-Assisted Laser Desorption Ionization Time-of Flight Mass Spectrometry as a Rapid Quality Control Method in Oligonucleotide Synthesis Analytical Biochemistry, vol. 246, pp. 185-194 (1997).
Ellington et al., Current Protocols in Molecular Biology, pp. 2.11. 1-2.11.25, John Whiley & Sons, Inc. (1998).
Becker et al., Real-Time Quantitative Polymerase Chain Reaction to Assess Gene, Transfer Human Gene Therapy, vol. 10, pp. 2559-2566 (1999).
Leary et al., Consensus oligonucleotide primers for the detection of GB virus C in human cryptogenic hepatitis, Journal of Virological Methods, vol. 56, pp. 119-121 (1996).
Eriksson et al., Independent Regulation of the Myotonic Dystrophy 1 Locus Genes Postnatally and during Adult Skeletal Muscle Regeneration, Journal of Biological Chemistry, vol. 275, pp. 19964-19969 (2000).
Office Action in Australian Appl. No. AU200420, dated Jun. 6, 2007.
Office Action in Canadian Appl. No. CA2474482, dated Jul. 4, 2007.
Office Action in European Appl. No. EP02784321.8, dated Sep. 18, 2007.
Supplementary Search Report in European Appl. No. EP02784321. 8, dated Jan. 8, 2005.
Supplementary Search Report in European Appl. No. EP03254410. 8, dated Apr. 8, 2005.
Supplementary Search Report in European Appl. No. EP03701976. 7, dated Jan. 4, 2008.
Office Action in Japanese Appl. No. JP2003564284, dated Dec. 21, 2005.
De La Vega et al., "Selection of Single Nucleotide Polymorphisms for a Whole-Genome Linkage Disequilibrium Mapping Set," Applied Biosystems®, poster presented at Cold Spring Harbor Laboratory Genome Sequencing & Biology Meeting, May 2002.
Geneworks, http//web.archive.org/web/20010924210557/www. geneworks.com.au/.
Hohashi, "Primers," Further Advanced Macintosh, Collection of software for medicine and biology, vol. 2, pp. 92-100 (1994).
Lipman et al., "Rapid and Sensitive Protein Similarity Searches," Science, 227:1435-1441 (1985).
Livak et al., "Oligonucleotides with Fluorescent Dyes at Opposite Ends Provide a Quenched Probe System Useful for Detecting PCR Product and Nucleic Acid Hybridization " *PCR Methods and Applications*, 4:357-362 (1995).
New England Biolabs, "Custom Oligonucleotide Synthesis Catalogue 2000-2001," pp. 120.
Syvänen, "Accessing Genetic Variation: Genotyping Single Nucleotide Polymorphisms," *Nature Reviews Genetics*, 2(12):930-942 (2001).
Chen et al., "Computer Program for Calculating the Melting Temperature of Degenerate Oligonucleotides Used in PCR of Hybridization," *BioTechniques*, 22:1158-1160 (1997).
Eberhardt, "A Shell Program for the Design of PCR Primers Using Genetics Computer Group (GCG) Software (7.1) on VAX/VMS™ Systems," *BioTechniques*, 13(6):914-917 (1992).
Hodgman et al. (Eds.), "Handbook of Chemistry and Physics," Forty-Fourth Edition, *The Chemical Rubber Publishing Co.*, pp. 9-10 (1961).
Hyndman et al., "Software to Determine Optimal Oligonucleotide Sequences Based on Hybridization Simulation Data," *BioTechniques*, 20(6):1090-1097 (1996).
Jaeger et al., "Improved Predictions of Secondary Structures for RNA," *Proc. Natl. Acad. Sci. USA*, 86(20):7706-7710 (1989).
Kress et al., "A Comparative Analysis of Thermal Blood Perfusion Measurement Techniques," *Journal of Biomechanical Engineering*, 109(3):218-225 (1987).
Kunitsyn et al., "Partial Thermodynamic Parameters for Prediction Stability and Washing Behavior of DNA Duplexes Immobilized on Gel Matrix," *J. of Biomolecular Structure and Dynamics*, 14(2):239-244 (1996).
Lockhart et al., "Expression monitoring by hybridization to high-density oligonucleotide arrays," *Nature Biotechnology*, 14(13):1675-1680 (1996).
Milner et al., "Selecting Effective Antisense Reagents on Combinatorial Oligonucleotide Arrays," *Nature Biotechnology*, 15(6):537-541 (1997).
Mitsuhashi, "Strategy for designing specific antisense oligonucleotide sequences," *Journal of Gastroenterology*, 32(2):282-287 (1997).
Mitsuhashi, "Technical Report: Part 2. Basic Requirements for Designing Optimal PCR Primers," *J. of Clinical Laboratory Analysis*, 10(5):285-293 (1996).
Mitsuhashi et al., "Oligonucleotide probe design— a new approach," *Nature*, 367(24):759-761 (1994).
Mitsuhashi, "Technical Report: Part 1. Basic Requirements for Designing Optimal Oligonucleotide Probe Sequences," *J. of Clinical Laboratory Analysis*, 10(5):277-284 (1996).
Patzel et al., "Theoretical design of antisense RNA structures substantially improves annealing kinetics and efficacy in human cells," *Nature Biotechnology*, 16(1):64-68 (1998).
Pease et al., "Light-Generated Oligonucleotide Arrays for Rapid DNA Sequence Analysis," *Proc. Natl. Acad. Sci. USA*, 91:5022-5026 (1994).
Rychlik et al., "A computer program for choosing optimal oligonucleotides for filter hybridization, sequencing and in vitro amplification of DNA," *Nucleic Acids Res.*, 17(21):8543-8551 (1989).
Santa Lucia et al., "Improved Nearest-Neighbor Parameters for Predicting DNA Duplex Stability," *Biochemistry*, 35(11):3555-3562 (1996).
Southern et al., "Analyzing and Comparing Nucleic Acid Sequences by Hybridization to Arrays of Oligonucleotides; Evaluation using Experimental Models," *Genomics*, 13(4):1008-1017 (1992).
Stull et al., "Predicting antisense oligonucleotide inhibitory efficacy: a computational approach using histograms and thermodynamic indices," *Nucleic Acids Res.*, 20(13):3501-3508 (1992).
Sugimoto et al., "Thermodynamic parameters to predict stability of RNA/DNA hybrid duplexes," *Biochemistry*, 34:11211-11216 (1995).
Weber et al., "Molecular dynamics simulation of polymers. I. Structure," *The Journal of Chemical Physics*, 71:4760-4762 (1979).
Wodicka et al., "Genome-wide expression monitoring in *Saccharomyces cerevisiae*," *Nature Biotechnology*, 15(13):1359-1367 (1997).

(56) References Cited

OTHER PUBLICATIONS

Primer Express® Software v2.0, Applications-Based Primer Design Software, User's Manual, Applied Biosystems, Foster City, CA (2001), available at www.bionet.nsc.ru/gep/materials/Primer_Express_v2_0_User_Manual.pdf (last visited Jul. 1, 2014).

Rychlik, W., "Selection of Primers for Polymerase Chain Reaction," Chapter 2 in *Methods in Molecular Biology, vol. 15, PCR Protocols Current Methods and Applications*, White, B.A. (Ed.), pp. 31-40, Humana Press Inc. (1993).

\* cited by examiner

Gene Exploration System

BioMolecule Library | Text Search | Sequence Analysis | Workspace

Search: Homo sapiens
Query: Chromosome 2 - scaffold greater than 150kb • map

Homo sapiens Chromosome 2 Map Report
Index Range 0 - 240,668,003

| | Scaffold | Location | | Length |
|---|---|---|---|---|
| 1. | GA_x5L2HTTHW5V | chr. 2 | 0 - 2,734 | 2,734 |
| 2. | GA_x5L2HTTHWVY | chr. 2 | 6,843 - 10,823 | 3,980 |
| 3. | GA_x5L2HTU50TQ | chr. 2 | 14,932 - 16,582 | 1,650 |
| 4. | GA_x5L2HTU50VB | chr. 2 | 20,691 - 22,341 | 1,650 |
| 5. | GA_x5L2HTTHW97 | chr. 2 | 26,450 - 29,791 | 3,341 |
| 6. | GA_x5L2HTTHWD2 | chr. 2 | 33,900 - 35,444 | 1,544 |
| 7. | GA_x5L2HTTHWPM | chr. 2 | 39,553 - 60,007 | 20,454 |
| 8. | GA_x5L2HTTHWH9 | chr. 2 | 64,116 - 67,125 | 3,009 |
| 9. | GA_x5L2HTTHW80 | chr. 2 | 71,234 - 76,109 | 4,875 |
| 10. | GA_x5L2HTTHWBA | chr. 2 | 80,218 - 86,341 | 6,123 |
| 11. | GA_x5L2HTTHY5A | chr. 2 | 90,450 - 92,415 | 1,965 |
| 12. | GA_x5L2HTTHWRP | chr. 2 | 96,524 - 97,867 | 1,343 |
| 13. | GA_x5L2HTTHWRR | chr. 2 | 101,976 - 103,639 | 1,663 |
| 14. | GA_x5L2HTTHWRT | chr. 2 | 107,748 - 109,326 | 1,578 |
| 15. | GA_x5L2HTTHW5R | chr. 2 | 113,435 - 114,636 | 1,201 |
| 16. | GA_x5L2HTTHWR5 | chr. 2 | 118,745 - 119,889 | 1,144 |
| 17. | GA_x5L2HTTHWL7 | chr. 2 | 123,998 - 125,676 | 1,678 |
| 18. | GA_x5L2HTUCHG0 | chr. 2 | 129,785 - 133,236 | 3,451 |
| 19. | GA_x5L2HTUCJ0H | chr. 2 | 137,345 - 139,124 | 1,779 |
| 20. | GA_x54KRE8WT9G | chr. 2 | 143,233 - 144,610 | 1,377 |
| 21. | GA_x54KRE8WTAL | chr. 2 | 148,719 - 153,513 | 4,794 |
| 22. | GA_x54KRE8WTDA | chr. 2 | 157,622 - 163,326 | 5,704 |
| 23. | GA_x54KRE902HB | chr. 2 | 167,435 - 332,677 | 165,242 |
| 24. | GA_x5L2HTTHY6C | chr. 2 | 336,786 - 337,997 | 1,211 |

*Fig. 3*

Gene Exploration System

BioMolecule Library | Text Search | Sequence Analysis | Workspace

Search: Homo sapiens
Query: GA_x9V1BB6 • [gene list] [map]

Homo sapiens Scaffold Report ○: GA_x9V1BB6
scaffold range 5000000
scaffold location - chr 17 ▷ 36,566,229 - 41,491,828 chromosome map report
⟲ previous scaffold • next scaffold ⟳

| Genome Assembly Id : Start ... End |
|---|
| 1.      GA_X9v1bb6 : 1..500000 |
| 2.      GA_x9V1BB6 : 500001..1000000 |
| 3.      GA_x9V1BB6 : 1000001..1500000 |
| 4.      GA_x9V1BB6 : 1500001..2000000 |
| 5.      GA_x9V1BB6 : 2000001..2500000 |
| 6.      GA_x9V1BB6 : 2500001..3000000 |
| 7.      GA_x9V1BB6 : 3000001..3500000 |
| 8.      GA_x9V1BB6 : 3500001..4000000 |

*Fig. 4*

Gene Exploration System

BioMolecule Library | Text Search | Sequence Analysis | Workspace

Search: Homo sapiens
[Export] • Query: GA_x9V1BB6:1..500000 • [gene list] [map]

Sequence Report ○: GA_x9V1BB6:1..500000
sequence location - chr 17 ▷ 36,566,229 -37,066,229

Chromosome map report | Scaffold report
next segment ⟳ type: Scaffold     species: *Homo sapiens* analyze [BlastN ▼] [go]    Sequence query limits: BlastN - 350kb, BlastX - 150kb

```
>GA_x9V1BB6:1..500000
1        11       21       31       41       51
ACTAGCCTGGGCAACAAGAGTGAAACTCCGTTCTCAAAAAAAAAAAAAGCCTTTTTTGA
61       71       81       91       101      111
GATGGAGTCTCGCTCTGTCGCCCAGGCTGGAGTGCAGCAGCGCGATTTCGGCTCACTGCA
121      131      141      151      161      171
```

*Fig. 5*

Gene Exploration System

BioMolecule Library / Text Search / Sequence Analysis / Workspace

Search: Genome Maps
Query: hCG22136 · [map]

analyze [Gene ▼] [BlastN ▼] [go]  View selected in Company Stock Assays [go]  view [Standard ▼] [go]

Hits 1-3 of 3 [page: (1)]

| | ID- Gene, Transcript, Protein | Gene Name | Gene Symbol | Location | Panther Best Hit | Best NRAA Definition | Company Assay ID | Transcript Class |
|---|---|---|---|---|---|---|---|---|
| clr all | | | | | | | | |
| ☐ 1. | hCG22136<br>• hCT1968196<br>• Hcp1782699 | apolipoprotein E | APOE | Chr. 19 △<br>42,918,445 - 42,922,033 | APOLIPOPROTEIN E<br>(CF11428:SF3) | gb\|AAB59397.1\|(M10065)<br>apolipoproteinE [Homosapiens] | Hs00171168_m1 | ✴ |
| ☐ 2. | hCG22136<br>• hCT1968195<br>• hCP1782694 | apolipoprotein E | APOE | Chr. 19 △<br>42,918,445 - 42,922,033 | APOLIPOPROTEIN E<br>(CF11428:SF3) | gb\|AAB59397.1\|(M10065)<br>apolipoproteinE [Homosapiens] | Hs00171168_m1 | ✴ |
| ☐ 3. | hCG22136<br>• hCT13229<br>• hCP39666 | apolipoprotein E | APOE | Chr. 19 △<br>42,918,445 - 42,922,033 | APOLIPOPROTEIN E<br>(CF11428:SF3) | gb\|AAB59397.1\|(M10065)<br>apolipoproteinE [Homosapiens] | Hs00171168_m1 | ✴ |

Hits 1-3 of 3 [page: (1)]

Key:

transcript class
- ✴ Expert Reviewed
- ▦ Expert Reviewed - Putative Pseudogene
- ● Celera computational annotation/Otto
- ▪ Gene prediction (4)

- ▦ Gene prediction (3)
- ● Gene prediction (2)
- ▪ Gene prediction (1)

location
△ forward orientation
▽ reverse orientation
◇ uncertain

*Fig. 6*

Gene Exploration System

BioMolecule Library | Text Search | Sequence Analysis | Workspace

Gene : hCG22136 • apolipoprotein E     species: *Homo sapiens*
symbol : APOE    location : chr. 19▷ 42,918,445 - 42,922,033    HGMD
alias:

Transcript / Protein pair(s)     Panther best hit
☐ mRNA : hCT13229    ☐ Protein : hCP39668    CF11428 APOLIPOPROTEIN view | Protein | mRNA | Chromosome id : hCT13229 • sequence revision 2

| nucleotides | exons | coding region | transcript class |
|---|---|---|---|
| 1156 | 4 | Complete | ★ |

| | accession | e-value | definition |
|---|---|---|---|
| NRAA best hit | 178853 | 0.0 | gbAAB59397.1 (M10065) apolipoprotein E (Homo sapiens) |

Best hits against Celera and Public sequence databases : hCP39668

[chromosome map showing positions 0–50M with cytobands 19p13.3 through 19q13.4, and exon map showing positions 42,918,500 through 42,921,500; Gene (Homo sapiens, hCG22136) hCG22136 APOE; Exons (Homo sapiens, hCG13229) Visible 4; positions 42,919,800 through 42,919,600; Exons (Homo sapiens, hCG13229) Visible 1]

Evidence     💡 About the Data

| type | present | |
|---|---|---|
| Reference Sequence Entry | Yes | [ 4557324 ] |
| Hits to CHGI Entry | Yes | |
| Hits to CMGI Entry | Yes | |
| Hits to Mouse Fragments | Yes | |
| Kits to Known Proteins | Yes | |

Transcribed Sequence (all exons)    ☐ Query CompleteSequence : [BLASTN ▼] go

```
>chgd_transcript|hCT13229_2 /len-1156 /transcript_uid-110005
95681219 /gn_name-01_z54KRC9BDAW /ga_uid-181000065561950 /cg
_name-hCG22186.2 /alignment=(1605984-1606021:1606781-1606847
:1607939-1608132:1608712-1609572| alias=EXPERT_REVIEW CCCAGCGGAGGTGAAGGACGTCCTTCCCCAGGAGCCGACTGGCCAATCACAGGCAGGAAG
ATGAAGGTTCTGTGGGCTGCGTTGCTGGTCACATTCCTGGCAGGATGCCAGGCCAAGGTG
GAGCAAGCGGTGGAGACAGAGCCGGAGCCCGAGCTGCGCCAGCAGACCGAGTGGGAGAGC
GGCCAGCGCCTGGGAACTGGCACTGGGTCGCTTTTGGGATTACCTGCGCTGGGTGCAGACA
CTGTGTGAGCAGGTGCAGGAGGAGCTGCTCAGCTCCCAGGTCACCCAGGAACTGAGGGGG
CTGATGGACGAGACCATGAAGGAGTTGAAGGCCTACAAATCGGAACTGGAGGAACAACTG
ACCCCGGTGGCGGACCACACGCCCCACGGCTGTCCAACGAGCTGCAGGCGCCCCAGGCC
CGGCTGGGCGCGCACATGGAGGACGTGCGCGCCCGCCTGCTCAGTACCGCGGCGAGGTG
```

Fig. 9

Gene Exploration System

BioMolecule Library | Text Search | Sequence Analysis | Workspace

HGMD - Human Gene Mutation Database
Report : APOE

Gene Name : Apolipoprotein E
OMN : 107741

Associations to Celera's Human Genome    Tips
Gene : hCG22136     Location : chr. 19 ▷ 42,918,445 - 42,922,033     Human RefSNP by gene 32

Mutations in this gene were first reported in 1986
- Funke (1986) Gtn Ctem 32, 1285

| HGMD classified mutation type | Mutations |
|---|---|
| Nucleotide substitutions (missense/nonsense) | 20 |
| Nucleotide substitutions (splicing) | 1 |
| Nucleotide substitutions (regulatory) | 2 |
| Small deletions | 4 |
| Small insertions | 0 |
| Small indels | 0 |
| Goss deletions | 1 |
| Gross insertions & duplications | 1 |
| Complex rearrangements (uncluding inversions) | 0 |
| Repeat variations | 0 |
| TOTAL : | 29 |

| Mutations by HGMD Phenotype (select to search HGMD Data) | Nucleotide substitutions | Mirco- lesions | Gross lesions |
|---|---|---|---|
| Alzheimer disease increased risk | 1 | 0 | ▯ |
| Alzheimer disease increased risk association | 1 | 0 | ▯ |
| Alzheimer disease susceptibility to association | 1 | 0 | ▯ |
| Apolipoprotein E deficiency | 14 | 1 | ▯ |
| Hyperipidaemia 3 | 1 | 0 | ▯ |
| Hyperipoproteinaemia | 0 | 1 | 1 |

*Fig. 11*

Gene Exploration System

BioMolecule Library | Text Search | Sequence Analysis | Workspace

Search Genome Maps species: Homo sapiens

□ Whole Chromosome Viewer
[select chr. ▼] (gene list) (map)     💡 About the Date □ Locate a Celera Gene     Flanking Region [0 Mb ▼]
[hCG (gene) ▼] [          ] (gene list) (map)

Tips  Get to a gene location on the chromosome map by
 • Celera gene, transcript or protein id  e.g. hCG22136
 • Gene symbol (HUGO) - e.g. APOE
 • RefSeq nt gi - e.g. 4557324
 Note: Multiple results may map to a single postion

Cytogenetic Band

Band [      ] to Band [      ] (gene list) (map)
 e.g. 17p11         e.g.17q11

Band [      ] (gene list) (map)
 e.g. 17cen

Position [select chr. ▼]     Flanking Region [0 Mb ▼]

Postion [      ] Mb, to Postion [      ] Mb (gene list) (map)
 by Mb e.g. 37.0       e.g. 39.0

Postion [      ] Mb (gene list) (map)
 by Mb e.g. 39.6

STS Marker     Flanking Region [0 Mb ▼]

Marker [      ] to Marker [      ] (gene list) (map)
 e.g. RH75541       e.g. RH55136

Marker [      ] (gene list) (map)
 e.g. RH732515

BAC Tile Map     Flanking Region [0 Mb ▼]

BAC ID [      ] to BAC ID [      ] (gene list) (map)
 e.g. AC067852       e.g. AC009283

BAC ID [      ] (gene list) (map)
 e.g. AC046171                  💡 About the Date

*Fig. 12*

Gene Exploration System

BioMolecule Library | Text Search | Sequence Analysis | Workspace

Search Genome Assembly

Get a Celera chromosome map, scaffold or sequence report by chromosome or known Genome Assembly number. For all searches please enter ID - no wildcard (*) or boolean variables. 💡 About the Date species: *Homo sapiens*

☐ Chromosome Report -

Lists all Celera scaffolds on a chromosome and includes their coordinates on the Celera reference chromosome axis.

Chromosome    Scaffold Lengths
[chr. 2 ▼]    [all ▼]   search

Optional: include chromosome position in search
Position [    ] Mb. to Position [    ] Mb.
    *e.g. 37*                      *e.g. 39*

☐ Scaffold Report -

Lists all genomic assembly segments associated with a single scaffold. For delivery in CDS, Celera scaffolds are broken into 500Kb segments
by Genome Assembly number
[        ] search
*e.g. GA_x9V1BB6*
To browse GA numbers search by chromosome report.

☐ Sequence Report -

Displays the genomic assembly segment's location on the Celera reference chromosome axis and the nucleotide consensus sequence (ungapped) in FASTA format
by Genome Assembly number
[        ] search
*e.g. GA_x9V1BB6 : 1..500000*
To browse GA numbers search by chromosome report.

Gene Exploration System

BioMolecule Library | Text Search | Sequence Analysis | Workspace ontology keyword: [ ] (find)

Ontology                                                                   tips 💡

┌─ Select a Species ─────────────────────────────────────────┐
│          ● Homo sapiens          ○ Mus musculus            │
└────────────────────────────────────────────────────────────┘

┌─ Gene Ontology ────────────────────────────────────────────┐
│   ☐   function                                          ▦  │
│       0003674 : 160/92335                                  │
│   ☐   cellular component                                   │
│       0005575 : 0/94113                                    │
│   ☐   process                                              │
│       0008150 : 0/151404                                   │
│                                                            │
│   Key:  ▦       Gene List (node hits - select to view)     │
│        node     GO Classification                          │
│        # : # / # GO id : genes (node) / genes (inclusive nodes) │
└────────────────────────────────────────────────────────────┘

Gene Exploration System

BioMolecule Library | Text Search | Sequence Analysis | Workspace

Ontology:   Keyword Results species:   Homo sapiens

Results by node > node > node
   search :    Ontology
   keyword :   {caspase*}

1. GO molecular function > enzyme > peptidase > cysteine-type peptidase > cysteine-type endopeptidase > caspase
2. GO molecular function > enzyme > peptidase > cysteine-type peptidase > cysteine-type endopeptidase > caspase > signaling (initiator) caspase
3. GO molecular function > enzyme > peptidase > cysteine-type peptidase > cysteine-type endopeptidase > caspase > signaling (initiator) caspase > caspase-1
4. GO molecular function > enzyme > peptidase > cysteine-type peptidase > cysteine-type endopeptidase > caspase > signaling (initiator) caspase > caspase-2

*Fig. 16*

| | SEARCH [        ] IN [Products ▼] [GO] |
|---|---|
| HOME | ABOUT US | STORE | ● PRODUCTS | APPLICATIONS | SERVICE & SUPPORT | LIBRARIES | EVENTS |

▷ Accessories
▷ Custom Services
▷ Disposables
▶ Genomic Assays
▷ Instrument Systems
▷ Reagents
▷ Software

Genomic Assays

Stock Assays Products translate the world's most comprehensive resource for public and private human genome sequence data into an immense catalog of validated, ready-to-use assays for gene expression and SNP genotyping. All assays are based on the familiar 5' nuclease chemistry with probes for single-tube convenience and reliable performance.

View the entire catalog, including our on line assay selection guide and evaluation data on each assay, free with no obligation by clicking on the appropriate link to the right. In addition, the Custom Assays Service lets you custom order assays for your particular gene expression or SNP genotyping application.

Stock Assays
Gene Expression Products
more info>                    search assays>

Stock Assays
SNP Genotyping Products
more info>                    search assays>

Custom Assays
more info>

Gene Exploration System

Expand your research horizons with the Gene Exploration System, a subscription-based, integrated research platform that provides the most comprehensive and curated biological data available along with validated assays.

*Fig. 17* seq_000001 AGTGAACG[A/G]GATAGGCA[G/T]CTCCTGCCC 1=s33d,2=s33g
           record name                    sequence                    coordinates seq_000004 AGTGAACGAGATAGGCAGCTCCTGCCCCATCCAAG 13=m13,20=txyz
           record name                 sequence                         coordinates Submission file contains:
- ☐ Header line
- ☐ Sequence record for each assay
- ☐ Sequences for one part number (only SNP assays and only one scale)

Each sequence record:
- ☐ Exists as a single line, with no carriage returns or end-of-line characters
- ☐ Contains all three components: record name, sequence, and at least one coordinate
- ☐ Contains only two spaces, each separating the three components
- ☐ Contains no spaces within the record name, sequence, or coordinate Header line contains:
- ☐ Greater-than symbol >
- ☐ Name
- ☐ Telephone number
- ☐ One part number
- ☐ No more than 255 characters Each record name:
- ☐ Is unique
- ☐ Contains no more than 10 characters
- ☐ Includes only alphanumberic, underscore, hyphen, and period characters
- ☐ Contains no spaces or tabs Each sequence:
- ☐ Is presented in the 5' to 3' orientation
- ☐ Contains no more than 5000 characters
- ☐ Contains no spaces or tabs
- ☐ Consists of only the characters A, C, G, T, or
- ☐ N, except where SNP or indel target sites are indicated.

Each SNP site:
- ☐ Is marked with square brackets
- ☐ Contains the bases for two alleles of the SNP, separated by a forward slash

```
>JohnSmith 9997865432 partnumber4332072
seq_000001 AGTGAACG[A/G]GATAGGCA[G/T]CTCCTGCCC 1=s33d,2=s33g
seq_000002 TTACGGCCCTGA[G/T]GGGACTGC[G/C]ATCATTTTCT 1=sn1f,2=sn3a
seq_000003 GAGTGGAGCAACA[TAGC/*]GCTTTCCGCAATTTAC 1=34d
```

Each indel site:
- ☐ Is marked with square brackets
- ☐ Contains no more than 6 bases to the left of a forward slash and an asterisk to the right of the forward slash Each coordinate:
- ☐ Contains a target site order position, equals sign, and target site name for each target site
- ☐ Contains a target site name with no more than four alphanumeric characters
- ☐ Contains commas to separate multiple sites
- ☐ Is presented in 5' to 3' order
- ☐ Contains no spaces or tab

*Fig. 25*

Submission file contains:
☐ Header line
☐ Sequence record for each assay
☐ ☐ Sequences for one part number (only SNP assays or gene expression assays and only one scale)

Each sequence record:
    ☐ Exists as a single line, with no carriage returns or end-of-line characters
    ☐ Contains all three components: record name, sequence, and at least one coordinate
    ☐ Contains only two spaces, each separating the three components
    ☐ Contains no spaces within the record name, sequence, or coordinate Each sequence:
    ☐ Is presented in the 5' to 3' orientation
    ☐ Contains no more than 5000 characters
    ☐ Contains no spaces or tabs
    ☐ Consists of only the characters A, C, G, T, or N
    ☐ Contains unmarked target sites Header line contains:
    ☐ Greater-than symbol >
    ☐ Name
    ☐ Telephone number
    ☐ One part number
    ☐ No more than 255 characters Each record name:
    ☐ Is unique
    ☐ Contains no more than 10 characters
    ☐ Includes only alphanumberic, underscore, hyphen, and period characters
    ☐ Contains no spaces or tabs

```
>JohnSmith 9997865432 partnumber4332079
seq_000004 AGTGAACGAGATAGGCAGCTCCTGCCCCATCCAAG 13=m13,20=txzy
seq_000005 TTACGGCCCTGAGGGGACGAATCGATCATTTTCT 15=tryk
```

Each coordinate:
    ☐ Contains a target site nucleotide position, equals sign, and target site name for each target site
    ☐ Contains a target site name with no more than four alphanumeric characters
    ☐ Contains commas to separate multiple sites
    ☐ Is presented in 5' to 3' order
    ☐ Contains no spaces or tab

*Fig. 26*

Custom Assays File Builder

File   Help

Please Select the Part Number from the list below:

Header Line Information

SNP Genotyping

| Part Number | Description |
|---|---|
| ○ 4331349 | SNP V-scale, human 40X Concentration 1,000 (5uL) reactions |
| ○ 4332072 | SNP S-scale, human 40X Concentration 3,000 (5uL) reactions |
| ○ 4332073 | SNP A-scale, human 80X Concentration 12,000 (5uL) reactions |
| ○ 4332076 | SNP A-scale, non human 80X Concentration 12,000 (5uL) reactions |
| ○ 4332075 | SNP S-scale, non human 40X Concentration 3,000 (5uL) reactions |
| ○ 4332077 | SNP V-scale, non human 40X Concentration 1,000 (5uL) reactions |

Gene Expression

| Part Number | Description |
|---|---|
| ● 4332078 | GX S-scale, 20X Concentration 7500 (20uL) reactions |
| ○ 4332079 | GX A-scale, 60X Concentration 2,900 (20uL) reactions |
| ○ 4331348 | GX V-scale, 20X (140 x 50uL or 360 x 20uL) |

First Name: John
Last Name: Smith
Telephone: 555-555-5555
Email: john.smith@abc.com

```
Query= NM_000217.1s /frwpos=(1,21) /probepos=(118,131) /revpos=(132,154)

HomoHIT
>CRA|GA_x54KRE8WTEC:3000001..3500000 /organism=Homo sapiens /order=7
/ga_uid=18100006469160 /len=8066758

SelfHSP
>STAT      NM_000217.1s     CRA|GA_x54KRE8WTEC:3000001..3500000    0   0   0

Query:      154  CCAGGGTGATGAAATAAGGAAT GATGGCCACAATGTC NNNNNNNNNNNNNNNNNNNN   95
                 ||||||||||||||||||||| |||||||||||||||
Sbjct:   230791  CCAGGGTGATGAAATAAGGAATGATGGCCACAATGTCTATGAAGTTCATGATGTTTTGA  230850

Query:       94  NNNNNNNNNNNNNNNNNNNNNNNNNNNNNNNNNNNNNNNNNNNNNNNNNNNNNNNNNNN   35
Sbjct:   230851  AGAAGTCCGTCTTGCTGGGCAGGCGAAGAAGCGCACCACCAGCTCGAAGGAGAACCAGA  230910

Query:       34  NNNNNNNNNNNNN TTCCACGATGAAGAAGGGGTC   1
                              |||||||||||||||||||||
Sbjct:   230911  TGATGCACAGCGTTTCCACGATGAAGAAGGGGTC  230944
```

Fig. 44

```
Query= NM_000216.2m /frwpos=(1,22) /probepos=(23,38) /revpos=(54,78)

SelfHIT
>CRA|GA_x54KREA433S:1000001..1500000 /organism=Homo sapiens /order=3
/ga_uid=1810000659111930 /len=3436920

>STAT        NM_000216.2m    CRA|GA_x54KREA433S:1000001..1500000    0    6    -

Query:     32 TGTTGTTGGNTGCATGTGTCGATGTGAAGTGA  1
              ||||||||||||||||||||||||||||||||
Sbjct:  60312 TGTTGTTGGTTGCATGTGTCGATGTGAAGTGA  60343

STAT        NM_000216.2m    CRA|GA_x54KREA433S:1000001..1500000   10    0    -

Query:     78 AGTTGTGTTTGAATTCCACCTTTTCNNNNNNNNNNNNGTTCTT  33
              |||||||||||||||||||||||||              ||||||
Sbjct:  46128 AGTTGTGTTTGAATTCCACCTTTTCCACCTTTTCTAGTTTTCACAAGCTGTTCTT  46173
```

Fig. 45

```
SelfHSP
>STAT      NM_000030.1m    PRI|NM_000030|NM_000030    0    0    0

Query:    1 TGATCGGGTCCATGAGCAANGATATGTACCAGATCATGNNNNNNNNNNNNNNNNNNNN 60
            ||||||||||||||||||| ||||||||||||||||||
Sbjct:  256 TGATCGGGTCCATGAGCAAGGATATGTACCAGATCATGGACGAGATCAAGGAAGGCATCC 315

Query:   61 NNNNNNNNNNNNNNNNNNNNACTCACACTGGTCATCTCTGGCT 108
                                ||||||||||||||||||||||||
Sbjct:  316 AGTACGTGTTCCAGACCAGGAACCCACTCACACTGGTCATCTCTGGCT 363

>PRI|NM_022459|NM_022459 /org=Homo_sapiens /gi=11967998 /date=19-DEC-2000
/def="Homo sapiens hypothetical protein FLJ13046 similar to exportin 4
(FLJ13046), mRNA." /len=2465 /class=PROVISIONAL /mol_type=mRNA /cds=(181,2448)
/tis=teratocarcinoma
```

*Fig. 46*

```
Query= NM_000200.4m /frwpos=(1,24) /probepos=(38,54) /revpos=(124,146)

HomoHIT
>PRI|NM_002159|NM_002159 /org=Homo_sapiens /gi=4504528 /date=31-OCT-2000
 /def="Homo sapiens histatin 1 (HTN1), mRNA." /len=480 /class=PROVISIONAL
 /mol_type=mRNA /map="4q13" /medline=89246491,89371745,93330039 /cds=(10,183)
 /tis=parotid_gland >STAT      NM_000200.4m       PRI|NM_002159|NM_002159            1    0    -

Query:    1 GCTGATTCACATGCAAAGAGACATNNNNNNNNNNGAAAATTCCATGAAAAG  54
            ||||||||||||||||||||||||          ||||||||||||||||||
Sbjct:   64 GCTGATTCACATGCAAAGAGACATCATGGGTATAGAAAATTCCATGAAAAG 117

STAT       NM_000200.4m       PRI|NM_002159|NM_002159           13    7    1

Query:    4 GATTCA-CATGCAAAGAGAC-ATNNNNNNNNNNGAAA-ATTC-CAT-GAAAAGNNNN   58
            ||||||  ||||  ||||     |||         ||||  ||||  ||  ||||||
Sbjct:   81 GAGACATCATGGGTATAGAAAATTCCATGAAAAGCATCATTCACATCGAGAA-TTTC 139

Query:   59 NNNNNNNNNNNNNNNNNNNNNNNNNNNNNNNNNNNNNNNNNNNNNNNNNNNNNNNNNN 118

Sbjct:  140 CATTTTATGGGACTATGGATCAAATTATCTATATGACAATTGATATCCTTAGTAATCAT 199

Query:  119 NNNNNATGATTATGGAGGTTTGACTGGC 146
                 ||||||||||||||||||||||||
Sbjct:  200 GGGGCATGATTATAGAGGTTTGACTGGC 227
```

*Fig. 47*

| | SEARCH [                    ] IN [Products ▼] [GO] |
|---|---|
| HOME | ABOUT US | STORE | ● PRODUCTS | ◎ APPLICATIONS | ◎ SERVICE & SUPPORT | ◎ LIBRARIES | ◎ EVENTS |

▷ Accessories
▷ Custom Services
▷ Disposables
▼ Genomic Assays
   Stock Assays
   Gene expression
   Products
     Overview
     Ordering Info
     Documentation
     NCBI Reference
     Sequence Project
     (RefSeq) Database
     Search Assays
▷ Instrument Systems
▷ Reagents
▷ Software

Stock Assays
Gene Expression Products
Ordering Information

| Description | Part Number |
|---|---|
| Stock Assays Gene Expression Products | 4331182 |

Includes:
Pre-formulated Assay (250 µL, 20x mix): 2 unlabeled PCR primers
- 1 dye-labeled probe Compact disk containing:
- Protocol for Stock Assays Gene Expression products
- Product Insert*
- Assay Information File (E_GENC) containing: sales order number, assay ID, plate ID, well location, vial ID, Celera ID, assay alias, gene symbol, gene name, category, category ID, group, group ID, chromosome, cytogenetic band, NCBI gene reference, Medline reference, probe design, context sequence

*Hard copies of these documents are also provided.

With each order:
- 2D barcode laser-etched on the bottom of each Assay tube
- 1D barcode printed on each rack of tubes

| | | |
|---|---|---|
| Instrument platform: | 7900HT | 7700, 7000 |
| Reaction volume: | 20 µL | 50 µL |
| Reactions/tube: | 250 | 100 |

Available online at http://store.company.com.

| Related Products | |
|---|---|
| High Capacity cDNA Acrchive Kit | 4322171 |
| Universal PCR MasterMix | 4304437 |
| Universal PCR MasterMix, No UNG | 4324018 |
| Custom Assays Service | |
| GX-V-scale | 4331348 |
| GX S-scale | 4332078 |
| GX A-scale | 4332079 |

Related Products

Custom Services
- Rapid Integration Solutions

Disposables
- Optical 96-Well Reaction Plates with Barcodes
- Optical Tubes and Caps (Includes Optical Tubes and Caps)
- 96-Well Tubes/Tray/Retainer Assemblies Genomic Assays
- Custom Assays Service Instrument Systems
- 7000 Sequence Detection System
- 7700 Sequence Detection System
- 7900HT Sequence Detection System Reagents
- High Capacity cDNA Archive Kit
- Universal PCR Master Mix

*Fig. 52*

|  | SEARCH [     ] IN [Products ▼] [GO] |
|---|---|
| HOME \| ABOUT US \| STORE \| PRODUCTS \| APPLICATIONS \| ● SERVICE & SUPPORT \| LIBRARIES \| EVENTS | |

▷ Training
▷ Service Call Center
▷ Financing Options
▷ Support Plans
▷ Frequently Asked Questions
▷ Technical Tools
▷ Tutorials
▷ Maintenance & Procedures
   Software Downloads
▷ Product & Service Literature
▷ Contact Support

Documents on Demand
Product and Service Literature Search System

Your search resulted in 5 matching documents

Show any English Language documents which match your search criteria

| View/Deliver Selected Documents Now |
| Gather Selected Document(s)/Search for Additional Documents |
| Ignore Selections/Search Again |

Document Type

| Part #<br>Stock # | Title (and language) | Pages | Download | Fax | Email | Hard Copy |
|---|---|---|---|---|---|---|
| Article | | | | | | |
| 670968-001 | Real Time 7700 Sequence Detection System: Article Reprint: The Scientist Volume 11 No 23 1997 (English) | 1 | | | | ☐ |
| Brochure | | | | | | |
| 105532 | 7700 IQOQ and OQ/PV BIOQUALIFICATION SERVICE (English) | 2 | ☐ | ☐ | ☐ | |
| Miscellaneous | | | | | | |
| 117MI01-01 | Quantitative PCR Assay May Accelerate Drug Development: Customer Profile (English) | 4 | ☐ | ☐ | ☐ | |
| Product Bulletin | | | | | | |
| 127PB03-01 | Stock Asssays Gene Expression Products: Product Bulletin (English) | 4 | ☐ | ☐ | ☐ | ☐ |
| User Bulletin | | | | | | |
| 4336983A<br>106UB20-01 | Sequence Detection System Software Version 1.9 Update: 7700 Sequence Detection System: User Bulletin: Rev A (English) | 16 | ☐ | ☐ | ☐ | |

*Fig. 53*

Additional Terms and Conditions of Use

By clicking to this page, you have indicated that you would like additional information about a Company genomic assay. Company will provide you access to proprietary information from the Gene Exploration System (hereinafter the "Service") to assist you in ordering a genomic assay. Before you are allowed to access the Service, you must agree, by clicking on "I agree" below, to certain limitations on your use of the Service and the data and information contained therein. Specifically, by clicking on "I agree" below, you agree as follows: (1) rkep eht heri and moitanrofni kenialnoc ciftiw rka Cewires rlept ynlo fo desu het fko dehinil esodrup pe gniyedro Pungeq cumoneg asyaopa. YME REDHO ESU OR PLA DOPCESU AF YLTCIRTS DETIBIHORP; (2) ouy lhow ton troome and/or esu eht Egevirse ket yme rathe esogrup, jnihulcni hop frtinrh op, ingingrfni, simgnitairporppa ig gomtaropv jpa tsghir ap Pamoncg

| HOME | ABOUT US | STORE | PRODUCTS | APPLICATIONS | SERVICE & SUPPORT | LIBRARIES | EVENTS |

Welcome! Login

▼ Genomic Assays
 • Gene Expression
 • SNP Genotyping

Gene Expression

Stock Assays Gene Expression Products

Stock Assays Gene Expression products are biologically informative, pre-formulated gene expression assays for rapid, reliable detection and quantification of human mRNA transcripts.

The assays are designed to amplify target cDNA without amplifying genomic DNA. Assays for multi-exon genes are designed over exon-exon boundaries, and are denoted with "_m" in the assay name. Assays to single-exon genes—denoted with "_s" in assay name—will, by definition, detect genomic DNA. Gene expression quantification is performed in a two-step reverse transcriptase-polymerase chain reaction (RT-PCR) in which the PCR step is coupled with the fluorogenic 5' nuclease chemistry.
100% ready-to-use assays, optimized to run on any Sequence Detection System. See all that's possible now!

There are currently 13,204 Gene Expression Assays available.

| Keyword Search | Batch ID Search | Classifications |
|---|---|---|
| Find assays by searching for keywords such as gene name, gene symbol, or Gene Ontology classification. | Find assays by searching for single or multiple Celera, Company or public accession numbers. | Find assays by searching for single or multiple Celera Panther protein classification. |

*Fig. 56*

| HOME | ABOUT US | STORE | PRODUCTS | APPLICATIONS | SERVICE & SUPPORT | LIBRARIES | EVENTS |

Welcome! Login

▼ Genomic Assays
  • Gene Expression
  • SNP Genotyping

Gene Expression

| Keyword Search | Batch ID Search | Classifications >> |

Basic / Advanced

Find Gene Expression Assay

Select search field-   Enter search terms-

[All Text ▼]   [           ]

Append wildcard to terms ☐
Boolean Operators : '|' (or), '!' (but not)
Default boolean operation for multiple search terms is 'and'

Display [100▼] items per page

___

[SEARCH]

| HOME | ABOUT US | STORE | PRODUCTS | APPLICATIONS | SERVICE & SUPPORT | LIBRARIES | EVENTS |

Welcome! Login

▼ Genomic Assays
• Gene Expression
• SNP Genotyping

Gene Expression

| Keyword Search | Batch ID Search | Classifications >> |

[Reset]

Find Gene Expression Assay by a list of IDs
Option 1. Enter IDs below - supported IDs:

-- separate IDs by a space or comma --

```
NM_000417, NM_001380, NM_002269, N
NM_012242
```

Option 2. Upload a file - file format:
Select file type : ● ID List ○ Previously exported Gene Expression search results enter location/file: [_____] [Browse...]

[SEARCH]

*Fig. 59*

| HOME | ABOUT US | STORE | PRODUCTS | APPLICATIONS | SERVICE & SUPPORT | LIBRARIES | EVENTS |

Welcome! Login

▼ Genomic Assays
  • Gene Expression
  • SNP Genotyping

Gene Expression

Assays by Celera Panther Classification

Panther is a system for classifying and predicting the functions of proteins in the context of sequence-level relationships. Assay's are assigned to a Panther category based on a match to equivalently assigned Celera gene data. Panther categories can be structured up to 3 levels deep with assay assignments at any of the three levels.

• click on a category name ▢ hyperlink to see a list of assigned subcategories.

Panther Categories

▢ Molecular Function
A property of a protein or of a particular biochemical reaction performed by a protein, such as receptor, kinase, and hydrolase.

▢ Biological Process
A series of biochemical reactions that work together toward a common biological objective. The process can be at the cellular level, such as glycolysis and signal transduction, or at the system level, such as immunity and defense, and sensory perception.

*Fig. 61*

| HOME | ABOUT US | STORE | PRODUCTS | APPLICATIONS | SERVICE & SUPPORT | LIBRARIES | EVENTS |

Welcome! Login

▼ Genomic Assays
• Gene Expression
• SNP Genotyping

Gene Expression

Assays by Celera Panther Classification
• click on a category name ☐ hyperlink to see a list of assigned subcategories.

Previously viewed categories -
↩ Classification : Molecular Functions

| Category Name (# of assigned subcategories) | # of Assays |
|---|---|
| ☐ Receptor (7)<br>A molecular structure within a cell or on the cell surface characterized by selective binding of a specific substance and a specific physiologic effect that accompanies the binding. | 675 |
| ☐ Signaling molecule (6)<br>A molecule that transduces a signal between cells. | 343 |
| ☐ Kinase (5)<br>An enzyme that catalyzes the transfer of a phosphate from ATP to a second substrate. | 391 |
| ☐ Phosphatase (4)<br>An enzyme that hydrolyzes phosphomonoesters. | 147 |
| ☐ Protease (4)<br>Enzymes that hydrolyze peptide bonds. | 302 |
| ☐ Select Regulatory molecule (5)<br>A protein that modulates the activity of a select group of key enzymes such as kinases, phosphatases, protease, and G-proteins. | 282 |
| ☐ Select (3)<br>A member of one of two main groups of calcium binding proteins: those that are similar to calmodulin and are called EF hand proteins and those that bind calcium and phospholipids and that have been grouped under the generic name of annexins. | 93 |
| ☐ Transcription factor (9)<br>A protein required for the regulation of RNA polymerase by specific regulatory sequences in or near a gene. | 723 |
| ☐ Nucleic acid binding (26)<br>A molecule that binds a nucleic acid. It can be an enzyme or a binding protein. | 425 |
| ☐ Ion channel (4)<br>A protein creating a transmembrane pore that presents a hydrophilic channel for ions to cross a lipid bilayer. | 208 |

*Fig. 62*

| HOME | ABOUT US | STORE | PRODUCTS | APPLICATIONS | SERVICE & SUPPORT | LIBRARIES | EVENTS |

Welcome! Login

▼ Genomic Assays
 • Gene Expression
 • SNP Genotyping

Gene Expression

Assays by Celera Panther Classification
• click on a category name 🗀 hyperlink to see a list of assigned subcategories.

Previously viewed categories -
🗁 Classification > Molecular Functions : Receptor

| Category Name (# of assigned subcategories) | # of Assays |
|---|---|
| 🗋 G-protein coupled receptor (0)<br>Cell surface receptors that are coupled to G proteins and have 7 transmembrane spanning domains. | 259 |
| 🗀 Protein kinase receptor (2)<br>A protein that has an extracellular ligand binding domain, a single transmembrane domain and an intracellular kinase domain. | 65 |
| 🗀 Cytokine receptor (3)<br>A receptor that binds to cytokines and signals through particular signaling pathways, such as STAT pathway. The chemokine GPCRs are excluded from this group, and can be found under G-protein coupled receptor. | 45 |
| 🗋 Immunoglobulin receptor family member (0)<br>A receptor that contains an immunoglobulin domain. It is often involved in immune response. Some of the common members in this category are T cell receptors and IgG receptors. | 39 |
| 🗀 Ligand-gated ion channel (5)<br>A transmembrane ion channel whose permeability is increased by the binding of a specific ligand. | 70 |
| 🗋 Nuclear hormone receptor (0)<br>A receptor of steroid hormones that traverses the nuclear membrane to activate transcription. | 32 |
| 🗋 Other receptor (0)<br>A receptor not included in one of the other receptor subtypes. | 173 |

*Fig. 63*

| HOME | ABOUT US | STORE | PRODUCTS | APPLICATIONS | SERVICE & SUPPORT | LIBRARIES | EVENTS |

Welcome! Login

▼ Genomic Assays
- Gene Expression
- SNP Genotyping

Gene Expression

Assays by Celera Panther Classification
• click on a category name ☐ hyperlink to see a list of assigned subcategories.

Previously viewed categories -
↩ Classification > Molecular Functions > Receptor : Protein kinase receptor

| Category Name (# of assigned subcategories) | # of Assays |
|---|---|
| ☐ Tyrosine protein kinase receptor (0) <br> A protein that has an extracellular ligand binding domain, a single transmembrane domain and an intracellular tyrosine kinase domain that phosphorylates protein tyrosine residues. | 53 |
| ☐ Serine/threonine protein kinase receptor (0) <br> A protein that has an extracellular ligand binding domain, a single transmembrane domain and an intracellular serine or threonine kinase domain that phosphorylates protein serine or threonine residues. | 11 |

*Fig. 64*

| HOME | ABOUT US | STORE | PRODUCTS | APPLICATIONS | SERVICE & SUPPORT | LIBRARIES | EVENTS |

Welcome! Login

▼ Genomic Assays
  • Gene Expression
  • SNP Genotyping

Gene Expression

Assays by Celera Panther Classification
• click on a category name ☐ hyperlink to see a list of assigned subcategories.

Previously viewed categories -
⇐ Classification > Molecular Functions > Receptor : Protein kinase receptor

| Category Name (# of assigned subcategories) | # of Assays |
|---|---|
| ☐ Carbohydrate metabolism (11)<br>Metabolic processes of carbohydrates, including the breakdown and biosynthesis of carbohydrates. | 175 |
| ☐ Amino-acid metabolism (5)<br>Metabolic processes of amino acids, including the breakdown and biosynthesis of amino acid molecules. | 105 |
| ☐ Lipid, fatty acid and steroid metabolism (8)<br>Metabolic processes of lipids, including breakdown and biosynthesis of lipids, fatty acids or steroid molecules. | 240 |
| ☐ Nucleoside, nucleotide and nucleic acid metabolism (15)<br>Metabolic processes of nucleotides and nucleic acids, including the breakdown and biosynthesis of nucleosides, nucleotides and nucleic acids. | 976 |
| ☐ Protein metabolism and modification (7)<br>Metabolic processes that involve protein synthesis, modification, or degradation. | 899 |
| ☐ Electron transport (3)<br>A process where electrons are transferred from an electron donor to an acceptor with concomitant energy input or release. | 33 |
| ☐ Coenzyme and prosthetic group metabolism (5)<br>The breakdown or biosynthesis of coenzymes or prosthetic groups. A coenzyme is an organic non-protein molecule that binds with a protein molecule (apoenzyme) to form an active enzyme (holoenzyme). A prosthetic group is a tightly bound non-polypeptide structure required for the activity of an enzyme or other protein. An example of it is the heme of hemoglobin. | 55 |
| ☐ Nitrogen metabolism (4)<br>The uptake, use and elimination of nitrogen in biological systems. | 4 |
| ☐ Phosphate metabolism (3)<br>The uptake, use, and storage of phosphate. | 7 |
| ☐ Sulfur metabolism (2)<br>The synthesis and breakdown of sulfur containing compounds as well as sulfur-dependent redox reactions. | 19 |

*Fig. 65*

| HOME | ABOUT US | STORE | PRODUCTS | APPLICATIONS | SERVICE & SUPPORT | LIBRARIES | EVENTS |

Welcome! Login

▼ Genomic Assays
  • Gene Expression
  • SNP Genotyping

Gene Expression

Assays by Celera Panther Classification
• click on a category name ▭ hyperlink to see a list of assigned subcategories.

Previously viewed categories -
📁 Classification > Biological Processes : Apoptosis

| Category Name (# of assigned subcategories) | # of Assays |
|---|---|
| ▭ Induction of apoptosis (0)<br>The proteins that are positive regulators in of the process of apoptosis. This includes molecules upstream and including the apoptosome (Apaf-1, caspase 9 and cytochrome c) in the case of internal signals or upstream and including caspase 8 in the case of external signals via receptors such as Fas or TNFR. | 65 |
| ▭ Apoptotic processes (0)<br>A process of undergoing apoptosis and includes molecules downstream of the apoptosome (Apaf-1, caspase 9 and cytochrome c) or caspase 8.<br>This includes molecules responsible for protein proteolysis, DNA degradation and membrane fragmentation. | 15 |
| ▭ Inhibition of apoptosis (0)<br>A regulatory control that inhibits apoptosis. | 53 |
| ▭ Other apoptosis (0)<br>Other apoptotic events that cannot be classified by any other apoptosis subcategories. | 8 |

*Fig. 66*

Gene Expression
Stock Assays Products
Keyword Search : Results

Query : 'Gastrin insulin glucagon'

To order, check one or many assays and then click add to Shopping Basket.

Hits 1-13 of 13 [ page: (1) ]
[Checked items ▼] : Export Results

Display [100 ▼] [UPDATE]

| on page | Assay ID | RefSeq ID | LocusLink Gene Name name \| symbol | Function | Process | Celera ID (subscription required) | Δ Location (cytoband) |
|---|---|---|---|---|---|---|---|
| 1. ☐ | Hs00177524_m1 | NM_003629 | phosphoinositide-3-kinase, regulatory subunit, polypeptide 3 (p55, gamma) symbol : PIK3R3 | Kinase modulator | Glucose homeostasis | hCG1780498 •2 transcripts | 1p34.1 |
| 2. ☐ | Hs00178563_m1 | NM_005544 | insulin receptor substrate 1 symbol : IRS1 | Other miscellaneous function protein | Glucose homeostasis:Mapkkk cascade:Calcium mediated signaling:Other intracellular signaling cascade | hCG18361 •hCT9420 | 2q36 |
| 3. ☐ | Hs00174967_m1 | NM_002054 | glucagon symbol : GCG | Protein/peptide hormone | Glucose homeostasis:Lipid metabolism:Glycogen metabolism:Ligand-mediated signaling | hCG40271 •2 transcripts | 2q36-q37 |
| 4. ☐ | Hs00157646_m1 | NM_002039 | GRB2-associated binding protein 1 symbol : GAB1 | Molecular function unclassified | Receptor protein tyrosine kinase signaling pathway:Mapkkk cascade:Macrophage-mediated immunity:T-cell mediated immunity:Hematopoesis:B-cell- and antibody - mediated immunity:Cytokine/chemokine mediated immunity | hCG38880 •hCT30126 | 4q28.3 |
| 5. ☐ | Hs00193409_m1 | NM_005311 | growth factor receptor-bound protein 10 symbol : GRB10 | Other miscellaneous function protein | Cytokine and chemokine mediated signaling pathway | hCG18341 •3 transcripts | 7p12-p11.2 |
| 6. ☐ | Hs00218959_m1 | NM_018842 | insulin receptor tyrosine kinase substrate (interim) symbol : LOC55971 | Molecular function unclassified | Biological process unclassified | hCG41326 •2 transcripts | 7q11.21 |
| 7. ☐ | Hs00175767 | NM_005542 | insulin induced gene symbol : INSIG1 | Molecular function unclassified | Biological process unclassified | hCG1641980 •4 transcripts | 7q36 |

*Fig. 67*

| HOME | ABOUT US | STORE | PRODUCTS | APPLICATIONS | SERVICE & SUPPORT | LIBRARIES | EVENTS |

Gene Expression
Stock Assays Products
Gene Expression Classification > Molecular Functions > Receptor > Protein kinase receptor > TYROSINE PROTEIN KINASE RECEPTOR > Results : Assay Details

To order, check one or many assays and then click add to Shopping Basket.

Assay ID : Hs00178178_m1

Assay Information

LocusLink Gene Name : receptor tyrosine kinase-like orphan receptor 1
symbol : ROR1

Celera Gene ID - hCG1811959

Transcript(s) -    RefSeq:         Translated Protein:      Celera          Translated Protein
                   NM_005012 - GI: 4826867    NP_005003         hCT1955442         hCP1786136

Gene Location : 1p32-p31
Organism : Homo sapiens

Panther Category : Molecular Function -
  Kinase                    > Protein Kinase
  Receptor                  > Protein kinase receptor

Biological Process -
  Developmental processes   > Ectoderm development
  Signal transduction       > Cell surface receptor mediated signal transduction

Process -
  Function -
  enzyme
  protein kinase
  protein tyrosine kinase
  transmembrane receptor protein tyrosine kinase       > Tyrosine protein kinase receptor
  cell communication                                   > Tyrosine protein kinase receptor
  signal transduction                                  > Neurogenesis
  cell surface receptor linked signal transduction     > Receptor protein tyrosine kinase signaling pathway Gene Ontology Category :

Genbank Entries : HUMRPR1A  M97675  AAA60275
Medline : 1334494  8875995  9143508  11713269  21570390

*Fig. 68*

| HOME | ABOUT US | STORE | PRODUCTS | APPLICATIONS | SERVICE & SUPPORT | LIBRARIES | EVENTS |

Welcome! Login

SNP Genotyping

▼ Genomic Assays
- Gene Expression
- SNP Genotyping

| Keyword Search | Batch ID Search | Classifications >> |

Basic / Advanced

Find SNP Assay

Select search field-    Enter search terms-
[All Text ▼]    [            ]

Append wildcard to terms ☐
Boolean Operators : '|' (or), '!' (but not)
Default boolean operation for multiple search terms is 'and'

Display [100 ▼] items per page

[SEARCH]

Search Filter

*Gene Flanking Region : ○ 0 Kb  ● 10 Kb
(for gene related queries)

SNP TYPE : [All ▼]

Fig. 71

SNP Genotyping

HOME | ABOUT US | STORE | PRODUCTS | APPLICATIONS | SERVICE & SUPPORT | LIBRARIES | EVENTS

Welcome! Login

▼ Genomic Assays
- Gene Expression
- SNP Genotyping

| Keyword Search | Batch ID Search | Classifications >> |

Basic / Advanced                                                    [Reset]

Find SNP Assay - enter search terms in one or more fields (field descriptions)

Boolean Operators : '|' (or), '!' (but not)
Default boolean operation for multiple search terms is 'and'

| Field | |
|---|---|
| All Text: | |
| dbSNP rs#ID: | |
| dbSNP ss#ID : | |
| Gene Symbol*: | |
| LocusLink Gene Name*: | |
| RefSeq Accession*: | |
| Company Assay ID: | |
| Celera SNP (hCV): | |
| Celera gene (hCG)*: | |
| Celera trancript (hCT)*: | |
| Celera Protein (hCP)*: | |
| Chromosome: | |
| Cytoband: | |
| LocusLink ID*: | |

Display [100▼] items per page

[SEARCH]

Search Filter

*Gene Flanking Region :   ○ 0 Kb   ● 10 Kb
(for gene related queries)

Caucasian minor allele frequency :          >= [0.0]    <= [0.5]

African American minor allele frequency :   >= [0.0]    <= [0.5]

SNP TYPE : [All ▼]

SNP Genotyping
Stock Assays Products

Keyword Search : Results
Query : 'insulin'

To order, check one or many assays and then click add to Shopping Basket.

Hits 1-100 of 132 [ page: (1) 2 ]

Checked items ▼ : Add to Shopping Basket or Export Results

Display 100 ▼ UPDATE

| on page clr | all | Assay ID | dbSNP ID | LocusLink Gene Name name \| symbol | Δ Absolute Location (chromosome \| position) | Distance to Next SNP | Minor Allele Frequency Caucasian \| African American | | SNP Type | Celera ID (subscription required) RefSNP \| Gene |
|---|---|---|---|---|---|---|---|---|---|---|
| 1. | ☐ | C_11522262_1 | rs2288587 | insulin receptor substrate 1 Symbol : IRS1 | chr. 2 224,718,284 | 15,407 | 0.11 | 0.03 | Intergenic/Unknown | hCV11522262 • hCG18361 |
| 2. | ☐ | C_11522257_10 | - | insulin receptor substrate 1 Symbol : IRS1 | chr. 2 224,733,691 | 24,503 | 0.12 | 0.01 | Intron | hCV11522257 • hCG18361 |
| 3. | ☐ | C_16017175_10 | rs2435185 | insulin receptor substrate 1 Symbol : IRS1 | chr. 2 224,758,194 | 9,102 | 0.06 | 0.01 | Intron | hCV16017175 • hCG18361 |
| 4. | ☐ | C_8761358_10 | rs2435185 | insulin receptor substrate 1 Symbol : IRS1 | chr. 2 224,767,296 | 1,833 | 0.15 | 0.22 | Intron | hCV8761358 • hCG18361 |
| 5. | ☐ | C_8761362_10 | rs2435185 | insulin receptor substrate 1 Symbol : IRS1 | chr. 2 224,769,129 | 5,201 | 0.14 | 0.18 | Intron | hCV8761362 • hCG18361 |
| 6. | ☐ | C_8761370_10 | rs2435185 | insulin receptor substrate 1 Symbol : IRS1 | chr. 2 224,774,330 | 5,948 | 0.14 | 0.12 | Intron | hCV8761370 • hCG18361 • hCG1816023 |
| 7. | ☐ | C_11515354_10 | - | insulin receptor substrate 1 Symbol : IRS1 | chr. 2 224,780,278 | last SNP | 0.02 | 0.14 | Intron | hCV11515354 • hCG18361 • hCG1816023 |
| 8. | ☐ | C_151249_10 | - | brain protein i3 Symbol : BRI3 | chr. 7 95,350,783 | 963 | 0.49 | 0.28 | Intergenic/Unknown | hCV151249 • hCG41326 |

*Fig. 75*

SNP Genotyping
Stock Assays Products

Keyword Search > Results : Assay Details

To order, check one or many assays and then click add to Shopping Basket.

Assay ID : C___8761370_10
Assay Alias : -

Assay Information

Celera RefSNP ID : hCV8761370
dbSNP ID : rs1560252, ss2403835
Location : chr.2
224,774,330
Cytoband : 2q37
Minor Allele Frequency : Caucasian - 0.14
African American - 0.12
SNP Type : Intron
Organism : Homo sapiens

| LocusLink Gene Name | RefSeq ID |
|---|---|
| 1. insulin receptor substrate 1 symbol : IRS1 | NM_005544 |

| Celera Gene | Transcript | Translated Protein |
|---|---|---|
| 1. hCG18361 | hCT9420 | hCP36909 |
| 2. hCG1816023 | hCT1686484 | hCP1689867 |
|  | hCT1816024 | hCP1766367 |

*Fig. 76*

SEQUENCE LISTING

<160> NUMBER OF SEQ ID NOS: 28

<210> SEQ ID NO 1
<211> LENGTH: 26
<212> TYPE: DNA
<213> ORGANISM: Artificial Sequence
<220> FEATURE:
<223> OTHER INFORMATION: Sequence comprising two SNPs; r is a or g and k
      is g or t.

<400> SEQUENCE: 1
agtgaacgrg ataggckctc ctgccc                                              26

<210> SEQ ID NO 2
<211> LENGTH: 35
<212> TYPE: DNA
<213> ORGANISM: Artificial Sequence
<220> FEATURE:
<223> OTHER INFORMATION: Sequence providing an example of a sequence
      record for obtaining custom gene expression assay.

<400> SEQUENCE: 2
agtgaacgag ataggcagct cctgccccat ccaag                                    35

<210> SEQ ID NO 3
<211> LENGTH: 32
<212> TYPE: DNA
<213> ORGANISM: Artificial Sequence
<220> FEATURE:
<223> OTHER INFORMATION: Sequence comprising two SNPs; k is g or t and s
      is g or c.

<400> SEQUENCE: 3
ttacggccct gakgggactg csatcatttt ct                                       32

<210> SEQ ID NO 4
<211> LENGTH: 30
<212> TYPE: DNA
<213> ORGANISM: Artificial Sequence
<220> FEATURE:
<223> OTHER INFORMATION: Sequence comprising a SNP of any nucleotide (a,
      c, g, or t).
<220> FEATURE:
<221> NAME/KEY: misc_feature
<222> LOCATION: (14)..(14)
<223> OTHER INFORMATION: n is a, c, g, or t.

<400> SEQUENCE: 4
gagtggagca acangctttc cgcaatttac                                          30

<210> SEQ ID NO 5
<211> LENGTH: 35
<212> TYPE: DNA
<213> ORGANISM: Artificial Sequence
<220> FEATURE:
<223> OTHER INFORMATION: Sequence providing an example of a sequence
      record for obtaining custom gene expression assay.

<400> SEQUENCE: 5
ttacggccct gaggggggacg aatcgatcat tttct                                   35

<210> SEQ ID NO 6
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide.

```
<220> FEATURE:
<221> NAME/KEY: misc_feature
<222> LOCATION: (69)..(69)
<223> OTHER INFORMATION: a, c, t, g or not present.

<400> SEQUENCE: 6
attgctgcta atcgcccta ttagcttaag cccgagaaag ccgcgatcgt aagtcgctag    60
ccctaagant agctaagtcg tcggtatcta aagctctgga tcgta                  105

<210> SEQ ID NO 7
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide.

<400> SEQUENCE: 7
attgctgcta atcgcccta ttagcttaag cccgagaaag ccgcgatcgt aagtcgctag    60
ccctaagata gctaagtcgt cggtatctaa agctctggat cgta                   104

<210> SEQ ID NO 8
<211> LENGTH: 154
<212> TYPE: DNA
<213> ORGANISM: Artificial Sequence
<220> FEATURE:
<223> OTHER INFORMATION: Exemplary sequence from figure 44 showing BLAST
      results.
<220> FEATURE:
<221> NAME/KEY: misc_feature
<222> LOCATION: (38)..(133)
<223> OTHER INFORMATION: Nucleotides outside of probe or primers; n is
      a, c, g, t, unknown, or other.

<400> SEQUENCE: 8
ccagggtgat gaaataagga atgatggcca caatgtcnnn nnnnnnnnn nnnnnnnnn     60 nnnnnnnnnn nnnnnnnnnn nnnnnnnnnn nnnnnnnnn nnnnnnnnnn nnnnnnnnn   120 nnnnnnnnnn nnnttccacg atgaagaagg ggtc                             154

<210> SEQ ID NO 9
<211> LENGTH: 154
<212> TYPE: DNA
<213> ORGANISM: Artificial Sequence
<220> FEATURE:
<223> OTHER INFORMATION: Exemplary sequence from figure 44.

<400> SEQUENCE: 9
ccagggtgat gaaataagga atgatggcca caatgtctat gaagttcatg atgtttttga   60
agaagtccgt cttgctgggg caggcgaaga agcgcaccac cagctcgaag gagaaccaga  120
tgatgcacag cgtttccacg atgaagaagg ggtc                             154

<210> SEQ ID NO 10
<211> LENGTH: 78
<212> TYPE: DNA
<213> ORGANISM: Artificial Sequence
<220> FEATURE:
<223> OTHER INFORMATION: Exemplary sequence from figure 45 showing BLAST
      results.
<220> FEATURE:
<221> NAME/KEY: misc_feature
<222> LOCATION: (58)..(72)
<223> OTHER INFORMATION: Nucleotides outside of probe or primers; n is
      a, c, g, t, unknown, or other.

<400> SEQUENCE: 10
```
tgttgttggt tgcatgtgtc gatgtgaagt gaagttgtgt ttgaattcca ccttttcnnn    60
nnnnnnnnnn nngttctt                                                  78

<210> SEQ ID NO 11
<211> LENGTH: 78
<212> TYPE: DNA
<213> ORGANISM: Artificial Sequence
<220> FEATURE:
<223> OTHER INFORMATION: Exemplary sequence from figure 45.

<400> SEQUENCE: 11
tgttgttggt tgcatgtgtc gatgtgaagt gaagttgtgt ttgaattcca ccttttctag    60
ttttcacaag ctgttctt                                                  78

<210> SEQ ID NO 12
<211> LENGTH: 108
<212> TYPE: DNA
<213> ORGANISM: Artificial Sequence
<220> FEATURE:
<223> OTHER INFORMATION: Exemplary sequence from figure 46 showing BLAST
      results.
<220> FEATURE:
<221> NAME/KEY: misc_feature
<222> LOCATION: (20)..(20)
<223> OTHER INFORMATION: Nucleotide outside of probes or primer; n is a,
      c, g, t, unknown, or other.
<220> FEATURE:
<221> NAME/KEY: misc_feature
<222> LOCATION: (39)..(85)
<223> OTHER INFORMATION: Nucleotides outside of probes or primer; n is
      a, c, g, t, unknown, or other.

<400> SEQUENCE: 12
tgatcgggtc catgagcaan gatatgtacc agatcatgnn nnnnnnnnn nnnnnnnnnn      60 nnnnnnnnnn nnnnnnnnnn nnnnnactca cactggtcat ctctggct                 108

<210> SEQ ID NO 13
<211> LENGTH: 108
<212> TYPE: DNA
<213> ORGANISM: Artificial Sequence
<220> FEATURE:
<223> OTHER INFORMATION: Exemplary sequence from figure 46.

<400> SEQUENCE: 13
tgatcgggtc catgagcaag gatatgtacc agatcatgga cgagatcaag gaaggcatcc    60
agtacgtgtt ccagaccagg aacccactca cactggtcat ctctggct                 108

<210> SEQ ID NO 14
<211> LENGTH: 54
<212> TYPE: DNA
<213> ORGANISM: Artificial Sequence
<220> FEATURE:
<223> OTHER INFORMATION: Exemplary sequence from figure 47 showing BLAST
      results.
<220> FEATURE:
<221> NAME/KEY: misc_feature
<222> LOCATION: (25)..(37)
<223> OTHER INFORMATION: Nucleotides outside probe or primers; n is a,
      c, g, t, unknown, or other.

<400> SEQUENCE: 14
gctgattcac atgcaaagag acatnnnnnn nnnnnnngaa aattccatga aaag           54

<210> SEQ ID NO 15
<211> LENGTH: 54

```
<212> TYPE: DNA
<213> ORGANISM: Artificial Sequence
<220> FEATURE:
<223> OTHER INFORMATION: Exemplary sequence from figure 47.

<400> SEQUENCE: 15
gctgattcac atgaaaagag acatcatggg tatagaagaa aattccatga aaag    54

<210> SEQ ID NO 16
<211> LENGTH: 13
<212> TYPE: DNA
<213> ORGANISM: Artificial Sequence
<220> FEATURE:
<223> OTHER INFORMATION: Second fragment from exemplary sequence from
      figure 47 showing BLAST results.

<400> SEQUENCE: 16
catgcaaaga gac                                                13

<210> SEQ ID NO 17
<211> LENGTH: 55
<212> TYPE: DNA
<213> ORGANISM: Artificial Sequence
<220> FEATURE:
<223> OTHER INFORMATION: First fragment from exemplary sequence from
      figure 47.

<400> SEQUENCE: 17
gagacatcat gggtatagaa gaaaattcca tgaaaagcat cattcacatc gagaa   55

<210> SEQ ID NO 18
<211> LENGTH: 40
<212> TYPE: DNA
<213> ORGANISM: Artificial Sequence
<220> FEATURE:
<223> OTHER INFORMATION: Exemplary sequence to illustrate masking.

<400> SEQUENCE: 18
acgtgacgtg acgtgacgtg acgtggatcg tggggtcct                    40

<210> SEQ ID NO 19
<211> LENGTH: 39
<212> TYPE: DNA
<213> ORGANISM: Artificial Sequence
<220> FEATURE:
<223> OTHER INFORMATION: Exemplary sequence to illustrate masking.
<220> FEATURE:
<221> NAME/KEY: misc_feature
<222> LOCATION: (29)..(29)
<223> OTHER INFORMATION: Masked nucleotide; n is a, c, g, t, unknown, or
      other.
<220> FEATURE:
<221> NAME/KEY: misc_feature
<222> LOCATION: (33)..(36)
<223> OTHER INFORMATION: Masked nucleotides; n is a, c, g, t, unknown,
      or other.

<400> SEQUENCE: 19
acgtgacgtg acgtgacgtg acgtggatng tgnnnntcc                    39

<210> SEQ ID NO 20
<211> LENGTH: 10
<212> TYPE: DNA
<213> ORGANISM: Artificial Sequence
<220> FEATURE:
<223> OTHER INFORMATION: Exemplary probe sequence.

<400> SEQUENCE: 20
```

<210> SEQ ID NO 21
<211> LENGTH: 10
<212> TYPE: DNA
<213> ORGANISM: Artificial Sequence
<220> FEATURE:
<223> OTHER INFORMATION: Exemplary probe sequence.

<400> SEQUENCE: 21
cagctcctgc                                                              10

<210> SEQ ID NO 22
<211> LENGTH: 120
<212> TYPE: DNA
<213> ORGANISM: Homo sapiens

<400> SEQUENCE: 22
actagcctgg gcaacaagag tgaaactccg ttctcaaaaa aaaaaaaaag cctttttttga      60 gatggagtct cgctctgtcg cccaggctgg agtgcagcag cgcgatttcg gctcactgca     120

<210> SEQ ID NO 23
<211> LENGTH: 215
<212> TYPE: PRT
<213> ORGANISM: Homo sapiens

<400> SEQUENCE: 23

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Pro Asp Pro Arg Pro Gly Arg Gly Glu Gly Ala Gly
            100                 105                 110

Gly Gly Gly Ala Arg Gln Ala Gly Gly Ala Gly Pro Ala Asp Thr Pro
        115                 120                 125

Ala Gly Arg Gly Leu Pro Gly Pro Pro Gln Glu Leu Val Arg Ala Pro
    130                 135                 140

Gly Gly Arg His Ala Ala Pro Val Gly Arg Ala Gly Gly Glu Gly Ala
145                 150                 155                 160

Gly Cys Arg Gly His Gln Arg Arg Pro Cys Ala Gln Arg Gln Ser Leu
                165                 170                 175

Asn Ala Glu Ala Cys Ser His Ala Thr Pro Arg His Pro Val Pro Pro
            180                 185                 190

Ala Ser Ala Gln Pro Ala Ala Gly Asp Pro Val Pro Ala Pro Ala Val
        195                 200                 205

Leu Leu Gly Trp Thr Leu Val
    210                 215

<210> SEQ ID NO 24
<211> LENGTH: 480

```
<212> TYPE: DNA
<213> ORGANISM: Homo sapiens

<400> SEQUENCE: 24
cccagcggag gtgaaggacg tccttcccca ggagccgact ggccaatcac aggcaggaag      60
atgaaggttc tgtgggctgc gttgctggtc acattcctgg caggatgcca ggccaaggtg     120
gagcaagcgg tggagacaga gccggagccc gagctgcgcc agcagaccga gtgggagagc     180
ggccagcgct gggaactggc actgggtcgc ttttgggatt acctgcgctg ggtgcagaca     240
ctgtgtgagc aggtgcagga ggagctgctc agctcccagg tcacccagga actgaggggg     300
ctgatggacg agaccatgaa ggagttgaag gcctacaaat cggaactgga ggaacaactg     360
accccggtgg cggaccacac gcccccacgg ctgtccaacg agctgcaggc gccccaggcc     420
cggctgggcg cgcacatgga ggacgtgcgc gcccgcctgc tgcagtaccg cggcgaggtg     480

<210> SEQ ID NO 25
<211> LENGTH: 540
<212> TYPE: DNA
<213> ORGANISM: Homo sapiens

<400> SEQUENCE: 25
tgatccaccc gccccggcct cccaaagtgc tgggattaca ggtgtgagcc accgcgcccg      60
gccgaccatg caatcttttc tgacggttcc tgaaaccacc gagttggttc taccccagga    120
ccgacgcaca ctctgtccct gctcgatgga attcttccct ctggtcttga catgactggg    180
aagggttgcg tgcgcatgtc gccctctgtc gtccaccatt gtccccatct tgcaaggcca    240
agaggaggtt ctccactaag ggcacatggc cagtgggact ccagtgtccc tgctcttcac    300
ggcgccagca accccgttcc ctgtgccgcc tcgctcgcct ggtccttttcg tgctccccag    360 cactggcctc ctggagccca gggccaccag tgacgctttg gtctctagtc ctttccagtg    420
cctcttcctt cccccagaca ccagtgagaa cagggcctgc cgtgtgccgg tcacgcctga    480
gctctcgagt ctcttgccac caacagctcc gacttgaccc agggtgtctc tacctccagg    540

<210> SEQ ID NO 26
<211> LENGTH: 19
<212> TYPE: DNA
<213> ORGANISM: Artificial Sequence
<220> FEATURE:
<223> OTHER INFORMATION: Third fragment from exemplary sequence from
      figure 47 showing BLAST results.
<220> FEATURE:
<221> NAME/KEY: misc_feature
<222> LOCATION: (3)..(15)
<223> OTHER INFORMATION: Nucleotides outside primers or probe; n is a,
      c, g, t, unknown, or other.

<400> SEQUENCE: 26
atnnnnnnnn nnnnngaaa                                                   19

<210> SEQ ID NO 27
<211> LENGTH: 98
<212> TYPE: DNA
<213> ORGANISM: Artificial Sequence
<220> FEATURE:
<223> OTHER INFORMATION: Sixth fragment from exemplary sequence from
      figure 47 showing BLAST results.
<220> FEATURE:
<221> NAME/KEY: misc_feature
<222> LOCATION: (7)..(75)
<223> OTHER INFORMATION: Nucleotides outside primers or probe; n is a,
      c, g, t, unknown, or other.
```

-continued

```
<400> SEQUENCE: 27
gaaaagnnnn nnnnnnnnnn nnnnnnnnnn nnnnnnnnnn nnnnnnnnnn nnnnnnnnnn      60
nnnnnnnnnn nnnnnatgat tatggaggtt tgactggc                              98

<210> SEQ ID NO 28
<211> LENGTH: 92
<212> TYPE: DNA
<213> ORGANISM: Artificial Sequence
<220> FEATURE:
<223> OTHER INFORMATION: Second fragment from exemplary sequence from
      figure 47.

<400> SEQUENCE: 28
tttccatttt atggggacta tggatcaaat tatctatatg acaattgata tccttagtaa      60
tcatggggca tgattataga ggtttgactg gc                                    92
```

METHODS FOR PLACING, ACCEPTING, AND FILLING ORDERS FOR PRODUCTS AND SERVICES

CROSS-REFERENCE TO RELATED APPLICATIONS

This application is a divisional of U.S. patent application Ser. No. 13/458,879, filed Apr. 27, 2012, which is a continuation of U.S. patent application Ser. No. 12/015,143, filed on Jan. 16, 2008 (now abandoned), which is a continuation of U.S. patent application Ser. No. 10/334,793, filed on Jan. 2, 2003 (now abandoned), which claims the benefit of U.S. Provisional Application No. 60/352,039, filed on Jan. 25, 2002, U.S. Provisional Application No. 60/352,356, filed on Jan. 28, 2002, U.S. Provisional Application No. 60/369,127, filed on Apr. 1, 2002, U.S. Provisional Application No. 60/369,657, filed on Apr. 3, 2002, U.S. Provisional Application No. 60/370,921, filed on Apr. 9, 2002, U.S. Provisional Application No. 60/376,171, filed on Apr. 26, 2002, U.S. Provisional Application No. 60/380,057, filed on May 6, 2002, U.S. Provisional Application No. 60/383,627, filed on May 28, 2002, U.S. Provisional Application No. 60/383,954, filed on May 29, 2002, U.S. Provisional Application No. 60/390,708, filed on Jun. 21, 2002, U.S. Provisional Application No. 60/394,115, filed on Jul. 5, 2002, and U.S. Provisional Application No. 60/399,860, filed on Jul. 31, 2002, all of which are hereby incorporated in their entirety by reference.

SEQUENCE LISTING

The instant application contains a Sequence Listing which has been submitted electronically in ASCII format and is hereby incorporated by reference in its entirety. Said ASCII copy, created on Jun. 2, 2017, is named 4797_C2D1_US_SL.txt and is 13,010 bytes in size.

FIELD

This application relates to methods for distributing products and services, and more particularly, to methods for placing, accepting, and filling orders for products and services, especially biotechnological products and services.

BACKGROUND

With the completion of the first draft of the human genome along with the sequencing of the genomes of other species, an enormous amount of genomic resource data has become available. This data has permitted extensive studies of gene expression as well as studies of single nucleotide polymorphisms and their linkage to disease conditions. However, these and other studies have been limited by the need of researchers to spend substantial time, money, and manual labor in the design of probes and primers for experimental assays. Once designed, the researcher can synthesize the probes and primers or order them from an oligonucleotide synthesis facility or service. Only a limited number of studies can be done given time constraints required for the individual researcher to complete each of the tasks leading up to a particular experiment, and, therefore, an overall provider of design, manufacturing, and validation services for probes and primers would be of significant value to the researcher.

SUMMARY

Accordingly, the present inventors have succeeded in developing web-based systems for ordering assays, which, in various embodiments, can comprise probes and primers. Included among various of these systems are systems for ordering probes and primers that have undergone design, manufacturing, and validation procedures. In some of these various systems, the ordered probes and primers are delivered to the researcher along with information detailing various parameters associated with production of the assay delivered.

Thus, in various configurations of the present invention, there can be provided a method for supplying to a consumer assays useful in obtaining structural genomic information, such as the presence or absence of one or more single nucleotide polymorphisms (SNPs), and functional genomic information, such as the expression or amount of expression of one or more genes. As such, the assays can be configured to detect the presence or expression of genetic material in a biological sample. The method includes providing a web-based user interface configured for receiving orders for stock assays, providing a web-based user interface configured for receiving requests for design of custom assays and for ordering said assays, and delivering to the consumer at least one custom or stock assay in response to an order for the one custom or stock assay placed by the consumer. In certain other aspects, the present invention can also be directed to a system and to methods for constructing a system for providing to a consumer assays configured to detect presence or expression of genetic material.

In various configurations of the invention as described above, the method can further include providing a web-based gene exploration platform configured to provide information to assist a consumer in selecting one or both of a stock assay and a custom assay.

The present invention, in various configurations, can also include a search resource provided to identify genetic material. The search resource may provide one or more parameters identifying gene structure or function for selection by the consumer. Assays that detect the presence or expression of genetic material may include assays for detecting SNPs or for detecting expressed genes. In various configurations, the ordering interface can be configured to receive criteria related to the SNP or to the expressed transcript for which an assay is ordered Stock SNP assays provided by the web-based user interface can include, in some configurations, a large number of SNP assays, for example, at least 40,000 SNP assays for detecting the at least 40,000 pairs of SNP alleles, or at least 100,000 SNP assays for detecting the at least 100,000 pairs of SNP alleles. In some configurations, SNP assays that can be ordered can be assays for SNPs that are known to be located in gene regions. In some configurations, SNPs that can be detectable may be located at intervals of about 10 kilobases (kb). Also in some configurations, the SNPs have a minor allele frequency of about 10% in a population (which may be, but is not necessarily, a human population).

Stock gene expression assays provided by the web-based user interface can include, in some configurations assays for at least about 10,000 or more expressed genes. In certain configurations, gene expression assays for multi-exon genes can be made up of probes and primers designed to lie on exon-exon boundaries to preclude amplification of genomic DNA.

For SNP assays and gene expression assays, either or both of pre-manufacturing quality control and post-manufacturing quality control can be provided in some configurations of the present invention. Pre-manufacturing quality control may include one or more of pre-processing selection, designing primers and probes, and performing in silico quality control. In the case of SNP assays, pre-manufacturing controls may include identifying optimal sequence regions which may not contain any SNPs or repeat sequences. In the case of gene expression assays, the optimal sequence regions in some configurations may not contain any SNPs other than a SNP for which the assay is designed to detect, and also does not contain any repeat sequences. The designing of primers and probes may comprise, in some configurations, avoidance of non-optimal regions as defined above as well as the use of specifications that optimize PCR reaction conditions for the designed assay. Such specifications include assay values for $T_m$, GC content, buffer and salt conditions, oligonucleotide concentration in assay, low secondary structure of oligonucleotide, amplicon size and low incidence of primer-dimer formation. In silico quality control can ensure that probes and primers match target sequences but do not match other sequences in the genome or other transcripts.

Post-manufacturing quality control provided in some configurations includes one or more of synthesis yield testing, analytical quality control testing, functional testing, and validation testing.

In some configurations, assays can be shipped with a data sheet which may be a hard-copy datasheet or an electronic datasheet, or both. The electronic datasheet may be in the form of a CD-ROM or other suitable machine readable form. Assays that are shipped can be identified, in some configurations, by identifiers which can include a two-dimensional (2-D) barcode, and an assay identification number. The assay components in certain configurations include, in a single tube, two primers and a TaqMan® probe. In the case of SNP assays, two primers and two TaqMan® probes can be included, i.e., one TaqMan® probe for each allele. In some configurations, the tubes also contain PCR reagents for performing assays.

In certain configurations, the present invention provides an assay kit. The kit contains at least one assay for detecting presence or expression of genomic material. The kit also contains an information source comprising an E-datasheet, an assay information file, or at least one printed-copy datasheet or combinations thereof.

Various configurations of the present invention also provide a method for building a submission file useful for ordering at least one of SNP genotyping assays and gene expression assays. The method includes providing a graphical user interface configured to accept, from a user, information relating to (a) recipient identification, (b) assay amount, and (c) at least one target sequence, electronically validating at least a portion of the information relating to the target sequence; and saving the information relating to recipient information, assay amount, and target sequence to a file, wherein the information relating to target sequence includes the validated information.

Various configurations of the present invention also provide genomic products and services to a consumer. The products and services provided can be used to detect presence or expression of genetic material in biological sample. The system comprises a first source of information regarding at least one of presence or expression of genetic material in biological samples, a second source of information regarding products and services for analyzing genetic material and an interface system communicating with the first source of information and the second source of information. The system is able to recommend to the consumer certain processes and services in response to inquires to said first source of information by the consumer.

In various configurations, the present invention can provide a web-based user interface configured to receive a request for design of one or more custom assays and an order for said custom assays; and deliver to the consumer at least one custom assay in a single tube in response to an order for said at least one custom assay placed by the consumer, wherein said assay comprises at least one probe, a forward primer and a reverse primer.

In various configurations, the present invention can also provide a web-based user interface configured to receive an order one or more stock assays; and deliver to the consumer at least one stock assay in a single tube in response to an order for said at least one stock assay placed by the consumer wherein said assay comprises at least one probe, a forward primer and a reverse primer.

The present invention also provides a web portal configured to provide an interface configured to accept orders for one or more stock assays; an interface configured to accept orders for one or more custom assays; a gene exploration platform configured to provide information to assist a user in selecting one or both of a stock assay and a custom assay.

BRIEF DESCRIPTION OF THE DRAWINGS

The present invention will become more fully understood from the detailed description and the accompanying drawings, wherein:

FIG. 3 is an exemplary window pane for a chromosome map report.

FIG. 4 is an exemplary window pane for a scaffold report.

FIG. 5 is an exemplary window pane for a sequence report, showing sequence (SEQ ID NO: 22)
ACTAGCCTGGGCAACAAGAGTGAAACTCCGTTCTCAAAAAAAAAAAAAGC

CTTTTTTGAGATGGAGTCTCGCTCTGTCGCCCAGGCTGGAGTGCAGCAGCG

CGATTTCGGCTCACTGCA.

FIG. 6 is an exemplary window pane for a gene list.

Figure 7:
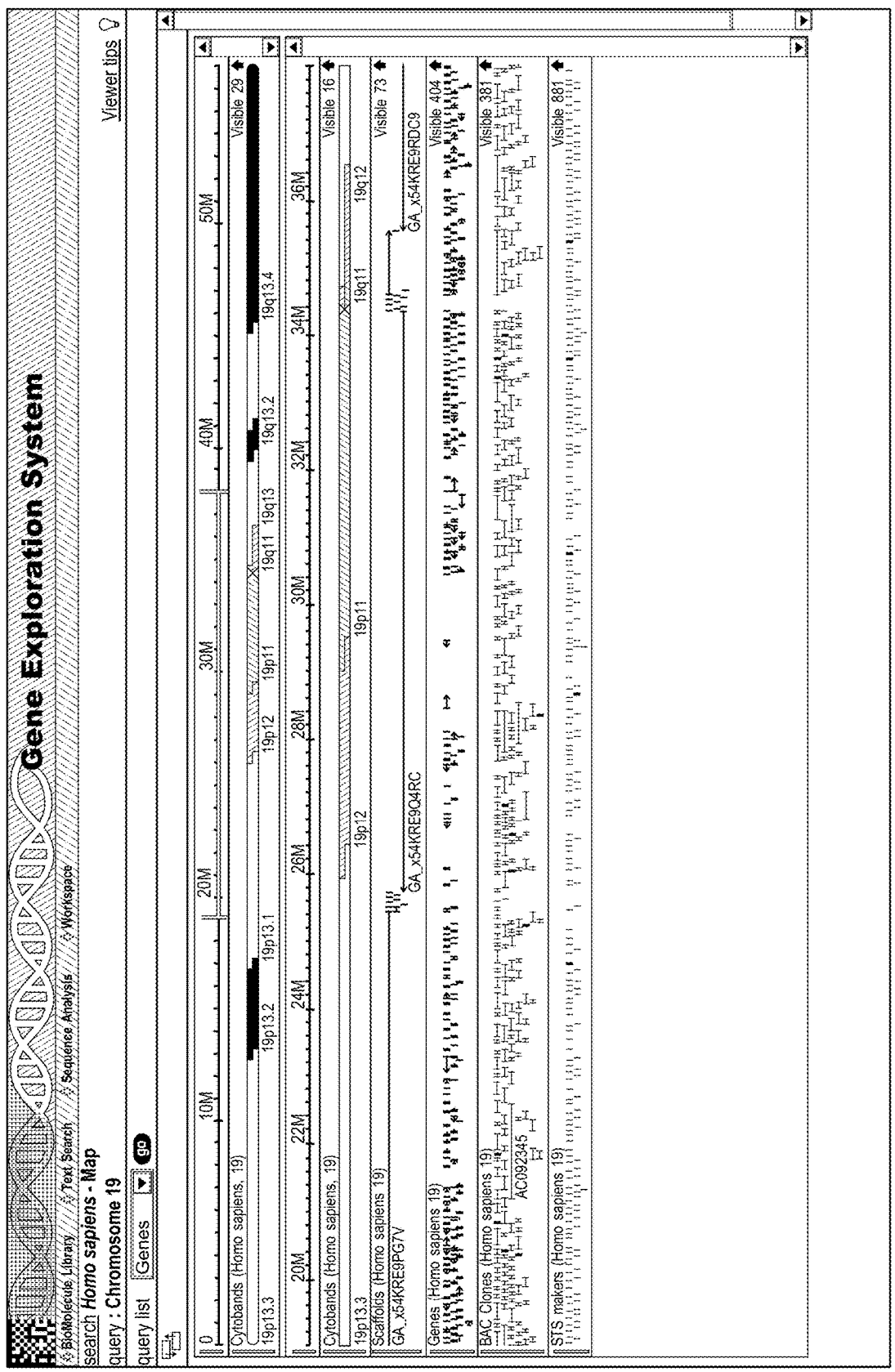

FIG. 7 is an exemplary window pane for a chromosome map display.

Figure 8:

FIG. 8 is an exemplary window pane for a biomolecule report, showing sequence (SEQ ID NO: 23)
MKVLWAALLVTFLAGCQAKVEQAVETEPEPELRQQTEWQSGQRWELALGRF

WDYLRWVQTLSEQVQEELLSSQVTQELRALMDETMKELKAYKSELEEQPDP

RPPGRGEGAGGGGARQAGGAGPADTPAGRGLPGPPQELVRAPGGRHAAPVG

RAGGEGAGCRGHQRRPCAQRQSLNAEACSHATPRHPVPPASAQPAAGDPVP

APAVLLGWTLV*.

FIG. 9 is an exemplary window pane for an mRNA view of a biomolecule report, showing sequence (SEQ ID NO: 24)
CCCAGCGGAGGTGAAGGACGTCCTTCCCCAGGAGCCGACTGGCCAATCACA -continued

```
GGCAGGAAGATGAAGGTTCTGTGGGCTGCGTTGCTGGTCACATTCCTGGCA

GGATGCCAGGCCAAGGTGGAGCAAGCGGTGGAGACAGAGCCGGAGCCCGAG

CTGCGCCAGCAGACCGAGTGGGAGAGCGGCCAGCGCTGGGAACTGGCACTG

GGTCGCTTTTGGGATTACCTGCGCTGGGTGCAGACACTGTGTGAGCAGGTG

CAGGAGGAGCTGCTCAGCTCCCAGGTCACCCAGGAACTGAGGGGGCTGATG

GACGAGACCATGAAGGAGTTGAAGGCCTACAAATCGGAACTGGAGGAACAA

CTGACCCCGGTGGCGGACCACACGCCCCACGGCTGTCCAACGAGCTGCAG

GCGCCCCAGGCCCGGCTGGGCGCGCACATGGAGGACGTGCGCGCCCGCCTG

CTGCAGTACCGCGGCGAGGTG.
```

Figure 10:

FIG. 10 is an exemplary window pane for a chromosome view of a biomolecule report, showing sequence

```
                                                (SEQ ID NO: 25)
TGATCCACCCGCCCCGGCCTCCCAAAGTGCTGGGATTACAGGTGTGAGCCA

CCGCGCCCGGCCGACCATGCAATCTTTTCTGACGGTTCCTGAAACCACCGA

GTTGGTTCTACCCCAGGACCGACGCACACTCTGTCCCTGCTCGATGGAATT

CTTCCCTCTGGTCTTGACATGACTGGGAAGGGTTGCGTGCGCATGTCGCCC

TCTGTCGTCCACCATTGTCCCCATCTTGCAAGGCCAAGAGGAGGTTCTCCA

CTAAGGGCACATGGCCAGTGGGACTCCAGTGTCCCTGCTCTTCACGGCGCC

AGCAACCCCGTTCCCTGTGCCGCCTCGCTCGCCTGGTCCTTTCGTGCTCCC

CAGCACTGGCCTCCTGGAGCCCAGGGCCACCAGTGACGCTTTGGTCTCTAG

TCCTTTCCAGTGCCTCTTCCTTCCCCCAGACACCAGTGAGAACAGGGCCTG

CCGTGTGCCGGTCACGCCTGAGCTCTCGAGTCTCTTGCCACCAACAGCTCC

GACTTGACCCAGGGTGTCTCTACCTCCAGG.
```

FIG. 11 is an exemplary window pane for a human gene mutation database report.

FIG. 12 is an exemplary window pane for a genome map search.

FIG. 13 is an exemplary window pane for a genome assembly search.

Figure 14:
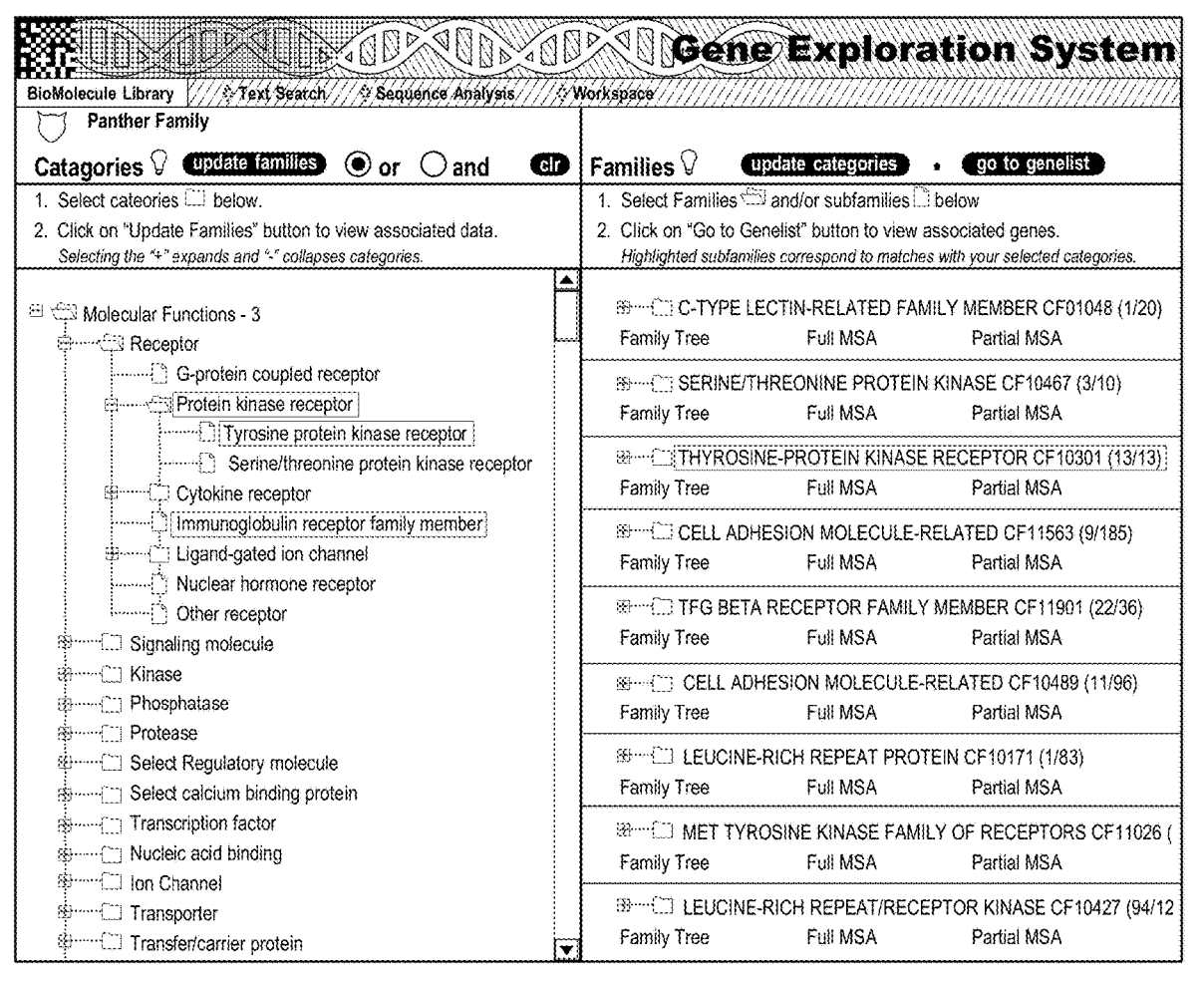

FIG. 14 is an exemplary window pane for a Panther protein function-family browser.

FIG. 15 is an exemplary window pane for an ontology investigation.

FIG. 16 is an exemplary window pane for an ontology keyword results investigation.

FIG. 17 is an exemplary introductory window pane for designing or selecting a genomic assay.

Figure 18:
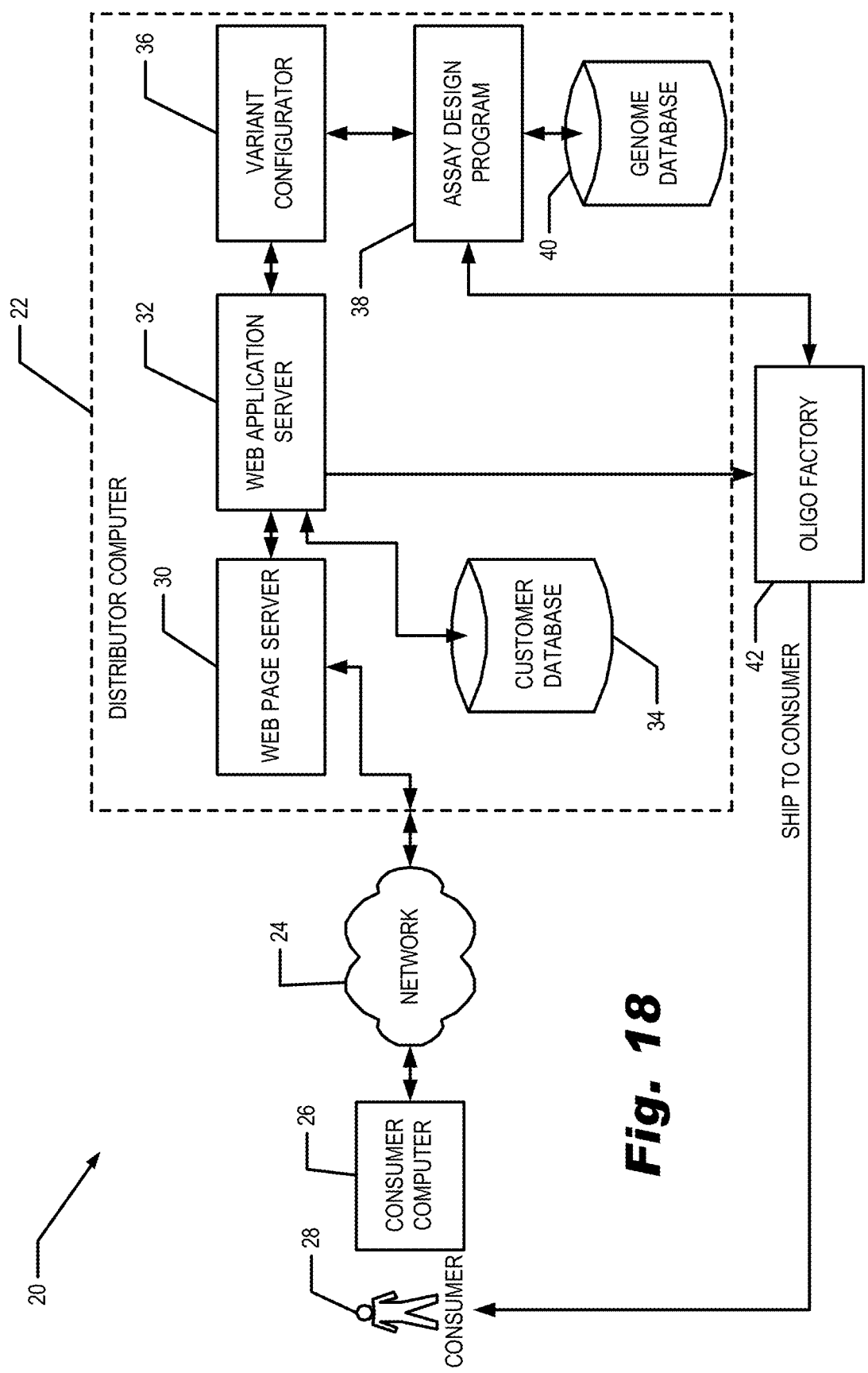

FIG. 18 is a block diagram representing the various configurations of a computer system of the present invention that is used for distributing biotechnology products to a consumer.

Figure 19:
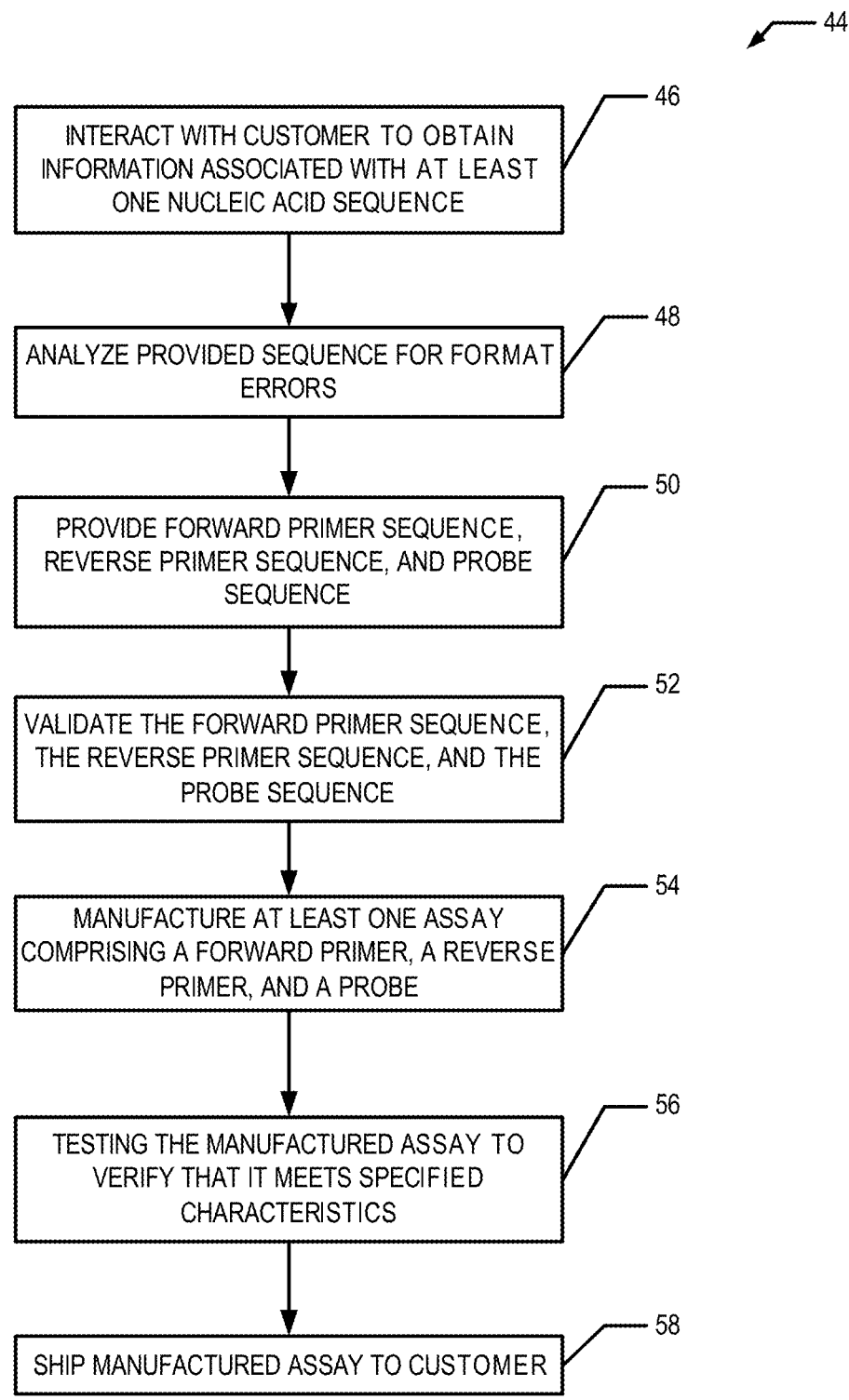

FIG. 19 is a flow chart representative of various method configurations of the present invention that can perform by computing system configurations such as those represented by FIG. 3, or by other computer system configurations.

Figure 20:
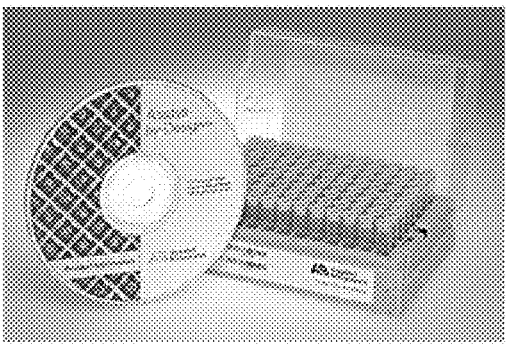

FIG. 20 is an exemplary window pane providing instructions to the user with respect to ordering custom assays according to one of the various embodiments of the present invention.

Figure 21:
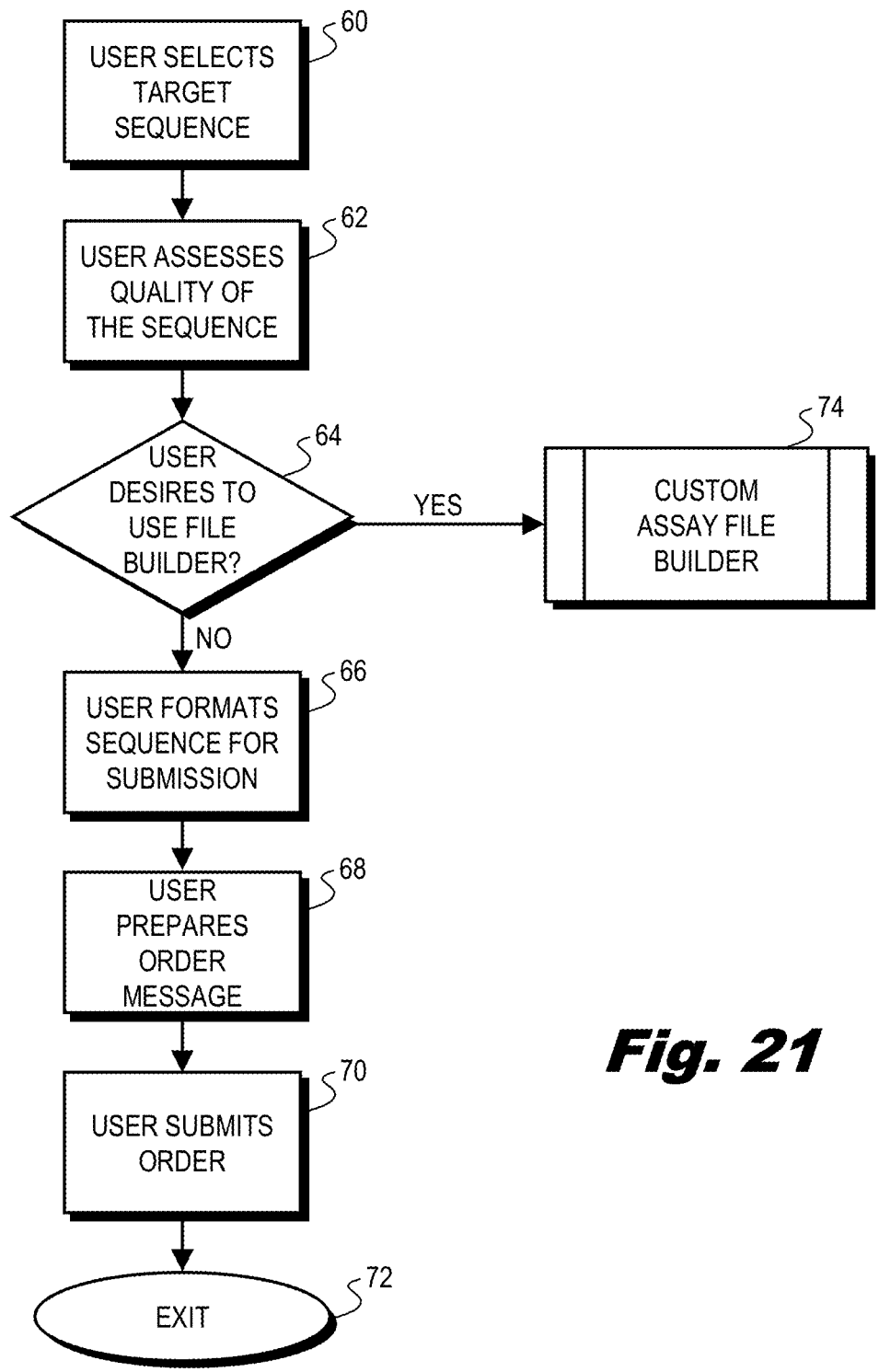

FIG. 21 is a flow chart illustrating the manner in which the user submits information for obtaining custom assays according to one of the various embodiments of present invention.

Figures 22, 23, 24:
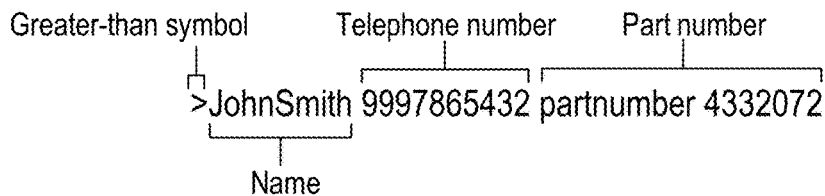

FIG. 22 illustrates the contents of the header portion of a submission file according to one of the various embodiments of the present invention.

FIG. 23 is an illustration of a sequence record used for obtaining custom SNP genotyping assays according to one of the various embodiments of the present invention, showing sequence AGTGAACGRGATAGGCKCTCCTGCCC (SEQ ID NO:1), wherein R is A or G, and K is G or T, in accordance with WIPO standard ST.25.

FIG. 24 is an illustration of a sequence record for obtaining custom gene expression assay according to one of the various embodiments of the present invention, showing sequence

```
                                                 (SEQ ID NO: 2)
AGTGAACGAGATAGGCAGCTCCTGCCCCATCCAAG.
```

FIG. 25 is a representation of a visual checklist for a SNP submission file according to one of the various embodiments of the present invention, showing sequences AGTGAACGRGATAGGCAKCTCCTGCCC (SEQ ID NO:1), TTACGGCCCTGAKGGGACTGCSATCATTTTCT (SEQ ID NO:3), and GAGTGGAGCAACANGCTTTCCGCAATTTAC (SEQ ID NO:4), wherein R is A or G, K is G or T, and N is A, C, G, or T in accordance with WIPO standard ST.25.

FIG. 26 is an illustration of a visual checklist for a submission file for gene expression assays according to one of the various embodiments of the present invention, showing sequences

```
                                                 (SEQ ID NO: 2)
AGTGAACGAGATAGGCAGCTCCTGCCCCATCCAAG
and (SEQ ID NO: 5)
TTACGGCCCTGAGGGGACGAATCGATCATTTTCT.
```

Figure 27:
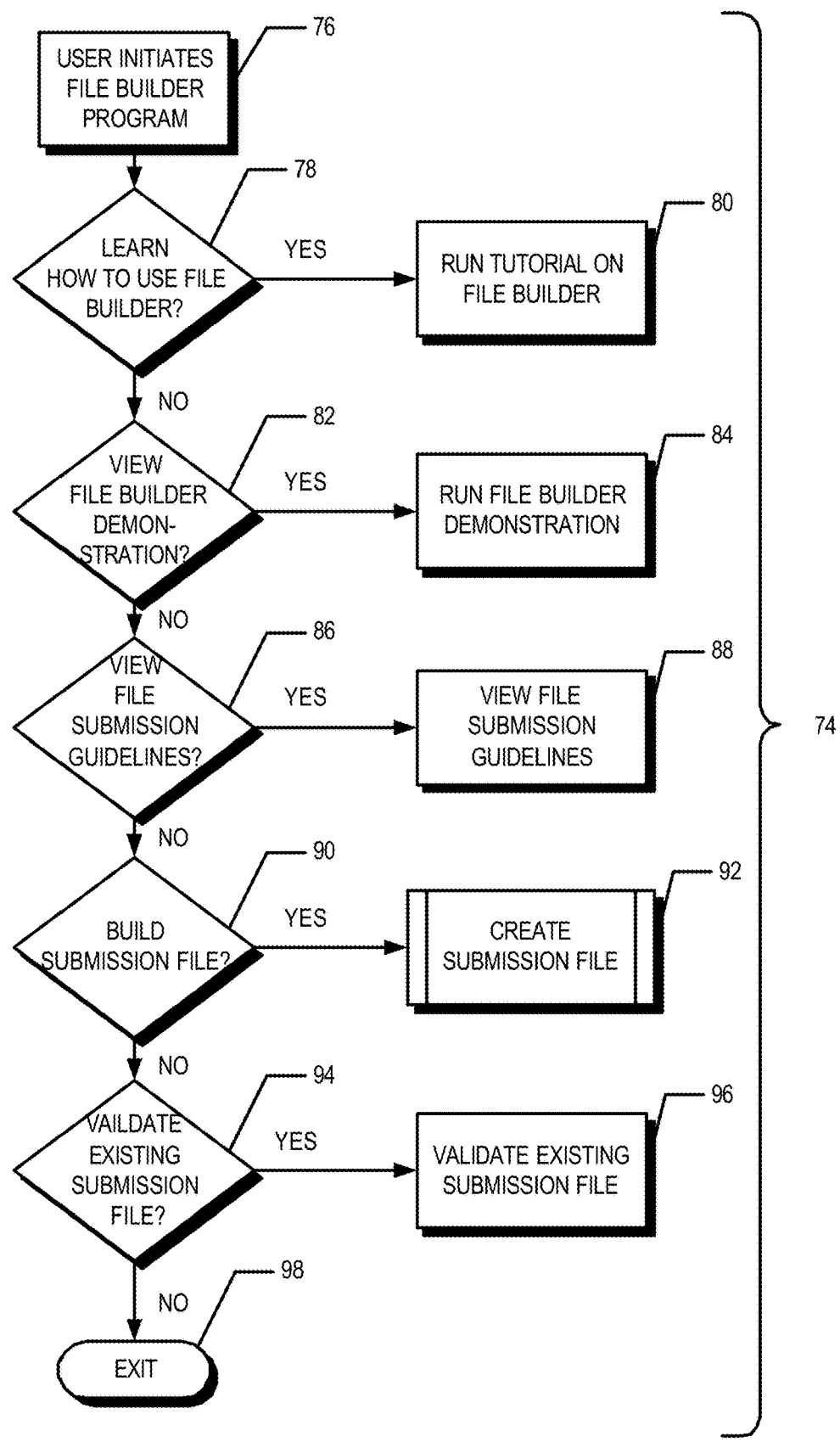

FIG. 27 is a flow chart of the file builder program according to one of the various embodiments of the present invention.

Figure 28:
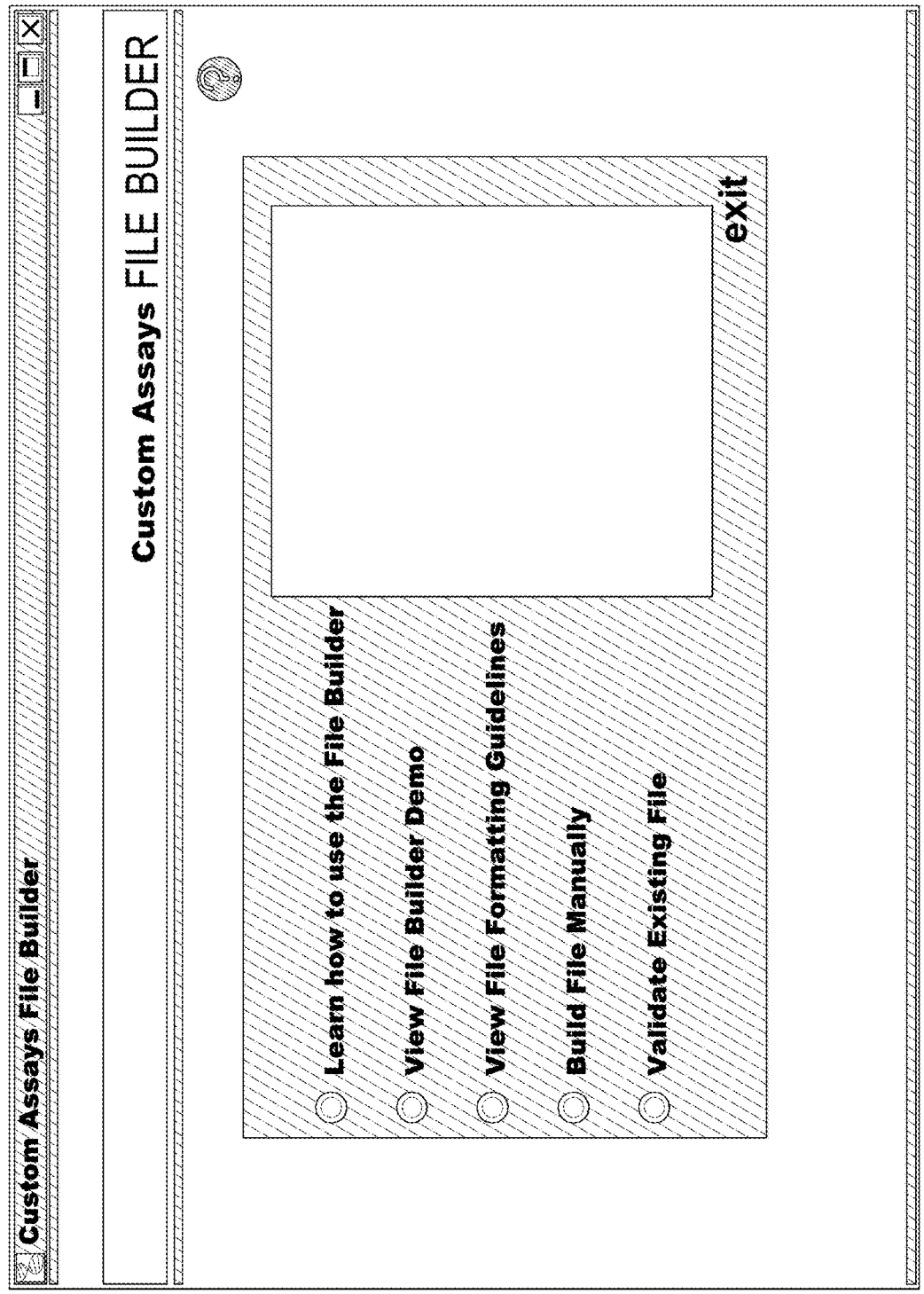

FIG. 28 is an exemplary window pane which allows the user to build a submission file when the using the file builder program according to one of the various embodiments of the present invention.

Figure 29:
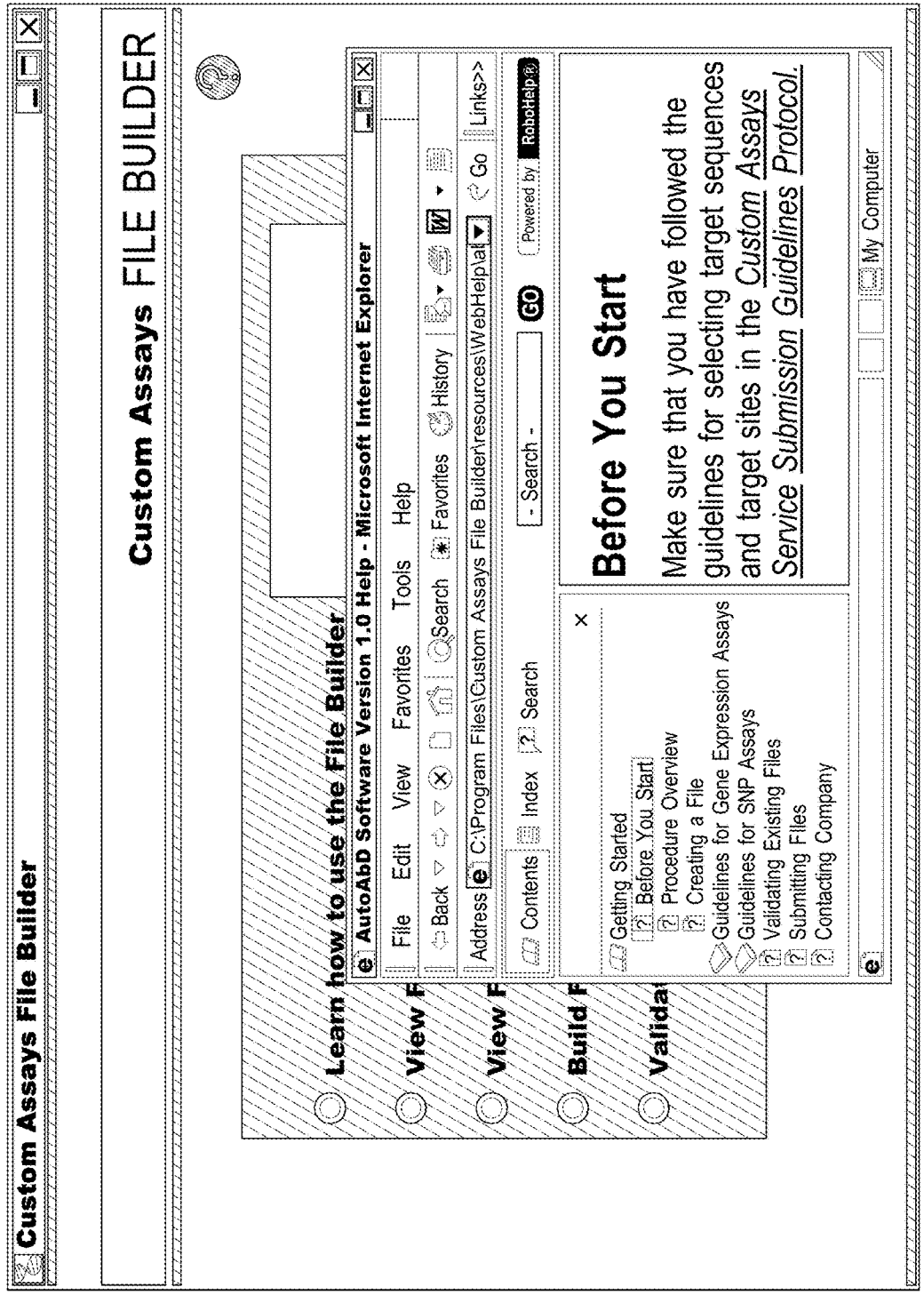

FIG. 29 is an exemplary window pane showing tutorial information being displayed according to one of the various embodiments of the present invention.

Figure 30:
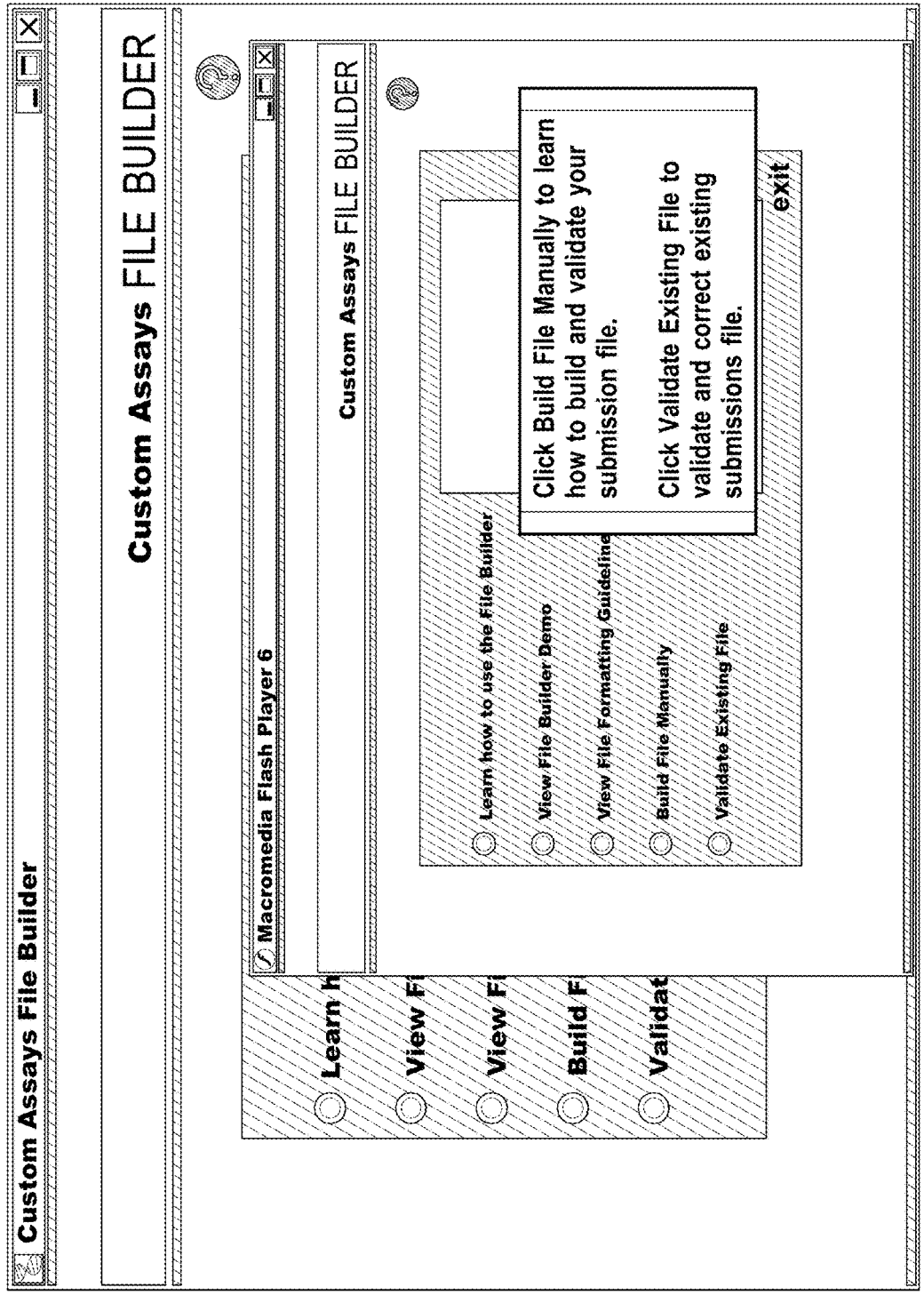

FIG. 30 is an exemplary window pane showing a demonstration of the file builder program according to one of the various embodiments of the present invention.

Figure 31:
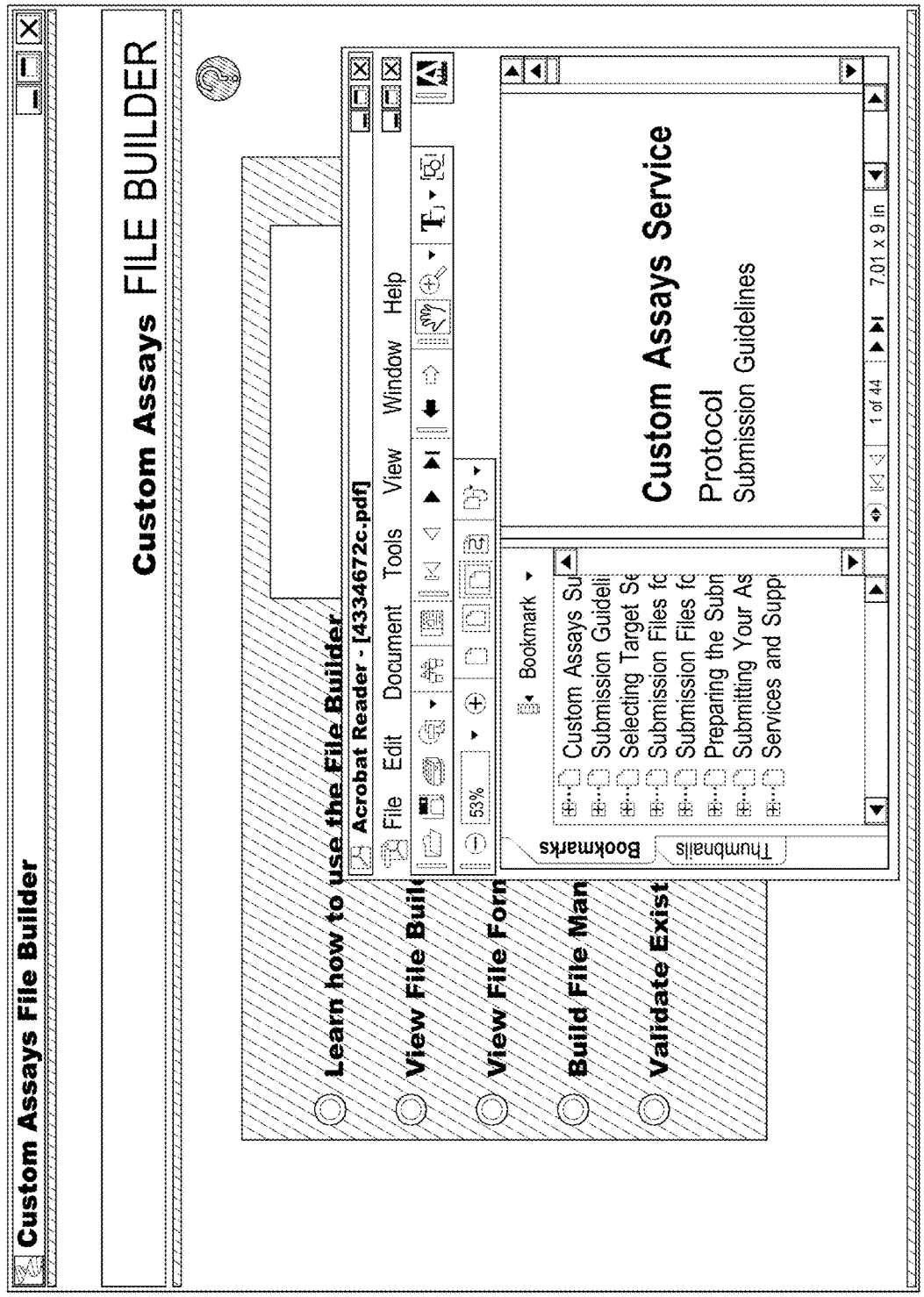

FIG. 31 is an exemplary window pane illustrating the submission guidelines for obtaining custom assays according to one of the various embodiments of the present invention.

Figure 32:
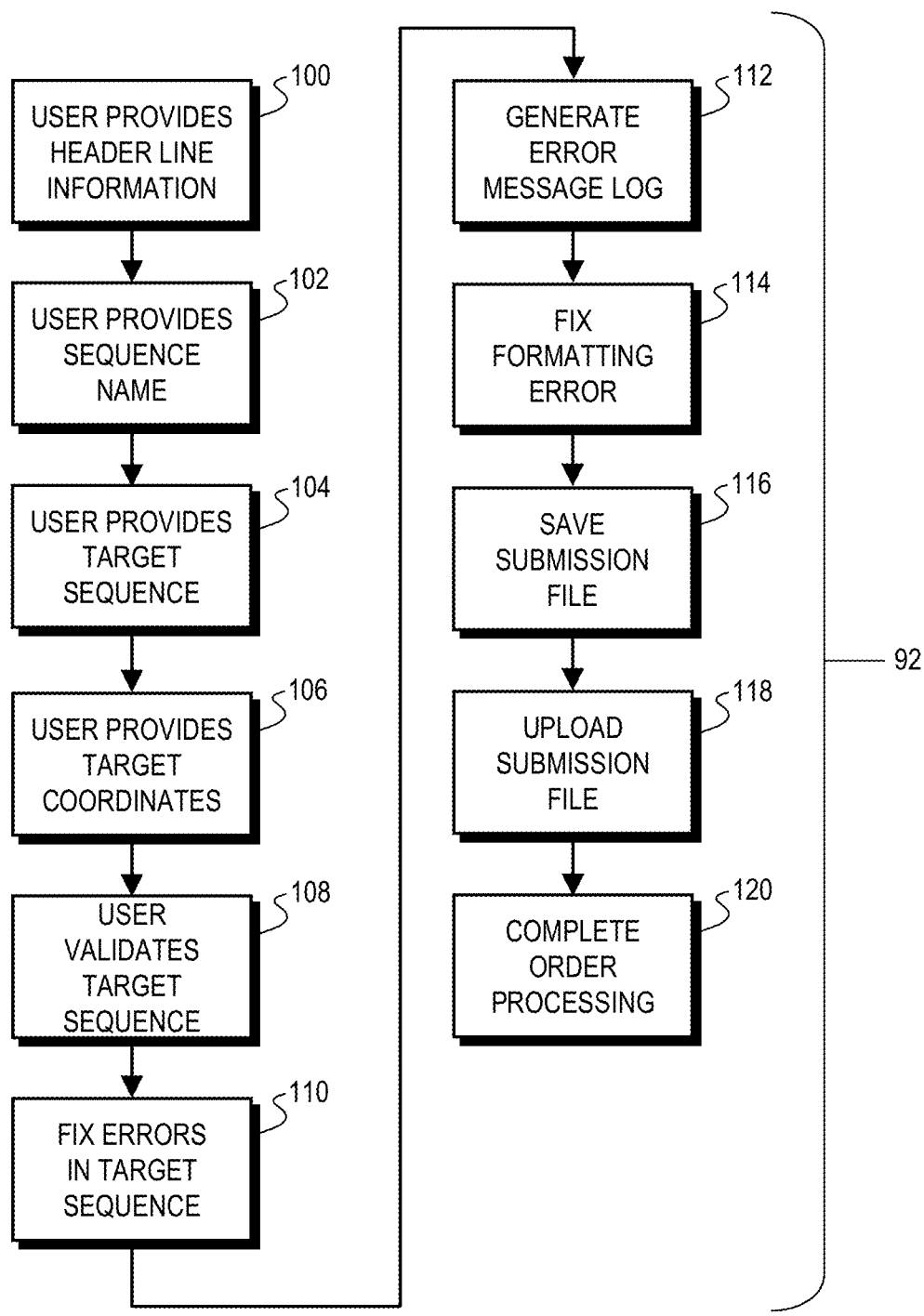

FIG. 32 is a flow chart illustrating how the file builder program issued according to one of the various embodiments of the present invention.

FIG. 33 is an exemplary window pane which allows the user to enter header line information for the submission file according to one of the various embodiments of the present invention.

Figure 34:
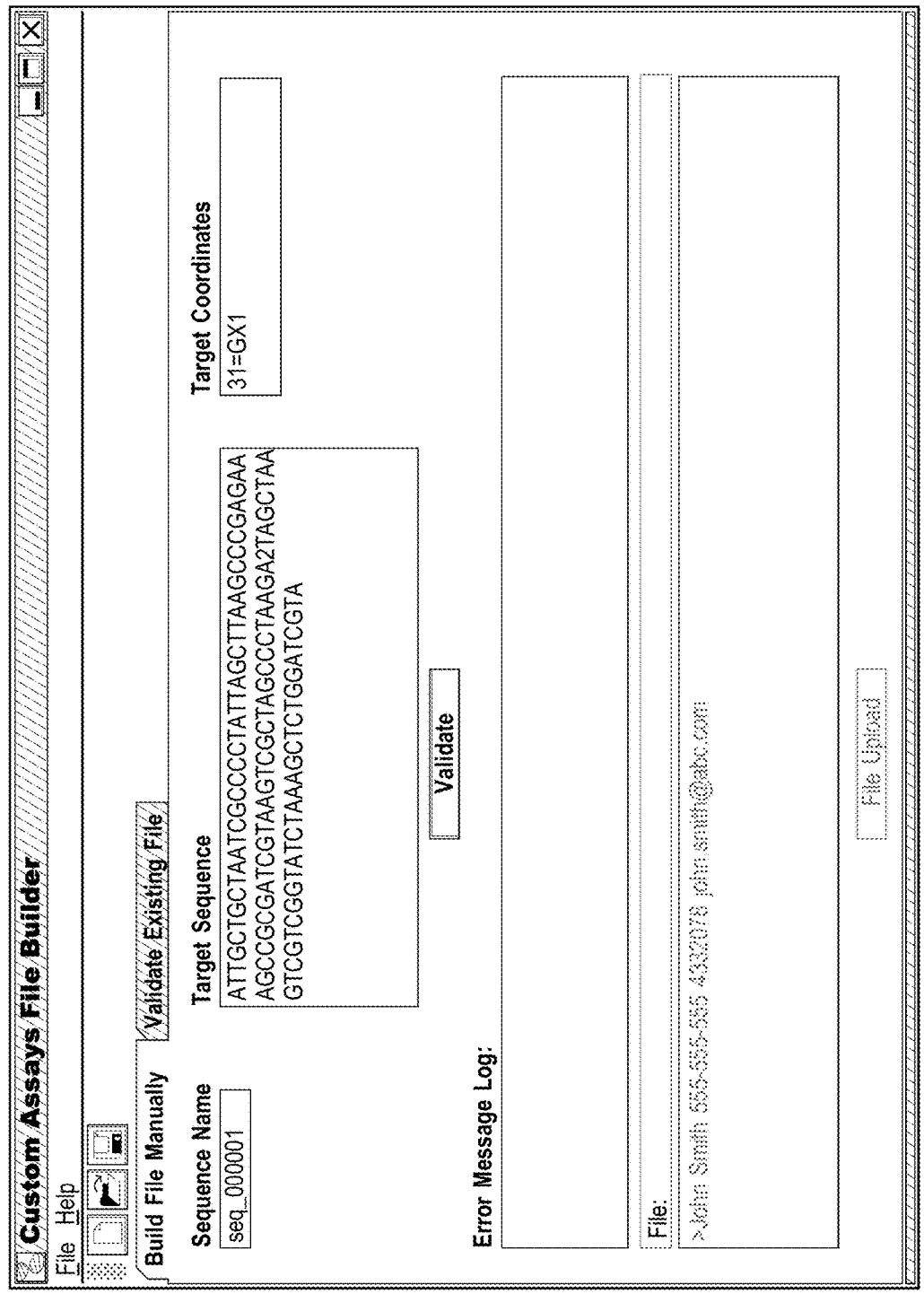

FIG. 34 is an exemplary window pane which permits the user to enter information associated with a sequence record according to one of the various embodiments of the present invention, showing sequence

```
                                           (SEQ ID NO: 6)
ATTGCTGCTAATCGCCCCTATTAGCTTAAGCCCGAGAAAGCCGCGATCGT

AAGTCGCTAGCCCTAAGANTAGCTAAGTCGTCGGTATCTAAAGCTCTGGA

TCGTA.
```

In the illustrated embodiment, a sequence input by the user includes an error, where the "N" listed in SEQ ID NO: 6 corresponds to a "2" typographical error input by the user.

Figure 35:
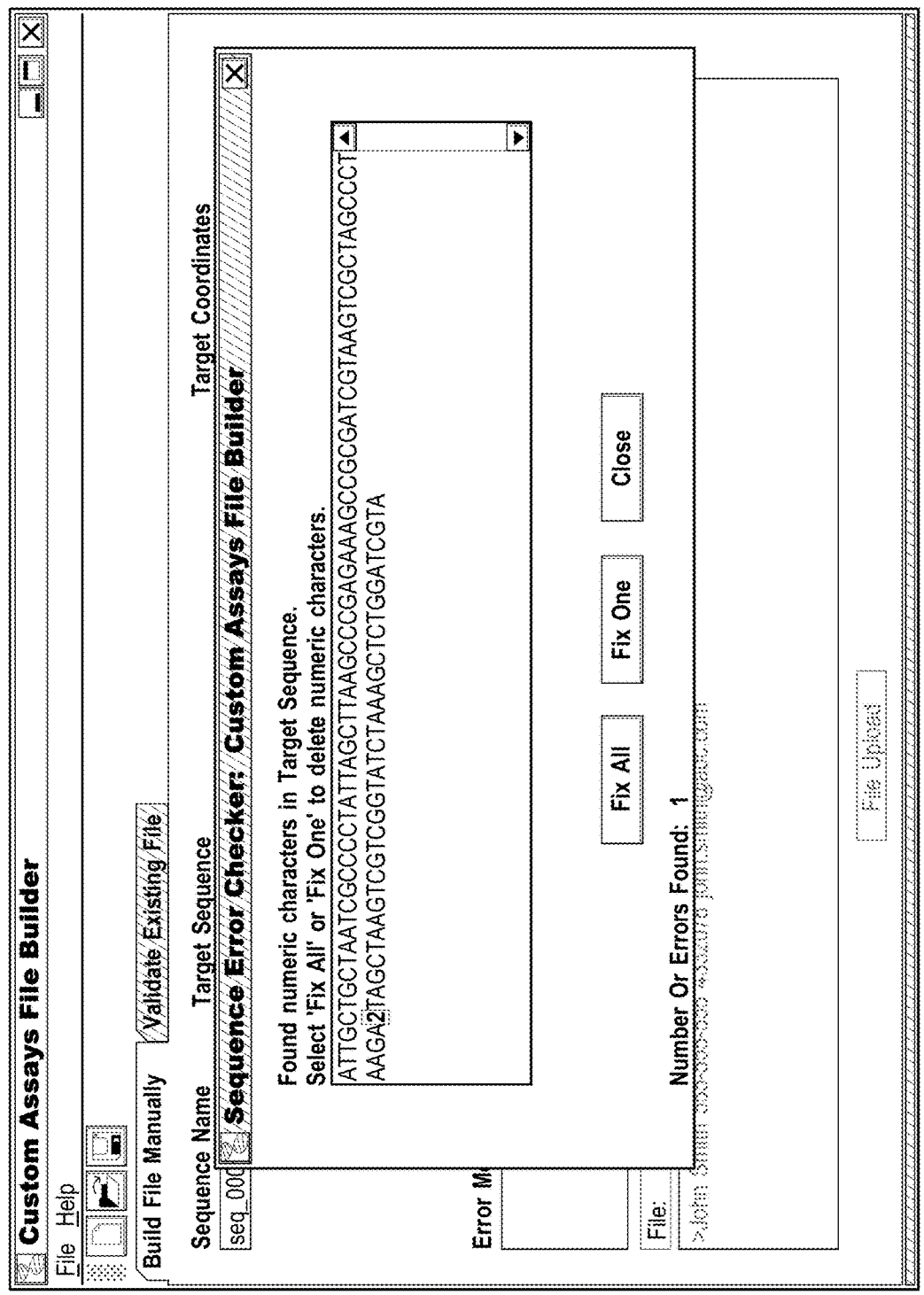

FIG. 35 is an exemplary window pane illustrating the manner in which errors are brought to the attention of the user while the file builder program is being executed according to one of the various embodiments of the present invention, showing sequence

```
                                           (SEQ ID NO: 6)
ATTGCTGCTAATCGCCCCTATTAGCTTAAGCCCGAGAAAGCCGCGATCGT

AAGTCGCTAGCCCTAAGANTAGCTAAGTCGTCGGTATCTAAAGCTCTGGA

TCGTA.
```

In the illustrated embodiment, the sequence input by the user includes an error, where the "N" listed in SEQ ID NO: 6 corresponds to a "2" typographical error input by the user.

Figure 36:
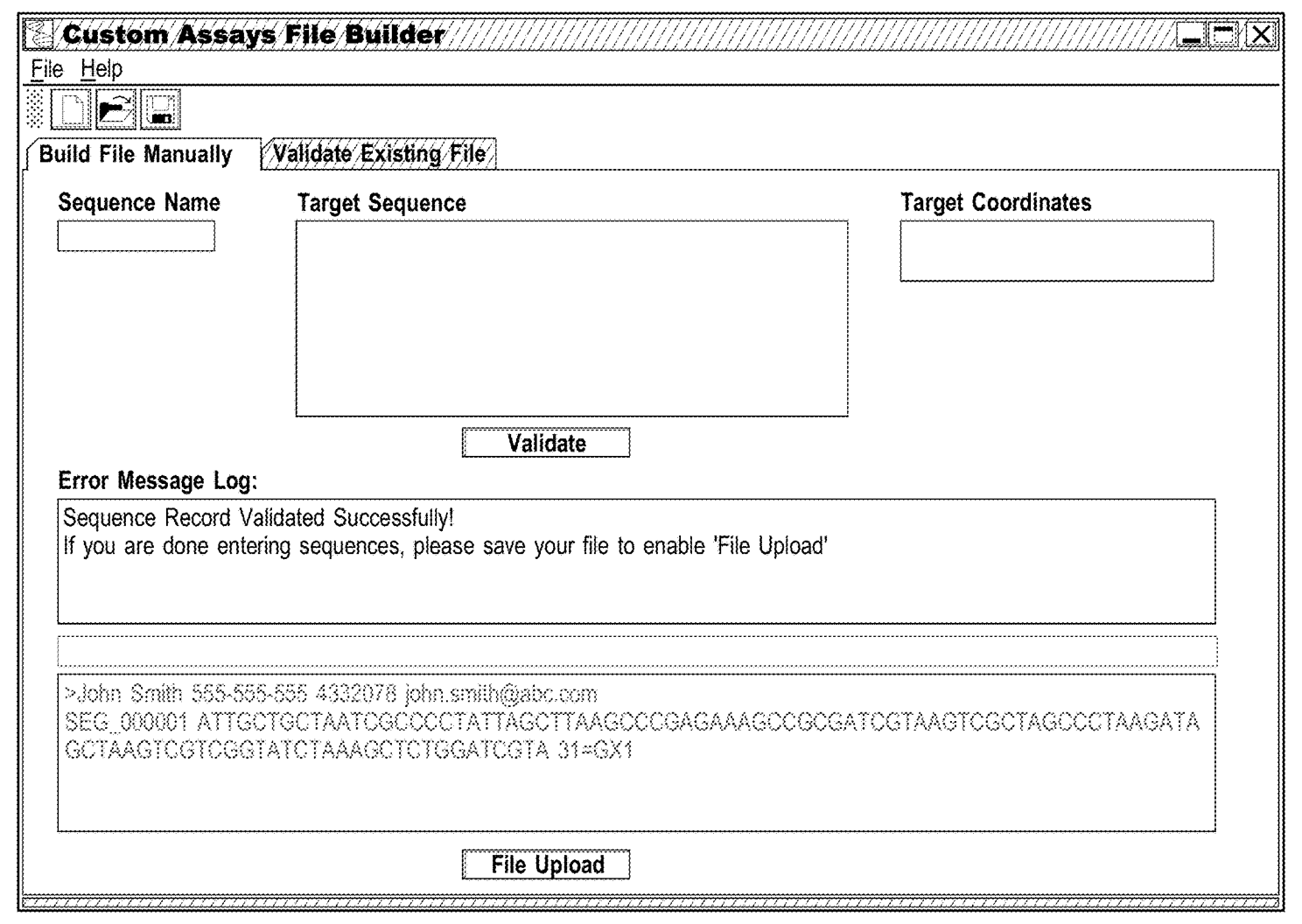

FIG. 36 is an exemplary window pane generated after a sequence is validated by the file builder program according to one of the various embodiments of the present invention, showing sequence

```
                                           (SEQ ID NO: 7)
ATTGCTGCTAATCGCCCCTATTAGCTTAAGCCCGAGAAAGCCGCGATCGT

AAGTCGCTAGCCCTAAGATAGCTAAGTCGTCGGTATCTAAAGCTCTGGAT

CGTA.
```

Figure 37:
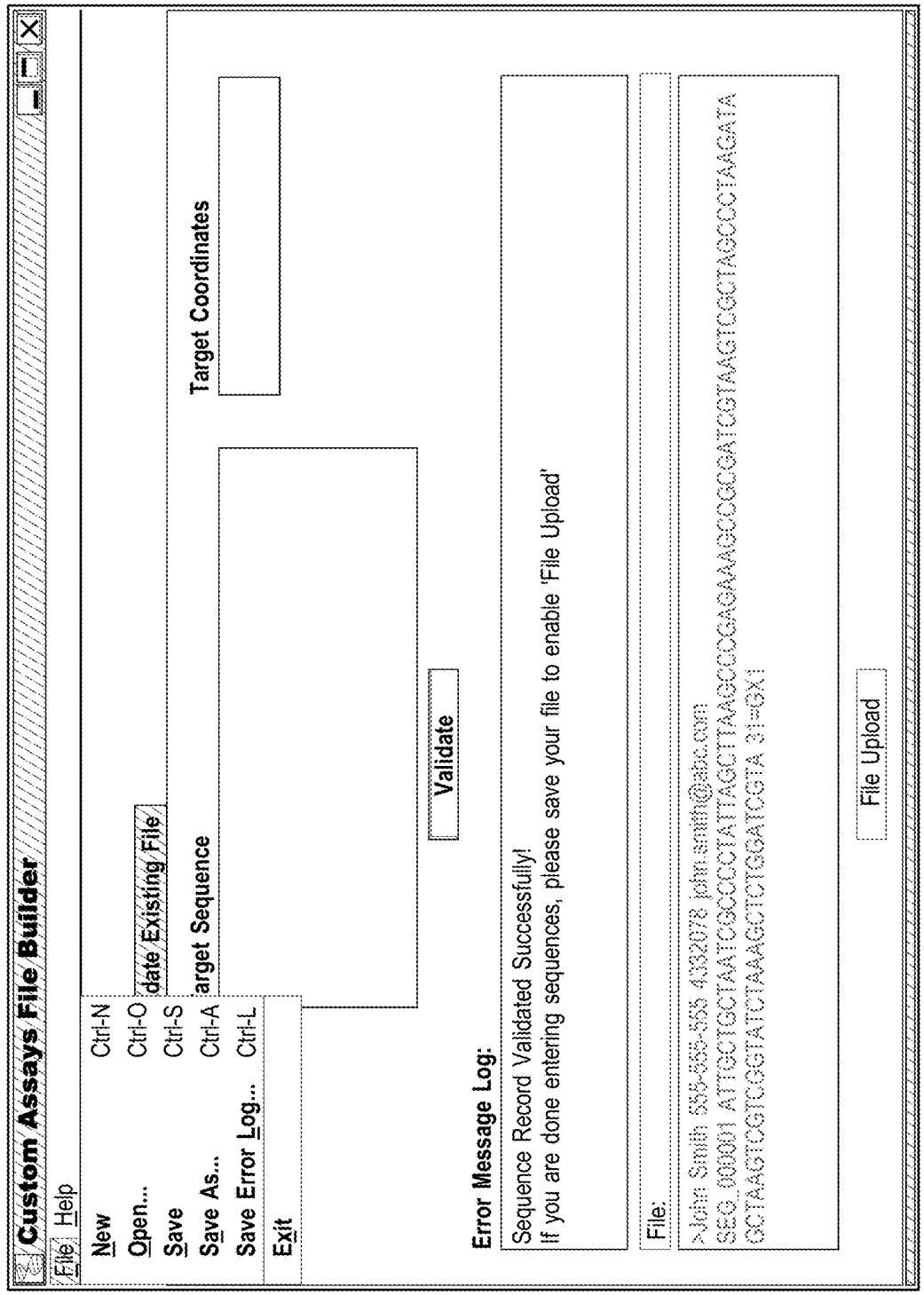

FIG. 37 is a representative window pane illustrating the manner in which the submission file may be saved according to one of the various embodiments of the present invention, showing sequence

```
                                           (SEQ ID NO: 7)
ATTGCTGCTAATCGCCCCTATTAGCTTAAGCCCGAGAAAGCCGCGATCGT

AAGTCGCTAGCCCTAAGATAGCTAAGTCGTCGGTATCTAAAGCTCTGGAT

CGTA.
```

Figure 38:
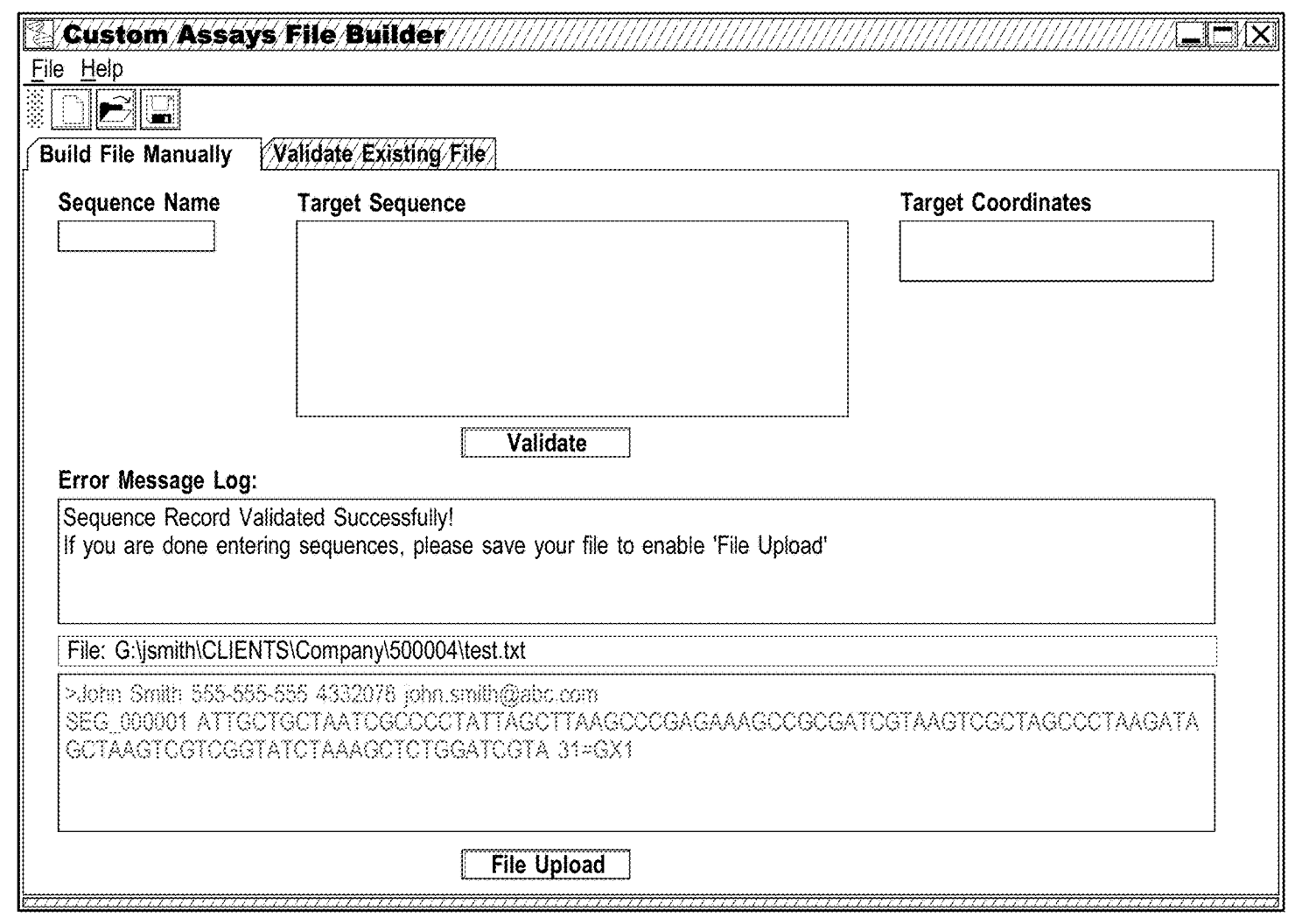

FIG. 38 is an exemplary window pane illustrating the display of the file builder program after the sequence record has been saved according to one of the various embodiments of the present invention, showing sequence

```
                                           (SEQ ID NO: 7)
ATTGCTGCTAATCGCCCCTATTAGCTTAAGCCCGAGAAAGCCGCGATCGTA

AGTCGCTAGCCCTAAGATAGCTAAGTCGTCGGTATCTAAAGCTCTGGATCG

TA.
```

Figure 39:
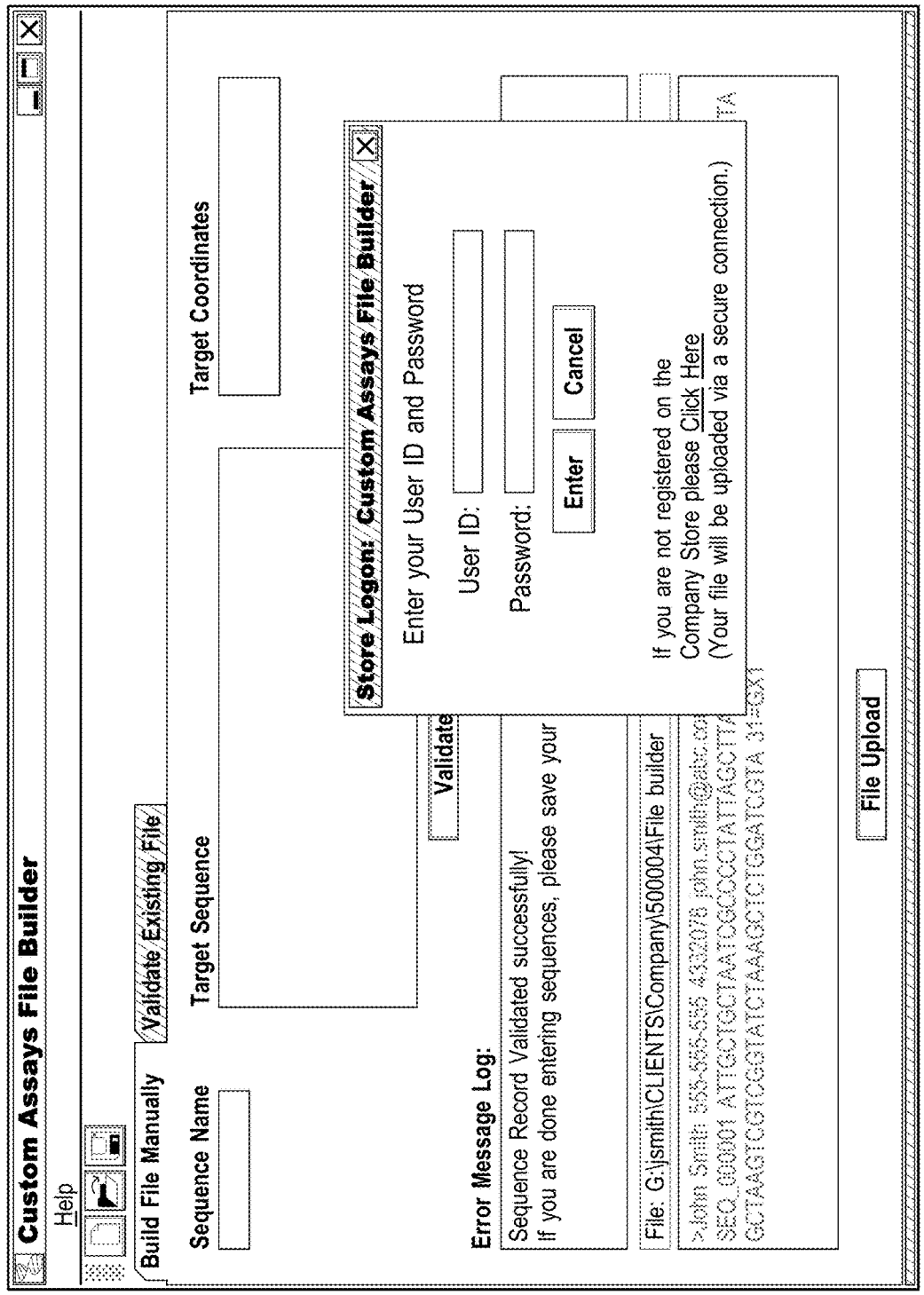

FIG. 39 is an exemplary window pane illustrating the manner in which the file builder program uploads information according to one of the various embodiments of the present invention, showing sequence ATTGCTGCTAATCGCCCCTATTAGCTTAAGCCCGAGAAAGCCGCGATCGTAAGT CGCTAGCCCTAAGATAGCTAAGTCGTCGGTATCTAAAGCTCTGGATCGTA (SEQ ID NO:7) partially obscured by a dialog box of a computer program.

Figure 40:
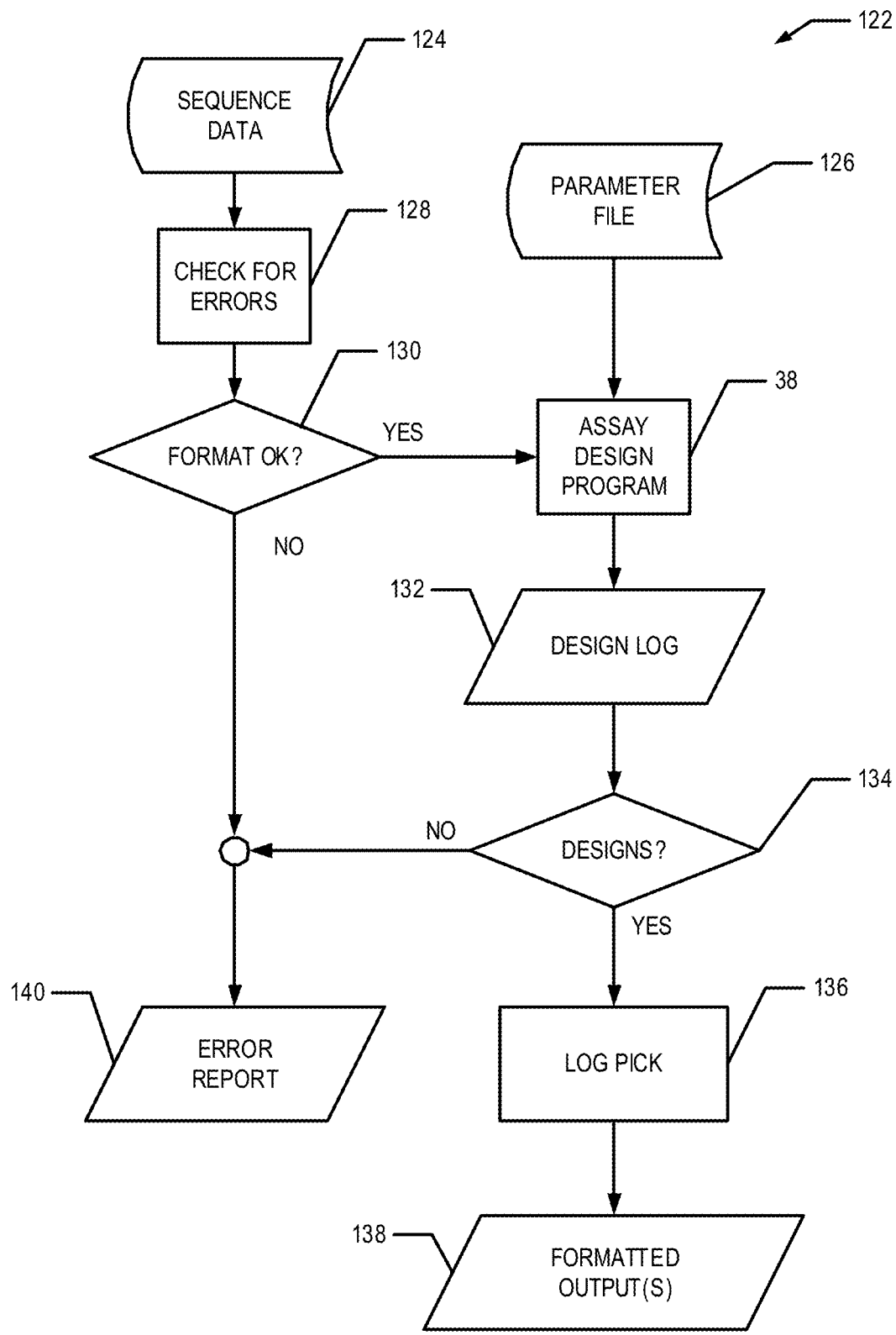

FIG. 40 is a block diagram representative of components and data flow at various configurations of an assay design system.

Figure 41:
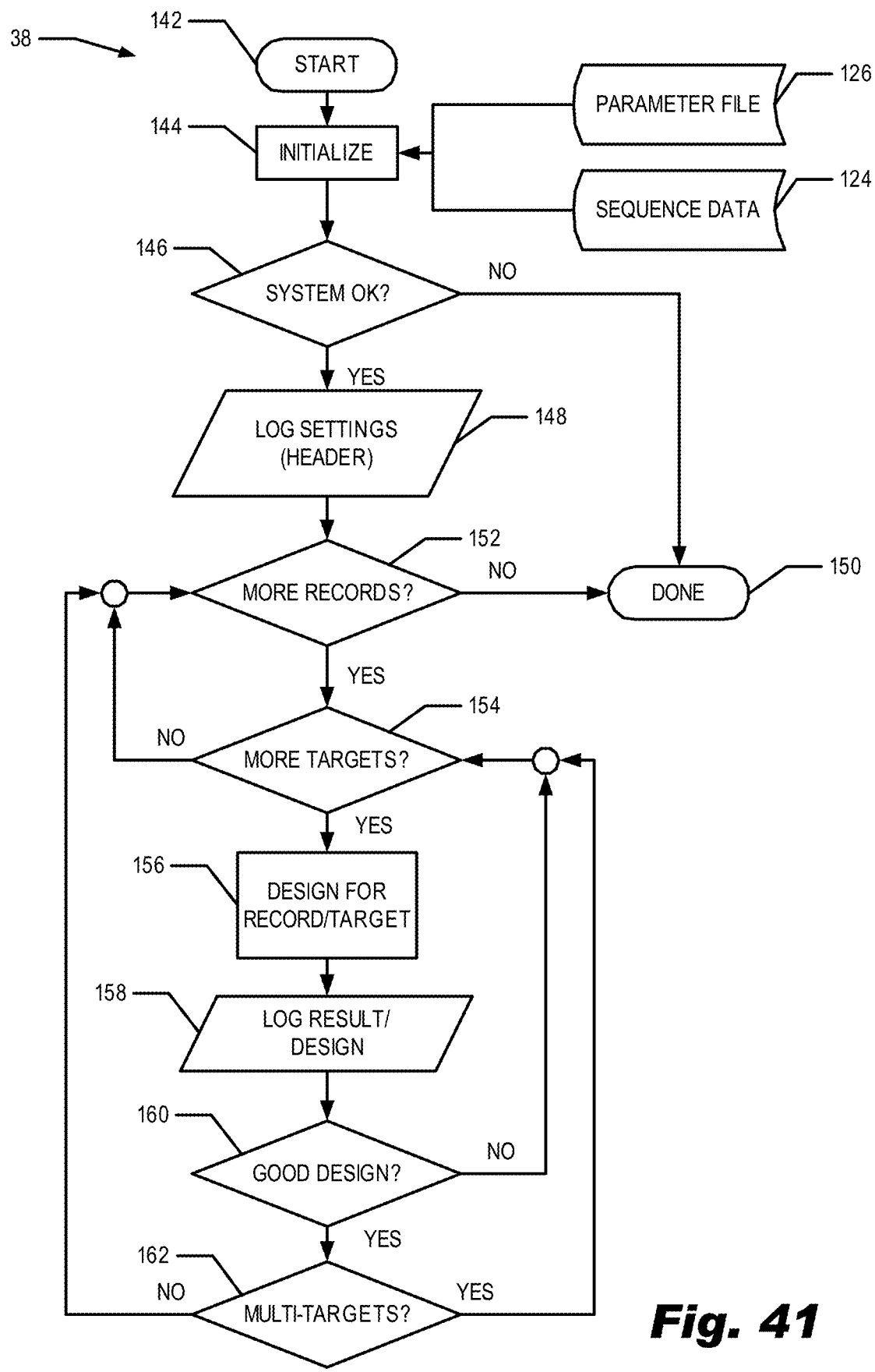

FIG. 41 is a diagram representative of various configurations of assay design program logic suitable for use in assay designs system configurations represented by FIG. 40.

Figure 42:
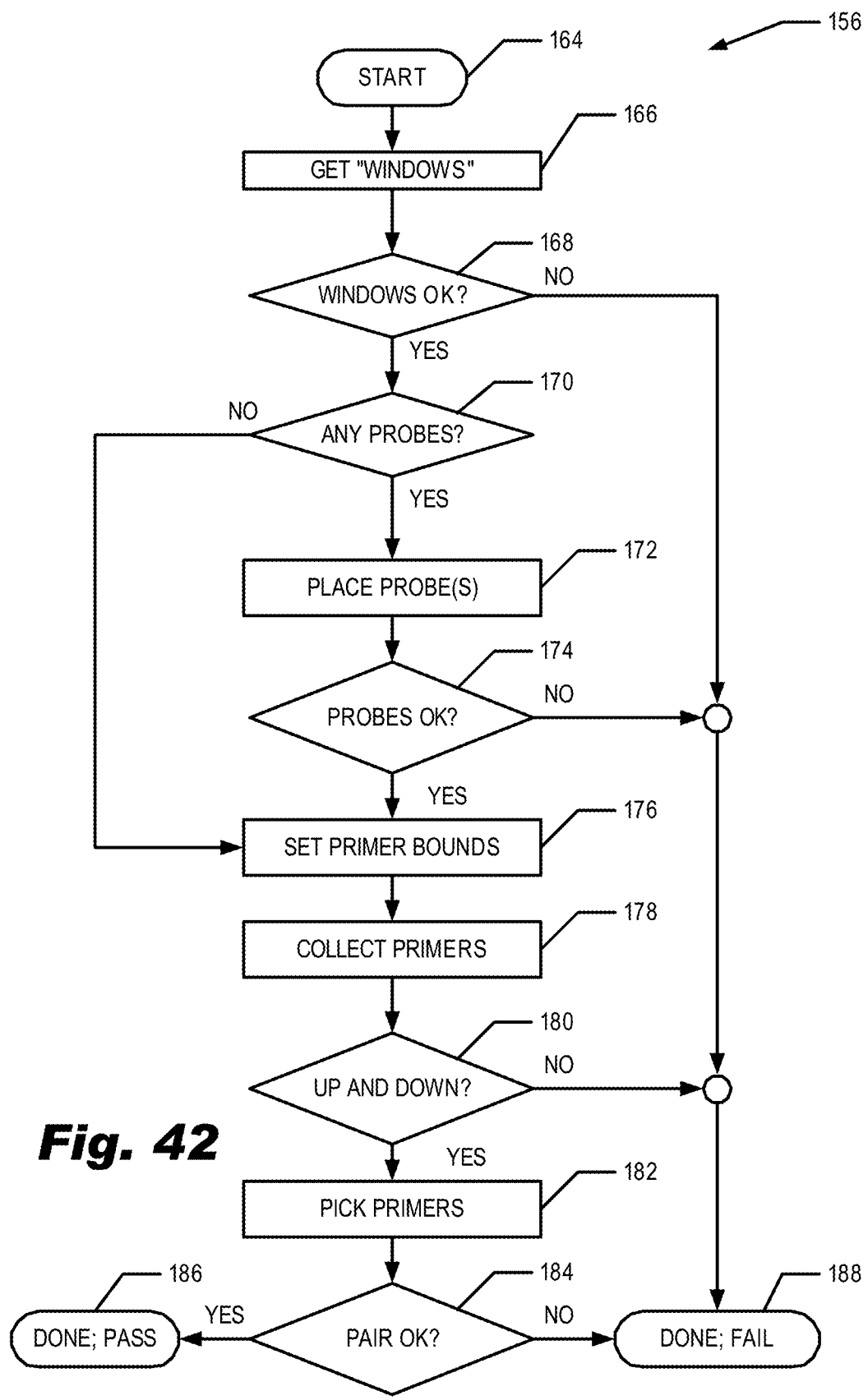

FIG. 42 is a diagram representative of various configurations of reagent design procedures suitable for use in assay design program logic configurations represented by FIG. 41.

Figure 43:
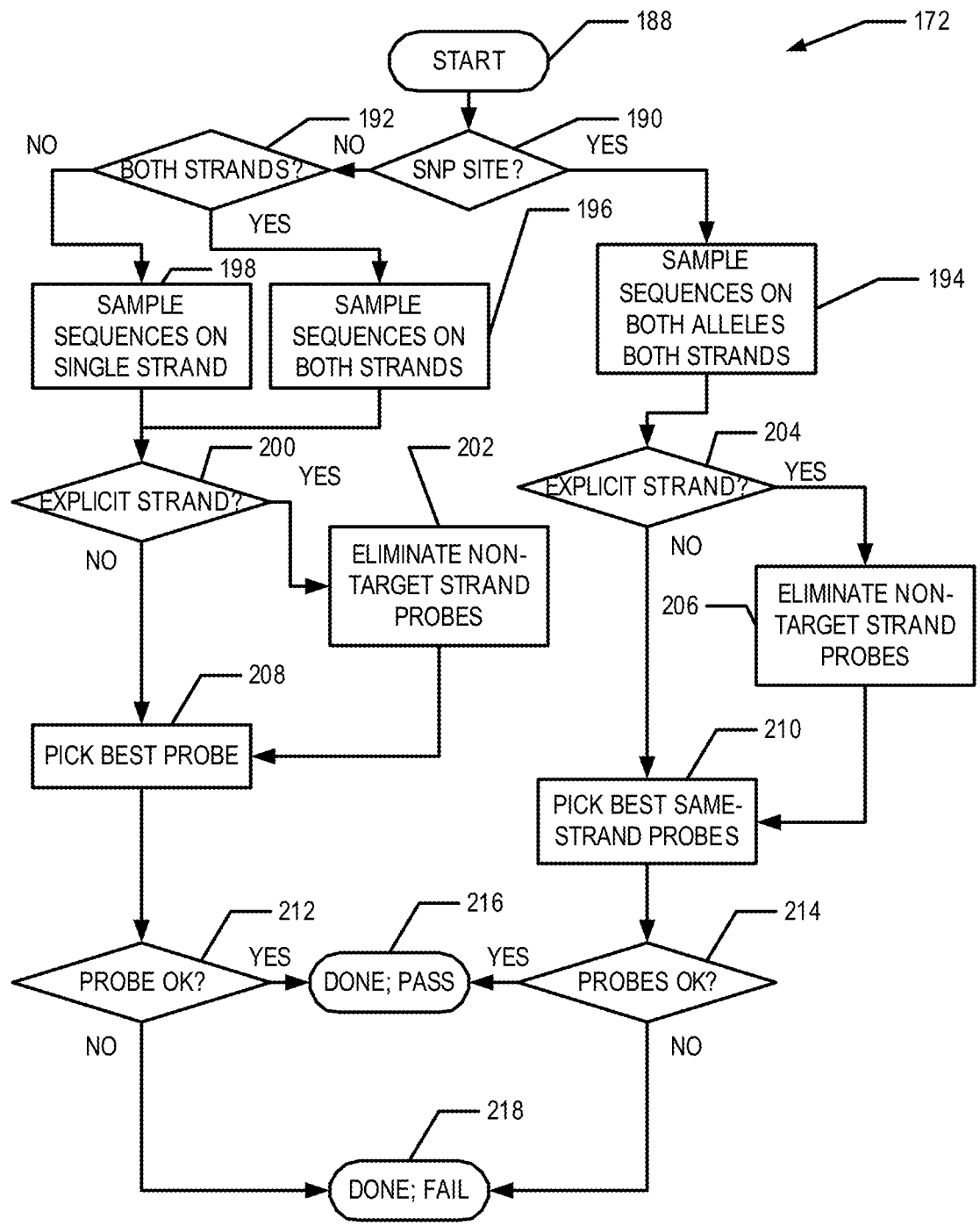

FIG. 43 is a diagram representative of various configurations of probe placing procedures suitable for use in reagent design procedure configurations represented by FIG. 42.

FIG. 44 illustrates the BLAST results against a human genome database showing gene NM_000217 which is a single-exon gene and the primers (shaded arrows) and probe (shaded box) align perfectly with the genomic DNA sequence, showing sequences

```
                                           (SEQ ID NO: 8)
CCAGGGTGATGAAATAAGGAATGATGGCCACAATGTCNNNNNNNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNTTCCACGATGAAGA

AGGGGTC,
and
                                           (SEQ ID NO: 9)
CCAGGGTGATGAAATAAGGAATGATGGCCACAATGTCTATGAAGTTCAT

GATGTTTTTGAAGAAGTCCGTCTTGCTGGGGCAGGCGAAGAAGCGCACC

ACCAGCTCGAAGGAGAACCAGATGATGCACAGCGTTTCCACGATGAAGA

AGGGGTC.
```

FIG. 45 illustrates the BLAST results against a human genome database showing gene NM_000216 which is a multi-exon gene and the assay is designed over the exon 6-exon 7 boundary in which the probe sequence is split between the two exons and over the intervening intron is about 14 kb in length, showing sequences

```
                                           (SEQ ID NO: 10)
TGTTGTTGGTTGCATGTGTCGATGTGAAGTGAAGTTGTGTTTGAATTCCAC

CTTTTCNNNNNNNNNNNNNNNNNNGTTCTT,
and
                                           (SEQ ID NO: 11)
TGTTGTTGGTTGCATGTGTCGATGTGAAGTGAAGTTGTGTTTGAATTCCAC

CTTTTCTAGTTTTCACAAGCTGTTCTT.
```

FIG. 46 illustrates a BLAST alignment of two primers and the TaqMan® probe sequence against the transcript to which the assay was designed, the primer sequences being indicated by shaded arrows and the probe sequence indicated by the shaded box, showing sequences

```
                                           (SEQ ID NO: 12)
TGATCGGGTCCATGAGCAANGATATGTACCAGATCATGNNNNNNNNNNNN

NNNNNNNNNNNNNNNNNNNNNNNNNNNNNNNNNNNNNNNACTCACACTGGTCAT

CTCTGGCT,
and
                                           (SEQ ID NO: 13)
TGATCGGGTCCATGAGCAAGGATATGTACCAGATCATGGACGAGATCAAG
```

-continued

GAAGGCATCCAGTACGTGTTCCAGACCAGGAACCCACTCACACTGGTCAT

CTCTGGCT.

FIG. 47 illustrates a BLAST hit to a non-self transcript showing an assay designed across exon 4-5 of NM_0002000 to provide a perfect BLAST alignment to the self transcript (not shown) with, however, a significant alignment to a second, non-self transcript (NM_002159) in which each of the primers have a single mismatch and the probe is a perfect match, showing sequences (SEQ ID NO: 14)
GCTGATTCACATGCAAAGAGACATNNNNNNNNNNNNNNGAAAATTCCATGA
AAAG, (SEQ ID NO: 15)
GCTGATTCACATGAAAAGAGACATCATGGGTATAGAAGAAAATTCCATG
AAAAG, (SEQ ID NO: 16(second fragment), SEQ ID NO:
26 (third fragment), and SEQ ID NO: 27 (sixth
fragment))
GATTCA-CATGCAAAGAGAC-ATNNNNNNNNNNNNNNGAAA-ATTC-

CAT-GAAAAGNNNNNNNNNNNNNNNNNNNNNNNNNNNNNNNNNNNNNNNNNN

NNNNNNNNNNNNNNNNNNNNNNNNNNNNNNNNNATGATTATGGAGGTTTGA

CTGGC
and (SEQ ID NO: 17 (first fragment), and SEQ ID NO: 28
(second fragment))
GAGACATCATGGGTATAGAAGAAAATTCCATGAAAAGCATCATTCACATC

GAGAA-TTTCCATTTTATGGGGACTATGGATCAAATTATCTATATGACAA

TTGATATCCTTAGTAATCATGGGGCATGATTATAGAGGTTTGACTGGC.

Figure 48:
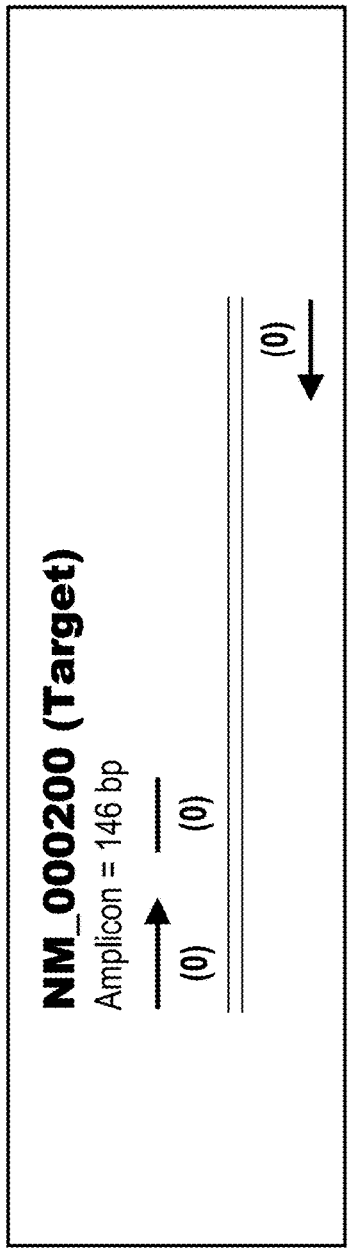

FIG. 48 illustrates the matching of the primers and probe with NM_0002000.

Figure 49:
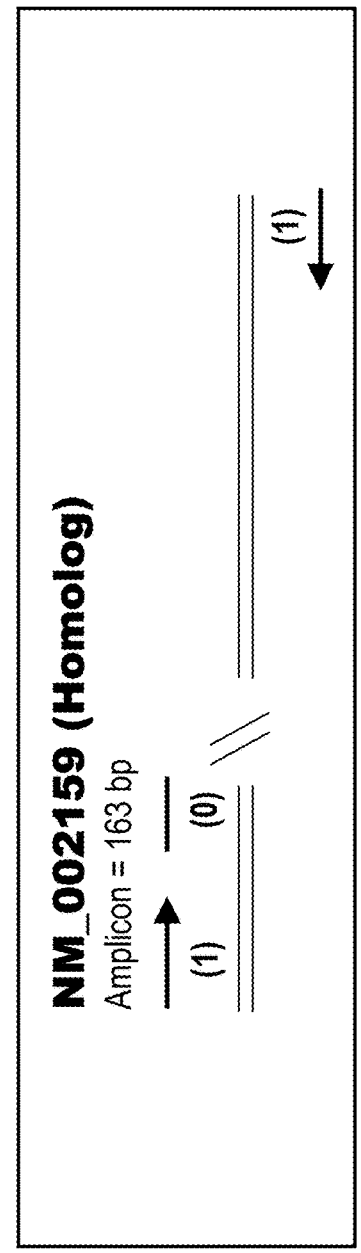

FIG. 49 illustrates the significant matching of the primers and probe with NM_0021590.

Figure 50:
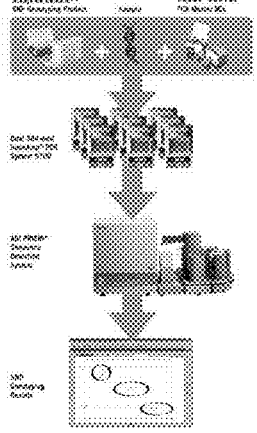

FIG. 50 is an exemplary window pane which may be used to initiate collection of information for gene expression assays according to one of the various embodiments of the present invention.

Figure 51:
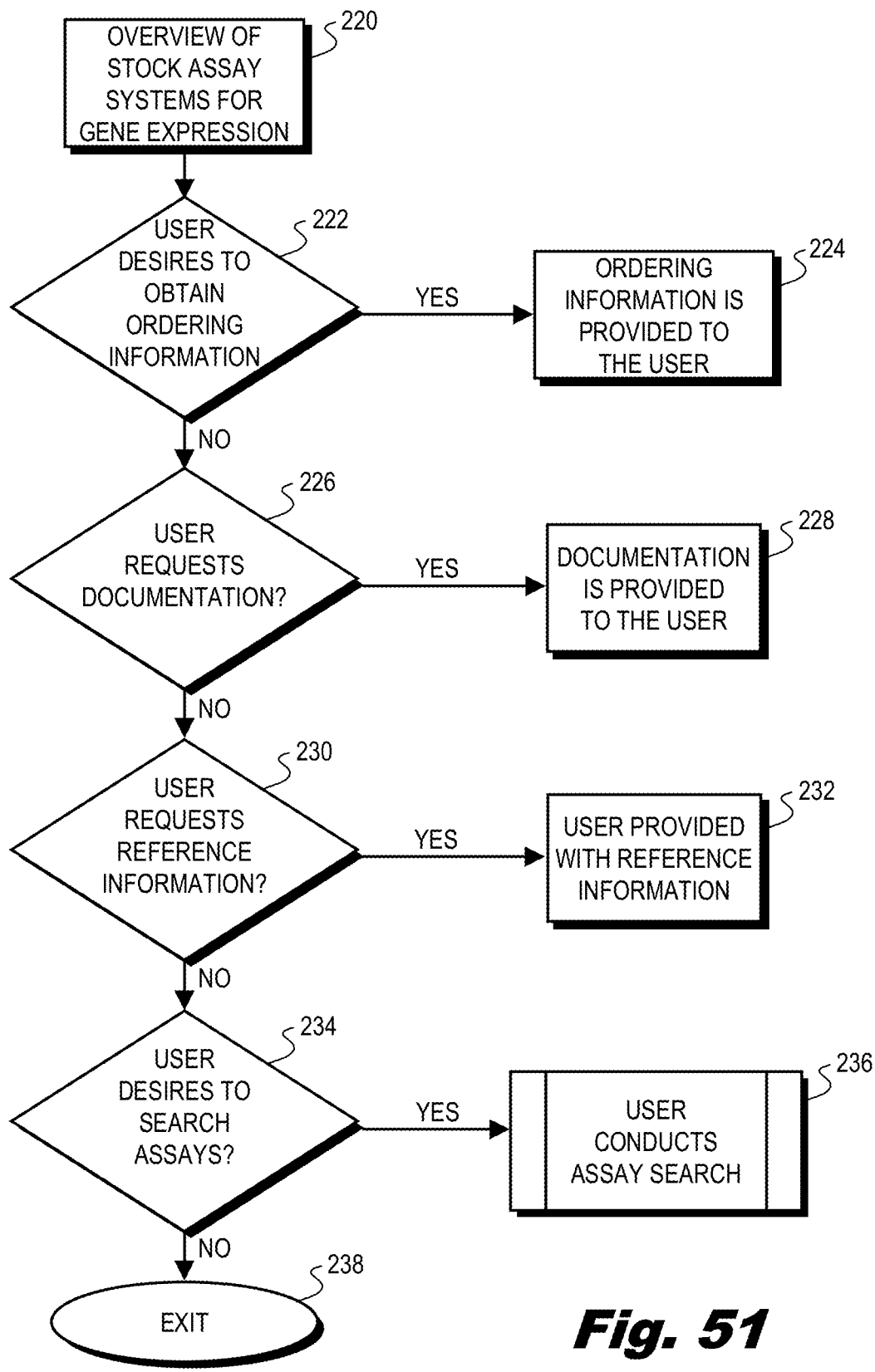

FIG. 51 is a flow chart illustrating the manner in which the user collects information for gene expression stock assays according to one of the various embodiments of the present invention.

FIG. 52 is an exemplary window pane illustrating ordering information associated with obtaining stock assays for gene expression according to one of the various embodiments of the present invention.

FIG. 53 is an exemplary window pane illustrating the manner in which documents are obtained relating to assays according to one of the various embodiments of the present invention.

Figure 54:
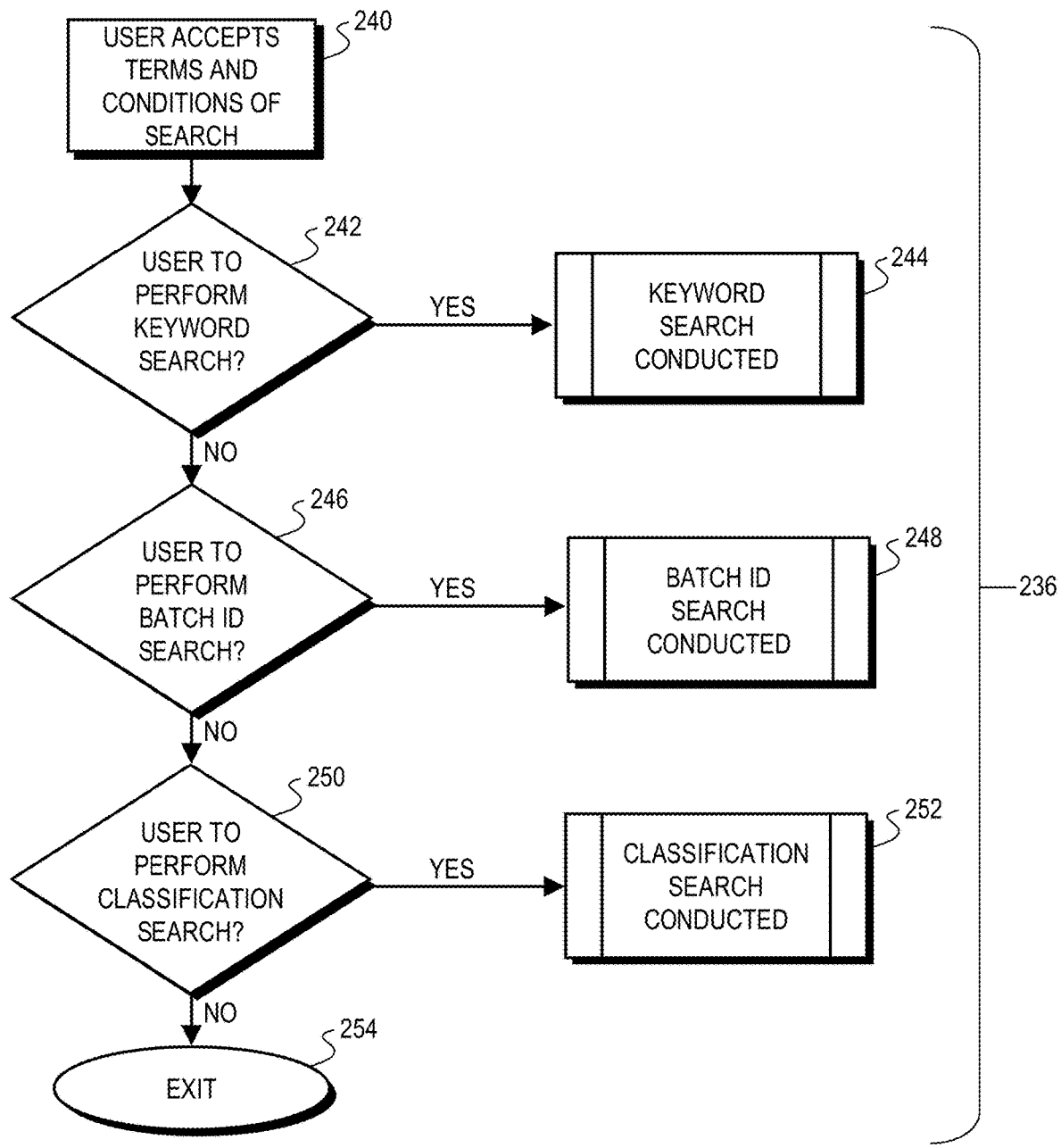

FIG. 54 is a flow chart illustrating the order in which the user performs a search for gene expression assays according to one of the various embodiments of the present invention.

FIG. 55 is a representative window pane illustrating the manner in which the user agrees to terms and conditions of use for searching assay information according to one of the various embodiments of the present invention.

FIG. 56 is an exemplary window pane allowing the user to search for a stock assays for gene expression according to one of the various embodiments of the present invention.

FIG. 57 is an exemplary window pane allowing the user to conduct a basic keyword search for gene expression assays according to one of the various embodiments of the present invention.

Figure 58:
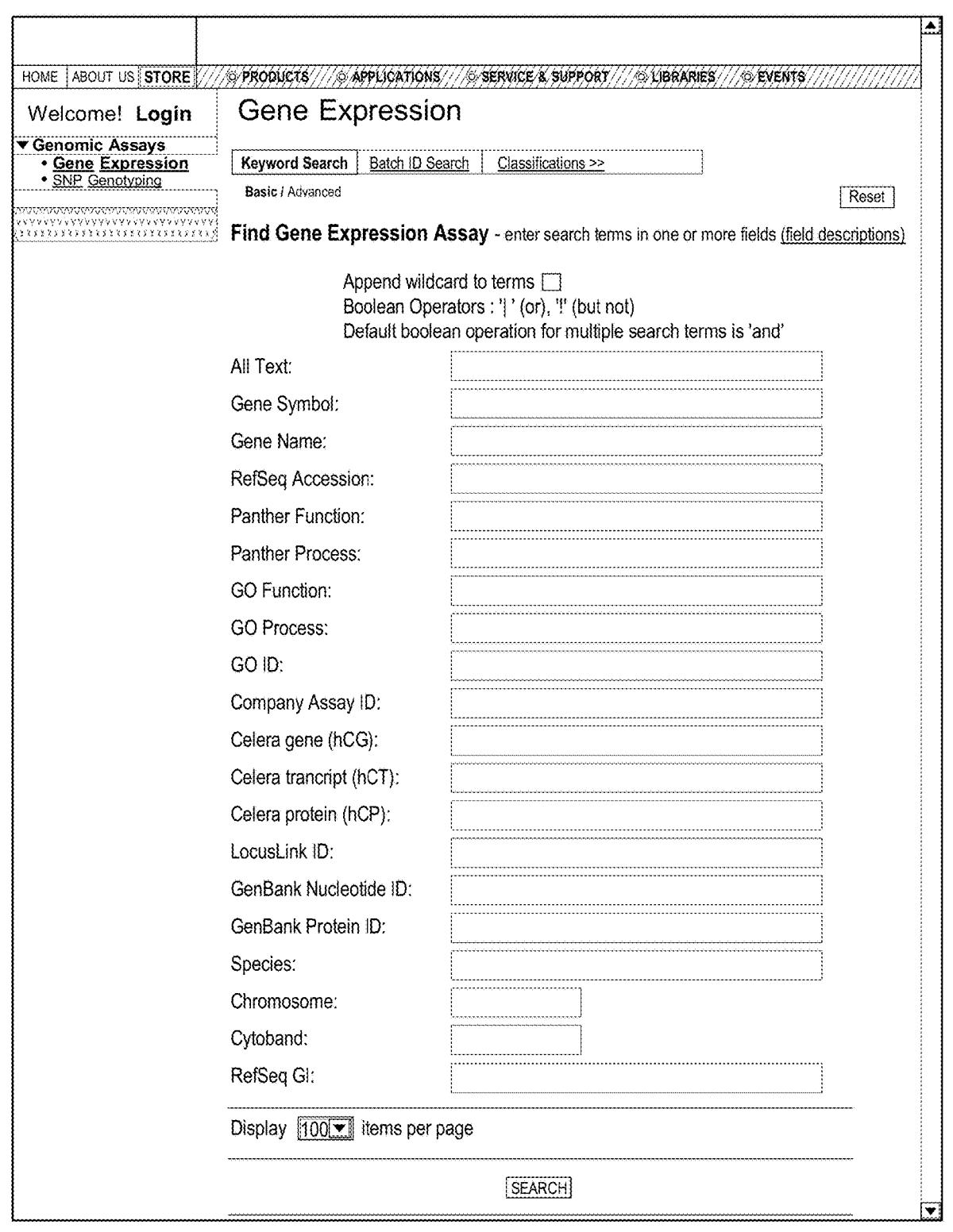

FIG. 58 is an exemplary window pane allowing the user to perform an advanced keyword search for gene expression assays according to one of the various embodiments of the present invention.

FIG. 59 is an exemplary window pane allowing the user to conduct a batch identification search for gene expression assays according to one of the various embodiments of the present invention.

Figure 60:
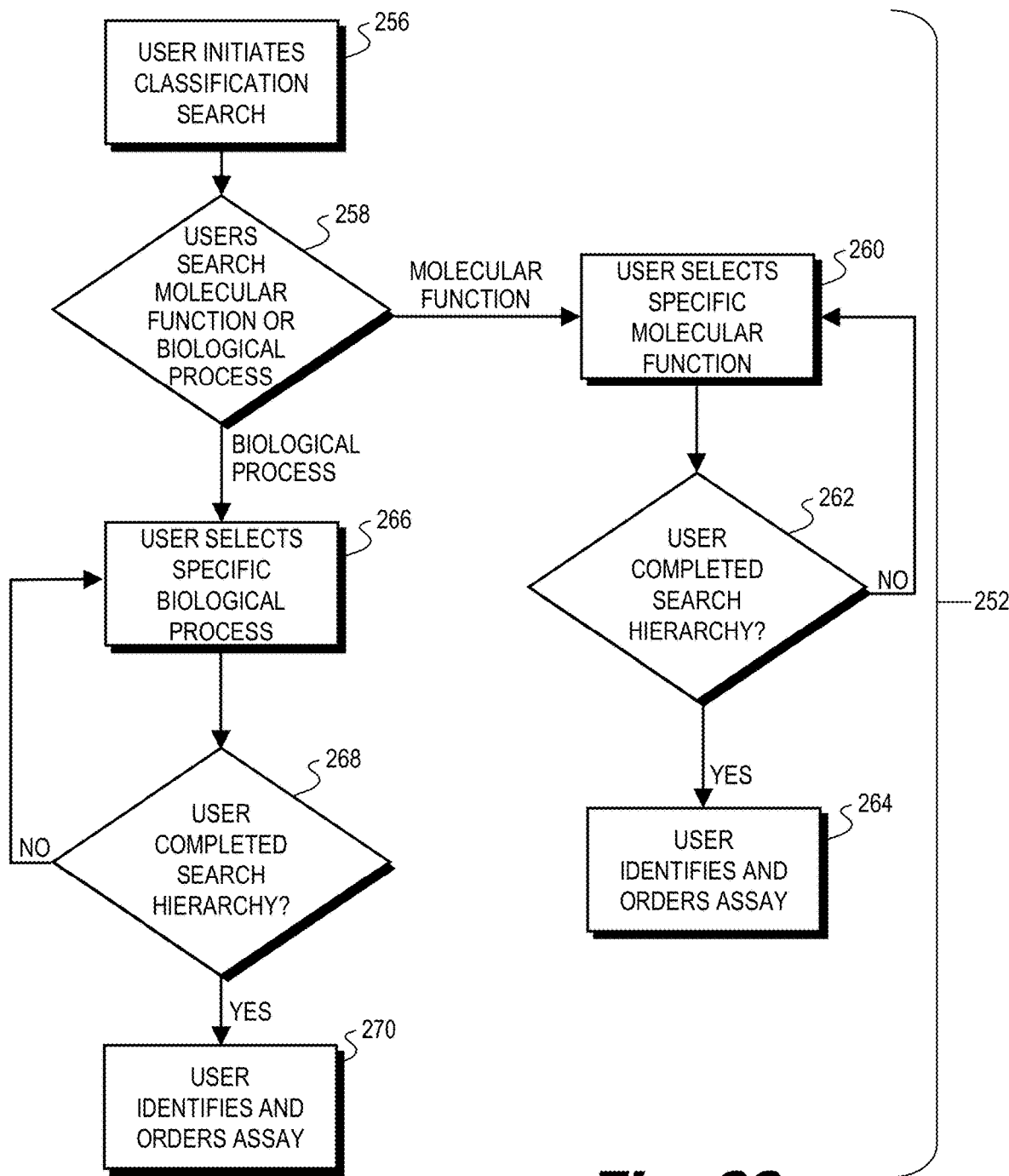

FIG. 60 is a flow chart illustrating the manner in which the user conducts a classification search according to one of the various embodiments of the present invention.

FIGS. 61-66 are exemplary window panes illustrating a classification search for gene expression products performed according to one of the various embodiments of the present invention.

FIG. 67 is an exemplary window pane illustrating the output of a search for gene expression assays according to one of the various embodiments of the present invention.

FIG. 68 is an exemplary window pane illustrating the information provided for a specific assay during a search for gene expression assays according to one of the various embodiments of the present invention.

Figure 69:
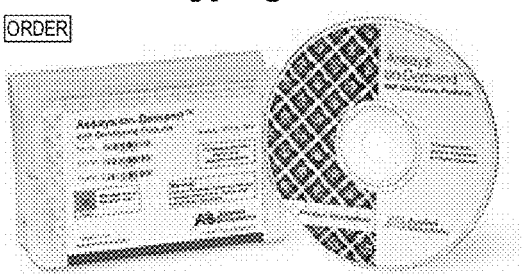

FIG. 69 is an exemplary window pane which provides the user with an overview of stock assays for SNP genotyping products.

Figure 70:
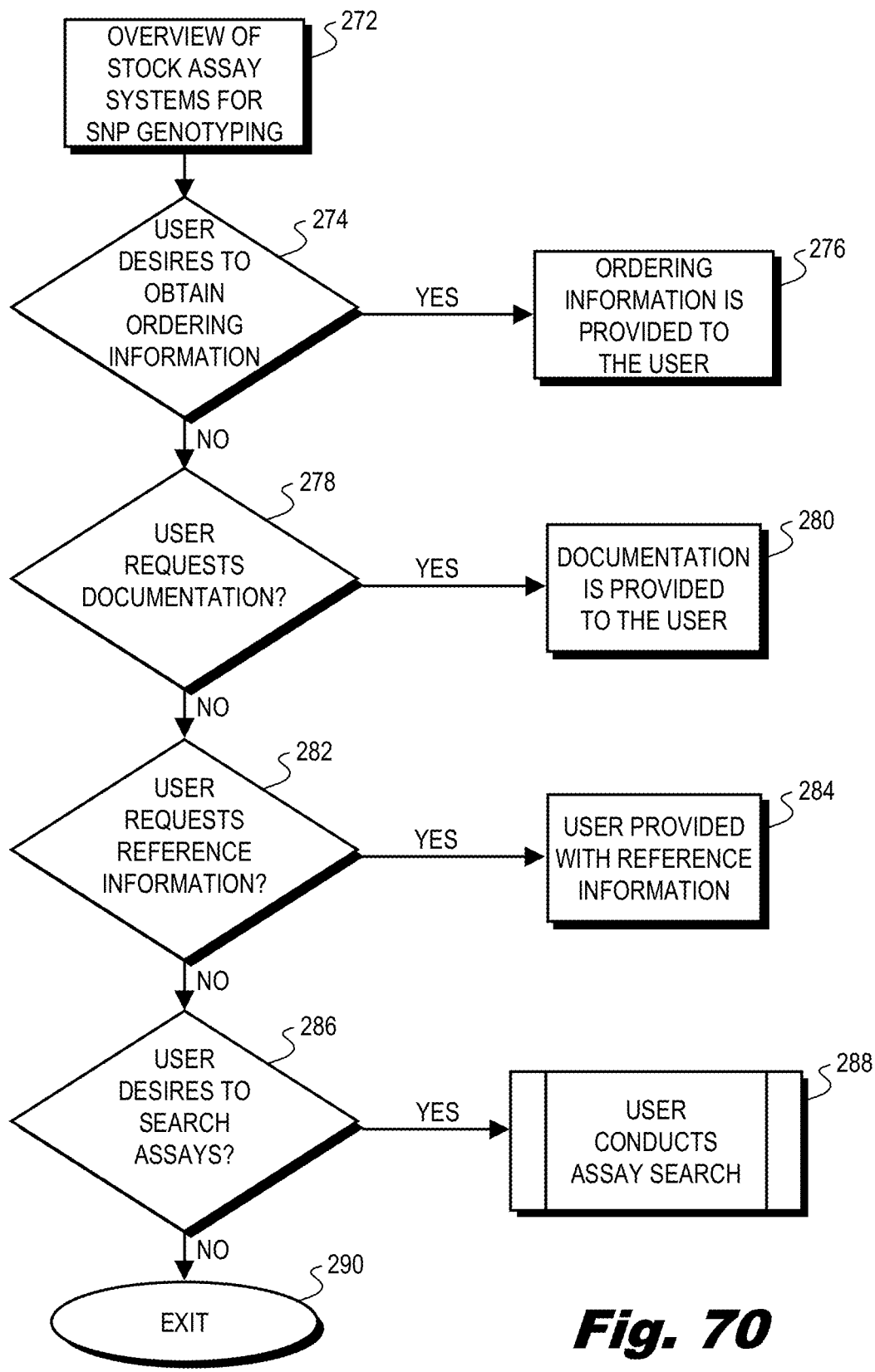

FIG. 70 illustrates the manner in which the user obtains information and orders stock assays for SNP genotyping according to one of the various embodiments of the present invention.

FIG. 71 is an exemplary window pane used to conduct a basic keyword search for selecting assays for SNP genotyping according to one of the various embodiments of the present invention.

FIG. 72 is an exemplary window pane used to perform an advance keyword search for searching SNP genotyping assays according to one of the various embodiments of the present invention.

Figure 73:

FIG. 73 is an exemplary window pane which allows the user to conduct a location search for a SNP genotyping assay according to one of the various embodiments of the present invention.

Figure 74:
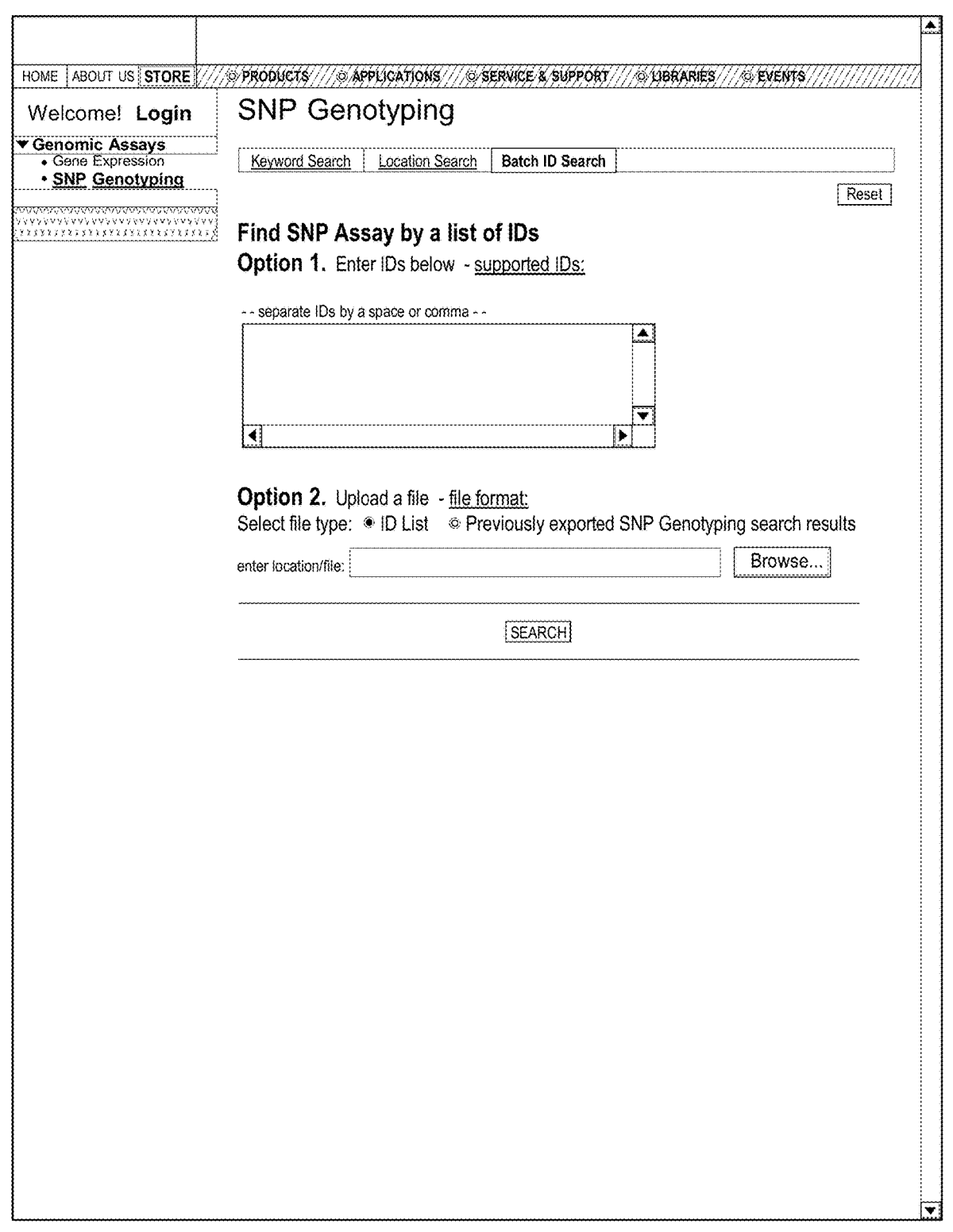

FIG. 74 is an exemplary window pane allowing the user to conduct a batch identification search for SNP genotyping assays according to one of the various embodiments of the present invention.

FIG. 75 is an exemplary window pane illustrating the output of a search for SNP genotyping assays according to some configurations of the present invention.

FIG. 76 is an exemplary window pane illustrating the output for a specific assay after conducting a SNP genotyping assay search according to one of the various embodiments of the present invention.

Figure 77:
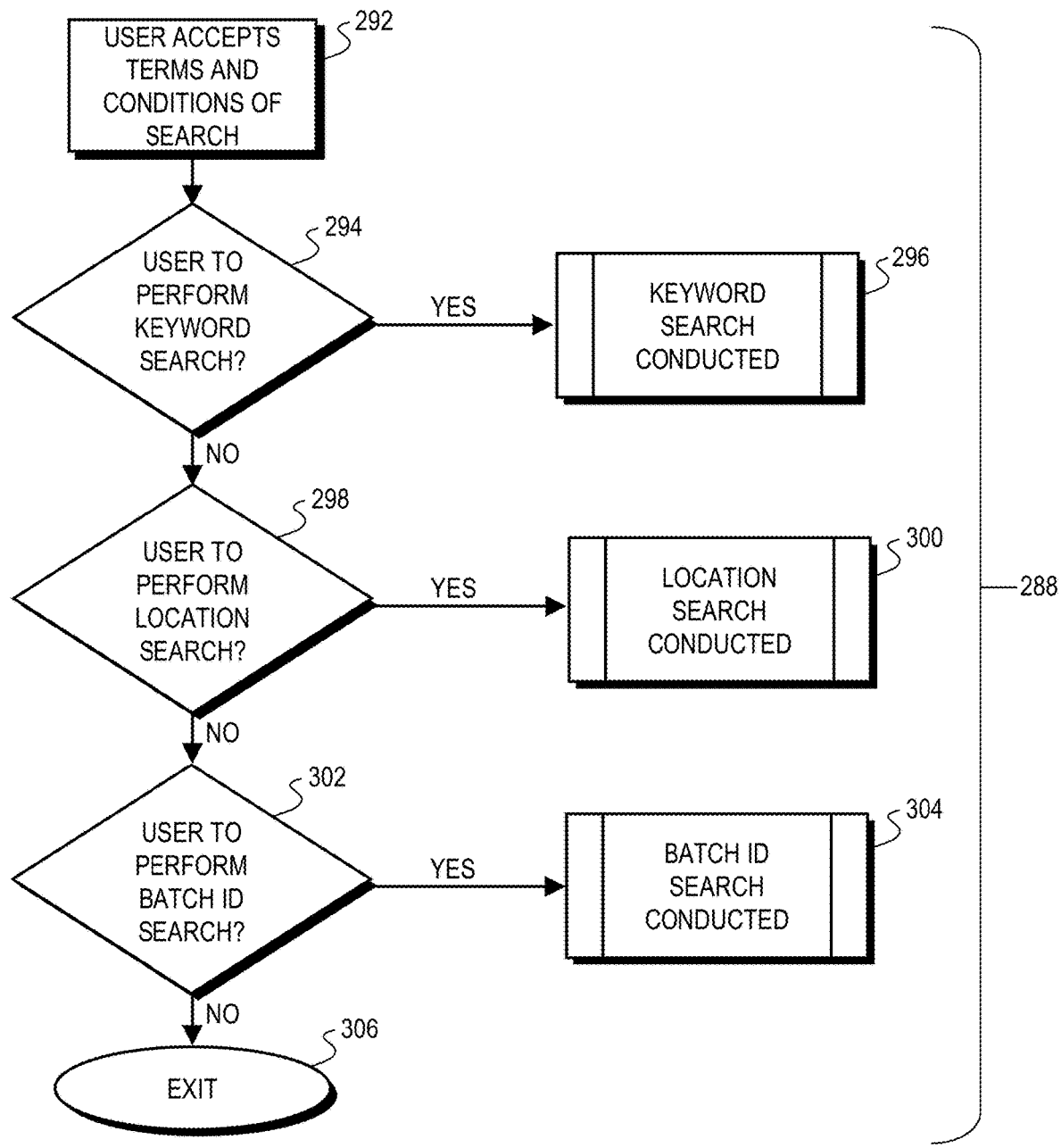

FIG. 77 illustrates the manner in which the user may perform a SNP genotyping search according to one of the various embodiments of the present invention.

Figure 78:
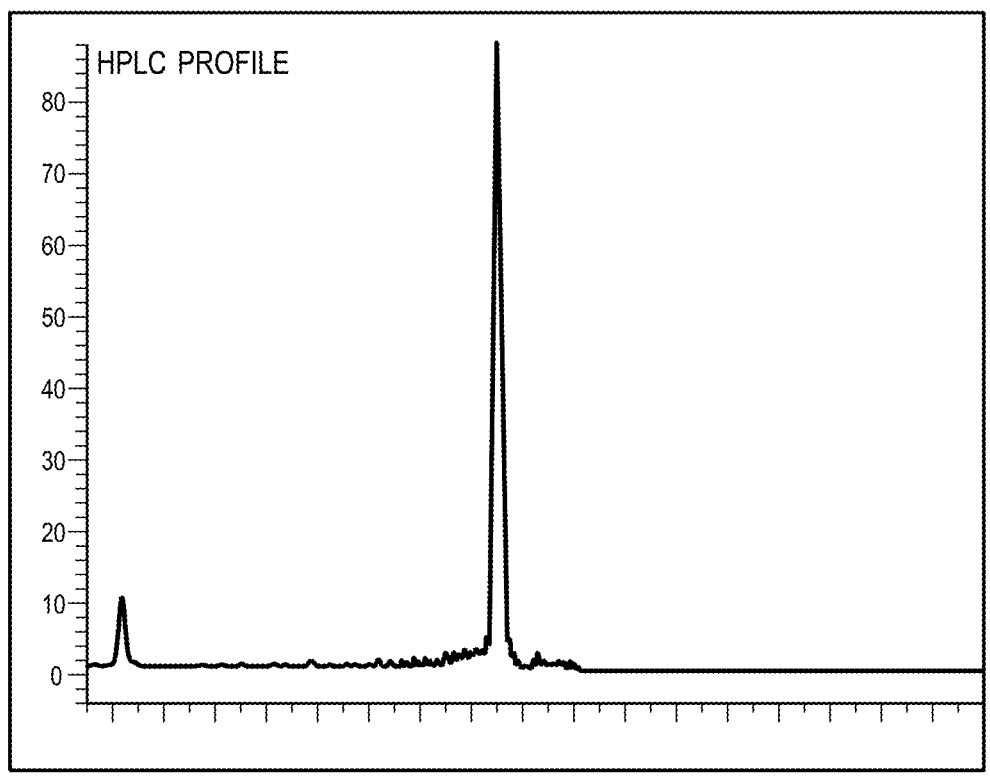

FIG. 78 illustrates an anion-exchange HPLC profile of a 0.2 µmol 23-mer showing 90% of product is full-length DNA molecule.

Figure 79:
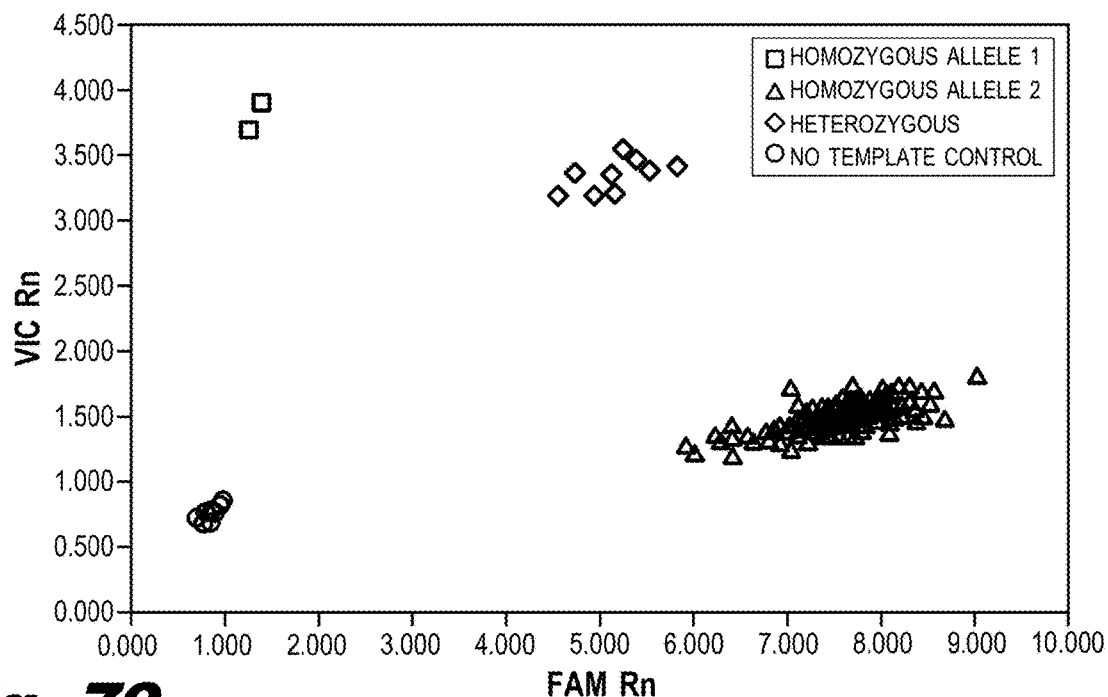

FIG. 79 illustrates a typical analyzed TaqMan® plate showing four genotype clusters for a particular SNP, each data point representing one sample plotted by intensity measures from each of two fluorescent dyes such that clusters of points are classified as being homozygous for either allele, heterozygous, or no amplification.

Figure 80:
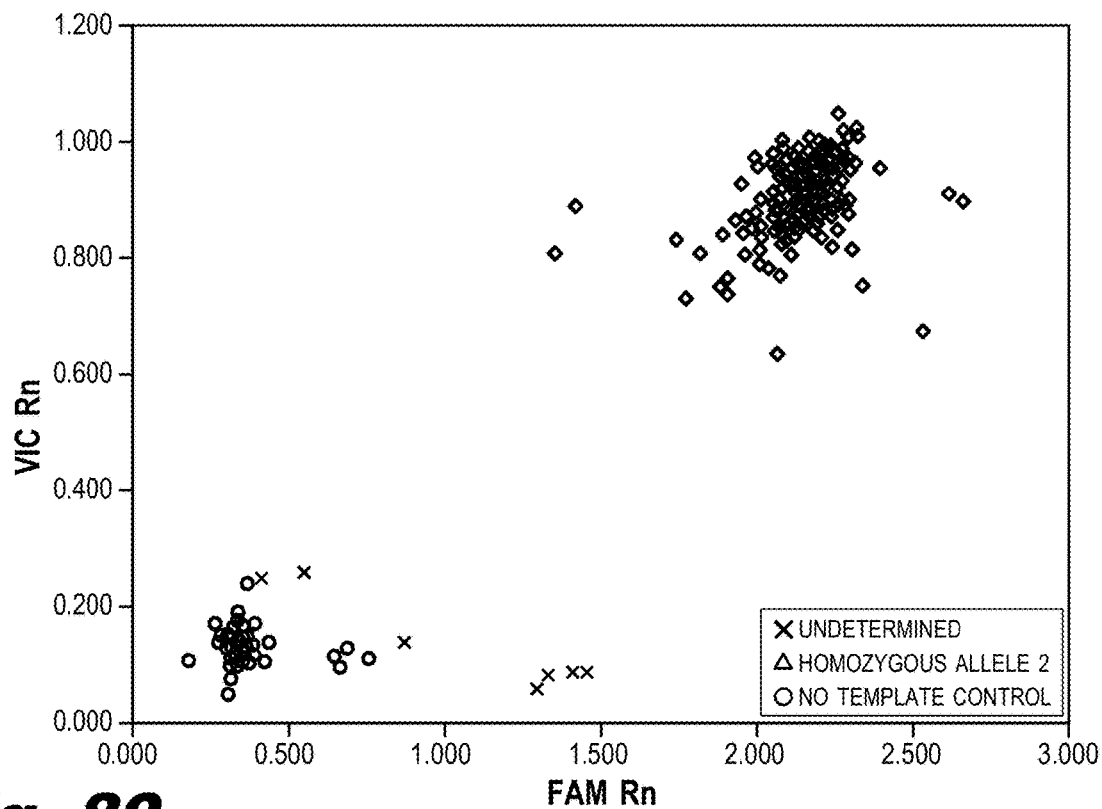

FIG. 80 illustrates a pseudo-SNP resulting in all samples appearing heterozygous.

Figure 81:
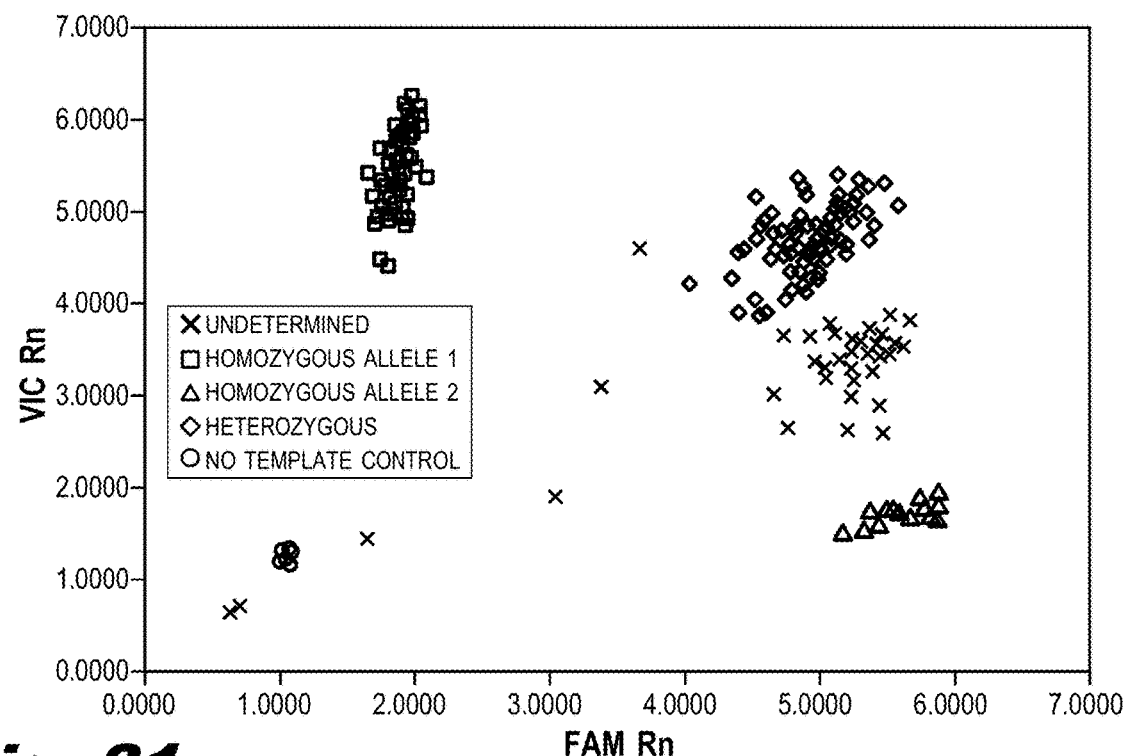

FIG. 81 illustrates undesired genotype clustering attributed to other unknown SNPs in the probes sequence.

Figure 82:
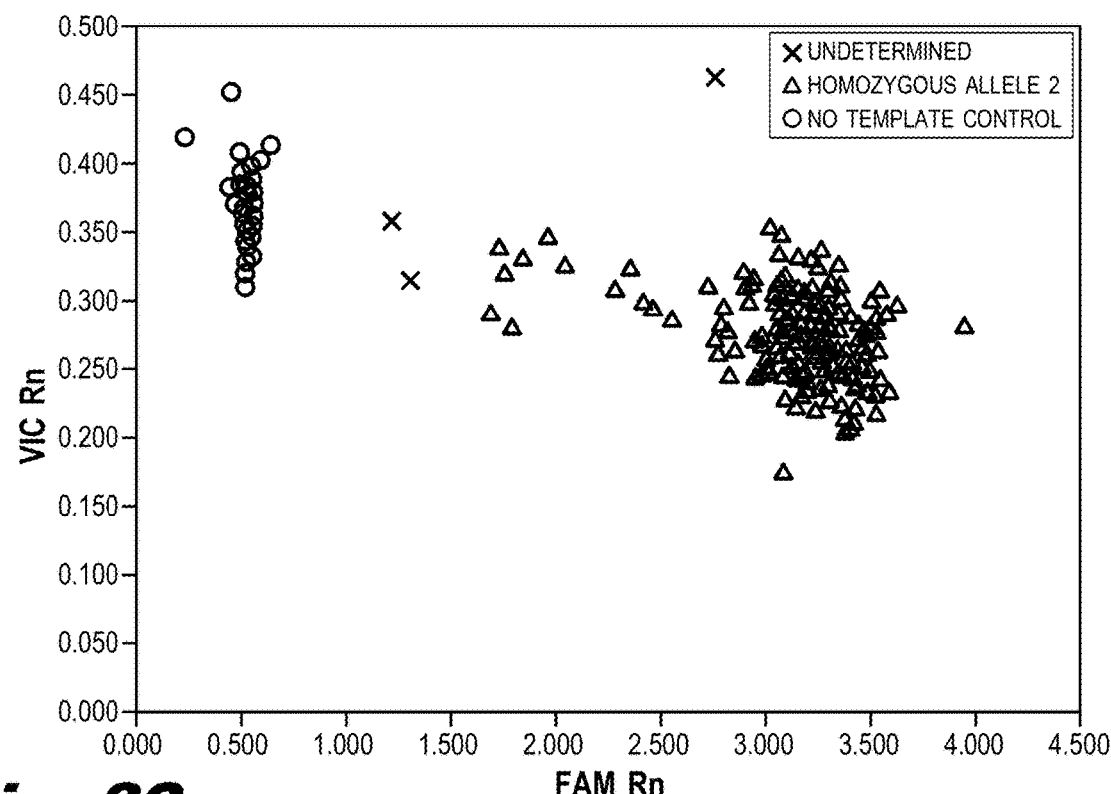

FIG. 82 illustrates the results from samples all of which are homozygous genotypes producing two clusters.

Figure 83:
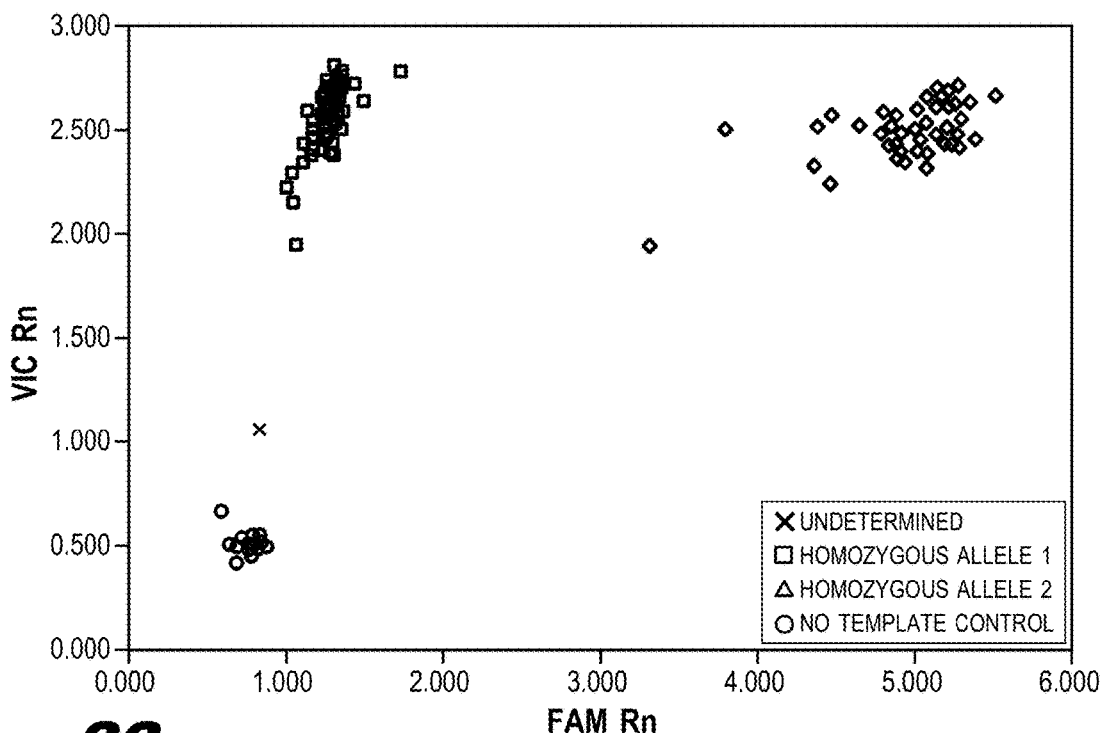

FIG. 83 illustrates the results from samples having a SNP with no rare allele homozygotes producing three clusters.

Figure 84:
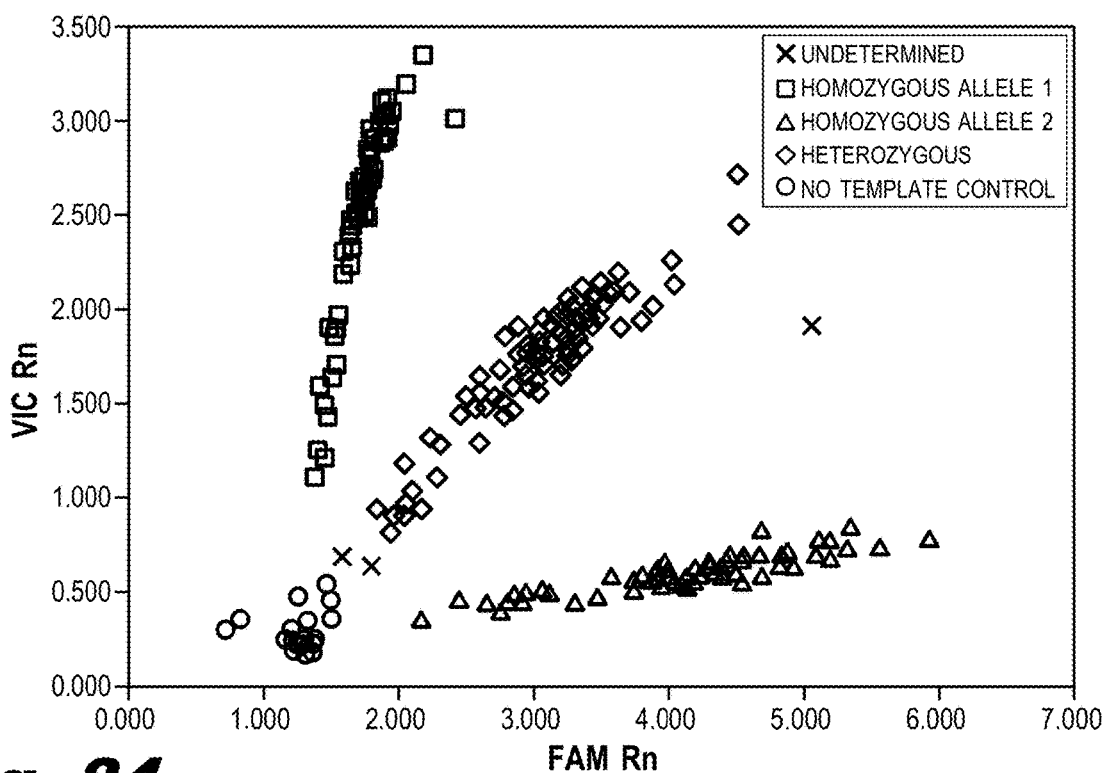

FIG. 84 illustrates four clusters that are not well defined resulting in the assay being deemed to fail to meet specifications.

Figure 85:
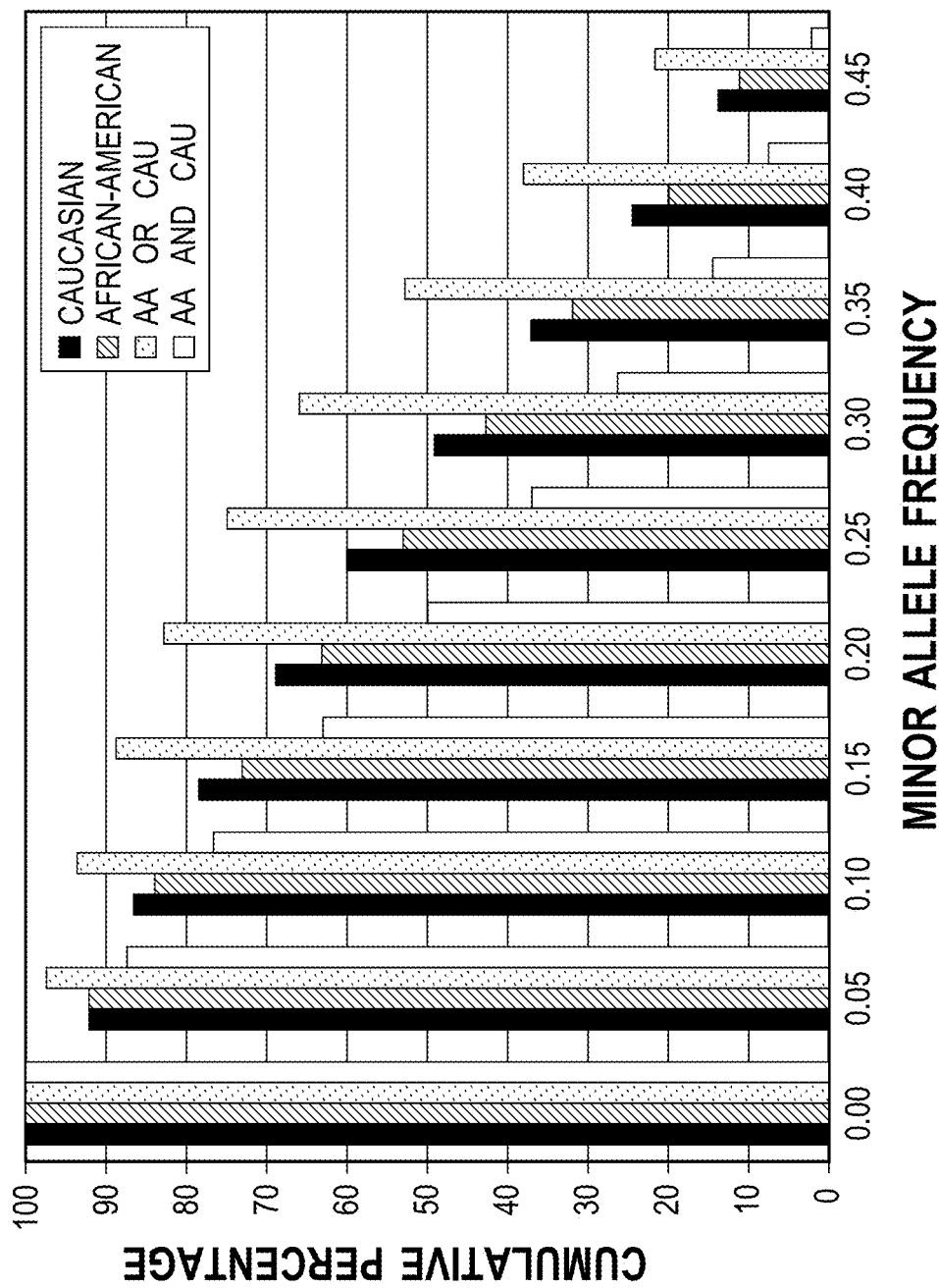

FIG. 85 illustrates allele frequency of SNPs tested for validation.

Figure 86:
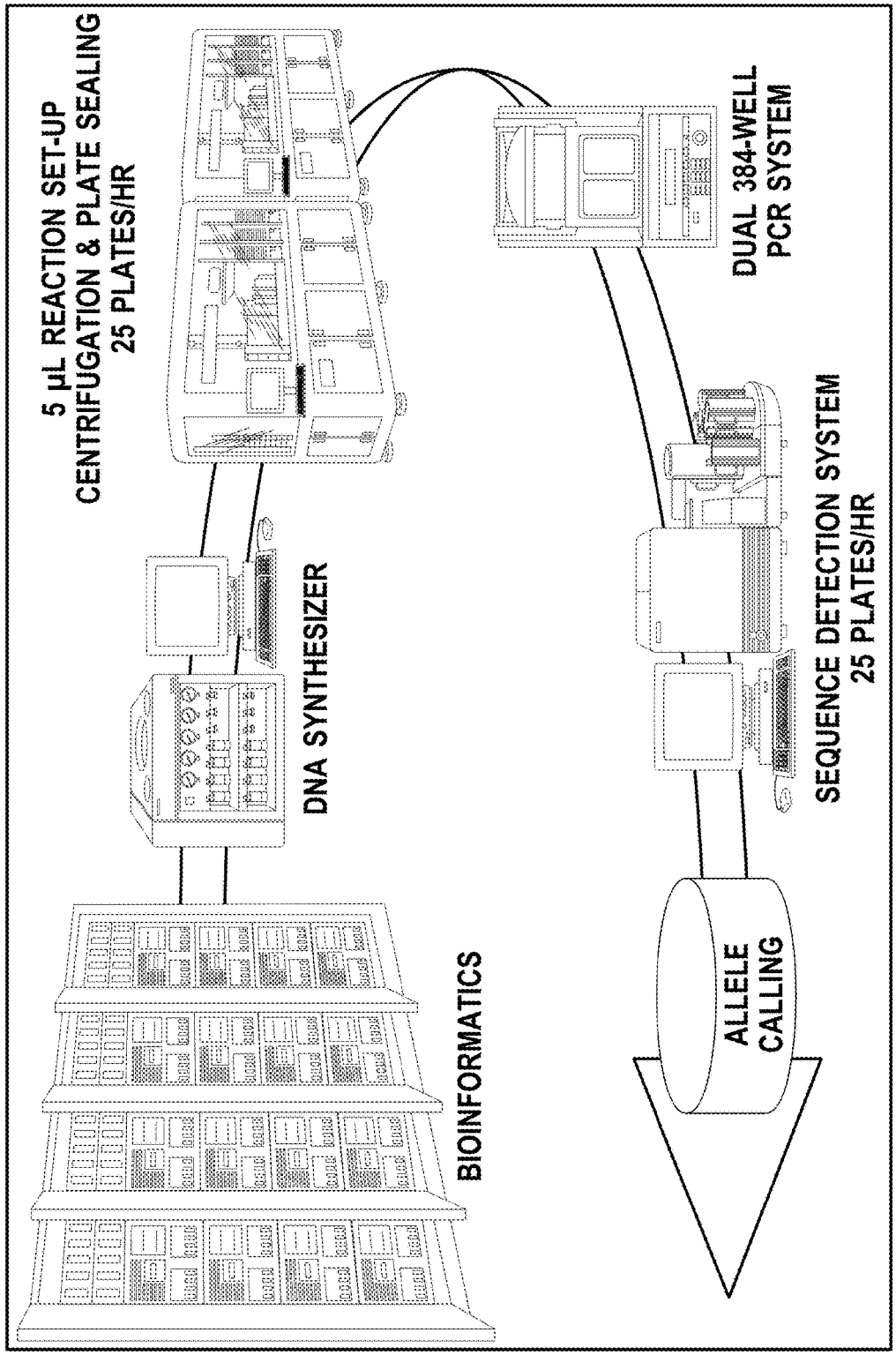

FIG. 86 illustrates SNP assay manufacture and validation.

Figure 87:
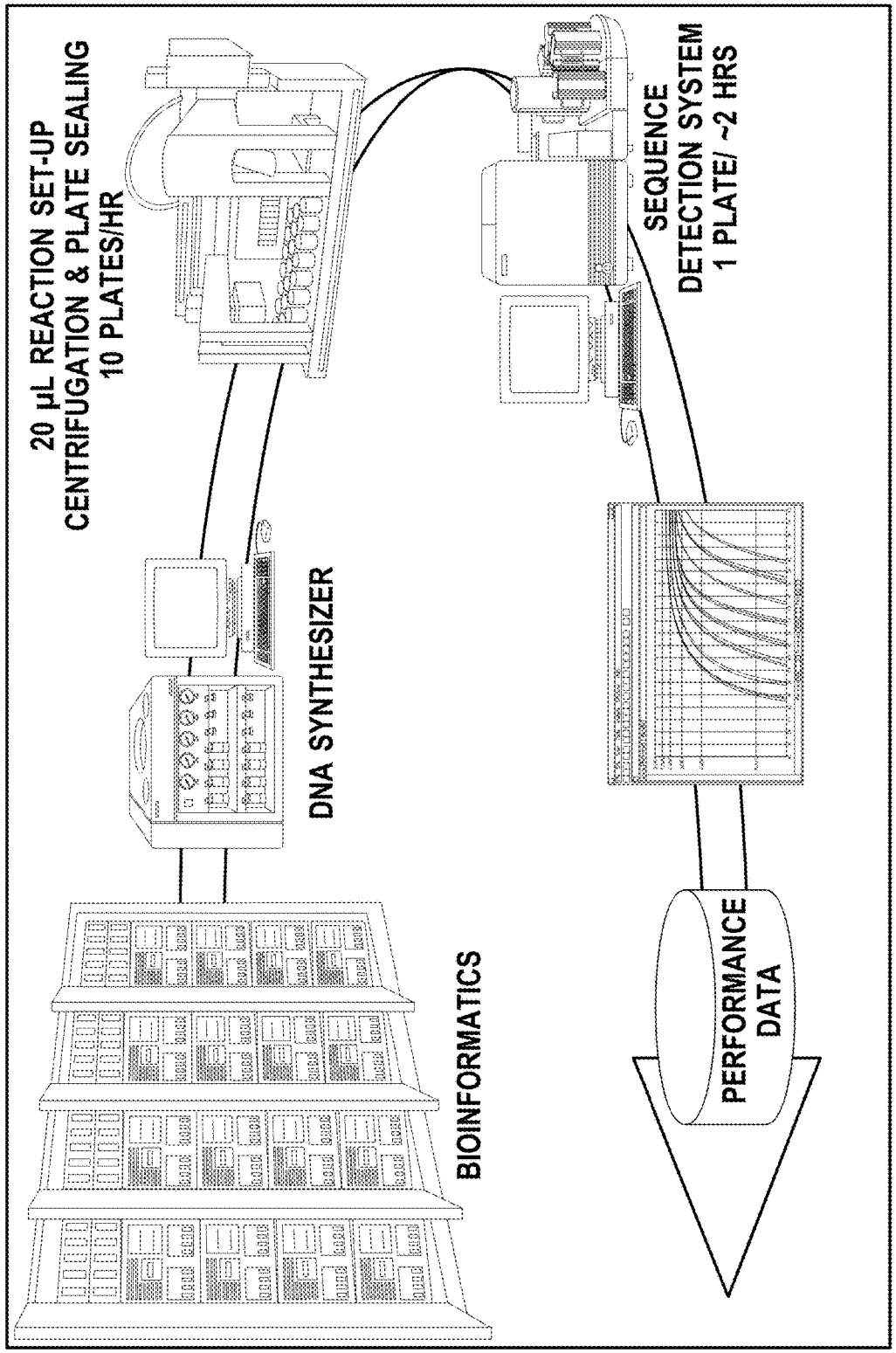

FIG. 87 illustrates gene expression assay manufacture and validation.

Figure 88:
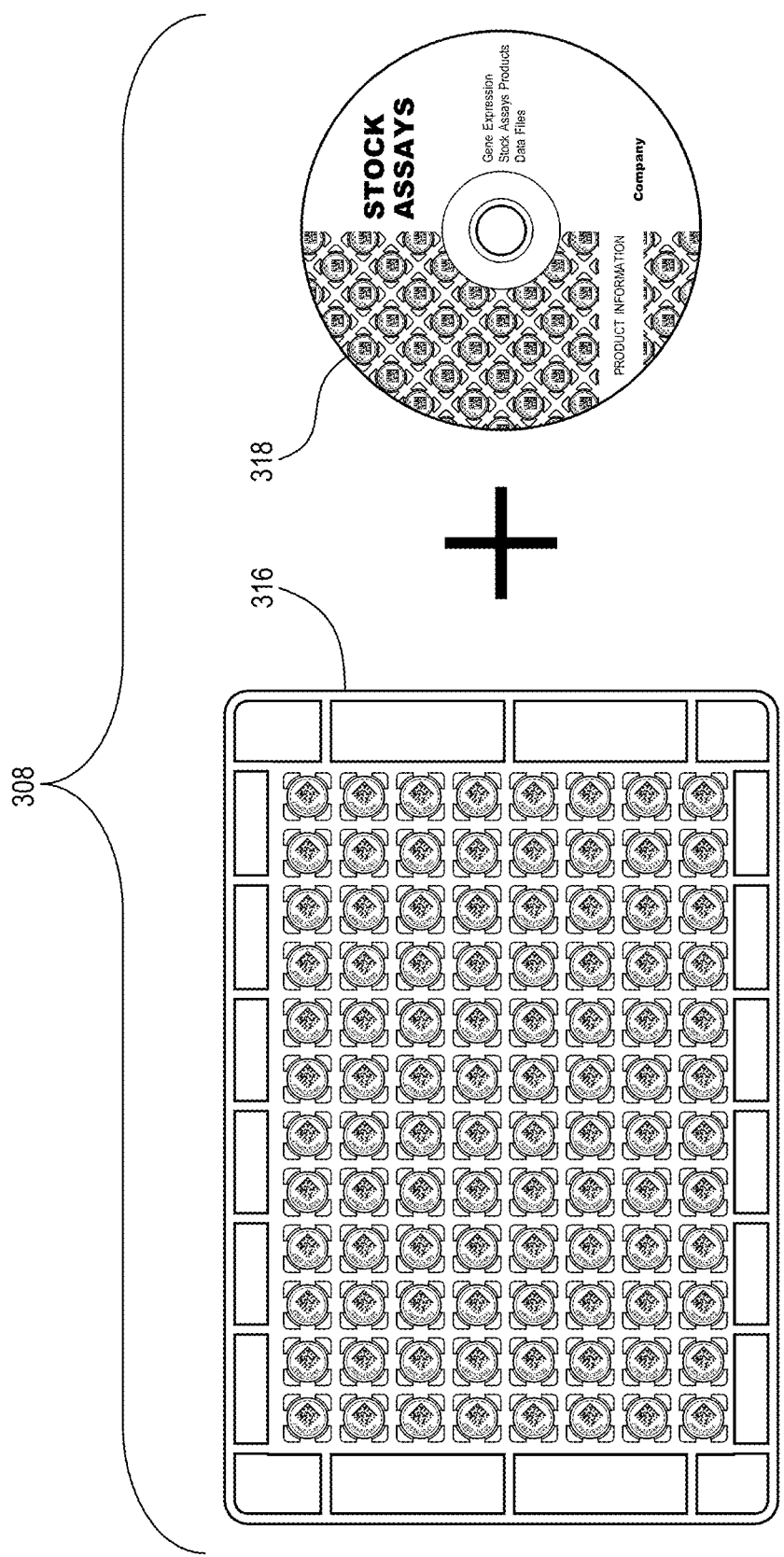

FIG. 88 illustrates an exemplary assay kit according to one of the various embodiments of the present invention.

Figure 89:
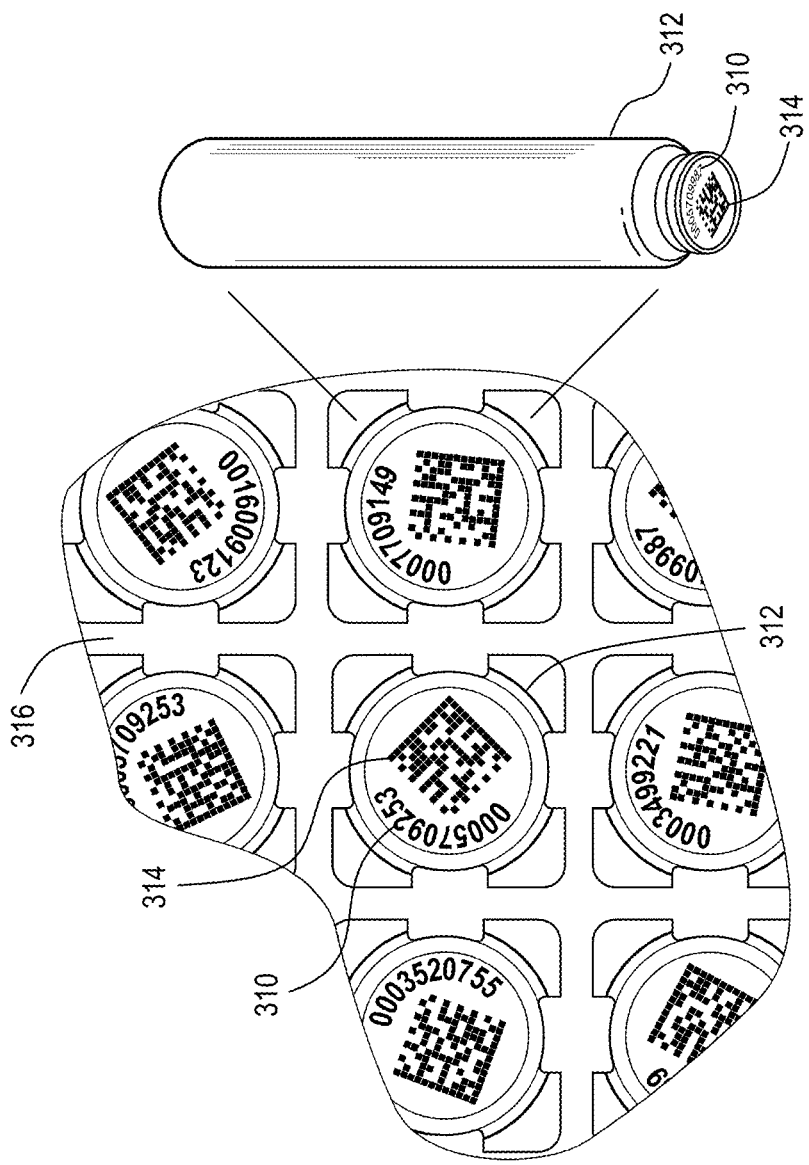

FIG. 89 illustrates a portion of the exemplary assay kit of FIG. 72, specifically, a portion of a rack of single-tube assays, illustrating human-readable identification numbers and two-dimensional bar code on the assay tubes and an exemplary illustration of the position of these identifying indicia on the assay tubes.

DETAILED DESCRIPTION

Definitions

Allele. One of several alternative forms of a gene or DNA sequence at a specific chromosomal location (locus). At each autosomal locus an individual possesses two alleles, one inherited from the father and one from the mother.

Allele-specific Oligonucleotide (ASO). A synthetic oligonucleotide, often about 20 bases long, which hybridizes to a specific target sequence and whose hybridization can be disrupted by a single base pair mismatch under carefully controlled conditions. ASOs can be often labeled and used as allele-specific hybridization probes. They can also be designed to act as allele-specific primers in certain PCR applications.

Allelic association. Any significant association between specific alleles at two or more neighboring loci.

Alternative splicing. The natural usage of different sets of exons, to produce more than one product from a single gene.

Assay. any of a number of nucleic acid assay systems (for review see Kricka, *Ann Clin Biochem.* 39:114-129, 2002; Shi, *Clin. Chem.* 47:164-172, 2001; Baner et al., *Curr. Opin. Biotechnol.* 12:11-15, 2001; Wittwer et al., U.S. Pat. No. 6,174,670, 2001). In various embodiments an assay can comprise nucleobase polymers, such as, for example, oligonucleotides, which constitute one or more probes and/or a forward and reverse primer. The assays can be configured to detect the presence of a SNP, the expression of a gene or the expression level of a gene. When using a TaqMan® procedure, the assay includes a TaqMan® probe, a forward primer and a reverse primer. See also "custom assay" and "stock assay."

Alu repeat (or sequence). One of a family of about 750,000 interspersed sequences in the human genome that are thought to have originated from the 7SL RNA gene.

Amplicon. A region defined by pairing of forward and reverse primers around a target site.

Anticodon. A sequence of three consecutive bases in a tRNA molecule that specifically binds to a complementary codon sequence in mRNA.

Autocalling. The use of an automated system to make a determination of genotype.

Bioinformatics. The collection, organization and analysis of large amounts of biological data, using networks of computers and databases.

BLAST. Basic Local Alignment Search Tool—Algorithms for sequence searching. A fast technique for detecting subsequences that match given query sequence. BLAST is a heuristic search algorithm employed by computer programs to ascribe significance to sequence findings using well-known statistical methods, for example, a fast search algorithm to search DNA databases based upon sequence similarities. (See, for example, Altschul et al. *J Mol Biol* 215: 403-10, 1990, Karlin et al., *Proc. Nat'l Acad. Sci. USA* 87: 2264-2268, 1990; Karlin et al., *Proc. Nat'l Acad. Sci. USA* 90: 5873-5877 1993; and Altschul et al., *Nat. Genet.* 6: 119-129 1994.) A BLAST analysis, in this context, refers to comparing sequences using a BLAST program such as blastp, blastn, blastx, tblastn, tblastx (accessible on the internet at http://www.ncbi.nlm.nih.gov/BLAST/) or MPBLAST (Korf et al., Bioinformatics 16: 1052-1053 (2000). "BLASTING," in this context, refers to comparing a sequence to sequences in a database, and identifying sequences contained in the database that are similar or identical to the sequence or its complement.

BLASTn. Search of a DNA sequence against a DNA sequence database.

Calling. The process of determining a genotype.

cDNA. Complementary DNA—a single stranded DNA sequence that was generated from and complementary to an mRNA sequence by reverse transcription. cDNA sequences contain only genes that code for protein (no non-coding DNA is included).

cDNA Library. A collection of single stranded DNA sequences that represent DNA that is translated into protein. cDNA libraries are generated from mRNA. They designed to represent the portion of the genome that is present as mRNA in a given cell on its way to synthesizing the proteins represented in that cell.

Centimorgan (cM). A unit of measure of recombination frequency. One centimorgan is equal to a 1% chance that a marker at one genetic locus will be separated from a marker at a second locus due to crossing over in a single generation. In human beings, 1 centimorgan is equivalent, on average, to 1 million base pairs.

Common SNPs. SNPs which have a minor allele frequency equal to or greater than a minimum percent of occurrence in an overall population, e.g. a population of humans or, in certain subsets of the overall population. Such subsets can include ethnically defined subset population. This can be assessed using samples from mixed populations or from specific populations such as Caucasian populations or African American populations as are available from repositories such as, for example, the Coriell Cell Repositories (Coriell Institute for Medical Research, Camden, N.J.).

Conserved sequence. A base sequence in a DNA molecule (or an amino acid sequence in a protein) that has remained essentially unchanged throughout evolution.

Consumer. Encompasses customers and other users of the products and services provided in configurations of the present invention. Unless explicitly stated otherwise, it is permitted but not required that configurations of the present invention precondition distribution on receipt of a payment or a promise to pay from the consumer for the distributed products or services. The terms "consumer," "requestor," "user" and "investigator" refer to entities different from the supplier and distributor. The terms "consumer," "requestor," "user" and "investigator" are often used interchangeably herein. However, in any given situation, it is possible that the consumer, the requestor, the user and/or the investigator are different entities or individuals, which themselves may (or may not) be related by agency. For example, the consumer, requestor, user and investigator in one instance may be a single individual engaged in research, such as at a college or university. As another example, the consumer may be a medical institution, the investigator may be a physician or researcher employed by the medical institution, and the requestor may be an assistant of the investigator. Also herein, the term "user" is frequently used to refer to an entity (such as a consumer, a requestor, or an investigator) who can be accessing a computer system.

Contig display name. The contig display name is the genome assembly (GA) name as used in some configurations of gene exploration systems.

Cryptic splice site. A sequence that resembles an authentic splice junction site and which can, under certain circumstances, participate in an RNA splicing reaction.

Custom assay. An assay that is designed from specifications that are generally related to the target sequence, but that do not contain information on the specific sequence of the probe or probes and primers.

dbSNP rs#ID. A specific field for searching for a SNP according to a dbSNP reference cluster ID.

dbSNP ss#ID. A specific field for searching for a SNP according to a dbSNP assay ID.

Deletions. can be generated by removal of a sequence of DNA, the regions on either side being joined together.

Discriminator. A procedure in which the "A-statistic" is used to screen out assemblies that are likely to be stacked regions of repetitive sequence that can be from more than one area of the genome.

Distribute. As used herein, the terms "distribute" and "provide" may be used synonymously, and are intended to encompass selling, marketing, or otherwise providing a product or service.

Distributor. As used herein the terms "distributor," "provider" and "supplier" are used to refer to an entity or entities that distributes and/or supplies products and/or services. The terms "distributor," "provider," and "supplier" can encompass sellers, marketers, and other providers of such products and services. The distributor, supplier, and provider may refer to the same entity, to two different entities, or to three different entities. In the description herein, it may be generally assumed that the manufacturer can be the supplier and distributor of the assay-related products and services described herein. However, in some configurations of the present invention, the distribution of the assay-related products and services described herein may be performed by an entity other than the manufacturer who supplies them.

DNA sequence. The relative order of base pairs, whether in a fragment of DNA, a gene, a chromosome, or an entire genome. See base sequence analysis.

Domain. A discrete portion of a protein with its own function and structure. The combination of domains in a single protein determines its overall function. The domain of a chromosome may refer either to a discrete structural entity defined as a region within which a supercoiling can be independent of other domains; or to an extensive region including an expressed gene that can have a heightened sensitivity to degradation by the enzyme DNAase I.

ENTREZ. NCBI's (National Center for Biotechnology Information) search and retrieval system for their data sets. It organizes GenBank sequences and links them to the literature sources in which they originally appeared.

EST. Expressed Sequence Tag. A sampling of sequence from a cDNA library. A short sequence of a cDNA clone for which a PCR assay is available.

Euchromatin. The fraction of the nuclear genome that contains transcriptionally active DNA and which, unlike heterochromatin, adopts a relatively extended conformation.

Exon(s). The protein-coding sequences of genes. Exons only comprise about 10% of the human genome. A segment of a gene that is decoded to give a mRNA product or a mature RNA product. Individual exons may contain coding DNA and/or noncoding DNA (untranslated sequences). See introns.

FASTA (file or format). A DNA sequence format that begins with a single line of text description that is less than 80 characters in length, followed by the DNA sequence file.

FASTA Search: A database search tool used to compare a nucleotide or peptide sequence to a sequence database. The program is based on the rapid sequence algorithm described by Lipman and Pearson.

Fragments. Small sections of DNA.

Frameshift mutation. A mutation that alters the normal translational reading frame of a DNA sequence.

GenBank. The public DNA sequence database maintained by the National Center for Biotechnology Information (NCBI), part of the National Library of Medicine.

Gene Exploration Platform (also referred to as Gene Exploration System). A web-based user interface configured to provide searchable information related to one or more genomes and/or transcriptomes and/or proteomes.

Gene families. Groups of closely related genes that make similar products.

Gene Ontology (GO). A controlled vocabulary for the description of the molecular function, biological process and cellular component of gene products which can be applied to all eukaryotes. The GO terms can be used as search identifiers.

Gene prediction. The process of using computational methods that search for known indicators of coding regions in the raw genomic sequence. These indicators include codon use bias, lack of stop codons, similarity of the translated protein sequence to known proteins, upstream regulators, splice sites, start codon. The outcome can be a set of exons that define a predicted gene.

Gene region. A linear stretch of genomic DNA which serves as a functional gene region consisting of cis-acting regulatory regions, transcribed regions, and intervening sequences as well as 10 kilobase pairs of 5' flanking sequence and 10 kilobase pairs of 3' flanking sequence.

Genomics. The study of the genetic material of an organism; the sequencing and characterization of the genome and analysis of the relationship between gene activity and cell function. The genetic material includes exons, introns, regulatory sequences, repeat elements and all other unidentified regions of the genome.

GI. GenBank Identifier, a unique number assigned to protein and nucleotide sequences in the GenBank database.

GT-AG rule. Rule that describes the presence of these constant dinucleotides at the first two and last two positions of introns of nuclear genes.

Haplotype. A series of alleles found at linked loci on a single (paternal or maternal) chromosome.

Heterochromatin. A region of the genome, which remains highly condensed throughout the cell cycle and shows little or no evidence of active gene expression.

Homologies. Similarities in DNA or protein sequences between individuals of the same species or among different species. Homologous chromosomes: a pair of chromosomes containing the same linear gene sequences, each derived from one parent. Homologous chromosomes (homologs): two copies of the same type of chromosome found in a diploid cell, one having being inherited from the father and the other from the mother. Homologous genes (homologs): two or more genes whose sequences can be significantly related because of a close evolutionary relationship, either between species (orthologs) or within a species (paralogs).

HSPs. High-scoring Segment Pairs; two sequence fragments of arbitrary but equal length with an alignment that can be locally maximal and for which the alignment score meets or exceeds a threshold (cutoff) score. These can be generated by BLAST.

Informatics. The study of the application of computer and statistical techniques to the management of information. In genome projects, informatics includes the development of methods to search databases quickly, to analyze DNA sequence information, and to predict protein sequence and structure from DNA sequence data.

Introns. DNA sequences in genes, which have no protein-coding function. Other non-coding regions include control or regulatory sequences and intergenic regions whose functions are unknown. Noncoding DNA separates neighboring exons eukaryote genes. During gene expression, introns, like exons, can be transcribed into RNA, but the transcribed intron sequences can be subsequently removed by RNA splicing and are not present in mRNA.

Investigator. See "consumer."

Linkage map. A map of the relative positions of genetic loci on a chromosome, determined on the basis of how often the loci are inherited together. Distance is measured in centimorgans (cM).

Linker (or adaptor oligonucleotide). A double-stranded oligonucleotide that can be ligated to a cloned DNA of interest in order, for example, to facilitate its ability to be cloned.

Marker. An identifiable physical location on a chromosome (e.g., restriction enzyme cutting site, gene) whose inheritance can be monitored. Markers can be expressed regions of DNA (genes) or some segment of DNA with no known coding function but whose pattern of inheritance can be determined. See RFLP, restriction fragment length polymorphism.

Master cluster. A "super cluster" that can be formed by joining clusters and singletons that have representative clones with significant matches (a Product Score of 40 or more) to the same gene. The master cluster is named after the cluster (or singleton) with the highest Product Score.

Mate pairs. A pair of reads that are in opposite orientations and at a distance from each other approximately equal to the insert length.

Messenger RNA (mRNA). RNA that serves as a template for protein synthesis. See genetic code.

Missense mutation. A nucleotide substitution that results in an amino acid change.

mRNA (Messenger RNA). The nucleic acid intermediate that can be used to synthesize a protein. The mRNA corresponds to one strand of the DNA and the sequence of the mRNA can be identical to the sequence of the DNA, except for the replacement of a T (thymine) with U (uracil).

Mutation frequency. Is the frequency at which a particular mutant can be found in a population.

NCBI. The National Center for Biotechnology Information, which can be accessed at the web site http://www.ncbi.nlm.nih.gov.

Nonsense mutation. A mutation that occurs within a codon and changes it to a stop codon.

Normalized library. A cDNA library from which most of the highly expressed sequences have been removed in order to represent a greater proportion of low-abundance messenger RNAs. Normalized libraries are not an accurate reflection of a tissue's gene-expression profile.

Nucleobase. Any nitrogen-containing heterocyclic moiety capable of forming Watson-Crick hydrogen bonds in pairing with a complementary nucleobase or nucleobase analog, e.g. a purine, a 7-deazapurine, or a pyrimidine. The present invention in some configurations uses assays based upon probes that can be polynucleotides or polymeric forms of other nucleobases such as nucleic acid analogs. Typical nucleobases can be the naturally occurring nucleobases adenine, guanine, cytosine, uracil, thymine, and analogs (Seela, U.S. Pat. No. 5,446,139) of the naturally occurring nucleobases, e.g. 7-deazaadenine, 7-deazaguanine, 7-deaza-8-azaguanine, 7-deaza-8-azaadenine, inosine, nebularine, nitropyrrole (Bergstrom, (1995) J. Amer. Chem. Soc. 117: 1201-09), nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine (Seela, U.S. Pat. No. 6,147,199), 7-deazaguanine (Seela, U.S. Pat. No. 5,990,303), 2-azapurine (Seela, WO 01/16149), 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, pyrazolo[3,4-D]pyrimidines, "PPG" (Meyer, U.S. Pat. Nos. 6,143,877 and 6,127, 121; Gall, WO 01/38584), and ethenoadenine (Fasman (1989) in *Practical Handbook of Biochemistry and Molecular Biology*, pp. 385-394, CRC Press, Boca Raton, Fl.). Nucleobases that are nucleic acid analogs include peptide nucleic acids in which the sugar/phosphate backbone of DNA or RNA has been replaced with acyclic, achiral, and neutral polyamide linkages. The 2-aminoethylglycine polyamide linkage with nucleobases attached to the linkage through an amide bond has been reported (see, for example, Buchardt, WO 92/20702; Nielsen (1991) *Science* 254:1497-1500; Egholm (1993) *Nature* 365:566-68).

Open Reading Frame (ORF). A stretch of nucleotide sequence with an initiation codon at one end, a series of triplet codons and a termination codon at the other end: potentially capable of coding for an as yet unidentified peptide or protein.

Ortholog. One of a set of homologous genes in different species (e.g. SRY in humans and Sry in mice).

Panther. Celera Genomics's proprietary protein classification software that allows hierarchical classification of protein families and subfamilies to further aid in identifying probable protein function. Panther facilitates target identification and prioritization by allowing more accurate predictions of protein function.

Paralog. One of a set of homologous genes within a single species.

Pharmacogenomics. The study of the stratification of the pharmacological response to a drug by a population based on the genetic variation of that population.

Phrap. Developed by Phil Green at the University of Washington, "Phil's Revised Assembly Program" is a tool for assembling shot-gun sequenced DNA fragments.

PHYLIP. Program Package created by J. Felsenstein for Phylogenicity.

Physical map. A map of the locations of identifiable landmarks on DNA (e.g., restriction enzyme cutting sites, genes), regardless of inheritance. Distance can be measured in base pairs. The relative positions of regions can be determined by physical measurements, such as by electron microscopy, restriction analysis, or sequence determination. For the human genome, the lowest-resolution physical map is the banding patterns on the 24 different chromosomes; the highest-resolution map would be the complete nucleotide sequence of the chromosomes.

Point mutation. A mutation causing a small alteration in the DNA sequence at a locus, often a single nucleotide change.

Polygenic character. A character determined by the combined action of a number of genetic loci. Mathematical polygenic theory assumes there can be very many loci, each with a small effect.

Polygenic disorders. Genetic disorders resulting from the combined action of alleles of more than one gene (e.g., heart disease, diabetes, and some cancers). Although such disorders can be inherited, they depend on the simultaneous presence of several alleles; thus the hereditary patterns can be usually more complex than those of single-gene disorders.

Polymorphism. Difference in DNA sequence among individuals. Genetic variations occurring in more than 1% of a population would be considered useful polymorphisms for genetic linkage analysis.

Precomputes. A series of computational analyses of Celera Genomics data to public data. The analyses used include gene prediction (GRAIL, Genscan, FgenesH), BLAST computes using several public and proprietary datasets (nraa, CHGD, RefSeq) to show similarity, and polishing of the BLAST results to find consensus splice sites using SIM4 or Genewise with sequences that can be highly similar to the genomic sequence.

Primer. A primer comprises a polymer of nucleobases, such as, for example, an oligonucleotide, the sequence of which is complementary to a target sequence, or to the complement of a target sequence. In certain aspects, the 3' end of an oligonucleotide primer can be extended by a DNA polymerase. The primer is short relative to the target nucleic acid. A primer sequence in some configurations comprises from about ten to about fifty nucleotides, and in some configurations comprises from about six, about eight, about ten, about thirteen up to about thirty nucleotides and any length there between. In most cases, PCR involves a forward primer and a reverse primer, which hybridize to opposite strands in a target sequence.

Probe. A "probe" comprises an oligonucleotide that hybridizes to a target sequence. In the TaqMan® assay procedure, the probe hybridizes to a portion of the target situated between the binding site of the two primers. A probe can further comprise a reporter group moiety. In some configurations, the reporter group moiety can be a fluorophore moiety. The reporter group can be covalently attached directly to the probe oligonucleotide, in some configurations to a base located at the probe's 5' end or at the probe's 3' end. The reporter group may also be attached to a minor groove binder (MGB), which can be itself covalently attached to the probe (Afonina et al., Nucleic Acids Research 25: 2657-2660 (1997); Kutyavin et al., Nucleic Acids Research 28: 655-661 (2000)). The MGB is, in some configurations, attached to the 3' end of the probe, either directly to the oligonucleotide or else to the fluorophore moiety or to the quencher moiety. A probe comprising a fluorophore moiety may also further comprise a quencher moiety. The quencher moiety is, in some configurations, a non-fluorescent quencher (NFQ). In some configurations, in probes designed for SNP detection, the fluorophore and the quencher can be attached to the oligonucleotide on opposites sides of the SNP nucleotide. A probe comprises about eight nucleotides, about ten nucleotides, about fifteen nucleotides, about twenty nucleotides, about thirty nucleotides, about forty nucleotides, or about fifty nucleotides. In some configurations, a probe comprises from about eight nucleotides to about fifteen nucleotides. As used herein, the use of the term "a probe" (singular) is intended to include or refer to two bi-allelic probes in the case of SNP assays, unless stated otherwise.

Proteome: The full set of proteins encoded by a genome.

Provide. See "Distribute."

Provider. See "Distributor."

Query. The DNA sequence used to search a database.

Radiation hybrid. A type of somatic cell hybrid in which fragments of chromosomes of one cell type can be generated by exposure to X-rays, and are subsequently allowed to integrate into the chromosomes of a second cell type.

Real time. The term "real time" is always spelled out in full. The abbreviation "RT," as used herein, always refers to "reverse transcriptase."

Receptor. A molecule (usually a protein) that spans a cell membrane and received extracellular signals and transmits them into the cell.

Regional overlay. Celera regional overlays can be created from Celera fragments and mate pair links, and external finished clones and unordered contigs from unfinished clones, which are referred to as BACs. The Celera Regional Assembler takes the external data and uses Celera fragments and mate pairs to order and orient the contigs within BACs, filling in gaps where possible.

Regulatory regions or sequences. A DNA base sequence that controls gene expression.

Repetitive DNA. A set of nonallelic DNA sequences which show considerable sequence homology.

Requestor. See "consumer."

Reverse transcriptase (RT). The abbreviation "RT" is used herein exclusively as an abbreviation for "reverse transcriptase." The term "real time" is always spelled out in full.

Scaffolds. Sets of contigs that can be ordered and oriented using enforcing mate pairs.

Sequence homology. A measure of the similarity in the sequence of two nucleic acids or two polypeptides.

Sequence tagged site (STS). Short (200 to 500 base pairs) DNA sequence that has a single occurrence in the human genome and whose location and base sequence are known. Detectable by polymerase chain reaction, STSs can be useful for localizing and orienting the mapping and sequence data reported from many different laboratories and serve as landmarks on the developing physical map of the human genome. Expressed sequence tags (ESTs) can be STSs derived from cDNAs.

Significant complementarity. Includes complementarity sufficient to interfere with the analysis of a target sequence. Significant complementarity can comprise, in non-limiting example, at least about 40% or greater sequence identity with the complement of a target sequence.

Single Nucleotide Polymorphism (SNP). Replacement, loss, or addition of one nucleotide (either A, C, G or T) in the DNA sequence. There are probably several million SNPs throughout the genome, and these alleles account for much of the variation seen in the human population. These predominately biallelic polymorphisms may exist in varying ratios in the population ranging from very rare alleles (1-5% frequency) to common alleles (20-50% frequency).

Splice acceptor site. The junction between the end of an intron terminating in the dinucleotide AG, and the start of the next exon.

Splice donor site. The junction between the end of an exon and the start of the downstream intron, commencing with the dinucleotide GT.

Stock assay. A pre-designed assay that does not require custom design. In some configurations of the present invention, an inventory of stock assays may be maintained from which users may place orders.

Stringency. A parameter for filtering the results of a query based on how closely related the sequences in a cluster must be.

Subject. A DNA sequence that produces a match in a blast search.

Supplier. See "Distributor."

SWISSPROT. European annotated non-redundant protein sequence database; most highly annotated protein database.

TA. Transcript assembly. Celera assembly of public EST.

Tandem repeat sequences. Multiple copies of the same base sequence on a chromosome; used as a marker in physical mapping.

Target. A biological sample comprising a nucleic acid. A target can comprise a single-stranded or double-stranded nucleic acid, and can comprise an RNA or a DNA. An RNA can be, in non-limiting example, a messenger RNA (mRNA), a primary transcript, a viral RNA, or a ribosomal RNA. A DNA can be, in non-limiting example, a single-stranded DNA, a double-stranded DNA, a cDNA, a viral DNA, an extrachromosomal DNA, or a mitochondrial DNA. A skilled artisan will recognize from the context of usage whether a target nucleic acid is single-stranded or double-stranded.

TBLASTn. A BLAST search of a protein sequence against a nucleotide sequence database that has been translated in all six frames.

Trace Files. The product of sequencing completed by the ABI 3700 Prism. After going through stringent quality control processes, trace files can be then used as data input for assembly.

Transcriptome. The full complement of activated genes, mRNAs, or transcripts expressed from a genome.

TREMBL. Translated EMBL, a compilation of the EMBL DNA data library.

UniGene database. A public database, maintained by NCBI, which brings together sets of GenBank sequences that represent the transcription products of distinct genes.

Unique clone. A sequence that has no match in GenBank or other public databases.

Unique singleton. A clone that does not cluster and has no match in the public databases.

UTR (untranslated region). Noncoding region found at the 5' or 3' termini of mRNA.

Untranslated sequences. Noncoding sequences found at the 5' and 3' termini of mRNA.

User. See "consumer."

Overview of Assays:

SNP Genotyping Assays:

In some configurations, the present invention includes methods of providing investigators with assays useful for detecting the presence of SNP alleles as well as assays useful for detection or quantification of gene expression. The elucidation and cataloguing of the sequences of genomes of various species, particularly the human genome, including the identification in public and/or private databases of more than 4,000,000 SNPs distributed throughout the genome, as well as the identification and cataloguing of a significant fraction of the approximately 30,000 expressed genes, provides the basis for establishing a collection of validated assays for SNPs or gene expression. Such assays can provide investigators with analytical tools for investigating virtually any gene in a mapped genome.

In some configurations, SNP databases can be used to develop assays that provide an investigator with the ability to analyze samples for the presence of identified SNP alleles. Testing samples from a particular individual allows SNP genotyping of that individual. SNPs from public and/or private databases can be selected for assay development. A number of approaches can be used in constructing SNP databases that can be useful in SNP genotyping (for review of SNP databases, see McCarthy et al., *Nat. Biotechnol* 18:505-508, 2000; Judson et al., *Pharmacogenomics* 3379-391, 2002, Miller et al., *Hum. Mol. Genet.* 10:2195-2198, 2001). In certain aspects, a gene-based approach can be used. In a gene-based approach, SNPs can be selected that reside on "gene regions." For example, a gene region comprising a 60 kb sequence including 10 kb upstream and 10 kb downstream from known functional sequences, can in certain instances have at least seven identified SNPs associated with it including at least one identified SNP that maps to a location approximately 10 kb upstream to its 5'-most cis-acting regulatory sequence, another identified SNP that maps to a location approximately 10 kb downstream to its 3'-most cis-acting regulatory or transcribed sequence, and at least 5 more identified SNPs mapping therebetween. Within the gene region, the SNPs can be selected such that they can be distributed across the gene region. As such, the selected SNPs can be located about 5 kb apart, about 10 kb apart, about 15 kb apart, or more, or at any selected separation distance between 5000 and 15000 bases, or at any selected separation distance without limitation. The availability of assays for SNP markers that can be spaced at intervals of approximately 10 kb for a gene affords an investigator the opportunity to obtain at least one SNP allele that can be used as a marker for the gene. SNP markers can serve as markers for genotypes or haplotypes and can be of value in investigating gene structure, haplotype structure, inheritance studies, and the like.

In certain aspects of the present invention, the inventors have focused on the selection of "common" SNPs. The minimum percent of occurrence in a population or population subset depends upon the requirements of a particular test and can be selected to be, in certain instances, about 8%, about 10%, about 15%, about 20% or greater or any value therebetween, or any selected frequency without limitation, depending upon the assay requirements. Particular minimum percent of occurrence values that can be considered to be generally applicable can be in certain embodiments, about 10% and in other embodiments, about 15%. In certain configurations, known SNPs that have been cataloged in at least one database can be subjected to a triage procedure to produce a reduced set of SNPs. In addition, SNPs can be selected whose minor alleles were observed in at least two distinct donors. Unless a minor allele is reported in at least two individuals, a SNP may be eliminated from further consideration for inclusion in the set of SNPs. Sequences comprising the selected SNPs, as well as sequences upstream and downstream from the SNPs, can be then analyzed to determine their suitability for use in SNP assays. SNPs deemed non-usable for assay development can be eliminated from further consideration for inclusion in the set. In a subsequent triage step, semi-empirical design quality control (QC) criteria can be used to reduce the SNPs included in the set.

The following properties of a candidate SNP may be considered in determining whether a candidate SNP is selected for inclusion in the reduced set of SNPs: 1) the SNP maps within or close to an annotated gene in a gene library, for example, within one of about 30,000 Celera-annotated genes or within 10 kb of an annotated gene; and 2) the SNP is spaced with respect to nearest neighbor to provide at least three SNPs per gene on intervals between SNPs of about 10 kb. Remaining gaps greater than about 10 kb in a gene region can be filled with at least two unscreened SNPs per 10 kb.

Assays that pass this selection procedure can be then validated in some configurations, based upon laboratory genotyping results using a panel of genomic DNA from, for example, about 90 individuals. For example, the DNA panel comprises genomic DNA from about 90 individuals representing a subset population of Caucasian individuals and a subset population of individuals of African American ancestry. Selected SNPs have a minor allele frequency of at least 10% or greater or at least 15% or greater in at least one population, or any selected minor allele frequency without limitation.

SNP assays can include any SNP assay known in the art. Methods for SNP detection include, in non-limiting example, variations of the INVADER™ method of Third Wave Technologies, and the TaqMan® method. In some configurations, assays can be developed for use in a TaqMan® method for identifying a SNP allele in a target sequence. The TaqMan® method uses two primer oligonucleotides and a DNA polymerase for PCR sequence amplification, as well as one or two probe oligonucleotides. For SNP detection using a TaqMan method, one primer oligonucleotide sequence maps to a site upstream from a target SNP sequence and a second primer oligonucleotide sequence maps to a site downstream from the target SNP sequence. A probe oligonucleotide sequence maps to the SNP, and comprises one allele of the target SNP, a reporter group moiety, which in some embodiments can be a fluorophore moiety, a fluorescence quencher moiety, which can be in some embodiments an NFQ moiety, and can also comprise an MGB moiety. In TaqMan analyses using two probes, the second probe sequence also maps to the SNP, and comprises an alternative allele of the target SNP, a second reporter moiety (for example, a second fluorophore moiety), a fluorescence quencher, and can also comprise an MGB. When two probes are used, the fluorophores can be selected to be distinguishable by virtue of their absorption or emission spectra. In non-limiting example, the fluorophores VIC™ and FAM as provided in kits by Applied Biosystems can be used as reporter fluorophore moieties in a SNP assay. The probe can further comprise an MGB. An MGB increases the melting temperature of a probe/target hybrid without increasing probe length, thereby allowing shorter probes to be used (Afonina et al., *Nucleic Acids Research* 25: 2657-2660 1997; Kutyavin et al., *Nucleic Acids Research* 28: 655-661 2000). In some configurations, the MGB moiety can be covalently attached to the 3' end of the probe. The structure of the MGB can be, in non-limiting example, a trimer of 1,2-dihydro-(3H)-pyrrolo[3,2-e]indole-7-carboxylate. This oligopeptide binds double-stranded DNA in the minor groove, with a high affinity for A-T-rich sequences in double stranded DNA. Because the presence of an MGB increases the stability of hybrid nucleic acids, oligonucleotide-MGB conjugates as short as 8-mers, or G-C-rich 6-mers are able to form stable hybrids with complementary sequences. These properties allow the use of probes as short as six nucleotides. MGBs furthermore increase the specificity of probe-target hybridization.

In the TaqMan® assay, each probe can be non-fluorescent or poorly fluorescent in spite of the presence of a fluorophore moiety, by virtue of the presence of the NFQ. However, during PCR amplification of the TaqMan assay, a probe bound to a target SNP can be digested by the polymerase, because of the enzyme's 5' exonuclease activity. Because the PCR conditions can be selected for high stringency hybridization, whereby a single nucleotide mismatch between probe and target does not permit stable hybridization, only probes perfectly complementary to the target are digested by the polymerase. Thus, if two probes representing alternative alleles of a SNP are used, only one probe will be subject to digestion by the polymerase. Because digestion of a probe releases a fluorophore from quenching by the quencher, measurement of the absorption or emission wavelength of a sample reveals which probe is digested by the polymerase, and hence, which SNP allele is present in the sample. Because SNPs can be heterozygous or homozygous, detection of absorption or emission spectra of one or both fluorophores in a sample during or following PCR amplification will reveal if the target sample is heterozygous or homozygous. Fluorophore released from a quenched primer can be quantified by any method known in the art. In some configurations, a fluorimeter can be used. In some configurations, the fluorimeter comprises a component of an integrated nucleic acid analysis system, in non-limiting example, an ABI PRISM® 7900HT Sequence Detection System.

In a SNP genotyping assay, two probes comprising identical sequences except for the SNP allele nucleotide, different fluorophores, and identical MGBs and NFQs can be used in various embodiments. For a biallelic SNP assay, any two spectrally distinguishable fluorophores for which the fluorescent signals can be quenched by the non-fluorescent quencher are used. In a non-limiting example, commercially available fluorophores, for example VIC™ and FAM™ from Applied Biosystems, can be used as probe labels in biallelic SNP genotyping.

In the design of an assay in various embodiments, at least one potential probe oligonucleotide sequence, as well as potential primer oligonucleotide sequences, can be analyzed in silico for suitability in a PCR assay. An in silico analysis of an oligonucleotide sequence can consider several criteria, such as, in non-limiting example, the predicted melting temperature of a duplex comprising the oligonucleotide sequence and its complement, the absence of significant self-complementarity (e.g., the absence of "hairpin loops"), the absence of significant complementarity with any other oligonucleotide expected to be used in the assay (e.g., "primer-primer dimerization"), and the absence of significant complementary with a genomic sequence outside of the target site. In certain embodiments, a candidate oligonucleotide sequence can be validated by "blasting" against the genome, and a candidate sequence is selected for further development for use in an assay only if its sequence appears no more than once in the genome.

Following in silico validation, each oligonucleotide designed for an assay can be synthesized using organic synthesis methods known in the art. The synthesis of probe oligonucleotides also includes the covalent attachment of a reporter group, a fluorescence quencher, and a minor groove binder.

Gene Expression Assays:

In some configurations of the present invention, information in databases on expressed sequences can be used to develop assays that provide an investigator with the ability to analyze a sample for the presence and quantity of expressed RNA. In certain configurations, a method is provided that permits an investigator to obtain a validated assay to a known expressed gene. In some configurations, assays can be designed for measuring gene expression levels using reverse transcription coupled to the polymerase chain reaction (Reverse Transcription-Polymerase Chain Reaction, RT-PCR) (Sambrook et al., 2d Edition, Cold Spring Harbor Laboratory Press, Cold Spring, N.Y. (1989)). In these configurations, primer or probe oligonucleotides comprising DNA sequences corresponding to mRNA sequences (or the complement thereof for a "reverse" primer sequence) can be designed and validated. In some configurations, at least one probe or primer spans an exon-exon boundary within a target mRNA (or cDNA) sequence to diminish any contribution from genomic nucleic acids.

Once a target expressed gene has been determined or designated, gene expression can be detected and quantified by the investigator using an assay designed using any of a number of methods. Thus, in some configurations, assays can be developed for use in an RT-PCR analysis using the TaqMan® method for quantifying a PCR-amplified cDNA of an target expressed mRNA. A TaqMan® gene expression assay utilizes a pair of oligonucleotide primers for PCR, as well as a probe oligonucleotide. The primer oligonucleotides hybridize to different sites within a double-stranded cDNA of an mRNA, in opposite orientations. The probe oligonucleotide comprises a sequence that hybridizes to a site between the primer hybridization sites. The hybridization stringency conditions can be selected such that at least one of the probe and primer oligonucleotides hybridizes uniquely to the genome. In some configurations, at least one of the probe and primer oligonucleotides comprises a sequence that spans an exon-exon boundary, in order to minimize spurious signal generated by contaminating genomic DNA acting as template. In some configurations, the probe comprises a sequence that spans an exon-exon boundary. The probe oligonucleotide further comprises a reporter moiety, in some configurations a fluorophore, as well as a fluorescence quencher, in some configurations an NFQ. Any fluorophore which can be subject to quenching by a quencher may be used as the reporter moiety. In non-limiting example, the fluorophore VIC™, as provided in kits by Applied Biosystems, can be used as a reporter fluorophore moiety in an RT-PCR gene expression assay. The probe can further comprise an MGB. In some configurations, the MGB moiety can be covalently attached to the 3' end of the probe. The structure of the MGB can be, in non-limiting example, a trimer of 1,2-dihydro-(3H)-pyrrolo[3,2-e]indole-7-carboxylate. Because the presence of an MGB increases the stability of hybrid nucleic acids, oligonucleotide-MGB conjugates as short as 8-mers, or G-C-rich 6-mers, are able to form stable hybrids with complementary sequences, and therefore allow the use of probes as short as six nucleotides. MGBs furthermore increase the specificity of probe-target hybridization.

Either a one-step or two-step process configuration can be used to analyze a sample for the presence or quantity of an RNA. In some configurations, a one-step process configuration can be used to detect and quantify an mRNA. In one-step process configurations, a thermostable polymerase that exhibits reverse transcription, DNA synthesis utilizing a DNA template, and 5'-to-3' exonuclease activity, in non-limiting example recombinant *Thermus thermophilus* DNA polymerase (rTth polymerase), can be used in a TaqMan® analysis. Because rTth polymerase exhibits all enzyme activities involving nucleic acids needed for an RT-PCR expression analysis, an assay can be provided to an investigator comprising all of the components for an RT-PCR analysis except for the target sample. Thus, following an investigator's request, a pre-validated assay can be sent to the investigator as a mixture in a single tube. The investigator need only add a target sample to the mixture, then subject the mixture to a standard thermal cycling protocol. In certain alternative configurations, the oligonucleotides of an assay can be supplied in a single tube, and the buffers, salts, and thermostable polymerase can be supplied separately. As a result of thermal cycling, fluorophore can be released if probes and primers are hybridized to a cDNA target. Measurement of released fluorophore provides a quantifiable signal, wherein fluorescence intensity can be monotonically related to RNA concentration in the target sample. Fluorophore released from a quenched primer can be quantified by any method known in the art. In some configurations, a fluorimeter can be used. In some configurations, the fluorimeter comprises a component of an integrated nucleic acid analysis system, in non-limiting example, an ABI PRISM® 7900HT Sequence Detection System.

In yet other, "two-step" RT-PCR analysis configurations, reverse transcription and PCR amplification can be conducted separately. Reverse transcription can be catalyzed using a reverse transcriptase, such as, in non-limiting example, a reverse transcriptase from Avian Myeloblastosis Virus or Moloney Murine Leukemia Virus. Second-strand synthesis, and amplification of cDNA can be subsequently effected in a second step using a DNA polymerase, such as, in non-limiting example, a heat-stable polymerase such as Taq polymerase. The Taq polymerase can be, in some configurations, a Taq polymerase that can be supplied complexed with a heat-denaturable blocking agent, for example, an antibody directed against the Taq polymerase, in order to prevent elongation of an oligonucleotide prior to an initial heat denaturation step at the start of a thermal cycling protocol.

In both SNP and gene expression assays, the assays can be run under uniform conditions to allow high-throughput analyses of samples. High-throughput capability lends itself to automation and robotics, wherein hundreds or thousands of individual gene expression analyses can be conducted within a single day. For example, 384 samples can be analyzed simultaneously by setting up 384 separate RT-PCR assays on a single 384-well tray, and conducting the reactions in a single thermal cycler apparatus. Robotics can be used to facilitate the rapid and accurate handling of the samples.

In various configurations, the invention includes provision of an assay for analysis of a SNP or an expressed gene using PCR or a variant or modification thereof. Variations of PCR include, for example, the TaqMan® assay, in which a pair of primer oligonucleotides and at least one probe oligonucleotide can be hybridized to a target nucleic acid. The DNA polymerase, in particular a heat stable DNA polymerase such as a taq polymerase, catalyzes the hydrolysis of the probe as a result of the polymerase's 5' to 3' exonuclease activity. If the probe comprises both a fluorophore moiety as a reporter group and a quencher moiety, such as a non-fluorescent quencher, hydrolysis of the probe results in separation of the fluorophore and the quencher, leading to an increase in the fluorescent signal obtainable from the reporter group.

Various configurations of the present invention make available to an investigator a system for obtaining validated assays and protocols for studying SNPs and their connection with disease or conditions as well as for studying the expression of genes. The assays can be made available in large number and in a standard format for performing tests involving SNPs or gene expression. The present invention also provides a system for rapid development of new assays, which can be based upon a specified target sequence or gene region provided by the investigator.

In some configurations of the present invention, stock gene expression products can be off-the-shelf quantitative gene expression assays that have been built on the 5' nuclease chemistry and that have been designed utilizing a bioinformatics pipeline that performs BLAST and other sequence analysis using, for example, either public or private data. An example of a database suitable for use with some configurations of the present invention can be the Celera Discovery System (CDS™), which is an example of a gene exploration system 19 (see FIG. 1). In some configurations, assays can be formulated into a 20× mix, quality control tested and functionally tested. Requestors can be provided with exon junction information and information relating the assay target sequence to the transcription sequence, and may, in some configurations, be provided with or have the option of being provided with the probe and primer sequence information as well as the full transcription sequence information.

In contrast, in configurations supplying custom assays, requestors can perform upfront BLAST or sequence analysis themselves, if desired, and then provide a target sequence and desired location or locations of a TaqMan® MGB probe to the supplier. Configurations of the present invention then utilize a suitable program such as, for example, Primer Express or a modified version thereof (which may, for example, execute in batch mode) to design the TaqMan® MGB probe and primer set. The primers and probes can be quality control-tested by the supplier and then formulated into a single-tube mix having, for example, concentrations of 20×, 60×, or other concentrations. In some configurations, requestors may select a concentration by ordering specific part numbers. The supplier supplies requestors with primer and TaqMan® MGB probe sequences.

Some configurations of the present invention provide both "custom" and "stock" options, and provide one or more predesigned, preformulated, quality control-tested assay in a single tube.

Web Based Portal System

According to various aspects of the system disclosed herein, the user may be able to use a web based portal to order products associated with conducting assays. The web based portal may be used to order custom assays and/or stock assays. In this regard, the user may initially navigate to the portal as shown in block 10 of FIG. 1. The portal may be similar to that shown in FIG. 17, although it will be understood that any other suitable portal may be used. Once the user arrives at the portal, the user determines the type of assay that is desired as represented by block 12. For example, a user may desire to order a custom assay, a stock assay that can be used for gene expression experiments, or a stock assay that can be used for SNP genotyping experiments. It will be understood, however, that this set of assays is only exemplary in nature and may also include other assays and/or related products.

Depending upon the type of assay which the user desires, the processing may differ. For example, if the user desires to obtain a custom assay, the system proceeds to obtain from the user information which may be useful to deliver the custom assay to the user as indicated by block 14. Similarly, if the user desires to obtain an assay for gene expression experimentation, the system proceeds to obtain the information which may be useful to generate such an assay as represented by block 16. In addition, if the user desires to obtain an assay for SNP genotyping, the system proceeds to collect information useful to providing such an assay as represented by block 18. Further, the user may desire to use the gene exploration system as indicated by block 19. The gene exploration system will be described below.

Gene Exploration System:

Some configurations of the present invention provide a gene exploration system or platform 19, that allows the user to perform in silico research which can assist the user in the process of assay selection. Gene exploration system 19 can be accessed directly from the portal 10 or from selection screens from custom assay and/or stock assay blocks 14, 16, and 18. For example, if a user has entered a custom or stock assay screen and wants to obtain further genomic information about a given assay, or if a user decides to perform further research prior to ordering a gene, an appropriate entry link to the gene expression system can be accessed.

Gene exploration platform 19 can provide access to a set of genomic and biomedical data from public and/or private sources. Some configurations provide integrated access to such data from Celera, GenBank, and other public and private data sources. Computational tools can also be provided to facilitate the viewing and analyzing of gene structure and function, genome structure and physical maps, and/or proteins classified by family, function, process, and/or cellular location. An intuitive user interface can be provided that organizes information for easy navigation and analysis.

Figure 2:
FIG. 2 is an exemplary window pane for navigating genome information.

In certain configurations the gene exploration system, block 19, can provide the user with a link to a genome navigation page such as that illustrated in FIG. 2. Several options can be provided for genome navigation, including, for example, human, mouse, human and mouse comparative genomics, protein classification, and pharmacogenomics. For example, in some configurations, the genome navigation option can be configured to provide users with the capability to browse and search genome maps, genome assembly, and genes data.

Protein classification option allows the user to browse and/or search one or more protein information databases. Database capabilities may include, for example, browsing and text searching Celera PANTHER™ families and gene ontology classification data.

The pharmacogenomics option available in some configurations can provide the user with the ability to search against one or more SNP databases, for example, the Celera Human SNP Reference Data database.

A navigation bar can be provided in some configurations of the present invention. The navigation bar provides access to one or more features, such as a biomolecule library; a text search (allowing the user to launch sequence analysis applications); a sequence analysis (allowing the user to launch sequence analysis applications); a workspace (allowing a user to start a new session and delete, rename, import, and/or export sessions, and/or select queries to delete and/or link with other queries, and perform complex queries); a queue display (permitting the user to display the status of his or her sequence analysis jobs and to retrieve the results); an options display (providing, for example, a display of user account information and/or display options); online help; and logoff. Some configurations can limit the number of sessions allowed to a user.

Some configurations of the present invention can provide a research facility based upon genome assembly and annotation data from one or more public and/or private databases. One or more of these databases may be Celera databases, from which chromosome map reports, scaffold reports, sequence reports, gene lists, chromosome map displays and/or biomolecule reports are available.

A representative example of a chromosome map report as provided in some configurations of the present invention is shown in FIG. 3. This report lists the scaffolds on a chromosome. Chromosome reports can be sorted by chromosome location in ascending order in some configurations. For each scaffold, one or more information items may be available, which may include a link to a corresponding scaffold report; the scaffold's coordinates and/or orientation on a reference chromosome axis; and/or the scaffold's length. From a chromosome map report, some configurations of the present invention provide access to the chromosome map display.

In some configurations of the present invention, to retrieve a chromosome map display, a user first searches a genome assembly (for example, the Celera genome assembly) to retrieve all scaffolds on a single chromosome. The user then clicks on a link to a chromosome map report from a scaffold report. A representative example of a scaffold report as provided in some configurations of the present invention is shown in FIG. 4.

In some configurations of the present invention, sequence reports can be provided. A representative example of a sequence report as provided by some configurations of the present invention is shown in FIG. 5. Sequence reports provided by some configurations of the present invention display the location of a genomic assembly segment on a reference chromosome axis and a nucleotide consensus sequence (ungapped) in FASTA format.

Various configurations of the present invention make gene lists available to users. A representative example of a gene list as provided in some configurations of the present invention is shown in FIG. 6. This gene list displays related information about genome annotation data in (for example) a tabular format.

Gene list information in some configurations can include, for example, one or more of the following items: gene ID, transcript ID, protein ID, gene name (if assigned), gene symbol (if assigned), gene alias (if assigned), reference sequence ID (if present).

Some configurations of the present invention provide a chromosome map display, as shown in FIG. 7. The chromosome map display can provide a graphical overview of a reference genome. In addition, it may provide access to one or more of the following: a corresponding scaffold report, a corresponding biomolecule report, and/or a corresponding gene list.

In some configurations a biomolecule report as provided as illustrated in FIG. 8. This report can contain one or more of three views: a protein view, an mRNA view, and a chromosome view. The protein view (such as the one illustrated in FIG. 8) can display one or more of the following information items for a selected protein ID (for example, a selected Celera Protein ID): a corresponding gene symbol, gene alias (if assigned), and/or gene ID; a corresponding transcript ID (e.g., Celera transcript ID); begin and/or end coordinates on the reference genome, and/or icons that indicate orientation: forward strand, reverse strand, or uncertain; a link to a human gene mutation database report, if available; the gene ontology classification; a Panther protein family classification; and/or protein domain hit identities.

The mRNA view (a representative example of which is shown in FIG. 9) can display one or more of the following information items for a selected transcript ID (for example, a selected Celera Transcript ID): corresponding gene symbol, gene alias (if assigned), and/or gene ID (e.g., Celera gene ID), begin and end coordinates on the reference genome, which can include icons to indicate the orientation; a link to a human gene mutation database report, if available; a corresponding protein ID (e.g., Celera Protein ID), the number of nucleotides and exons in the transcript; a Panther protein family classification; a link to best hits against one or more sequence databases (e.g., Celera and public databases); evidence; and/or a link to transcribed sequence for all exons.

The chromosome view (of which a representative example is shown in FIG. 10) can display one or more of the following information for a selected gene ID (for example, a selected Celera gene ID): corresponding gene symbol and/or gene alias (if available); begin and end coordinates on the reference genome, which can include icons to illustrate the orientation; link to human genome mutation database report, if available; corresponding transcript ID (e.g., Celera transcript ID); corresponding protein ID (e.g., Celera protein ID); and/or link to the gene sequence (e.g., the Celera gene sequence).

In some configurations of the present invention, a human gene mutation database (HGMD) report can be provided, as shown in FIG. 11. An HGMD report may include one or more of the following: corresponding gene name; link to corresponding OMIM record; links to SNP results (e.g., links to Celera SNP results), which may be made accessible only to subscribers; begin and end coordinates on the reference genome, which may include icons to indicate the orientation; HGMD classified mutation types; and/or mutations by HGMD phenotypes.

Some configurations of gene exploration platform 19 allow navigation of a genome by searching a genome map and/or by searching a genome assembly. For example, to search by chromosome number, some configurations allow a user to click on a "genome map" link (shown in FIG. 2), and respond by serving a "Search Genome Maps" web page, a representative example of which is shown in FIG. 11. In some configurations, a user can then select a chromosome from the "whole chromosome viewer" pull-down list. After selecting a chromosome from the pull-down list, the user can click "gene list" to view the list of genes for the selected chromosome, or click "map" to view the chromosome display.

In some configurations, the user can search by gene ID, gene symbol, and/or RefSeq ID. To do so from the web page shown in FIG. 11, for example, the user can select one of a number of ID types from a pull down list. The user can then type an ID for which to search in a text box, for example, "hCG14571" and select a flanking region from a pull-down list. A default value, for example, 0 Mb, may be provided. The user may then click on "gene list" to view the gene list results, or may click on "map" to view the chromosome display for the specified ID.

Some configurations permit a user to perform a search by cytogenetic band. In some of these configurations, the user can be presented with a "Search Genome Maps" page such as that shown in FIG. 12. The user can then type a begin value in the first "band" text box and an end value in the "to band" text box. A flanking region can be selected from the pull-down list, if desired. Next, the user can click on "gene list" to view the list of genes that exist between the two cytogenetic bands, or click on "map" to view the chromosome display for the specified region. Some configurations permit a user to perform a search for a single cytogenetic band. For example, in the "Search Genome Maps" page represented in FIG. 12, a user can type a value in the second "band" text box, select a flanking region from the pull-down list, and click "gene list" to view the gene list results, or click "map" to view the chromosome display for the specified band.

Some configurations permit a user to search by position on a chromosome. For example, in the "Search Genome Maps" page shown in FIG. 12, the user can select a chromosome from a pull-down list, type a begin value (e.g., in Mb) in the first "position" text box, type an end value in the "to position" text box, select a flanking region from the pull-down list (if desired), and click "gene list" to view the list of genes that exist between the two positions, or "map" to view the chromosome display for the selected region. In some configurations, a user can specify a single position by selecting a chromosome from the pull-down list, typing the desired position in the second "position" text box, selecting a flanking region from the pull-down list, and clicking on "gene list" or "map."

Some configurations allow a user to search for STS markers from, e.g., a radiation hybrid database (RHdb) or a database of sequence tagged sites (dbSTS). To search for a region bounded by two markers in some configurations, a user clicks on "genome maps" (see FIG. 2), and, in the "Search Genome Maps" page that appears (see FIG. 12), the user types an STS marker ID in the first "marker" text box. Searches for RHdb IDs and dbSTS IDs can be distinguished, in some configurations, by the user typing "RHn," where n can be the ID number, to search for an RHdb ID, or by the user typing "dbSTSn" to search for a dbSTS ID. The user then types an STS marker ID in the "to marker" text box, selects a flanking region from the pull down list, if desired, and clicks on "gene list" to view the list of genes that exist between the two STS markers, or on "map" to view the chromosome display for the selected region. In some configurations, to search for a single marker, the user follows a similar procedure, except that the user types the STS marker ID in the second "marker" text box and can be required to select a flanking region.

Some configurations of the present invention allow a user to search for a region between two BACs. For example, in the "Search Genome Maps" page shown in FIG. 12, the user may type a BAC ID in the first "BAC ID" text box, and a BAC ID in the "to BAC ID" text box. The user can then select a flanking region from the pull-down list, if desired. A default flanking region (e.g., 0 Mb) may be provided. The user then clicks on "gene list" to view the list of genes that exist between the two BACs, or on "map" to view the chromosome display for the specified region. In some configurations, the user may search for a single BAC by a similar procedure, except that the BAC ID can be typed in the second "BAC ID" text box.

Some configurations of the present invention provide a capability that allows a user to search a genome assembly by chromosome number or by genome assembly number to retrieve one or more of the following: a chromosome map report that can displays all scaffolds on a single chromosome; a scaffold report that can display all genomic assembly segments associated with a single scaffold; and/or a sequence report that can display a single genomic assembly sequence segment.

For example, in some configurations, to retrieve a list of all scaffolds on a single chromosome, the user can search by chromosome number to generate a chromosome map report by clicking on "genome assembly" on a page such as that illustrated in FIG. 2. A "search genome assembly" web page such as that shown in FIG. 13 can be then served from the server to the user's web browser. The user then selects a chromosome from the pull-down list. Optionally, the user may select a size from the "scaffold lengths" pull-down list to filter results, and/or the user may specify a target on the chromosome by typing values in the "position" and "to position" text boxes. After clicking "search," a chromosome map report appears.

Some configurations allow the user to search by genome assembly number to generate a scaffold report. For example, in the "search genome assembly" web page of FIG. 13, a genome assembly number can be typed into the "scaffold report" text box, and the user clicks on "search." A scaffold report then appears.

Some configurations allow the user to search by genome assembly number segment to generate a sequence report. For example, in the "search genome assembly" of FIG. 13, the user can type a genome assembly number segment in the sequence report text box and click "search." A sequence report then appears.

Some configurations of the present invention provide the user with the capability of finding genes by Panther families protein classification. Thus, some configurations provide a Panther protein function-family browser, which allows a user to perform one or more of the following: browse functional categories and protein families/subfamilies; text search functional categories or protein families/subfamilies; create a gene list; view the Panther tree for a given family; view the Panther multiple sequence alignment (MSA) for a given family; and/or view the Panther "Partial" MSA for a given family.

In some configurations, a Panther protein function-family browser can be made available when the user clicks on "Panther families" on the web page illustrated in FIG. 2. A representative example of a Panther protein function-family browser screen is shown in FIG. 14. This browser screen contains a "categories panel" and a "families panel." The families panel can also show subfamilies, as is illustrated in FIG. 14.

In various configurations, the browser may also provide facilities for accepting text searches (for example, the user might search for the text "kinase"), so that folders can be opened and categories containing the search term can be made visible (and can be highlighted, in some configurations). Some configurations also provide a sub-family search.

Some configurations of the present invention provide a Panther gene list. For example, a user can browse or text search to select desired protein families/subfamilies in the families panel, and go to a gene list listing all proteins assigned to the selected families/subfamilies. Various sorting and modification options can be provided, and export facilities can be provided (e.g., exporting the list to the user's local disk in a format suitable for other uses).

A Panther tree viewer can be provided in some configurations of the present invention. Panther distance trees allow users to explore the relationships between sequences in a particular family, and may also show some of the information used to annotate the families and subfamilies. In various exemplary configurations, the tree viewer has two panels that can be mapped to each other. One panel graphically displays the relationship between the different sequences. An attribute table contains one row for each sequence in the tree, and each column displays a different attribute of the sequence, such as the GenBank accession number for the sequence; the brief definition line parsed out of, for example, a SwissProt or GenBank record; the organism from which the sequence was derived; and/or links to open relevant abstracts from PubMed. In some configurations, the page also links to MSA views, and/or highlights selected subfamilies.

Some configurations also provide the user with a Panther MSA viewer. This viewer can be useful because Panther MSAs are used in producing Panther distance trees, and therefore, the family/subfamily classification. In some configurations, there can be two viewer modes: full MSA, which can include all publicly available sequences in the family that are related closely enough to produce an informative multiple alignment; and partial MSA, which shows the alignment only for the currently selected subfamilies. In some configurations, the MSA view can be divided into subfamilies in the same ordering as in the tree, so that the most closely related sequences appear closest to one another in the alignment. Also, some configurations of MSA viewers have two panels: an information panel, and an MSA panel. The information panel can contain information about each subfamily and sequence. This information may include hyperlinks to more detailed information. The MSA panel can display the multi-sequence alignment, which can be generated by aligning the sequences to the family hidden Markov model (HMM).

A Panther HMM alignment view can be provided. This view shows the query sequence aligned to the consensus sequence for the HMM. Also, a Panther family/subfamily hits view can be provided that shows all the Panther family/subfamily HMMs that hit a query sequence with a score better than a certain threshold.

In some configurations, certain genes (e.g., Celera genes) can be found by gene ontology protein classification. These configurations may provide either or both of a text search or a "drill down" search, for example.

To perform a text search in some configurations, a user clicks on "gene ontology" on the page illustrated in FIG. 2. An "ontology" page then appears. A representative example of an ontology page used in some configurations of the present invention is shown in FIG. 15. The user then types a search string into the ontology keyword text box and clicks on "find." An "ontology keyword results" page can be then generated and served to the user's browser. A representative example of an "ontology keyword results" page as can be produced in some configurations of the present invention is shown in FIG. 16. The user may then click on a link to drill down to the gene ontology (GO) classification list for that result. The user may continue to drill down until he or she accesses the desired category that also has a corresponding gene list link.

In some configurations, a user may drill down gene ontology classifications. For example, in some configurations, from the "ontology" page of FIG. 15, the user may select a species and a GO classification. The user can then drill down until he or she accesses the desired category that also has a link to a gene list.

In some configurations, GenBank human nucleotide sequences can be mapped to the human genome assembly (e.g., the Celera human genome assembly) using a combination of BLASTN and a modified version of the SIM4 algorithm. Also, some configurations map public sequences using repetitive hits (e.g., a sequence that maps to greater than 10 locations on the genome), orphans (e.g., a sequence fails to map to a genome), and best hit (e.g., if a sequence maps to between 2 to 10 locations, an attempt can be made to identify the best mapping.

Some configurations of the present invention provide browsing capabilities that permit a user to map public IDs (e.g., GenBank accession) to a human genome project (e.g., the Celera human genome) by searching a mapping database. In some configurations, for example, an ID mapper provides searching capabilities for one or more mapping databases, which may include GenBank DNA, GenBank mRNA, dbEST, and/or RefSeq.

In some configurations, text searches of data may also be performed by a user. For example, both Celera and non-Celera data may be searched by text.

Various configurations of the present invention can also include facilities for performing sequence analysis. For example, one or more of the following protein analysis types may be provided and made accessible to the user's browser window: BLASTP; TBLASTN; TFASTA; FASTA; PSI-BLAST; and/or HMMPFAM. Also, one or more of the following nucleotide analysis types may be provided and made accessible to the user's browser window: BLASTN; BLASTX; and/or TBLASTX.

Some configurations of the present invention provide workspaces that allow a user to start a new session, delete an entire session and its results, delete selected query results, rename a session, import session results, export session results, copy query results from one session to a different session, and/or perform additional queries from existing queries. For example, results can be exported to the user's local hard disk memory and re-imported for use later.

Computational System

In various configurations of the present invention and referring to FIG. 18, a computing system 20 comprising a plurality of computers 22, 26 may be utilized to distribute information, products and services such as the custom assays and/or stock assays described above, to a user or consumer 28. A first computer 22 (i.e., a distributor computer) on a computer network 24 (e.g., a public network, such as the Internet) interacts with a consumer 28 using a second computer 26 (i.e., a consumer computer) to obtain information that can be associated with a human or nonhuman target DNA (or RNA) sequence, which may include SNP and/or exon locations, i.e., the sequence itself, the SNP and/or exon locations themselves, or other information from which these items may be determined such as, for example, a gene name, accession number, etc. In some configurations, this interaction can be initiated by consumer 28 typing a uniform resource locator (URL) into a web browser running on consumer computer 26 and downloading a hypertext mark-up language (HTML) or other type of web page serving as a web portal (such as to which the user navigates in block 10 of FIG. 1) from a server 30 running on distributor computer 22.

The web page displayed on consumer computer 26 may include various types of introductory and sales information, provide a login for authorized user/purchasers, and solicit the DNA (or RNA) sequence and other information, as is necessary or desirable. In some configurations, the initial web page can be one of several web pages provided by server 30 that interact with consumer 28 to obtain information. For example, in some configurations, the initial web page accessed by consumer 28 can be a corporate web site that provides information for consumer 28 as well as a form in which consumer 28 types identifying information using consumer computer 26. Distributor computer 22 receives the information entered by consumer 28 and sent by consumer computer 26 via computer network 24.

In some configurations, distributor computer 22 verifies the identity of consumer 28 and his or her qualifications to access a sales page and to purchase assays from the distributor. For example, this verification may be performed by a web application server 32 (for example, the IBM® WEBSPHERE® Application Server available from International Business Machines Corporation, Armonk N.Y.) running on distributor computer 22 with reference to a consumer database 34 of qualified consumers and consumer identifications. If consumer 28 cannot be verified or is not qualified to make a purchase, this information may be returned by web application server 32 and web page server 30 via computer network 24 to consumer 28, and consumer 28 will not be allowed to complete a purchase and/or to access additional information.

Custom Assays:

Referring to FIGS. 18 and 19, various configurations of the present invention perform a method 44 for distributing a biotechnology product to a consumer. More particularly, the method includes utilizing a computer network 24 to interact at 46 with a consumer 28 to obtain information associated with (i.e., indicative of) at least one nucleic acid sequence. The target nucleic acid sequence obtained from the consumer can be, for example, a target RNA or DNA sequence, which itself may include an exon or a portion thereof, and/or a single nucleotide polymorphism (SNP). The information may further include information associated with a SNP location and/or an exon location. The provided nucleic acid sequence can be analyzed at 48 for format errors. If errors are detected, further interaction at 46 may be performed to correct the format errors. (In some configurations, prior to interacting at 46 with consumer 28 to obtain information comprising a nucleic acid sequence, consumer 28 can be required to verify his or her identity via computer network 24, and/or confirm his qualifications to place an order.)

Upon obtaining information from consumer 28, various methods of the present invention provide, at 50, a forward primer sequence, a reverse primer sequence, and a probe sequence having specified characteristics.

The forward primer sequence and the reverse primer sequence together define an amplicon sequence. The amplicon lies within the target nucleic acid sequence. The probe sequence can be complementary to a portion of the amplicon sequence. Next, in various configurations, one or more of the forward primer sequence, the reverse primer sequence, and the probe sequence can be validated at 52, using, for example, a genome database such as database 40. Validation may include BLASTing of one or more of the sequences, as described above. At least one assay can be manufactured at 54. The manufactured assay comprises a forward primer in accordance with the forward primer sequence, a reverse primer in accordance with the reverse primer sequence, and a probe in accordance with the probe sequence. In some configurations, the forward primer sequence, the reverse primer sequence, and/or the probe sequence can be a validated sequence from 52. The assay can be shipped at 58 to consumer 28. Some configurations of the present invention ship the assay in a single tube format with a two-dimensional bar code. In some configurations, the probe in the manufactured assay comprises a fluorescence quencher. The fluorescence quencher can be a non-fluorescent dye. In some configurations, the fluorescence quencher can be configured to reduce background fluorescence and increase quenching efficiency. The assay itself can be suitable for use in a sequence detection system, such as, for example, a real-time PCR system.

Some configurations test, at 56, the manufactured forward primer, the manufactured reverse primer, and/or the manufactured probe before delivery to verify that the assay meets specified characteristics. Tests at 56 may include, for example, performing mass spectroscopy on the manufactured assay to determine that an oligonucleotide sequence is correct, and/or performing a functional test to determine that an amplification has occurred and at least one allelic discrimination can be confirmed.

Figure 1:
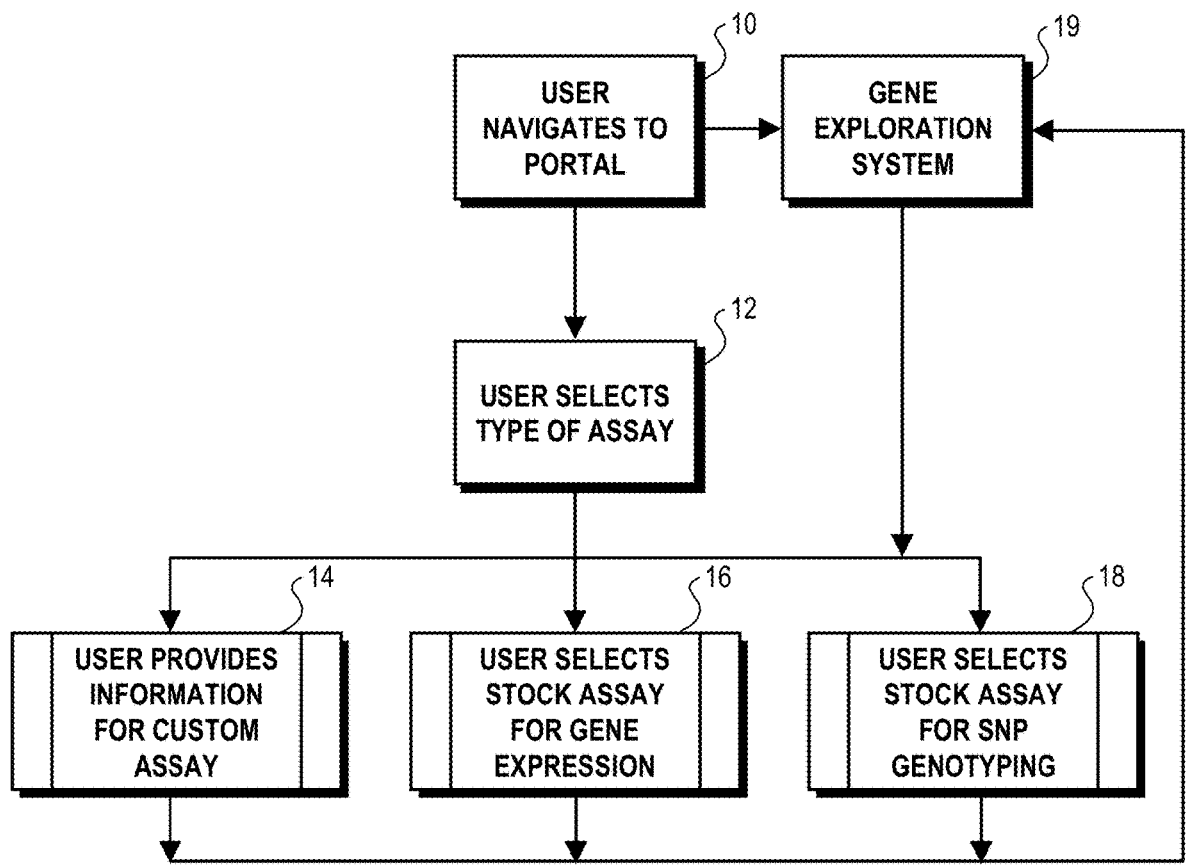
FIG. 1 is a block diagram representing one method of providing assays to a consumer according to one of the various embodiments of the present invention.

According to the various embodiments, if the user selects to obtain a custom assay at block 14 as shown in FIG. 1 (and, in configurations in which verification and/or qualification can be required, the user is verified and qualified), a window pane can be presented to the user which provides introductions to the user as to the manner of submission of an order for a custom assay. A non limiting example of one such window pane is shown in FIG. 20. In this regard, the user may be requested to follow certain procedures relating to: selecting the target sequence, assess the quality of the sequence, prepare the submission file, format the sequence for submission, prepare the order message, and submit the order by e-mail, by regular mail or over the internet. Each of these elements will be more fully discussed below with reference to FIG. 21.

As shown in FIG. 21, the user may, according to the various embodiments of the present invention, select the target sequence (60) for which an assay is to be delivered. There can be various factors which may be considered in selecting a target sequence. These factors may include: biological significance of the sequence, sequence length, sequence quality, uniqueness of sequence, and repetitive elements. With respect to biological significance, it will be appreciated that the quality assurance assays performed during the manufacture of the primer and probe as discussed herein may be used to determine whether the yielding content of the primers and probe meets specifications. For this reason, it may be desirable to initially determine whether the biological performance of the assay will accomplish the desired result.

With respect to target sequence length, in certain embodiments the length of the sequence can range from about 60 bases to about 5000 bases. However, larger and shorter sequences may also be used. Short sequences (e.g., fewer than 300 bases) may limit the number of potential assays that can be designed. For this reason, in some configurations, a sequence length of approximately 600 bases can be submitted, though increasing the sequence length may increase the number of possible assays. In addition, the sequence may be selected such that the target site can be directed towards the center of the submitted sequence.

In addition, a user can determine the quality of the sequence (62), e.g., to determine whether the sequence is unique in public databases when selecting the submission sequence. If there are similar versions of the sequence in a public database, how closely they agree can be a factor that can be used to determine the quality of the sequence. If other versions of the target sequence are different in public databases, it is possible to mask the ambiguous bases using N's as described below. Examples of databases with curated sequences include RefSeq (http://www.ncbi.nlm.nih.gov/LocusLink/refseq.html), which contains mRNA sequences, and dbSNP (http://www.ncbi.nlm.nih.gov/SNP), which contains SNPs. The NCBI RefSeq project provides reference sequence standards for the naturally occurring molecules of the central dogma, from chromosomes to mRNAs to proteins.

When ambiguous bases are determined to exist, it may be desirable to annotate the submission sequence to avoid ambiguous bases in the regions of the sequence used for designing assays. When an ambiguous base occurs, the ambiguous base may be substituted with an N. For example, if the lowercase bases in the sequence (SEQ ID NO: 18)
ACGTGACGTGACGTGACGTGACGTGGATcGTGggggTcCT are ambiguous, the lowercase bases can be substituted as follows:

(SEQ ID NO: 19)
ACGTGACGTGACGTGACGTGACGTGGATNGTGNNNNTCC

It may be desirable to minimize the number of substitutions of ambiguous bases with Ns. This is because the system does not include Ns in the primer or probe and therefore sequences with Ns reduces the number of available primer and probes from which to select the optimal assay. In addition, it may also be desirable not to have Ns that are too close to the target site. In this regard, it may be desirable not to have Ns within five bases of the target site when submitting sequences for gene expression assays, as well as 2 bases of the target site when submitting sequences for SNP assays. It will be understood, however, that a larger or smaller separation between the target site and the location of Ns may be used.

In various configurations, the user can, if desired, further assess the quality of the sequence (62) by determining whether unique primers and probes can be generated for the specific sequence. Various methods may be used to determine whether unique primers and probes may be manufactured. In one non-limiting example for determining whether a unique primer and probe can be generated for a DNA sequence a BLAST search tool can be used as follows. Such a BLAST search tool can be useful for determining the uniqueness of the target region. Using either the entire target sequence or a portion thereof, e.g. 50 bp upstream and downstream from a SNP a BLAST search can be performed (e.g. at the web site http://www.ncbi.nlm.nih.gov/BLAST). The BLAST search can detect regions with sequence similarities and repetitive elements.

After the sequence has undergone a BLAST search, the sequence can be run through a program such as Repeat Masker to detect common repetitive elements. Repeat Masker may be found at http://repeatmasker.genome.washington.edu. If many regions with similar sequences are located after running a program such as Repeat Masker, a filter may be used to limit the number of regions with similar sequences. For example, it may be useful to limit the search to human genomic DNA for SNPs or mRNA/cDNA for gene expression. It will be noted that the BLAT server at the University of California, Santa Cruz carries out searches using assembled genomic sequence. The BLAT server at the University of California, Santa Cruz, is located at http://genome.ucsc.edu/goldenPath/octTracks.html.

In another non-limiting example a user can assess whether useful probes and primers can be manufactured for a gene expression assay by performing a BLAST search of a target region which encompasses an exon-exon boundary. N's can be substituted for small regions of repeats, SNPs, and ambiguous sequences. If the target region is found not to be unique, a different exon-exon boundary can be selected and a BLAST search performed on a target region which encompasses the alternate exon-exon boundary.

After the target sequence has been selected but before the submission file is prepared, the sequence data again can be reviewed to determine whether sequence problems may cause failure in the assay design. As discussed above, these problems may occur if the sequences are too short, a low confidence in the sequence is present, the sequence is of poor quality, there are masked bases, too many Ns limit the design, and there are Ns too close to the target site for the probe. Each of these issues are discussed above.

After the user selects the target sequence at block 60, and assesses the quality of the sequence at block 62, the user can prepare the submission file which includes the relevant information for ordering the assay, such as the target sequence data from which the primers and probes can be designed. As a design choice, programs utilized in configurations of the present invention may impose formatting requirements on input data to simplify parsing of the input data. For example, a submission file in some configurations can contain a header line and one sequence record for each assay, and some configurations may require the submission file to be formatted in this manner. An example of a submission file for a SNP assay (showing SEQ ID NO:1, SEQ ID NO:3, and SEQ ID NO:4) with the header line and sequence records formatting according to exemplary formatting requirements can be as follows:

```
>JohnSmith 9997865432 partnumber4332072
seq_000001
AGTGAACG[A/G]GATAGGCA[G/T]CTOCTGCCC 1 = s33d,
2 = s33g seq_000002
TTACGGCCCTGA[G/T]GGGACTGC[G/C]ATCATTTTCT
1 = sn1f, 2 = sn3a seq_000003
GAGTGGAGCAACA[TAGC/]GCTTTCCGCAATTTAC 1 = 34d
```

Similarly, an example of a submission file for a gene expression assay, including a header line and sequence records, can be as follows (showing SEQ ID NO:2, and SEQ ID NO:5):

```
>JohnSmith 9997865432 partnumber4332079
seq_000004
AGTGAACGAGATAGGCAGCTCCTGCCCCATCCAAG 13 = m13,
20 = txyz seq_000005
TTACGGCCCTGAGGGGGACGAATCGATCATTTTCT 15 = tryk
```

According to various embodiments of the present invention, user 28 may prepare the submission file manually. Alternatively, user 28 may use a file builder program (described below) which queries user 28 for relevant information, automatically constructing the sequence file, and allows user 28 to upload the sequence file through the portal. As shown in FIG. 21, user 28 makes this selection at block 64.

Manual Preparation of Submission File:

If user 28 selects to prepare the submission file manually at 64, then user 28 prepares the submission file without using the file builder program. The structure of the submissions file will now be described. The contents of the submission file may vary depending on whether the assay being designed is to be used for creating a SNP genotyping assay or an assay which will be used for gene expression.

As discussed above, the submission file may contain two components: a header line and one or more sequence records. The header line contains information regarding the individual ordering the assay, and may have the same contents if user 28 orders one or more SNP genotyping assays or one or more gene expression assays. The header line of a submission file may contain one or more the following fields: a greater-than (>) symbol (or another symbol or token that can serve to identify the line as a header line of a submission file), a name field, a telephone number field, and a part number field. In some configurations, this formatting may be imposed as a requirement. In addition, also as a design choice, some configurations limit the header line to no more than 255 characters. The orientation of these fields in the header line is as shown in the FIG. 22. Also in some configurations, as a design choice, each sequence record may be limited to a single line regardless of length.

To create a header consistent with these formatting conventions, a standard text editor such as Microsoft® Notepad can be used. A greater-than symbol (>) can be entered as the first character, followed by the contact name and phone number. A part number can be then entered which is used to select the parameters of the resulting assay. In some configurations, part numbers can be assigned by the supplier that indicate a type of assay and a scale of synthesis. The supplier may, but need not, require separate submission files for each requested assay. In some configurations, SNP human assays, SNP non-human assays, and gene expression assays can be assigned different part numbers. Also in some configurations, different part numbers can also be assigned according to the scale of the assay. As a non-limiting example, in some configurations in which SNP human assays, SNP non-human assays, and gene expression assays are each supplied in three different scales, a total of nine different part numbers can be used.

A non-limiting example of part numbers and designations are shown in the tables reproduced below:

| Scale | Number of Reactions | | Part Number |
|---|---|---|---|
| | 25-μL Reaction 96-Well | 5 μL Reaction 384-Well | |
| SNP Human Assay Part Numbers | | | |
| V-Scale | 200 | 1,000 | 4331349 |
| S-Scale | 600 | 3,000 | 4332072 |
| A-Scale | 2,400 | 12,000 | 4332073 |
| SNP Non-Human Assay Part Numbers | | | |
| V-Scale | 200 | 1,000 | 4332077 |
| S-Scale | 600 | 3,000 | 4332075 |
| A-Scale | 2,400 | 12,000 | 4332076 |
| Gene Expression Assay Parts Numbers | | | |
| V-Scale | 140 | 360 | 4331348 |
| S-Scale | 300 | 750 | 4332078 |
| A-Scale | 1,160 | 2,900 | 4332079 |

It will be noted that in this example there can be only one part number for each record. Accordingly, a separate submission file can be created for each assay type or each scale which is desired. A completed header line may be varied so long as the general rules here are satisfied.

The sequence record contains the sequence data for designing the primers and probes and may vary depending upon whether the assay being requested is a SNP assay or a gene expression assay. If the assay is a SNP assay, then the sequence record may have the following fields as shown in FIG. 23: a record name field, a sequence field, and a coordinate field which provides the position and name for specific target site. The record name field may be a unique name to identify the sequence record and may be limited to no more than 10 characters in length as a design choice in some configurations. Also as a design choice, the record name field may be limited to containing only letters, numbers, underscore, hyphen or period character combinations with no spaces or tabs. In the example shown in FIG. 23, the record name is seq_000001. The sequence field may be used to contain the nucleic acid sequence with the SNP target site marked. In the example shown in FIG. 23, there are two SNP target sites: [A/G] and [G/T]. Configurations of the present invention can be permitted to require that the entries in the sequence field are in 5' to 3' orientation, that they contain no more than 5,000 characters, that there can be no tabs or spaces in the field, and the only characters that appear are A, C, G, T, or N, except where SNP or insertion or deletion target sites are indicated. Insertion or deletion target sites are sometimes referenced herein as "insertion/deletion" target sites or as "indel" target sites. Although an exemplary configuration is described that imposes these rules, other configurations may impose more or less restrictive rules and/or different rules. Configurations of the present invention can also be permitted to convert all lower case letters to uppercase to simplify processing of data.

Although other conventions may be used, configurations can be permitted to require that SNP target sites be indicated with square brackets around each site, with two sequences corresponding to the individual alleles separated by a forward slash. For example, ACAC[G/T]TCT can be denoted by two alleles: ACACGTCT or ACACTTCT. Also, configurations can be permitted to require that indel target sites be indicated with square brackets around each site, and that, within the brackets, base(s) present be indicated, followed by a forward slash and an asterisk, wherein the asterisk indicates a deletion. For example, ACAC[GA/*]TC can denote two alleles: ACACGATC or ACACTC. It will be noted that the indel target sequence can in various embodiments contain 6 bases in addition to the insertion/deletion base or bases.

Finally, the coordinate field identifies and names a marked target site. Configurations can be permitted to require that the target site be indicated in 5' to 3' order. Although other conventions may be used, configurations can be permitted to require that the coordinate field include the target site order position, an equal (=) sign, and an alphanumeric target site name of no more than four characters. Multiple coordinates may be specified in some configurations, and it can be permissible for these configurations to require that the coordinates be separated by commas without spaces. For example, in the sequence record shown in FIG. 23, the sequence record identifies two coordinates, one identifying each target site. In this regard, "1=s33d" identifies the first SNP target site from the 5' end, and resulting probe sequences can include CGAGA and CGGGA. In addition, "2=s33g" identifies the second SNP target site from the 5'end, and the resulting probe sequences can include CAGCT and CATCT. It will be understood, however, that the sequence record may contain any number of different fields of many different lengths.

In some configurations, only one assay will be synthesized for each record. The assay name associated with a particular assay that can be ultimately synthesized may be defined by the record name and coordinate. For example, in the sequence record shown in FIG. 23, the assay name associated with record "seq_000001" with the coordinate "1=s33d" may be "seq_00001-s33d". In addition, the assay name associated with the record "seq_000001" with the coordinate "2=sgg" may be "seq_000001-s33g".

As discussed above, configurations of the present invention can be permitted to require (or allow) that the format of a sequence record for a gene expression assay vary from the sequence record for a SNP genotyping assay. In this regard, the sequence record for a gene expression assay can include three fields: a record name field, a sequence field, and a coordinate field. The record name field may be a unique name that can be used to identify the sequence record. Configurations of the present invention can be permitted to impose restrictions on the unique name, for example, limiting it to no more than 10 characters. In the example of sequence record for a gene expression assay shown in FIG. 24, the record name is "seq_000004". The sequence field can be the nucleic acid sequence with the target sites unmarked. The coordinate field can be used to identify and name a gene expression target site. A convention that can be used, and which can be permitted to be imposed by some configurations of the present invention, is that the coordinate field include the target site nucleotide position, an equal sign and a target site name. Configurations of the present invention can be permitted to impose restrictions on the target site name, for example, that the name be alphanumeric and no more than four characters. Various configurations can allow multiple coordinates to be present and can require, for example, that multiple coordinates be separated by commas and no spaces. For example, in the sequence record shown in FIG. 24, there are two coordinates one for each target site. In this regard, "13=m13" identifies the 13$^{th}$ nucleotide from the 5' end, which is located at the center of the target sequence, and the resulting probe sequence can include AGATAGGCAG (SEQ ID NO:20). In addition, the coordinate "20=txyz" identifies the 20$^{th}$ nucleotide from the 5' end, which is located at the center of the target sequence, and the resulting probe sequence can include CAGCTCCTGC (SEQ ID NO:21). In this example, the txyz user-supplied coordinate can be selected for assay design and this can be added to the record name as a unique identifier to create a new record name, e.g., seq_000004txyz.

Sequence field information can be (and in some configurations, can be required to be) arranged in 5' to 3' orientation and it can be permitted in some configurations to limit the sequence field information to no more than about 5,000 characters. However, it is to be understood that the sequence field may have (or may be allowed to have) more than 5,000 characters in some configurations. By design choice, configurations may also require that there be no spaces or tabs between the characters, and that only permissible characters can be A, C, G, T, or N. Configurations can be permitted to automatically convert lowercase letters to uppercase, for example, for ease in processing.

Although not required, at least one coordinate in the coordinate field of the sequence record can contain the target position, an "equals" sign, and a target site name for each site. It is permitted to require that the coordinate field contain no spaces, and that multiple sites be separated by commas. As discussed above, at least one coordinate can be required for each sequence record. If a specific target site is not present, multiple sites can be selected across the sequence.

When entering sequence records, the record name can be entered according to the guidelines set forth above. A single space or a tab may then be entered followed by the sequence data also according to the guidelines discussed above. Another space or tab can then be entered followed by the coordinate(s) also set forth above, then the enter key can be depressed. These steps can be repeated for each sequence record.

In some configurations, File>Save can be selected to save the file as a text (i.e., ".txt") document. If Microsoft Notepad is being used on a Microsoft WINDOWS® 2000 operating system, ANSI encoding can be selected. Configurations of the present invention can be permitted to impose restrictions on the name selected for the saved file. For example, some configurations can require file names of no more than eight alphanumeric characters, and may require the extension .txt to be present.

After the file has been saved, a further check may be performed to determine whether the submission file satisfies the format requirement set forth in FIG. 25. A visual checklist for a gene expression assay submission files is set forth in FIG. 26.

Once the submission file has been checked for errors and is ready for submission, an order message can be prepared as indicated by block 70. The order message contains order information which includes the submission file and the part number listed in the header of the submission file. If more than one submission file is being submitted, the submission file and the corresponding part number for each submission file can be present. In addition, the order message can include either a purchase order number or credit card information with the name as it appears on the card, the card number and the expiration date. The order message can also contain contact details such as name, e-mail address, phone number, address and e-mail address of primary contact in case of difficulties with the submitted file. Shipping information can also be provided which can include identification of the person to receive shipment, for example, that person's name, address (including room number, building and department) and/or phone number. An invoice number and identification of a purchasing agent or person to receive invoice details may also be included, and such identification may include that person's name, address, e-mail address and/or phone number.

Once the submission files have been checked for errors, the submission file can be submitted to the system either by e-mail, by regular mail or by web access. If the order is to be sent by e-mail, the submission file can be attached to the order message and an indicia of the processing can be placed in the subject line of message. For example, the text "CA" may be placed in subject line to indicate that the order can be processed as a custom assay. The e-mail message can then be sent to the facility conducting the design process, for example an e-mail message sent to custom.assay@Company.com.

If the order is being submitted by regular or express mail, a copy of the order message can be included. The submission file may be placed on a machine readable medium, for example, a 3.5 inch floppy disk or CD ROM in a format readable on (for example) Microsoft Windows operating systems. The order message and submission file can be then submitted to the service using the invention.

File Builder:

To assist user 28 in preparing a sequence for submission to the custom assay system, various embodiments of the present invention include a file builder program to prepare the submission file as represented by block 74. The file builder program can be used for submitting sequences for SNP genotyping assays and for submitting sequences for gene expression assays. File builder program configurations of the present invention can include a DNA sequence checker as well as a text editor to facilitate building, editing, and correcting new as well as validating imported sequence submission files. Once the submission files are created using the file builder program, the submission files can be uploaded over the Internet to the system for synthesis or otherwise submitted. A file builder program may be resident on consumer computer 26, or it may be a web-based application or resident on the host computer.

Exemplary configurations of a file builder program will now be described in greater detail with reference to FIG. 27 and FIG. 28. When user 28 initiates an exemplary configuration of a file builder program at block 76, user 28 can select one or more options to facilitate the building of a submission file. It will be understood that options available in various file builder configurations may vary from those described herein. However, in some exemplary configurations, user 28 can initially select to learn more about the file builder program at block 78. If user 28 selects to learn about the file builder program at block 78, user 28 can be directed toward a set of instructions which can be either resident on consumer computer 26 or a web site that contains information regarding custom assay submission guideline protocol as indicated by block 80. An example of a window pane associated with one such tutorial is represented in FIG. 29.

In some configurations, user 28 can also select an option of viewing a file builder demonstration program at decision block 82. The file builder demonstration program shows how user 28 can complete the fields for preparing a submissions file using the file builder program (as will be described below). In this regard, the file builder demonstration program provides step-by-step instructions regarding the use of the file builder program to format an assay request. If user 28 selects to view a file builder demonstration at decision block 82, file builder demonstration program can be displayed for user 28 at block 84. As a design choice, some configurations of the file builder demonstration program may utilize Macromedia Flash. An exemplary window pane generated by the file builder demonstration program is shown in FIG. 30.

User 28 may also select to view the submission guidelines for preparing the submission file as indicated by decision block 86. If user 28 selects to view the submission guidelines at decision block 86, the file builder program displays at block 88 a file containing the submission guidelines in a suitable display format, one example of which is portable document format (PDF). An exemplary window pane showing the submission guidelines displayed at block 88 illustrated in FIG. 31.

User 28 can also select to build a submission file at decision block 90. If user 28 selects to build a submission file at decision block 90, user 28 can be directed to a series of window panes at block 92 that allow user 28 to enter header line information of the type described above. In this regard, user 28 at block 100 of FIG. 32 selects the part number associated with the SNP genotyping or gene expression assays. Additional information about the assay can be included with the part number, including one or more of the following: assay scale, e.g. V scale, A scale, or S scale, target species, e.g. human or non-human, assay concentration, and assay volume. In addition, user 28 can be requested to provide a first name, last name, telephone number and e-mail address of the person receiving the order. An example of a window pane that may be used for this purpose is shown as FIG. 33.

After user 28 enters the relevant header file information at block 100, the file builder program requests entry at block 102 of a sequence name which can be the name given by user 28 to the specific sequence. In addition, user 28 can also be requested to provide a target sequence as indicated by block 104. Finally, user 28 also provides at block 106 the target coordinates. An exemplary window pane for which this information can be entered, is shown in FIG. 34.

After the sequence name, target sequence and target coordinates have been entered, user 28 is able to validate the sequence (i.e., check for formatting and typographical errors) at block 108. User 28 may instruct the file builder program to validate the sequence by clicking on a "validate" button, such as that shown in FIG. 34. When user 28 chooses to validate the sequence, the file builder program reviews the text of the sequence for errors.

If the file builder program detects typographical errors in the target sequence, some configurations generate a window pane that indicates to user 28 that typographical errors are present. In the example shown in FIG. 34, there were two errors present, the number 2 and the number 5 being present in the sequence. The file builder program can provide suitable output to bring the errors to the attention of user 28, such as the output shown in FIG. 35. User 28 then has the option at block 110 of fixing either one or all of the errors in the target sequence information provided to the file builder program. After the target sequence errors have been corrected in block 110, an error message log can be generated at block 112 which further provides information on whether the sequence is formatted properly as described above. If the error message log indicates that there is an error in the formatting of information, user 28 can then fix the formatting errors at block 114. If the file is formatted properly, the error message log can indicate that the sequence record was validated. A non-limiting example showing a window pane in which information provided by that user 28 was successfully validated is shown in FIG. 36.

After the information from user 28 has been successfully validated, the information can be saved to disk as indicated by block 116 (see FIG. 37). It will be noted that the location at which the file is saved can be displayed by the file builder program, as can be the contents of the submission file (see FIG. 38).

By convention, files in some configurations can be saved with a file extension of ".txt". After the file has been saved, user 28 is able to upload the submission file at block 118 to the system by clicking on or depressing an appropriate button. Before or after user 28 has requested sequence information be uploaded to the system, user 28 may be requested to provide appropriate identification and password information. Configurations of the present invention can be permitted to make such identification mandatory. A non-limiting example of a window pane requesting such identification information is shown in FIG. 39. After user 28 has entered the appropriate identification and password information, the file can be uploaded to the ecommerce web site store. Once the submission file is uploaded to the store, user 28 may complete the order process at block 120. In some configurations, user 28 logs into the web site of the store using the same user identification and password and then chooses to proceed to the electronic shopping basket at which point the order can be displayed to user 28. User 28 can then review the order and continue shopping or proceed to process the order. In some configurations, the user will have identified more than one assay to be ordered and all of the identified assays can be ordered and added to the shopping basket. In addition, the user can place one or more assays in the shopping basket and then return to continue shopping and subsequently place one or more additional assays in the shopping basket.

In some configurations, if user 28 selects to process the order, the store provides stored contact and shipping information and asks that user 28 verify the information as well as provide any special instructions. User 28 can then verify payment information and place the order if all the information can be correct.

Returning to FIG. 18, in some configurations, a variant configurator 36 (such as SELECTICA® Configurator™, available from Selectica, Inc., San Jose, Calif.) interacts with consumer 28 via network 24 to produce a list of specified characteristics, as discussed below. Configurator 36 can be essentially an automated decision tree that produces the input for assay design program 38 and that ensures that input parameters to assay design program 38 are within bounds that can be handled by program 38. If there are no errors, assay design program 38 then uses a lookup process, a design process, or another suitable method to provide a forward primer sequence, a reverse primer sequence, and a probe sequence that have the specified characteristics.

Upon successful validation, oligo factory 42 accepts the order from consumer 28, manufactures at least one assay having components including a forward primer, a reverse primer and a probe and ships the manufactured assay to the consumer. The forward primer, reverse primer, and probe can be manufactured in accordance with the validated sequences.

In some configurations and referring to FIG. 40, an assay design system 122 can be provided as computer software that allows automated, high-throughput design of assays such as, for example, TaqMan® assays. The designed assays can in various embodiments, include primers and probes for allelic discrimination and gene expression assays in a batch format. This computer software can be particularly useful when designing hundreds or thousands of assays. Assay design program 38 can be a non-interactive pipeline of algorithms for the design of TaqMan® or other probe and primer reagents. In some configurations, heuristic rules can be utilized in assay design program 38. Pre- and post-processing utility programs and wrapper scripts can be utilized as components of the complete assay design system 122.

In various configurations, input to assay design program 38 includes a parameter file 126 that specifies design rules and one or more sequence data files 124. Output includes a log file 132 that reports system settings and attributes describing each successful reagent design (including probe, primer, and amplicon sequences). Additional output indicating a system status can be reported to a display screen as the program is running, in some configurations.

Sequence input file 124 can contain formatted and annotated sequence data. Parameter file 126 can contain keyword-associated settings that govern rules and scoring applied during designs. Prior to attempting any designs, the format of supplied sequence data can be checked at 128 for errors. If errors are found at 130 in the sequence data from input file 124, they can be reported to an error log 140 and the process can be terminated.

In various configurations, assay design program 38 starts by parsing parameter file 126 to set up rules and scoring schemes. If initialization errors occur, they may be caused by conflicting options or incorrect file names or formats. If there are any errors encountered during the initialization phase, they can be reported to log file 140 and assay design program 38 can then stop. Following successful initialization, assay design program 38 sequentially attempts to design assay sets for each target site in each sequence listed in the input sequence data from parameter file 126. As designs are processed, they can be recorded in a design log file 132. Design attempts that fail can also be recorded in log file 132. Design failures can occur when no acceptable set of reagents satisfying all rules and scores can be found for a sequence target.

If, at 134, there are no valid designs present in design log file 132, this fact can be reported in error report 140. Otherwise, following the core design process, design log file 132 may be used to generate output sequence data in a number of different formats. Log pick program 136 can perform this post-processing of design log 132 data to produce formatted outputs 138. A script can be implemented utilizing the UNIX operating system to integrate the whole system by tying together all of the processes shown in FIG. 40. The script can also log runs of process 122 and assign each output batch a serial number for tracking purposes.

Separate design rules and constraints can be applied to potential probes, primers, and amplicons. All designs resulting from a given run share a common set of rules. Probe constraints include limits on size (i.e., probe length), $T_m$ (target, minimum, and maximum temperatures), internal loops (total and contiguous matching bases in a "hairpin stem"), G+C content (i.e., combined G and C percentage), and runs of a given base, such as G. Analogous constraints can also be separately applied to primers, which have an additional limit on G+C at the 3' end (5 bases) of the primers. Constraints applied to amplicons include length (including primers), G+C content, and the number of ambiguous bases (note that ambiguous bases are generally not allowed within probes or primers). In addition, the primers defining amplicons can be constrained to limit the maximal size of internal priming sites (i.e., the number of contiguous matching bases starting at the 3' end of one primer that complements any part of the other primer).

For many of the constraints listed above, system 122 may apply either a filter or a score. When applied as a filter, a constraint will be either satisfied or not with the corresponding design being either accepted or rejected. When applied as a score, attributes may be given a graded value that reflects how "optimal" a given design is. For example, a design with all constrained attributes near optimum values will be favored over one with attributes deviating from the optimum values. Scoring provides finer tuning of the constraints that system 122 will use to evaluate and select designs.

Logic flow representative of some configurations of assay design program 38 is shown in more detail in FIG. 41. Upon starting program 38 at 142, an initialization phase 144 reads parameter data from parameter file 126 and sequence data from sequence data file 124. (As shown in FIG. 40, sequence data 124 may be checked for errors at 128 and 130 before being read by assay design program 38.) Initialization 144 includes parsing parameter file 126 and setting up for subsequent probe design. If any problems are encountered at 146 as a result of initialization 144, assay design program 38 reports a diagnostic message and stops at 150. Otherwise, processing continues. In some configurations of the present invention, most parameter file 126 options have default values and may be superceded by command line options. Options actually used during design can be reported in log file header 148, which is or becomes part of design log 132 of FIG. 40.

Various configurations of assay design program 38 attempt to acceptably design assay sets for each target site at 156. These designs can be logged at 158. An attempt can be made to identify acceptable designs at 160 for each input sequence record from sequence data file 124. When records are exhausted at 152, assay design program 38 is done at 150. Otherwise, for each record, each target can be tried at 156 in the order listed. If no target information is supplied, the sequence midpoint (if the sequence contains no SNP annotations) or the first SNP (if annotated) can be used as a target. When no targets are left for a given record at 154, assay design program 38 progresses at 152 to the next record.

For target sites, some configurations of assay design program 38 identify, at 160, successful and unsuccessful designs, according to the design metrics and scoring metrics. If program 38 fails to design for a target, this fact along with the corresponding unsuccessful design can be reported to log file 132 and the program progresses at 154 to the next target associated with the record. If it succeeds to design for a target, the details of the chosen record can be reported to log file 132. Normally, a single successful design causes assay design program 38 to move to the next record at 152. However, in some configurations, if an option to evaluate all targets listed for each record is enabled, assay design program 38 progresses, at 162, to the next target at 154 rather than to the next record at 152 following a successful design.

Representative logic for designing reagents for a simple target suitable for various configurations of procedure 156 is shown in more detail in FIG. 42. Upon starting at 164, design for record/target program 156 extracts design "windows" at 166, e.g., one or two subsequences around the target can be extracted. For SNP targets, two separate windows can be extracted at 166 around the SNP target site, one for each allele. In addition, any other SNP that is known to be within the sequence of the window can be masked by converting it to an N, which represents any nucleotide. For non-SNP targets, a single subsequence window can be extracted at 166. Windows can be limited in size by the supplied input sequence length or by the maximum allowable amplicon size. Problems encountered at 168 during window extraction (for example, an incorrectly formatted SNP annotation) cause a failure at 188. (In general, failures in this and other procedures or functions may be reported to the consumer and result in no product being shipped. Failures resulting from data that is improper, inconsistent, out-of-bounds, etc. need not be fatal. Thus, in various configurations, the software can be configured to reset itself after an order or failure therefore, to be ready for the next order.)

If no problems are encountered, placement of probes can be normally attempted next at 172, unless an option to design only primers is enabled at 170, in which case, execution continues at 176. (A primer-only option may be enabled, for example, by a command line option, such as "-op".) Probe placement at 172 yields either one or two acceptable probes (non-SNP and SNP cases, respectively), or not. If acceptable probes are not identified at 174, target design process 156 fails at 188. Otherwise, bounds can be set for primers at 176.

In some configurations of the present invention, to set primer bounds at 176, three sub-regions within the design window can be defined. In cases in which probes can be designed (e.g., cases in which not only primers are designed), a central mask region corresponding to coordinates of the probes can be defined. Bounds for the mask region may be explicitly designed relative to target site coordinates. For example, in some configurations, a command line option (such as "-pm") can be used to specify that the mask region is to be designed relative to target site coordinates. In this case, the actual mask region can be the larger of the specified bounds or the mask formed by the probes. Fixing the central mask region determines the two sub regions where primers may be designed. The "upstrand" sub-region begins at the start of the window and extends to the start of the mask region. The "downstrand" sub-region follows the mask and extends to the end of the window. The three sub-regions of the window (i.e., upstrand, mask, and downstrand) do not overlap.

With the upstrand and downstrand sub-regions determined, design procedure 156 attempts to collect a number of primers in each sub-region at 178. Forward primers can be taken from the upstrand region and reverse primers can be taken from the downstrand region. Potential primers can be evaluated at each nucleotide position starting from the coordinates closest to the mask (i.e., the end and start coordinates of the upstrand and downstrand regions, respectively). Such evaluation may, for example, determine whether a potential primer is acceptable according to standards known and recognized in the art. In some configurations, design procedure 156 collects up to ten forward and ten reverse primers, but by setting a command line option (such as "-np"), the limit of ten can be changed to another number.

If at least one potential forward and one potential reverse primer is not found at 180, design process 156 fails at 188. With two lists of primers, design process 156 next attempts to identify an acceptable forward/reverse pair at 182. If no acceptable primer pair is identified at 184, design process 156 fails at 188. Otherwise, a complete design has been found at 186.

The logic of a representative configuration of procedure 172 for placing probes in various configurations of the present invention is shown in more detail in FIG. 43. When a design attempt is begun at 188, a probe placement can be attempted. The logic follows slightly different but similar paths depending upon a determination of whether the target is a SNP site or a non-SNP site at 190. For SNP sites, sample sequences on both alleles of both strands can be considered at 194. For non-SNP sites, a determination can be made at 192 as to whether both strands or only a single strand is used at 194, 196, or 198. Explicit strands can be then determined at 200 or 204 and non-target strand probes can be eliminated at 202 or 206 to pick the best probe at 208 or 210. Features that can be used to pick the best probe can be determined on the basis of $T_m$ value and filter or score values. Minimal target overlap can be an input parameter. For non-SNP targets this value may be negative, allowing a larger sequence region to be sampled. For SNP targets, the minimum value of target overlap can be two bases, but the overlap may be increased. Probes targeting both forward and reverse strands can be evaluated. Probes may not start with G and normally the requirement that G content does not exceed C content can be applied, but an option can be provided to eliminate the G≤C rule. In some configurations, and in some cases, both forward and reverse strands can be considered explicitly for $T_m$ delineation. If probe scoring is being applied, the best scoring probe can be selected. Otherwise, the constraint satisfying probe most overlapping the target site can be selected. From this determination of whether a probe is acceptable or not at 212 or 214, probes can be selected that pass, at 216, or alternatively can be selected against, at 218, for failing the criteria.

For SNP target sites, sequences corresponding to both alleles (only bi-allelic SNP sites can be supported in some configurations) can be explicitly constructed and the best probes for both strands of both allele sequences can be identified as described above. An acceptable pair of SNP probes must target the same sequence strand. If acceptable probe pairs can be found for both strands, the strand yielding the pair with the largest total score can be selected. When input sequences have multiple SNP sites denoted, the non-targeted SNP sites can be masked (i.e., set to base N) when the sequences for each explicitly targeted allele are constructed.

If no acceptable probe (or, for SNPs, no acceptable probe pair) can be found for a given target, the system reports this fact and attempts to continue, depending upon the number and format of sequence targets supplied. If a single sequence is supplied as input, failure to select a probe (or pair) results in a program termination. If multiple target coordinates (or SNPs) are listed for a given sequence, failure to place a probe at one target coordinate causes probe placement process 172 to consider the next listed coordinate until all listed targets are exhausted. For multiple sequence input, failure to place a probe at any target coordinate leads the program to address the next listed sequence until all input sequences are exhausted. If there are multiple targets for a given sequence, whether or not a probe can be placed on any one individual target, all targets will be tested and the best design chosen.

Once a probe (or probe pair) sequence is selected, a list of upstream (forward) and downstream (reverse) primers can be delineated starting immediately before and after the probe position. These can be delineated via $T_m$ (in some configurations using a different algorithm than used for probe design), and filtered or scored. If SNP probe pairs can be being designed, primers are delineated starting immediately before and after the footprint corresponding to both SNP-targeting probe positions. At least one forward and one reverse primer must be identified. By default, up to ten forward and ten reverse primers can be collected, but the number of upstream and downstream primers may be changed, such as by using a command line switch. Failure to identify any forward or any reverse primers results in probe placement process 172 to report the problem and continue with the next target coordinate or next sequence as described above.

Forward and reverse primers can be checked for pair-wise compatibility and the corresponding amplicons can be filtered or scored. The compatibility check can include screening the 3' ends of the primers across the amplicon associated with a given primer pairing. If too great a 3' match is identified, the primers may not be paired. The pair of primers with the best score, by default, the shortest amplicon, can be chosen in some configurations of the present invention. Failure to select an acceptable primer pair results in probe placement process 172 reporting the problem and continuing as described above.

Acceptable designs comprising one or two probe sequences (such as, for example, probe sequences that can be used to make TaqMan® probes) together with corresponding forward and reverse primer sequences can be recorded in the log file. Along with the sequences, the coordinates, $T_m$ values, and scores may be reported for each probe and primer. Any associated auxiliary data (e.g., tracking information) loaded during sequence and target input may be also reported to the log file when a successful design is obtained. If no acceptable designs can be found for a target sequence, only the target name may be recorded in the log file.

Stock Assays: Gene Expression

In some configurations, custom gene expression products include off-the-shelf assays. In some configurations, assays can be provided for 15,000 genes based upon the NCBI Reference Sequence Database Project (RefSeq). In some configurations, off-the-shelf assays can be provided for about 30,000 genes (i.e., every human gene or almost every human gene). Various configurations use 5' nuclease chemistry with TaqMan® MGB probes and/or operate with universal formulation and thermal cycling parameters (for example, in some of these configurations, 900 nM primers, 250 nM probe). Some configurations provide assays designed utilizing a bioinformatics pipeline that includes private and public data, such as a combination of Celera data and Public data, or either private data or public data alone.

Gene Expression Assay Preparation:

In some configurations, gene expression assays include two unlabeled oligonucleotide primers and a single Taq-Man® probe (Livak et al., PCR Methods Appl 4:357-362) with an MGB moiety. Assay design can include transcript pre-processing, actual design of the primers and probe and in silico quality control prior to manufacturing the probe.

Pre-Processing:

In some configurations, certain sequence regions within the transcript can be identified in the pre-processing step for designing the oligonucleotide primers and probe for a 5' nuclease assay. For example, sequence regions may be selected that do not contain any known single nucleotide polymorphisms or repeat sequences. Also, 5' nuclease assays for gene expression may be designed across exon-exon boundaries, and thus, in some configurations, the position of each of the exon boundaries within a multi-exon transcript can be determined prior to the design of each assay.

In some configurations, transcript pre-processing begins once a batch of transcripts is compiled into a multi-fasta file. Repetitive and low complexity regions in each transcript can be masked (i.e. nucleotides replaced by an N) in some configurations. Repetitive sequences that can be masked include, for example, simple repeats (di- and tri-nucleotide repeats), Alu restriction site repeats, long interspersed nuclear elements (LINEs), and short interspersed nuclear elements (SINEs).

Exon-exon boundaries can be identified by mapping the masked transcripts to the human genome using alignment software. The positions of each exon-exon boundary can be marked for each multi-exon transcript, with single-exon transcripts being identified as such. Mapping may be performed against the Celera genome assembly, with supplemental mapping information provided by public sequence data. If sequence discrepancies are found between the public transcripts and the Celera genome during this step, the discrepant bases may be masked.

In some configurations, in the final pre-processing step, all known single nucleotide polymorphisms (SNPs) can be masked after performing a BLAST analysis against a genomic database using methods known in the art (see Altschul et al., J. Mol. Biol. 215:403-410, 1990). All of the known SNPs can be identified within each transcript. Both the SNP-masking and sequence discrepancy-masking steps can be useful in preventing oligonucleotide primer and probe assays from being designed over ambiguous or known variant nucleotide(s).

Assay Design:

The gene expression assay design can be based upon specifications as described above including optimal Tm requirements, GC-content, buffer/salt conditions, oligonucleotide concentrations, secondary structure, optimal amplicon size, and reduction of primer-dimer formation. As noted above, each gene expression assay can include, in some configurations, two unlabeled oligonucleotide primers and a single TaqMan® probe. The TaqMan® probes incorporate both an MGB and an NFQ at the 3' end of the oligonucleotide. The use of MGB probes increases the probability of designing an assay in traditionally difficult sequence regions (e.g., AT-rich sequences). Additionally, the relatively short MGB probes increase the probability that a probe can be designed over every exon-exon boundary of a multi-exon gene.

For transcripts from multi-exon genes an assay target position can be selected at each exon-exon boundary. The probe rather than one of the primers can be generally, but not always placed over the exon-exon boundary to ensure that the primers bind in two distinct exons. Placing the probe over the exon-exon boundary ensures that the primers can be in two different exons, and that fluorescent signal can be only generated from amplicons to which the probe can specifically bind and be cleaved. Assays designed over exon-exon boundaries can be designated by Hs********_m*, where the "m" indicates multiple exons.

For single-exon genes, both the primers and probe must be placed within the exon. Any assays that have the primers and probe placed within a single exon can, therefore, be designated Hs********_s*, where the "s" indicates a single exon. This designation provides an indication to users that there can be the potential to amplify contaminating genomic DNA in an RNA sample, and thus the appropriate experimental design controls can be implemented to avoid this problem.

For multi-exon genes, n−1 assays can be designed where n can be the number of exons. For transcripts from single-exon genes, multiple assays can also be designed by designating target positions that can be dispersed across the entire length of the transcript. The design of multiple assays for each transcript provides two advantages: 1) it increases the probability that a successful assay will emerge at the end of the entire design and quality control process, and 2) having assays that can be designed from the 5' to the 3' ends of every transcript provides great flexibility in the choice of a high-quality assay at any position on the transcript.

In Silico Quality Control:

In some configurations, after design, primer and probe sets are processed through a quality control step. This process penalizes, and thus helps to screen out: 1) assay designs that are not highly specific for the gene of interest, and 2) assay designs that may not accurately report the quantitative expression results for a particular target (i.e., an accurate threshold cycle (Ct) value) in a 5' nuclease assay.

In some configurations, the in silico quality control comprises three major parts, and each step generates a penalty score specific to a given assay design. A final penalty score for each assay design comprises the sum of each of the three individual penalty scores. The assay design with the lowest cumulative penalty score for each transcript can be the assay that can be chosen for manufacturing.

In some configurations, the three parts comprising the in silico quality control process include:

1) Transcript BLAST Scoring, which comprises determining the degree of homology, through BLAST, between the assay and other closely-related transcripts. A penalty can be assigned if an assay detects any closely homologous transcript(s) other than the intended target.
2) Genome BLAST Scoring, which comprises determining the degree of homology, through BLAST, between the assay and non-self regions of genomic DNA (e.g.

homologous genes and pseudogenes). A penalty can be assigned if an assay hits a second (or greater number) physical location on the genome in addition to the location of the gene-of-interest.
3) Determining the size of the intron across which the probe spans (for assays to multi-exon genes). A penalty can be assigned when the assay is designed across an exon-exon boundary that spans a small intron (for example, <2 Kb).

In various configurations, for all BLAST searches, a quality control query construct can be made by generating an amplicon sequence that includes each of the two primers and the intervening probe; the amplicon can be created by padding the specific number of nucleotides between the primers and the probe with N's (FIG. 44 and FIG. 45).

1) Transcript BLAST Scoring: The quality control query construct for each 5' nuclease assay can be BLASTed against transcript database(s) in some configurations to ensure that 1) each primers/probe trio in the quality control query sequence matches the target transcript sequence, and that 2) each assay can be specific for the gene of interest and will not amplify transcripts from other genes. Primers with homology to other genes (with an intervening homologous probe) can produce an unwanted fluorescent signal, and thus an artificially low Ct value. Primers to homologous genes (without an intervening homologous probe) may amplify homologous transcript(s) in addition to the target transcript and cause competition for reagents in the PCR reaction, resulting in an artificially high threshold cycle (Ct) value if the competing homologous transcript is expressed at high levels. These types of side reactions can skew the Ct for the gene of interest and thus produce an erroneous quantitative result for the target transcript. If homology exists, an assay can be assigned a penalty score based on the degree of homology to other transcripts. In some configurations, three sets of numbers can be reported in this transcript BLAST step as described below.

(a) BLAST Hit to Self (Transcript_SelfHSP):

The high scoring pair (HSP) from this BLAST can produce a match of 100% homology with self. This HSP represents the alignment of the quality control query construct to the target transcript in the transcript database, and shows a "0 0 0" (representing 0 mismatches in the forward primer sequence, 0 mismatches in the probe sequence, and 0 mismatches in the reverse primer sequence) result when BLASTed against the database from which the target transcript was retrieved (FIG. 46). If the quality control query construct has no hits against a particular transcript database, then the mismatch can be reported as an artificially high mismatch value (e.g., "50 50 50") and the assay can be flagged as being problematic.

(b) Continuous BLAST Hits to Non-Self Transcripts (Transcript_HomoHSP)

In this set of BLAST results the top non-self HSPs can be reported (i.e. BLAST results to homologous transcripts). The highest penalty can be assigned to the HSP that is the closest homolog but that is not a perfect match to the quality control query construct. If two HSPs have the same homology score to the query construct, then the one with the higher homology to the probe region can be chosen as the top hit.

This approach will skip all of the homologs that have a "0 0 0" match and will only report the top non-zero HSPs. Therefore, a primer/probe set that can amplify alternative splice variants for the same gene will not be penalized, since these alternatively-spliced transcripts may be present as unique transcripts within the database being queried. This step helps to ensure that assays can be gene-specific, but not necessarily transcript-specific.

Two or more highly homologous genes may end up with identical assay design in regions where the genes have identical sequence. In such a situation a transcript penalty can not be assigned (because of the "0 0 0" match). Situations in which an assay could detect transcripts from more that one gene can be penalized in a downstream part of the in silico quality control process when BLASTing can be done against the genome assembly (see below). Designing the process in this manner facilitates differentiation between an assay detecting an alternatively-spliced variant of the same gene versus an assay that detects a transcript from a different gene locus.

(c) Non-Continuous BLAST Hits to Non-Self Transcripts (Transcript_HomoHIT):

In some configurations, a BLAST query can be performed to analyze any alignments with high homology to each of the two primers, but which come from non-continuous regions of a homologous transcript. The quality control query construct hits two different (non-contiguous) parts (HSPs) of a non-self transcript. This BLAST result can be indicative of an amplicon from a homologous transcript being of a different size than the target amplicon. These BLAST results can be from two different HSPs (FIGS. 47, 48, and 49). The higher the homology between the primers and the HIT, the greater the penalty. A penalty can be assigned to minimize the likelihood of non-specific amplification of transcripts other than the target and thus competition for reagents in the PCR reaction that could affect the threshold cycle (Ct) of the target of interest.

2) Genome BLAST Scoring: In some configurations, the same quality control query construct that can be BLASTed against the transcript databases can also be BLASTed against the human genome assembly and the output can be reported in a similar manner. This quality control step avoids missing homologous transcripts that may not yet be known in transcript databases, facilitates, via genomic alignment, the distinguishing of different genes from alternative splice variants of the same gene, reduces amplification of artifacts due to the possible presence of contaminating genomic DNA in a total RNA sample, and penalizes those primers/probe that would amplify pseudogenes in total RNA samples that contain contaminating genomic DNA.

(a) Blast hit to self (Genome SelfHIT). As with the BLAST search to align the primers and probe to the target sequence in the transcript databases, similar BLAST searches can be used to align the primers and probe to the unique gene in the genome to which they were designed. For multi-exon genes the match must be "0 X 0" for the primer/probe set to avoid a penalty. The two zeros represent no mismatches between the forward and reverse primer sequences and the genome sequence, and the fact that they come from two different HSPs indicates that the primers can be on two different exons, separated by an intron. The non-zero value of X reflects the fact that the probe is interrupted by an intron, and thus does not align itself to contiguous sequence in genomic DNA. For single exon genes, the BLAST search alignment returns a value of "0 0 0" because there are no intronic regions to interrupt the probe sequences and lead to mismatches.

(b) Continuous BLAST hits to non-self gene(s) (Genome_HomoHSP): The Genome_HomoHSP BLAST results identify genomic regions that have high homology to the primers and probe, and can amplify a PCR product of similar size to the target transcript from contaminating genomic DNA present in an RNA template. This situation can most often occur because of the presence of a pseudogene in genomic DNA. This BLAST result identifies the HSP with the highest homology to the amplicon, with the focus primarily in the two primer regions. If two HSPs have the same degree of homology in the primer sequences, then the HSP with a higher homology to the probe region can be chosen as the top hit, and the degree of mismatch in the primers and probe can be used to generate the penalty. The higher the degree of homology between the primers and probe and the HSP, the greater the penalty. This, in effect, over-penalizing assays by assigning this genomic DNA penalty. However, this penalty can be applied in order to maximize the ability of an assay to accurately quantitate the target of interest in RNA preparations that may be contaminated with genomic DNA.

(c) Non-continuous BLAST hits to non-self gene(s) (Genome_HomoHIT): This genomic BLAST alignment identifies the genomic sequences that have the highest homology to each of the primers but come from two different HSPs. If the intervening sequence between the two HSPs is short, then the penalty can be high. This minimizes the chance of amplifying a non-target template in an RNA preparation with genomic DNA contamination. If the genomic interval between the two primers is large the penalty can be smaller because it is unlikely the primers can actually produce an amplicon from this type of secondary template.

As described above, there can be no penalty for non-self "0 0 0" hits in the transcript BLAST quality control step, and thus the Genome_HomoHIT BLAST results can be used to penalize assays that cannot discriminate between homologous genes. If two or more highly homologous genes have identical assays designed (for example, in a region where the two different genes have identical sequence) then the assays can be penalized at this step. If the Genome_HomoHIT results shows "0 X 0" hits at least one genomic location in addition to self, then the assay can be assigned a large penalty because it can be assumed that this second hit is to a separate and distinct gene.

3) Intron Size Scoring: The third part of the in silico quality control scoring process can be the determination of intron size for assays to multi-exon genes that have the probe spanning an exon-exon boundary. Although a penalty for small intron size can be integrated into the genome_HomoHIT rule, a separate rule also penalizes primer/probe sets that span introns of small size. This reduces the possibility of competition for reagents in RNA samples contaminated with genomic DNA, and also decreases the chance of amplifying incompletely spliced transcripts. The intron penalty can be based on the size of the intron: the larger the intron, the smaller the penalty.

Linking Assays to Transcripts:

A large number of BLAST searches against a variety of databases can be performed during the assay design process, as outlined above. In one non-limiting example, as many as about 100 BLAST results can be stored for each assay. The BLAST files that can be loaded into TaqDB contain the mismatch information resulting from the comparison of the primers and probe to these various databases. When there is a BLAST file showing a perfect match (0,0,0) to a transcript (this will, by definition, occur for the transcript from which the assay was originally designed) then a link can be created in the database between the assay and the accession ID of that transcript. When there are additional transcripts that perfectly match the primers and probe, they can also be added to the database and "virtually" linked to that particular assay. These links can be considered virtual because they can be links to transcripts that the assay was not originally designed to detect, but which it will detect. Alternative splice forms of a particular gene are the most common source of virtual links. Cross referencing all of the BLAST files with all of the assays in this manner allows the creation of many-to-many relationships between assays and transcripts, thus defining which transcripts an assay may amplify. As a result of this process, an assay can match multiple transcript accession IDs, for example, multiple RefSeq entries. In addition, other BLAST files that contain small mismatches can also be loaded into the database and linked to the assay as BLAST quality control data.

The assay-to-many-transcripts relationships can be displayed on the website online ordering system so that a researcher will have information on all of the transcripts an assay will detect, prior to purchasing the assay.

Remapping:

Transcript databases change over time inasmuch as new transcripts are continually being discovered, and occasionally entries that were originally thought to be transcripts can be found to be faulty and can be purged. In certain configurations, in order to keep the collection of assays current, BLAST searching can be used to map the assays to the new set of transcripts after a new transcript database is released (e.g., RefSeq is updated approximately every four weeks). This process keeps the information current through the identification of every known transcript that a particular assay can amplify, and it also allows the removal of any assay in the collection that no longer maps to the up-to-date transcripts. An additional benefit of the remapping process is that it is not necessary to design assays for every sequence in every transcript database. Rather one can often find a link from an existing assay to new sequences, and thus save time in delivery of assay products to researchers.

sequences. This in turn, decreases the failure rate in subsequent manufacturing, and results in better functional assays.

Evaluation of Designed Assays:

In a non-limiting example of an assay design process, over 16,000 RefSeq transcripts were run through the assay design process. From these transcripts, 13,633 assays were sent to manufacturing. There are 2000 transcripts for which no order was to manufacturing, and these assays fall into the following categories:
1. No assay designed
2. No designed assay passes the current penalty cut-off
   a. Intron size penalty (multi-exon genes only)
   b. Transcript penalty
   c. Genome penalty Although many of the assays that do not pass the in silico quality control standards may be suitable assays under certain circumstances, especially rigorous standards can be used in certain embodiments, to avoid manufacturing assays that have the potential to produce difficult-to-interpret quantitative gene expression results. There can be a variety of reasons why a designed assay may not be a robust assay for quantitative determination of mRNA transcript levels in a particular RNA sample. Thus, not all of these in silico quality control steps may be important to all users of an assay, but it can be, nevertheless desirable to provide the most robust quantitative assays that will fit the requirements of the entire spectrum of sample types and sample preparation methodologies utilized by the broad range of users of a particular assay.

Table 1 provides an example of how the process works, showing all of the assays designed across the exon-exon boundaries of the human plakophilin 4 (PKP4) mRNA (RefSeq ID NM_003628).

TABLE 1

| RefSeq ID | AssayID | Final Score | Assay Design Score | Intron Penalty | Intron Size | Transcript Penalty | Genomic Penalty | Status |
|---|---|---|---|---|---|---|---|---|
| NM_003628 | Hs00269305_m1 | High | High | 0 | >10 Kb | 0 | 0 | Ordered |
| | Hs00269306_m1 | High | High | 0 | >10 Kb | 0 | 0 | N.O. |
| | Hs00269307_m1 | High | High | 0 | >10 Kb | 0 | 0 | N.O. |
| | Hs00269308_m1 | mid | High | High | <200 bp | 0 | 0 | N.O. |
| | Hs00269309_m1 | High | High | 0 | >3 Kb | 0 | 0 | N.O. |
| | Hs00269310_m1 | High | High | 0 | >3 Kb | 0 | 0 | N.O. |
| | Hs00269311_m1 | Low | High | Low | >1 Kb | 0 | High | N.O. |
| | Hs00269312_m1 | Low | High | 0 | >10 Kb | 0 | High | N.O. |
| | Hs00269313_m1 | Low | High | 0 | >3 Kb | 0 | High | N.O. |
| | Hs00269314_m1 | Low | High | Low | >1 Kb | High | High | N.O. |
| | Hs00269315_m1 | Low | High | High | <200 bp | 0 | High | N.O. |
| | Hs00269316_m1 | Low | High | 0 | >2 Kb | 0 | High | N.O. |
| | Hs00269317_m1 | Low | High | 0 | >3 Kb | 0 | High | N.O. |
| | Hs00269318_m1 | Low | High | High | <200 bp | 0 | High | N.O. |
| | Hs00269319_m1 | High | High | 0 | >2 Kb | 0 | 0 | N.O. |
| | Hs00269320_m1 | High | High | Low | >1 Kb | 0 | 0 | N.O. |
| | Hs00269321_m1 | Low | High | Low | >1 Kb | 0 | High | N.O. |

Data Mining:

From failure analyses, it can be possible to recognize oligonucleotide sequences that can be problematic so that subsequently assays can be designed to be robust 5' nuclease assays. Thus, a database containing failed assay designs can provide a basis for improving the design process. For example, extracting the oligonucleotide sequences from assays that failed in the manufacturing process (e.g., quantitation, or analytical quality control) allows comparison of problematic sequences to identify commonalties. Certain types of sequences may tend to be difficult to manufacture and such difficult to manufacture sequences can be assessed a penalty for oligonucleotides containing such problematic As shown in the table, seventeen assays were designed for this transcript. Of the 17 assays designed, only the top-scoring assay that had no design penalties assigned was sent to manufacturing. However, there are six other candidate assays that met the manufacturing quality control cut-off for this particular target that can be chosen if for some reason the top-scoring assay fails along the downstream manufacturing and functional testing processes. Of the assay designs that did not pass the in silico quality control cut-off, one had a mid-level score because it was designed over an intron shorter than 200 bp. The rationale for this penalty score is that if the assay was being used to detect the transcript in a total RNA sample contaminated with genomic DNA, then the contaminating genomic DNA could be co-amplified with the mRNA target, potentially leading to inaccurate quantitation of the mRNA template. The likelihood of this occurring is low, since the primers are at 900 nM each in the final reaction and the probe does not detect genomic DNA, but these assays can be still penalized to provide a robust assay to the customers. Co-amplifying targets that do not bind to the probe will not interfere with quantitation when present in small amounts. Such targets can be often spiked into a reaction to serve as Internal Quantitation Controls (IQC) for quantitation (Furtado et al., N. Engl. J. Med. 340:1614-1622, 1999; Mulder et al., J. Clin. Microbiol. 32:292-300, 1994). Ten of the assays designed to the PKP4 target received a low final score because the primers/probe sequences for these assays exhibited high homology to at least one other portion of the genome. This penalty signals one of three possible situations: 1) that the domain which these exons encode is conserved and is present in other genes, 2) that there exists at least one pseudogene elsewhere in the genome, or 3) that there is random sequence at another site in the genome with very high homology to these particular exon sequences. Regardless of the reason, the potential exists for these low-scoring assays to generate less accurate quantitative results in a total RNA sample contaminated with genomic DNA than in a highly purified RNA sample. This points to the need for high-quality RNA template preparation upstream of any RT-PCR methodologies.

In some configurations, gene expression products ordered by a requestor on demand can be available from the supplier with a FAM label and the TaqMan® MGB probe technology, which utilizes a nonfluorescent quencher for improved sensitivity and quantitation precision. Addressing of the whole collection of human genes can be facilitated by advantageously utilizing the design flexibility of the shorter MGB probes. Also, in some configurations, TAMRA TaqMan probes can be made available to requestors by the supplier of customized products.

PCR efficiency of a given assay (or PCR reaction) can be defined as follows. An assay that results in a doubling of the amplicon with each PCR cycle has an efficiency of 100%. Efficiency can be of interest when using the comparative Ct method of quantification. One assumption in the equations used to calculate fold-differences by the comparative Ct method is that the assays/genes being compared must be of equivalent efficiency. A test can be conducted in some configurations to find outliers, i.e., assays of clearly poor efficiency, which may result from design as opposed to contamination. Subsets of genes designed and tested for high efficiency can be offered in some configurations.

Ordering Gene Expression Assays:

As discussed above, if the user desires at block 12 (see FIG. 1) to obtain stock assays for gene expression experimentation, the user can be directed through a series of inquiries at block 16 in which information regarding the nature of the gene expression assays can be collected.

In some configurations, custom gene expression assays made available for purchase may be selected by accession number (NCBI RefSeq ID) gene name, gene family, and/or functional groups and categories. For example, "Oncogene" is a category comprising three groups. For each group, some configurations provide a list of assays that a requestor can order as a set or individually. If a requestor does not find their particular gene expression assay of interest, the requestor can check back on a regular basis to determine if a new assay has become available for the gene expression of interest. Alternatively, a requestor may use the by design service. In some configurations, stock assays and custom assay designs can be made available for key splice variants. In addition, other search options and information associated with assays can be made available as desired.

A non-limiting example of a window pane which initiates the collection of information for gene expression assays is shown in FIG. 50. In this regard, the user can be provided with a description of a stock assay service for gene expression as well as the products which can be received upon submission of the information necessary to obtain the stock assay for gene expression.

Referring to FIG. 51, if, after viewing the overview of stock assay systems at 220, the user desires to obtain ordering information regarding stock assays for gene expression as indicated by block 222, ordering information can be then provided to the user at block 224. In this regard, the user can be provided with information regarding the contents of the assay which will be provided as well as technical information regarding the assay. In addition, information regarding the volume and reactions to produce can be provided as well as the necessary instrument platform. Part number information can also be available for the assay, as well as part numbers for related equipment. In one non-limiting example, the user can be informed of the components of the gene expression assays which will be received by the user. An exemplary window pane in which this information is provided to the user is shown in FIG. 52.

The user may also be able to request documentation from the system as indicated in FIG. 51 at decision block 226. If at block 226 the user requests documentation regarding gene expression assays, the system delivers documentation regarding the stock assay at block 228. This information may be brochures, product bulletins, user bulletins as well as other type of instructional or other information. This information may be delivered either via download, fax, e-mail or hard copy. A representative window pane illustrating the manner in which documents may be delivered to the user is shown in FIG. 53. In some configurations, the user may be able to select for delivery any number of the listed documents in any or all of the available formats for delivery.

Further, the user may also be able to request reference information at decision block 230. If the user requests reference information at decision block 230, the user can be provided at block 232 with reference information which may be links to publicly available databases. For example, the user at block 232 may be linked to the NCBI Reference Sequence Project (RefSeq) database. It is to be understood, however, that other suitable database may be referenced.

The user may also decide to search gene expression assays as represented by block 230. If the user decides to search gene expression assays at block 234, the user can be requested to accept certain terms and conditions of use for the assay search at block 240 (see FIG. 54). In addition to providing terms and conditions of use, the user can also be requested to provide information concerning the user such as name, institution, e-mail, phone number and/or address. In addition, the user can also be asked at block 240 whether the user would like information regarding products or services. A representative window pane is shown in FIG. 55.

If the user accepts the terms and conditions of use, the user can be directed at block 242 to a window pane which allows the user to search for stock assays for gene expression products. An exemplary window pane is shown in FIG. 56. The user can be then given the opportunity to search for gene expression assays by various techniques. For example, the user may at decision block 242 use keyword searching to find assays by searching for keywords such as gene name, gene symbol or gene ontology classification. If the user selects a keyword search at decision block 242, a keyword search can be conducted at block 244 as more fully disclosed below. The user may also decide to conduct a batch ID search at block 246 so as to find assays by searching for multiple accession numbers from public or private sources such as, for example, from Celera, Applied Biosystems or public databases. If the user selects to perform a batch ID search at block 246, a batch ID search can be performed at block 248 as will be more fully disclosed below. Finally, the user may decide to perform a classification search at decision block 250 to find assays by a suitable classification system such as the Celera Panther protein classification system.

If the user selects to perform a keyword search at block 242, the user may be able to perform either a basic or an advanced keyword search. If a basic keyword is to be performed, the user is able to select the search field in which the search is to be conducted, as well as enter a specific search term. The specific fields which can be searched include the non-limiting examples:

Gene Symbol
Gene Name
RefSeq Accession
Panther Function
Panther Process
GO Function
GO Process
GO ID
AB Assay ID
Celera gene (hCG)
Celera transcript (hCT)
Celera protein (hCP)
LocusLink ID
GenBank Nucleotide ID
GenBank Protein ID
Species
Chromosome
Cytoband
RefSeq GI A non-limiting example of a window pane which permits the entry of information for basic keyword searching is shown in FIG. 57.

If an advance keyword search is selected by the user, the user can insert search criteria for all of the fields described above. A non-limiting example of a window pane which permits entry of information for advanced keyword searching is shown in FIG. 58.

If the user determines that it is desirable to conduct a batch ID search at block 246, a batch ID search can be conducted at block 248. The batch ID search finds assays by using a list identification numbers. In this regard, the user is able to search by identification numbers from a variety of sources such as:

RefSeq accession number
GenBank Protein (GenPept) accession number
GenBank GI number
LocusLink
LocusLink gene symbol
Celera Gene (hCG)
Celera Transcript (hCT)
Celera Protein (hCP)
AB Assay ID The information can be entered in a number of formats such as, for example, the identification numbers can be separated by either a tab, carriage return, line return, comma or space. In addition, it is possible to upload a file containing the identification numbers, or identification numbers, such as a file which was previously exported following a gene expression search. An exemplary window pane which allows the user to enter information for a batch ID search is shown in FIG. 59.

Finally, the user may also be able to decide at block 250 whether a classification search, such as using the Celera panther classification system, is be conducted. The Celera Panther classification system is a system for classifying and predicting the functions of proteins in the context of sequence-relationships (see for example, U.S. Provisional Patent Application No. 60/433,431, filed Dec. 14, 2002, entitled "Methods for identifying, viewing, and analyzing syntenic and orthologous genomic regions between two or more species," which is hereby incorporated by reference in its entirety). Assays can be assigned to a Panther category based upon a match to equivalently assigned Celera gene data. The Panther categories can be constructed up to three levels deep with assay assignments at any one of the three levels.

If the user desires to perform a classification search at block 250, a classification search can be conducted at block 252. The user is then able to search by molecular function categories involving a property of the protein or of a particular biochemical reaction performed by a protein, such as receptor, kinase or hydrolase. In addition, the user may also be able to search by biological process categories involving the biochemical reactions that work together towards a common biological objective. The process can be at the cellular level, such as glycolysis and signal transduction, or at the system level, such as immunity and defense, in sensory perception.

An example of the manner in which a classification search at block 252 can be conducted is shown in FIG. 60. In this regard, the user initiates a classification search at block 256. After the user initiates the classification search, the user decides whether the classification is to be conducted with respect to molecular function or biological process at block 258. An exemplary window pane which allows the user to make this selection is shown in FIG. 61. If the user decides at block 258 to search by molecular function, then the user may be able to review a hierarchy of molecular functions until a set of assays can be presented to the user for the desired molecular function. In this regard, the user selects at block 260 a category of molecular functions. The processing then proceeds to block 262 to allow the user to decide whether the hierarchy search has been completed. This can occur if there are no further subclassifications within the category searched. For example, if the category of molecular function which is selected is "receptor", there are seven categories associated with this molecular function, including three subcategories (i.e., protein kinase receptor, cytokine receptor and ligand-gated ion channel receptor). An exemplary window pane showing the categories associated with the receptor molecular function is illustrated in FIG. 62. If at block 262, the user has decided to search a subcategory of molecular function, the user then selects another specific molecular function at block 260. For example, if the user selects the subcategory of "protein kinase receptor" as shown in FIG. 63, an exemplary window pane as shown in FIG. 64 may be displayed indicating the categories of protein kinase receptors. When the user has completed the hierarchal search at block 262, the user can then identify and order the assay at block 264.

Similarly, the user can select at block 258 to conduct a search based on biological processes. If the user makes the selection, the user selects one of a number of broad categories of biological processes which the system provides to the user at block 266. An exemplary window pane showing the biological processes from which the user may select is illustrated in FIG. 65.

After selecting one of the broad categories of biological process at block 266, the user determines whether the search hierarchy has been completed at block 268. If the user has not completed the search hierarchy (i.e., the relevant biological process displayed to the user contains subcategories), the user then again selects one of the subcategories at block 266. If the user has completed this search hierarchy at block 268, the user then identifies and orders the assay at 270.

A non-limiting example of a classification search relating to biological processes is shown in FIG. 66. In this example, if the user selects the biological processes associated with apoptosis at block 266, the user is presented with a window pane similar to that shown in FIG. 66. The user then may select the category associated with the particular field of interest and the assays associated therewith by clicking on the number associated with the number of assays column.

After the user inputs the search information, the results of the search can be provided to the user. One non-limiting example of a window pane providing results to the user is shown in FIG. 67. In this regard, the user can be provided with the assay ID, the RefSeq ID, the LocusLink gene name, function, process, Celera ID and location for the assays that satisfy the search criteria. The user may sort the results alphabetically by depressing any of the captions associated with each column. The window pane also includes check boxes allowing the user to select one or more particular assays which can then be added to the users "Shopping Basket" after login, for subsequent purchase. The user can also select one or more assays to be exported for purposes of, in non-limiting example, archiving or sequence comparison analyses conducted "off-line." A link can also be present which allows information regarding the associated gene to be obtained from third party or public databases, such as NCBI LocusLink. In addition, the user can obtain information concerning the molecular function and/or biological processes associated with the gene detected by the assay.

If the user selects a given assay, information concerning this specific assay can be presented in a manner similar to that shown in FIG. 68. In this regard, the information regarding the specific gene identification and location can be given as well as information regarding its biological significance. In particular, the information provided concerns both the molecular function as well as the biological processes which can be present.

In some configurations, endogenous controls can be available for relative quantitation of gene expression. For easy identification and ordering, the controls can be highlighted in the ordering system in some configurations.

Stock Assays: SNP Genotyping

In some configurations, at least 40,000 stock SNP genotyping products can be available. In some of these configurations, at least 77,000 such products can be available. In some of these configurations, at least 150,000 such products can be available, and in some of these configurations, at least 200,000 stock SNP genotyping products can be available.

In various configurations, SNP genotyping products can include, for example, 2 primers and 2 probes, each probe having a different label such as vic or fam, in a single tube, with or without assay information which can be provided on CD or other media. Various configurations can include some or all of the above.

In various configurations, at least 40,000 assays can be available using TaqMan® MGB probe technology under universal assay conditions. In some of these configurations, at least 150,000 such assays can be available, and in some of these configurations at least 200,000 assays can be available using TaqMan® MGB probe technology under universal assay conditions.

SNP Genotyping Assay Preparation:

In some configurations, SNP detection products include off-the-shelf assays. Various configurations use 5' nuclease chemistry with TaqMan® MGB probes and/or operate with universal formulation and thermal cycling parameters (for example, in some of these configurations, 900 nM primers, 250 nM probe). Some configurations provide assays designed utilizing a bioinformatics pipeline that includes private and public data, such as a combination of Celera data and public data, or either private data or public data alone.

The design of SNP genotyping assays can be similar to the design of gene expression assays in a number of aspects In some configurations, each SNP assay can include two unlabeled oligonucleotide primers and two TaqMan® probes, each probe having a fluorophore, a fluorescence quencher, and a minor groove binder. Assay design can include selection of SNPs for assay design in a pre-processing selection process, design of the primers and probes, and in silico quality control prior to manufacture of the primers and probes.

Pre-Processing:

In some configurations, certain sequence regions within the transcript can be identified in the pre-processing step for designing the oligonucleotide primers and probes for a 5' nuclease assay as described above for gene expression assay design. Repetitive and low complexity regions in can be masked (i.e. nucleotides replaced by an N) along with any SNP other than the SNP for which the assay is to be designed. Non-limiting examples of repetitive sequences which can be masked include simple repeats (di- and trinucleotide repeats), Alu restriction site repeats, long interspersed nuclear elements (LINEs), and short interspersed nuclear elements (SINEs).

SNPs can be identified in a gene region by performing a BLAST analysis against genomic databases using methods known in the art (see Altschul et al., J. Mol. Biol. 215:403-410, 1990), or can be identified in a SNP database (for example, the dbSNP database accessible at http://www.ncbi.nlm.nih.gov/SNP/). If discrepancies are discovered, discrepancy masking steps can be used to help ensure that no oligonucleotide primers or probes are designed over ambiguous nucleotide(s).

Assay Design:

The SNP assay design can be based upon specifications such as optimal Tm requirements, GC-content, buffer/salt conditions, oligonucleotide concentrations, secondary structure, optimal amplicon size, and reduction of primer-dimer formation as described above for gene expression assays.

In Silico Quality Control:

In some configurations, after design, primer and probe sets can be processed through a quality control step. This process, although conceptually similar to that described above for gene expression assays, involves quality control steps applicable to SNP genotyping assays as described below. The quality control step penalizes an assay at each phase of testing to generate a penalty score specific to a given assay design. A final penalty score for each assay design comprises the sum of each of the individual penalty scores. The assay design with the lowest cumulative penalty score for each SNP can be the assay that is chosen for manufacturing.

In some configurations, the in silico quality control process for SNP genotyping assays can involve genome BLAST scoring, which involves determining the degree of homology, through BLAST, between the assay and non-self regions of genomic DNA (e.g. homologous genes and pseudogenes). A penalty can be assigned if an assay hits a second (or greater number) physical location on the genome in addition to the location of the gene-of-interest.

For all BLAST searches, a quality control query construct can be made by generating an amplicon sequence that includes each of the two primers and the intervening probes; the amplicon can be created by padding the specific number of nucleotides between the primers and the probes with N's. The quality control query construct for each 5' nuclease assay can be BLASTed against a genomic database to ensure that 1) each primer/probe set in the quality control query sequence matches perfectly to the target SNP sequence (except for the SNP alleles in the probes), and that 2) each assay is specific for the SNP of interest and will not detect SNPs from any other regions of the genome. Primers with homology to other genes (with an intervening homologous probe) can produce an unwanted fluorescent signal, and thus mask the analysis of a true SNP. Primers to homologous genes (without an intervening homologous probe) may amplify homologous genes in addition to the gene comprising the target SNP and cause competition for reagents in the PCR reaction, causing spurious results. If homology exists, an assay can be assigned a penalty score based on the degree of homology to other SNPs. Two sets of numbers can be reported in this SNP BLAST step and are described below.

(a) BLAST Hit to Self.

The high scoring pair (HSP) from this BLAST can produce a match of 100% homology with self. This HSP represents the alignment of the quality control query construct to the target SNP in a SNP database, and shows a "0 0 0" (representing 0 mismatches in the forward primer sequence, 0 mismatches in the probe sequence (except for the SNP allele), and 0 mismatches in the reverse primer sequence) when BLASTed against the database from which the target SNP was retrieved. If the quality control query construct has no hits against any SNP in a SNP database, then the mismatch can be reported as "50 50 50" (an artificially high mismatch value) and the assay can be flagged as being problematic.

(b) Continuous BLAST Hits to Non-Self SNPs.

In this set of BLAST results the top non-self HSPs can be reported (i.e. BLAST results to homologous SNPs). The highest penalty can be assigned to the HSP that is the closest homolog but that is not a perfect match to the quality control query construct. If two HSPs have the same homology score to the query construct, then the one with the higher homology to the probe region can be chosen as the top hit.

Two or more highly homologous genes may end up with an identical assay design in regions where the genes have identical sequence. If two or more highly homologous genes have identical assays designed (for example, in a region where the two different genes have identical sequence) then the assays can be assigned a large penalty because it can be assumed that a second hit is to a separate and distinct gene.

Linking Assays to SNPs:

A large number of BLAST searches against a variety of databases can be performed during the assay design process, as outlined above. In one non-limiting example, about 100 BLAST results can be stored for each assay. The BLAST files that can be loaded into a database such as TaqDB contain the mismatch information resulting from the comparison of the primers and probes to these various databases. When there is a BLAST file showing a perfect match to a set of primers and SNP probes (this will, by definition, occur for the SNP from which the assay was originally designed) then a link can be created in the database between the assay and the accession ID of that SNP. When there are additional SNPs that perfectly match the primers and probe, they can also be added to the database and can be "virtually" linked to that particular assay. These links can be considered virtual because they can be links to SNPs that the assay was not originally designed to detect, but which it will detect. Cross referencing all of the BLAST files with all of the assays in this manner allows creation of many-to-many relationships between assays and transcripts, thus defining which SNPs an assay may amplify. As a result of this process, an assay can match multiple SNP accession IDs, for example, multiple RefSeq entries. In addition, other BLAST files that contain small mismatches can also be loaded into the database and linked to the assay as BLAST quality control data.

The SNP to genome relationships can be displayed on the online ordering system so that a researcher will have information on the SNP prior to purchasing the assay (see, for example, FIG. 76).

Remapping:

In certain configurations, BLAST searching can be repeated for SNP genotyping assays as updated SNP databases are released in a manner similar to that described above for gene expression assays. This process keeps the information current through the identification of every known SNP that a particular assay can amplify, and it also allows the removal any assay in the collection that no longer maps to the up-to-date SNPs. In addition, it can often be the case that a link from an existing assay can be found to new sequences identified in an updated SNP database, thus saving time in delivery of assay products to researchers.

Data Mining:

In certain configurations, as was described above for gene expression assays, analysis of assay design failures can be performed to provide information for improving the design process. This decreases the failure rate in subsequent manufacturing, and results in better functional assays.

Evaluation of Designed Assays:

In a non-limiting example of an assay design process, several hundred thousand SNPs were run through the assay design process. From these SNPs, over 100,000 assays were sent to manufacturing. There can be many SNPs for which no order has been sent to manufacturing, and these assays fall into the following categories:

1. No assay designed
2. No designed assay passes the current penalty cut-off

Although many of the assays that do not pass the in silico quality control standards may be suitable assays under certain circumstances, especially rigorous standards can be used in certain situations, to avoid manufacturing assays that have the potential to produce difficult-to-interpret results. There can be a variety of reasons why a designed assay may not be a robust assay for a SNP. Thus, not all of these in silico quality control steps may be important to all users of an assay, but it can be, nevertheless desirable to provide the most robust quantitative assays that will fit the requirements of the entire spectrum of sample types and sample preparation methodologies utilized by the broad range of users of a particular assay.

Ordering SNP Genotyping Assays:

If the user desires to obtain a stock assay for SNP genotyping products, the user selects this feature at block 12, as shown in FIG. 1. When a user selects a stock assay for SNP genotyping, the user can be directed through a series of inquiries at block 18 in which information regarding the nature of the SNP assay can be collected. An exemplary window pane, which provides the user with an overview of the Stock Assays for SNP genotyping products is shown in FIG. 69.

After the user reviews an overview of the stock assay system for SNP genotyping at block 272 (see FIG. 70), the user decides whether it would be useful to review ordering information at block 274. If the user desires to review ordering information, the system provides the user with ordering information at block 276. The ordering information includes the part number of the SNP genotyping product, as well as the contents of the assay. For example, the ordering information may include the following:

Pre-formulated Assays (187.5 µL, 20× mix)
    2 unlabeled primers
    1 FAM™ dye-labeled TaqMan® MGB probe
    1 VIC® dye-labeled TaqMan® MGB probe
Compact disk containing:
    Protocol
    Product insert hard copies of these documents can also be provided.
    Assay Information File containing: sales order number, well location, assay ID, vial ID, Celera ID, gene name, gene symbol, category, category ID, group name, group ID, chromosome, cytogenetic band, NCBI gene reference, NCBI SNP reference, SNP minor allele frequencies, SNP type, context sequence, reporter dyes
With each order:
    2-D barcode laser-etched on the bottom of each assay tube
    1-D barcode printed on each rack of tubes

| Instrument platform: | 7900HT | 7700, 7000 |
|---|---|---|
| Reaction volume: | 5 µL | 25 µL |
| Reactions/tube | 750 | 150 |

The user may also be able to also order documentation describing the SNP genotyping products. In this regard, the user selects to order documentation at block 278. If the user selects to order documentation at block 278, documentation relating to SNP genotyping assays can be provided to the user at block 280. In particular, the documentation can be provided by a window pane in a manner similar to that associated with gene expression assays (see FIG. 53).

In addition, the user may also be able to decide whether the user would like to receive reference information at block 282. This information may include the general steps for using SNP genotyping products as well as for providing general information regarding allele frequency. If the user decides to obtain reference information at block 282, the user can be provided with this information at block 284. In addition, the user may be able to search for assays used for SNP genotyping at block 286. If the user decides to search for assays at block 286, the user conducts a search at block 288.

Referring to FIG. 77, after the user accepts the terms and conditions of the search at block 292, the user can be then given the opportunity to search for SNP genotyping assays by various techniques. For example, the user may at decision block 294 use keyword searching to find assays by searching for keywords, such as gene name, gene symbol or gene ontology classification. If the user selects a keyword search at decision block 294, a keyword search can be conducted at block 296 as more fully disclosed below. The user may also decide to conduct a location search at block 298 so as to find assays. If the user selects to perform a location search at block 298, a location search can be performed at block 300, as will be more fully disclosed below. Finally, the user may decide to perform a batch ID search at decision block 302 to find assays by searching for multiple accession numbers from public or private sources such as, for example, from Celera, Applied Biosystems or public databases. If the user selects to perform a batch ID search at decision block 302, then a batch ID search can be performed at block 304. Finally, the user may decide to exit the system at block 306.

If the user decides to perform a keyword search at block 294 with respect to SNP genotyping, the user is able to search by selective fields for select terms. The specific fields which may be searched can be as follows:
    dbSNP rs#ID
    dbSNP ss#ID.
    Gene Symbol
    LocusLink Gene Name
    RefSeq Accession
    AB Assay ID
    Celera SNP (hCV)
    Celera gene (hCG)
    Celera transcript (hCT)
    Celera protein (hCP)
    Chromosome
    Cytoband
    LocusLink ID In addition, it is possible to filter the search by the specific SNP type which include:
    acceptor splice site
    coding region
    donor splice site
    intergenic/unknown
    intron
    mis-sense mutation
    nonsense mutation
    putative utr (untranslated region) 3
    putative utr 5
    repeats
    silent mutation
    utr 3
    utr 5

In addition, it is possible to search all these SNP types together.

In addition, the system also permits the use of a filter to exclude 10 kb flanking sequence. For a given gene, all the RefSeq sequence data associated with the gene in LocusLink are mapped on the genome. A gene may be defined as the furthest 5' and furthest 3' base of RefSeq sequence data associated with the gene. When searching on gene-related fields, the user may choose whether to include or exclude 10 Kb flanking sequence. Accordingly, when the system searches it can include up to 10 Kb of upstream sequence and downstream sequence in the query. This filter can be valid for the following fields:
    Gene Symbol
    LocusLink Gene Name
    RefSeq Accession
    Celera Transcript (hCT)
    Celera Protein (hCP)
    Celera Gene (hCG)
    LocusLink ID In certain configurations, the system will ignore this filter if the user searches on fields not listed above. If searching for SNP assays by Celera Gene (hCG) ID, a user can select a search within a gene by setting a search filter at 0 Kb or within a gene region which includes 10 Kb of 5' and 3' flanking sequence. An exemplary window pane permitting the user to perform a keyword search with search filter is shown in FIG. 71.

Alternatively, it can also be possible to perform an advance keyword search in which search terms can be placed in one or more various field for SNP genotyping as described above. An exemplary window pane allowing the user to perform an advanced keyword search is shown in FIG. 72.

In addition, the system also allows users to select ranges of Caucasian and African-American minor allele frequency. The allele frequency indicates the number of occurrences of an allele seen in the total number of chromosomes sequenced at the SNP site. The allele frequency for stock assay SNP genotyping products may be obtained from 90 individual human genomic DNA samples, 45 African-Americans and 45 Caucasian from the Coriell Human Variation collection. The samples can be run in a validation laboratory in order to ensure that every SNP provided in the stock assay SNP genotyping product is polymorphic and that the allele frequency can be adequate for association studies in a variety of populations. The results obtained from such a validation step also allow inference of haplotype blocks and the analysis of the extent of linkage disequilibrium among these makers. A selection and validation criteria for a set of SNP Genotyping Assays is described in Francisco de la Vega, et al., "Selection of Single Nucleotide Polymorphisms for a Whole Genome Linkage Disequilibrium Mapping Set". To access the poster, go to www.allsnps.com.

When the user selects to search by location at a block 298, the user initially selects the mapping type and relevant identification information at block 300. In this regard, the user can select the assay by SNP, gene or marker location within a given range. Alternatively, the SNP assay may also be determined on the position of the chromosome. This can be done by initially selecting the available chromosome and then the position within the chromosome, which may be reported in units of megabases. Alternatively, the SNP assay may be determined by location using ABI PRISM® Linkage Mapping Sets v2.5. ABI PRISM® Linkage Mapping Sets v2.5 consist of 811 fluorescent-labeled PCR markers selected to amplify high informative two base-pair repeat microsatellite loci. These markers can be arranged in two sets to provide coverage of the human genome at 5 $C^M$ and 10 $C^M$ average resolution. The markers can be from the 1996 Genethon Human genetic map and were selected based on chromosomal location and heterozygosity. More information regarding ABI PRISM® Link Mapping Sets v2.5 can be obtained from Applied Biosystems.

After the mapping type and identification information has been entered, the user also has the opportunity to select flanking region display results. A flanking region of 10 Kb can be selected, or alternatively, the system can be configured so that the user can select 0 Kb, 100 Kb, 500 Kb, and 100 Mb. Finally, the user may be able to filter the results using Caucasian and African-American minor allele frequency as well as SNP type. An exemplary window pane allowing the user to search by location is shown at FIG. 73.

Finally, the user can also decide whether to search for SNP genotyping assays using a batch ID search at decision block 302. In this regard, the user enters a valid ID type into the system at block 288. The valid ID types can be, for example, one or more of the following:

dbSNP reference cluster or assay ID
Celera hCV
AB Assay ID
LocusLink gene symbol
RefSeq accession number
Celera Gene (hCG)

Alternatively, the user can upload a file on the user's computer from a previously exported results from a SNP genotyping search. In this case, if the file contains a list of identification numbers, each of the identification numbers can, in various embodiments, be separated by a tab, a carriage return, a line return, a comma or a space. If the user selects to use previously exported assays results, then a tab delimited file resulting from the stock assay export feature may be used. An exemplary window pane allowing the user to conduct a batch ID search is shown in at FIG. 74.

The results from a SNP genotyping assay search can be provided to the user in a manner similar to that described above for gene expression assays. One non-limiting example of a window pane providing results to the user is shown in FIG. 75. In this regard, the user can be provided with the dbSNP ID, the LocusLink gene location by name and symbol, the absolute position, the distance to the next SNP, the main minor allele frequency in Caucasians and African-Americans as well as the Celera ID. The window pane also includes check boxes which allow the user to select one or more particular assays for order by added those assays to the users "Shopping Basket". In addition, the user can also select one or more assays and information related to the assays for export and for further in silico work such as, in the non-limiting examples, archiving or sequence comparison analyses or for linkage to genomic databases such as NCBI LocusLink.

If the user selects a given assay, information concerning this specific assay can be presented in a manner similar to that shown in FIG. 76. In this regard, data can be provided such as the specific gene associated with the assay, the gene's location, as well as information pertaining to the gene's biochemical and biological functions.

High Capacity Manufacturing

In various configurations, high capacity and high throughput equipment can be used for oligonucleotide synthesis and validation. Manufacturing activity can be process driven with well defined and validated procedures for every step in the manufacturing process.

DNA synthesizers are well know in the art. A DNA synthesizer may be used to manufacture oligonucleotides beginning with a primary residue which is the 3'-most nucleotide, anchored to a solid support. Each additional nucleotide can then be added in the desired order to assemble the nucleotide chain while proceeding in the 3'-to-5' direction.

Phosphoramidite chemistry may be employed for the addition, although alternative chemistries such as the H-phosphonate method can be used (for review see Brown et al, "Modern machine-aided methods of oligonucleotide synthesis", in *Oligonucleotides and Analogues a Practical Approach*. Ed. F. Eckstien, IRL Press, Oxford UK, 1995). Four steps are performed in the synthesis. The first base is attached to a solid support which can be typically controlled pore glass, via an ester linkage to the 3'-hydroxyl of the base. The 5'-trityl blocking group of the base can be then cleaved to initiate synthesis using brief treatment with an acid such as, for example, dichloroacetic acid or trichloroacetic acid in dichloromethane. The next monomer of the oligonucleotide being synthesized is then added in the form of a DNA phosphoramidite in tetrazole and coupled to the available 5'-hydroxyl group of the first base. The resulting phosphite linkage is then oxidized to phosphate by treatment with iodine in an aqueous solution containing THF and pyridine to complete the first cycle of oligonucleotide synthesis. This can be then repeated for each base being added.

The DNA synthesizer used in some configurations of the present invention can be capable of producing oligonucleotides in amounts of about 40 nmol, about 0.2 μmol or about 1 μmol. In various configurations, a DNA synthesizer can be used that can produce at least about 100, at least about 200 or more primer length oligos in 40 and 200 nmol amounts over a period of about 10 hours.

The DNA synthesizer used in some configurations of the present invention can also be capable of attaching appropriate fluorophores or quenchers to probes after synthesis.

For SNP assays based upon TaqMan® methods, probes and primers can be synthesized for performing TaqMan® assays. In certain embodiments, two TaqMan® MGB probes can be designed and manufactured to distinguish between two SNP alleles. Each TaqMan® MGB probes contains, in some configurations a reporter dye at the 5' end of each probe. The reporter dyes can be any of a number of suitable dyes, such as, for example, a VIC™ dye or a b-FAM™ dye. Thus, for example a VIC™ dye can be linked to the 5' end of a first probe specific for one allele of a SNP and a 6-FAM™ dye can be linked to the 5' end of a second probe specific for the second allele for use in a given assay. An MGB, as described above, can also be included in each probe. This increases the melting temperature ($T_m$) without increasing probe length, thereby permitting the design of shorter probes. The use of MGBs results in greater differences in $T_m$ values between matched and mismatched probes, which produces more accurate allelic discrimination.

In certain other configurations, probes and primers of gene expression assays can be synthesized. In some configurations a reporter dye can be attached at the 5' end of each probe. The reported dye can be any suitable dye, for example, a dye such as a VIC™ dye or a 6-FAM™ dye. An MGB, as described above, can also included in the probe. Thus, for example, one FAM™ dye-labeled, TaqMan® MGB probe can be synthesized along with two target-specific primers for use in a given assay.

In certain aspects, a quencher can also be attached to the probes for both SNP and gene expression assays. The quencher, in various configurations, can be an NFQ attached to the 3' end of each probe.

In various configurations of the present invention, the synthesized oligonucleotide can be subjected to purification methods which may include, for example, polyacrylamide gel electrophoresis (PAGE) for oligonucleotides of greater than 50 bases in length and high performance liquid chromatography (HPLC) for oligonucleotides of less than 50 bases in length. A typical anion-exchange HPLC profile of a 23-mer is shown in FIG. 78, which shows that 90% of the output product can be the full-length oligonucleotide.

The DNA synthesizer used in some configurations of the present invention can be coupled to a computer which allows conditions to be set for automatic performance the DNA synthesis.

In some configurations of the present invention, the DNA synthesizer used can be capable of synthesizing DNA oligonucleotides with rapid cycle times, low reagent consumption and reliability. One such high-capacity, high-throughput DNA synthesizer suitable for use is the commercially available ABI 3900 DNA Synthesizer (Applied Biosystems, Foster City, Calif.).

In various configurations, a large number of at least 10, at least 20, at least 50, at least 70 or more DNA synthesizers can be employed in the manufacturing facility. Multiple manufacturing facilities can also be used and the production of oligonucleotides in the individual facilities can be coordinated if desired. The multiple manufacturing facilities may be located in strategic geographic sites so as to efficiently supply a world-wide market.

Post-Manufacturing Validation and Quality Control

In various configurations of the present invention, selected quality checks can be performed by the supplier. Quality checks may include synthesis yield, analytical quality control (which may be performed, for example, using mass spectrometry), functional testing and validation testing. Validation testing can be performed on the manufactured assay prior to delivering to the consumer to verify that the assay meets the specified characteristics. If the assays do not meet the quality check or checks, they may be resynthesized before shipping or other appropriate corrective action taken before the assays are shipped to the requestor. The testing may include confirming that a synthesized oligonucleotide sequence is correct by testing primers and/or probes individually by mass spectroscopy, and/or, for human SNP assays, functionally testing using human genomic DNA to confirm that amplification occurs and at least one allelic discrimination cluster (heterozygous or homozygous, compared to no template controls).

Synthesis Yield Testing:

In various configurations, each component that makes up an assay. i.e. probes and primers, can be tested for yield after synthesis. Such testing can be done as part of the purification process and any suitable method known in the art can be used including PAGE and HPLC. Ion exchange HPLC can be, in various configurations, used for oligonucleotides having a length of less than about 40 to about 50 bases. Such anion exchange HPLC can be performed as an integrated function of the ABI 3900 DNA Synthesizers (see FIG. 78 for HPLC percent yield plot).

In various configurations, individual components of assays must meet a minimum yield specification. Such minimum yield specification may be, for example, at least about 60% (w/w), at least about 80% (w/w), at least about 90% (w/w) or at least about 95% (w/w) or greater expressed as the weight of the desired oligonucleotide to the total weight of the synthesis product multiplied by 100. The particular percent yield set as the minimum yield specification will depend upon the application, however, typically at least about 90% yield is desirable. Low yield synthesis reactions, i.e. reactions producing less than about 40%, less than about 80%, less than about 90% or less than about 95% can be rejected in some configurations of the present invention.

In certain aspects, the synthesis yield testing can be performed for each of the probes and primers of every assay.

Analytical Quality Control:

In various configurations, each of the probes and primers can be individually tested to ensure the accuracy of its sequence. Any method known in the art can be used to validate the sequence accuracy of the probes and primers. One such method used in some configurations of the present invention and which is adaptable to high-throughput manufacturing and validation is mass spectrometry. Mass spectrometry is an analytical tool that detects ions and measures their mass to charge ratio. Ionization techniques such as matrix assisted laser desorption-ionization and electrospray ionization allow the measurement of high molecular weight molecules such as DNA. The matrix assisted laser desorption ionization coupled with time of flight mass spectrometry (referred to as MALDI-TOF) allows high-throughput analysis of DNA molecules. One such mass spectrometer suitable for use in analytical quality control is the commercially available ABI Voyager-DE™ STR MALDI-TOF Mass Spectrometer (Applied Biosystems, Foster City, Calif.)

In various configurations, the DNA sample can be mixed with an organic matrix and co-crystallized on a sample plate. A fixed, pulsed laser beam then irradiates the sample plate. The matrix absorbs and transfers the laser energy to the DNA to produce an ionized gaseous phase. An electric field then accelerates the ionized DNA molecules according to their mass such that molecules of smaller mass are accelerated faster than molecules of larger mass. Thus, the mass of the DNA molecule can be determined.

The measured mass can be then compared to the calculated mass of the probe or primer. The probe or primer must be of the same mass as calculated or within acceptable deviation to pass specification. Acceptable deviations in various configurations of the present invention can be, for example, such that the actual mass of the DNA molecule may be not more than about 1%, not more than about 2%, not more than about 5%, not more than about 10% or not more than about 20% greater or lesser than the calculated mass.

In some configurations, this analytical quality control test can be performed for every assay.

Functional Testing:

In various configurations of the present invention, functional testing can be performed on the assays as well, however, different functional tests can be performed on the SNP assays and gene expressions assays in some configurations.

SNP Tests:

In various configurations, all human SNP assays can be tested on samples from a panel of at least 10 to 20 human genomic DNA samples. A sequence detection system capable of performing the assays of the present invention can be used. In some configurations, the sequence detection system can be capable of performing fluorogenic 5' nuclease chemistry assays using TaqMan® probes. One suitable sequence detection system is the ABI Prism® 7900HT Sequence Detection System (Applied Biosystems Foster City, Calif.).

Reference human genomic samples can be from a mixed ethnic group or from a single ethnic group and samples can be obtained from human cell repositories such as the Coriell Cell Repositories (Coriell Institute for Medical Research, Camden, N.J.).

In some configurations, a universal master mix, including test probes and primers, can be added directly to plates of dry or fresh DNA samples using standard robotics. Plates can be sealed and cycled using a standard thermal cycler such as, for example, Applied Biosystems Dual 384-well GeneAmp® PCR System 9700 thermal cycler (Applied Biosystems, Foster City, Calif.). Following cycling, plates can be automatically read on the 7900HT Sequence Detector. The availability of thermal cyclers such as the 9700 with automated lid handling can increase throughput by enabling robotics integration for 24-hour unattended operation.

In a two-allele system, TaqMan® probes for each allele can be multiplexed in a single tube, each probe having a different 5' fluorescent dye. Endpoint fluorescence can be measured by the 7900HT system and experimental results can be displayed on an allelic discrimination viewer. The discrimination viewer displays fluorescence values of one of the dyes which represents one allele against fluorescence values of the other dye.

Typically four clusters of points, each from a different sample, fall into separate quadrants of a rectangle (FIG. 79). One cluster of points will fall in a quadrant showing high fluorescence from one dye and little or none from the other indicating samples can be homozygous for one allele. This is the case for the squares and triangles in FIG. 79. Another cluster will show fluorescence from both fluorescent dyes such as illustrated with the diamonds in FIG. 79. The fourth cluster of points, represented by circles in FIG. 79, results from the no template control (NTC) sample.

Pseudo-SNPs can be a common problem that arises from misassemblies, paralogs, or repeat elements. Similar sequences from different regions in the genome may erroneously align due to matching at only a few bases. These differing bases may then incorrectly assumed to be SNPs. If a pseudo-SNP is genotyped, every sample will appear to be heterozygous since each sample contains both the pseudo-alleles (see FIG. 80)

Another problem that can arise can be the unexpected clustering of dye intensities as shown in FIG. 81, which can be caused by, among other things, unknown SNPs residing within the probe or primer sequences. This makes accurate genotype decisions difficult. Thus, in some configurations, information about the sequence surrounding the SNP can be obtained and consulted before attempting to design a SNP assay.

Although, clustering can be normally in four quadrants as shown in FIG. 79, other variations are possible. For example, two clusters can be the result of all homozygous genotypes as shown in FIG. 82. Three clusters can result from a SNP with no rare allele homozygotes as shown in FIG. 83. Five clusters can be produced by the presence of an unknown SNP (FIG. 81). FIG. 84 shows scattered clusters.

Determination of genotype can be done by a trained observer in some configurations or by an automated system in others (see for example, Mein et al., *Genome Research* 10:330-343, 2000).

In various configurations, an assay can be considered to meet specifications if it amplifies at least one cluster and it can be distinguishable from the No Template Control (NTC). Excess scattering of clusters such that genotype cannot be distinguished results in the assay not being considered to meet specifications. In some configurations, this test can be performed for both custom assay products and stock assay products.

Gene Expression Tests:

In various configurations, gene expressions assays can be tested against both a genomic DNA (gDNA) template and a no-template control (NTC).

In some configurations, gene expression assays can be performed in a two step RT-PCR reaction. In the reverse transcription (RT) step, cDNA can be reverse transcribed from total RNA samples using a reverse transcriptase. Commercially available RT kits can be used such as the High-Capacity cDNA Archive Kit (Applied Biosystems, Foster City, Calif.). The PCR step uses a DNA polymerase. The process involves preparing the master mix from the kit, preparing the cDNA archive reaction plate and performing the reverse transcription. The RT reaction can be performed in any suitable system such as, for example, the Applied Biosystems Dual 384-well GeneAmp® PCR System 9700 thermal cycler (Applied Biosystems, Foster City, Calif.) or the ABI PRISM™ 6700 Automated Nucleic Acid Workstation (Applied Biosystems, Foster City, Calif.). Target amplification, using cDNA as the template, can be the second step in the gene expression assays in various configurations of the present invention. In this step, AmpliTaq Gold DNA polymerase from the TaqMan® Universal PCR Master Mix (Applied Biosystems, Foster City, Calif.) can be used. This amplifies target cDNA synthesized from the RNA sample, using sequence-specific primers and TaqMan® MGB probe from the Gene Expression Assay Mix (Applied Biosystems, Foster City, Calif.). The PCR step must be performed on an ABI PRISM™ Sequence Detection System such as, for example the 7900HT Sequence Detection System. Performing the PCR step for singleplex assays in 384-well format may involve configuring the sequence detector plate document, preparing the reaction plate and running the plate.

In various configurations, assays to multi-exon genes (denoted with an "_m" in the Assay ID) must show no amplification against gDNA, while assays to single-exon genes (denoted with an "_s" in the Assay ID) will amplify the target in gDNA.

Validation Testing:

In various configurations of the present invention, SNP assays and Gene Expression assays undergo validation testing.

SNP Tests:

In some configurations, for all human SNP assays, each target can be run against a large number of human genomic DNA samples to verify functionality, judge the "robustness" of the assay and validate an allele frequency. One such group of 90 human genomic samples has been obtained from both Caucasian and African American populations. Genomic DNA samples of 45 African Americans and 45 Caucasians can be obtained from the Coriell Human Variation Collection (Coriell Cell Repositories, Coriell Institute for Medical Research, Camden, N.J.).

In various configurations of the present invention, SNP assays can be performed as described above. This validation process provides allele frequency data and confirms assay performance. In some configurations, to pass validation, SNPs must have a minimum defined allele frequency to provide a meaningful assay. In various configurations, the minimum allele frequency can be at least about 8%, at least about 10%, at least about 12%, at least about 15%, at least about 18% or at least about 20% or more or at any desired allele frequency. This test verifies that the SNP can be a true SNP, that the allele frequency meets the minimum defined allele frequency and that the system performs in a manner suitable for a viable assay.

FIG. 85 shows an allele frequency distribution of validated SNPs. As can be seen in the figure greater than about 93% of the SNPs had an allele frequency of 10% or greater in either the Caucasian or the African-American groups.

Thus, in various configurations, manufactured and validated products can exhibit low background signal, adequate signal generation, allele signal specificity and at least 2 allele clusters.

In some configurations, only assays that yield a minimum allele frequency and produce robust assay may be manufactured for sale.

Gene Expression Tests:

In various configurations of the present invention, for gene expression assays, each target can be run against one or more pools of human cDNA produced from RNA to verify functionality. In certain aspects, at least about 10 human cDNA samples comprise such pools.

In various configurations, functional testing of custom assays can be performed in accordance with the procedures described above. For example, a primary template useful in some configurations can be the Universal Human Reference RNA (Stratagene, La Jolla, Calif.); while useful secondary templates include Discovery Line™ pre-isolated human total RNA (Invitrogen, Carlsbad, Calif.) from brain, heart, kidney, liver, and lung, and a pool of the 5 tissues; and Raji-Control human Total RNA (Applied Biosystems, Foster City, Calif.).

TABLE 2A $C_T$ (PCR Thresold Cycle) Values Determined in Various Tissues Using Assays-on-Demand ™ products.

| | Source Tissue for RNA | | | | | | | |
|---|---|---|---|---|---|---|---|---|
| Gene Symbol | Universal human Reference RNA (Statagene) | Pooled Tissue RNAs | Brain | Heart | Kidney | Liver | Lung | Raji-Control Total RNA |
| AARS | 22.39 | 24.58 | 26.24 | 25.97 | 24.91 | 27.61 | 27.39 | 21.8 |
| ALAD | 23.26 | 22.22 | 26.27 | 24.94 | 24 | 23.18 | 24.51 | 24.37 |
| WNT8B | 40 | 40 | 40 | 38.93 | 40 | 40 | 40 | 40 |
| ATP7B | 24.43 | 27.75 | 29.61 | 27.81 | 25.99 | 25.9 | 27.3 | 28.54 |
| GRIN2C | 40 | 31.71 | 31.04 | 40 | 40 | 40 | 40 | 40 |
| SERPING1 | 25.38 | 20.1 | 26.57 | 21.99 | 20.94 | 19.62 | 21.91 | 25.86 |
| C3 | 21.81 | 19.88 | 27.91 | 24 | 27.01 | 19.87 | 23.19 | 22.07 |

TABLE 2B

Summary of Gene Expression Across Tissues Using Assays-on-Demand ™ Products.

| | | |
|---|---|---|
| Total Number of assays processed | 2348 | |
| Total number expressed (Ct <35) in at least 1 tissue | 2293 | 97.7% |
| Total number not expressed (Ct >35) in any tissues | 55 | 2.3% |

As seen in the tables in this example, approximately 98% of the manufactured assays gave positive results in a functional use test in at least one tissue sample tested.

In some configurations, only assays that yield amplification on the human cDNA pools within the specifications, i.e. showing expression against sample tissue RNA references may be manufactured for sale.

Overall manufacturing and validation systems for some configurations of the present invention are illustrated for SNP and Gene Expression assays in FIGS. 86 and 87, respectively.

As shown in FIG. 86, in some configurations, probes and primers can be designed based upon bioinformatics and manufactured using a DNA synthesizer such as the ABI 3900. Following synthesis yield testing and analytical quality control testing (not shown) functional and validation testing can be performed using a ABI PRISM® 7900HT Sequence Detection System. Probes and primers suitable for assays which can distinguish allele pairs can be validated.

As shown in FIG. 87, in some configurations, probes and primers can be designed based upon bioinformatics and manufactured using a DNA synthesizer such as the ABI 3900. Following synthesis yield testing and analytical quality control testing (not shown) functional and validation testing can be performed using GeneAmp® PCR System 9700 and ABI PRISM® 7900HT Sequence Detection System. Probes and primers which may be able to detect reference RNA samples can be suitable for assays and can be considered validated.

Shipping:

In various configurations of the present invention, customers can be informed of assays accepted for order, and of final shipment of assays passing quality control (QC) functional testing. Depending at least in part upon the capacity of the supplier's manufacturing and testing facilities, delivery of assays together with associated information and materials (the "assay kit" 308, a non-limiting example of which is illustrated in FIG. 88) may be made, in some configurations, in about 14 days from the date the order is accepted. Delivery may also take more or less time, depending upon the number of assays ordered. For example, in some configurations, turn around time can be 14 working days from when an order is accepted for under 3,000 assays.

In some configurations, the assay probes include a non-fluorescent dye that can be configured to reduce background fluorescence and increase quenching efficiency. Thus, such assays can be particularly suitable and provide a substantial benefit to consumers using PCR sequence detection systems such as the Applied Biosystems PRISM® 7900HT Sequence Detection System, enabling high-throughput SNP genotyping in which approximately 250,000 genotypes per day can be analyzed, each needing only a small amount of sample DNA. In some configurations, MGB technology can be utilized with non-fluorescent quenchers. Shorter MGB probes provided in these configurations provide more flexibility in assay design, yielding more robust assays as well as a larger number of assays for more targets. The non-fluorescent quencher eliminates background fluorescence, and improves sensitivity.

In various configurations, components of SNP assays (human or non-human) supplied by the supplier may include one or more of the following:

One TaqMan® MGB 6-FAM™ dye-labeled probe;
One TaqMan® MGB VIC™ dye-labeled probe; and/or
Two target-specific primers configured to distinguish between two alleles.

The two TaqMan® MGB probes can be configured to distinguish between two alleles. Each TaqMan® MGB probe contains, in some configurations:

a reporter dye at the 5' end of each probe, wherein a VIC™ dye is linked to the 5' end of the allele 1 probe and a 6-FAM™ dye is linked to the 5' end of the allele 2 probe;

an MGB, which increases the melting temperature ($T_m$) without increasing probe length, thereby permitting the design of shorter probes. The use of MGBs results in greater differences in $T_m$ values between matched and mismatched probes, which produces more accurate allelic discrimination; and an NFQ at the 3' end of the probe. Because the quencher does not fluoresce, various sequence detection systems, including those of Applied Biosystems, can measure reporter dye contributions more accurately.

During PCR, each TaqMan® MGB probe anneals specifically to a complementary sequence between the forward and reverse primer sites. When the probe is intact, the proximity of the reporter dye to the quencher dye results in suppression of the reporter fluorescence primarily by Förster-type energy suppression.

AmpliTaq Gold® DNA polymerase cleaves only probes that can be hybridized to the target. (AmpliTaq Gold® DNA Polymerase is a thermostable polymerase complexed with a non-thermostable polymerase inhibitor, for example, an antibody directed against the polymerase. The combination has its activity inhibited until it is heated.)

Cleavage separates a reporter dye from the quencher dye, which results in increased fluorescence by the reporter. The increase in fluorescence signal occurs if the target sequence is complementary to the probe and is amplified during PCR. Thus, the fluorescence signal generated by PCR amplification indicates which alleles are present in the sample.

A correlation exists between fluorescence signals and sequences present in a sample, in various configurations of the present invention. More particularly, in various configurations, a VIC dye fluorescence without a 6-FAM dye fluorescence indicates a homozygosity for allele 1. A 6-FAM dye fluorescence without a VIC dye fluorescence indicates a homozygosity for allele 2. Fluorescence of both dyes indicates an allele 1-allele 2 heterozygosity.

Also in various configurations, components of gene expression assays supplied by the supplier include one or more of the following:

One TaqMan MGB 6_FAM dye-labeled probe; and/or
Two target-specific primers.

In some configurations, custom assays combine two PCR primers and one FAM™ dye-labeled, TaqMan® MGB probe in a single-tube, ready-to-use, 20× mix (250 uL). Various configurations can be designed and optimized for two-step RT-PCR using TaqMan® Universal PCR Master Mix and complementary DNA (cDNA). An AB High Capacity cDNA Archive Kit (P/N 4322171) for converting RNA to cDNA, for example, can be used. Assays may also be tested for use on the ABI PRISM® 7900HT, 7700, and 7000 Sequence Detection Systems. In various configurations, products can be formulated at preselected universal concentration conditions (for example, final reaction concentrations of 900 nM primer and 250 nM probe) and configured to run using preselected universal thermal cycling parameters. As a result, in a variety of configurations, multiple assays can be run on a single plate, laboratory methods can easily be transferred to other researchers, and gene expression results can be directly compared to those of other researchers and other labs. In some configurations, assays can be configured for running in singleplex format with external endogenous controls run in separate wells on a plate.

Gene expression products ordered from stock may be used in RT-PCR protocols in configurations in which assays can be optimized for the two-step RT-PCR protocol. If, to use these products with RNA, RNA must be converted to cDNA, an AB High Capacity cDNA Archive Kit (P/N 4322171) or other suitable conversion product can be used for this conversion. A one-step protocol may be used in some configurations, such as by using the TaqMan® One-Step RT-PCR Master Mix Reagents Kit Protocol (P/N 4310299).

Stock assays for gene expression provided by some configurations of the present invention can be used for multiplexing. To use in single-plex reactions, users choose an appropriate endogenous control to be run in a separate well. A set of external, endogenous controls can be provided that have the same concentration and labeling (e.g., a TaqMan® MGB probe, labeled with the FAM™ dye) as the gene expression products. For multiplex reactions the endogenous control of choice can be run in separate wells (single-plex) as it does not require time-consuming validation experiments for the user to confirm that there is no PCR competition. However, if users choose to try multiplex experiments, the user can perform an experiment in which a multiplex versus singleplex assay can be performed to confirm that the PCR reactions and relative quantitation calculations can be unaffected by multiplexing.

Stock assays may be delivered with certain sequence information. For example, some sequence context information (forward primer location in the RefSeq sequence) and denote which exon-exon junction the assay covers so that users can get a sense of where the assay can be positioned in the transcript. More information can also be provided.

In some configurations, standardized assay designs can be provided for custom assays and/or stock assays, including either universal concentration or uniform thermal cycling parameters, or both, allowing results to be more easily compared with and/or transferred to other researchers and labs. Also, in some configurations, assays can be formulated in a single-tube 20× mix format that is convenient and easy to use, requiring no preparation or clean-up and providing faster time to results.

In some configurations, the manufactured assays can be shipped as homogenous assays in a single tube format. For example, in at least some configurations, a single tube, ready to use format can be provided that is suitable for immediate use on an ABI PRISM® Sequence Detection System platforms for one or more applications.

Referring to FIGS. 88 and 89, in addition to a human-readable label 310 (for example, a label on which appears the assay name) on each tube 312, in some configurations, a 2-D barcode 314 can be laser-etched on the bottom of each assay tube, and a 1-D barcode (not shown) on each 96-tube rack 316 of assays, making the assay tubes and racks machine-identifiable, so that the assays can be compatible with automation for high throughput applications.

In various configurations, an E-datasheet, or Assay Information File, can be provided with an assay. The E-datasheet or Assay Information File can be, in some configurations, an electronic file or data electronically stored on a data storage medium 318. This file or data can contain, for example, information on one or more assays, information on one or more polynucleotide sequences, an alphanumeric sequence representing a polynucleotide sequence, or the like. Alternatively, or in addition, a print copy or a printout of the E-datasheet or E-datasheet information can be provided.

In some configurations, a printed copy of a data sheet can also be provided, containing information about each assay. This information may include, among other things, the position of each assay in the plate rack. Some configurations provide, either in place of, or in addition to the printed copy of the data sheet, a CD-ROM with one or more data files recorded thereon. The data files may include, for example, any or all of the following files: an electronic assay workbook, including data sheet(s) and shipped worksheet(s); an electronically readable and/or printable copy of instructions for assay protocol; an electronically readable and/or printable copy the order request as well as the submission request protocol; and/or an electronically readable copy of a product insert.

In some configurations of the present invention, a data sheet and/or an electronic assay workbook can be provided with custom assays. In some configurations, an electronic assay workbook can be included with each order of up to 92 assays. In various configurations, the workbook file name includes the number on the bar code on the plate for easy correlation. In some configurations, the workbook contains two worksheets, namely, the "data sheet" worksheet and the "shipped" worksheet. Also in some configurations, the workbook can be a spreadsheet file, such as a Microsoft® Excel® file, which may contain macros and/or be password protected. Cells of the workbook can be copied and pasted into a new worksheet and modified in the new worksheet. A printed copy of the datasheet from the electronic file may be included with a shipment of assays ordered by design. The datasheet includes a correlation of the 2-D barcodes on the tubes to the corresponding assay names and primer and probe specific information.

In some configurations, a datasheet included with an order includes all of the following information: an identification of the assay in each tube; assay names; which target site was used, if the requestor submitted a sequence record that included more than one target site; locations of each tube in the assay rack; sequences of the primers and probes; and concentrations (µM) of primers and probes. Other configurations do not necessarily include all of this information and may include either more or less information.

For example, in some configurations, data sheets have the following columns:

Customer name (assigned by the supplier);
Order number (assigned by the supplier, in some configurations, corresponds to a number on a 1-D bar code on the plate);
Ship date (date shipped by the supplier)
Set ID (an assay name created from the record information in the requestor's submission file, including the record name and the target site name from the target site coordinate; if the sequence record submitted contained multiple target sites, the value of the Set ID can be used to determine which site was used to create the assay);
Set No. (may be used for internal quality control by the supplier)
Plate ID (assigned by the supplier, includes the order number value, and appears on the plate rack as the 1-D bar code);
Vial ID (a 2-D bar code number that appears on the bottom of each tube; entry in the datasheet may have leading zeros dropped in some configurations);
Well location (location of assay tube in the plate rack)
Line item (may be used for internal quality control by the supplier)
VIC probe name (may be used for internal quality control by the supplier);
VIC probe sequence (5' to 3' sequence of the probe labeled with VIC dye; in some configurations, the 3' non-fluorescent quencher-minor groove binder (NFQ-MGB) is not listed but is present on the probe);
VIC (µM) concentration (probe concentration)
Line item (may be used for internal quality control by the supplier)
6FAM probe name (may be used for internal quality control by the supplier)
6FAM probe sequence (5' to 3' sequence of the probe labeled with 6-FAM dye; note that in some configurations, the 3' NFQ-MGB is not listed but is present on the probe)
6FAM (µM) concentration (probe concentration)
Line item (may be used for internal quality control by the supplier)

Forward primer name (may be used for internal quality control by the supplier)
Forward primer sequence
Forward (µM) primer concentration
Line item (may be used for internal quality control by the supplier)
Reverse primer name (may be used for internal quality control by the supplier)
Reverse primer sequence
Reverse (µM) primer concentration
Part number (the part number ordered by the requestor).

The shipped worksheet can be provided to enable a user of the assays to determine that the tubes can be in the same positions in the plate rack as when the assays were shipped. For example, in some configurations, the following columns appear in the shipped worksheet:

Position (position in the plate)
Vial ID (a 2-D bar code number on the bottom of the tube at the indicated position; in some configurations, leading zeros can be dropped).

Usage of Assays:

The 5' nuclease allelic discrimination method used in TaqMan®·platforms utilized by some configurations of the present invention reduces human labor while in the laboratory. Unlike other methods that may require hybridization to chips or separate allele reactions, TaqMan® PCR preparation avoids hybridization to chips or separate allele reactions by adding a pre-made master mix containing buffer, deoxyribonucleotides, and DNA polymerase to the sample template and SNP specific oligonucleotides.

TaqMan® chemistry for SNP genotyping assays employs two allele specific probes for each SNP in addition to the common PCR primers. Each probe contains a 5' fluorescent dye, such as, for example, VIC or FAM, to detect the presence of the specific allele, and a 3' quencher to absorb fluorescence when the allele may not be present. The result can be much like any microarray or molecular beacon technology, one of the dyes will fluoresce for homozygous alleles and both dyes will fluoresce for heterozygotes.

In some configurations, ABI Prism® 7700 and ABI Prism® 7900HT Sequence Detection Systems available from Applied Biosystems may be used for endpoint analysis of 96 and 384 well plates, respectively, to record the fluorescence of the PCR product of each well. The latter may be bundled with an 84 plate robot for long term hands-free automation.

About 26 dual plate GeneAmp® PCR System 9700 thermal cyclers can be used in some configurations to keep one 7900HT supplied with an adequate number of PCR plates for continuous operation. However, different quantities and/or types of thermal cyclers may be used in some configurations, for example, if continuous operation and/or greater or lesser capacity is desired. Also in some configurations, barcoding can be used to record information hardware used, plates, assay probes and primers, technicians and times to evaluate performance.

In some configurations, assays themselves can be configured to be stored at between −15 and −25° C., but the number of freeze-thaw cycles can be minimized by storing multiple aliquots of the working stocks. In addition, the fluorescent probes can be protected by avoiding direct exposure of the assays to light.

In some configurations, assays can be diluted and aliquoted for routine use to minimize freeze-thaw cycles and to protect assay mixes from exposure to light. To dilute assay mixes, 40× or 80×SNP assay mixes can be diluted to a 20× working stock with 1×TE. The 1×TE can be 10 mM Tris-HCl, 1 mM EDTA pH 8.0, and made using DNase-free, sterile-filtered water. Multiple aliquots of the assay mixes may then be stored at −15 to −25° C.

A manual method may be used by a user of the assays to validate each tube position in the rack plate. In these configurations, the rack plate position and assay name on the tube label can be compared with the values in the well location and set ID columns in the data sheet worksheet. (This "validation" can be different from the validation of assays, in that validation of each tube position in a plate rack can be performed by the user, and merely confirms that the tubes are in positions matching the "shipped" worksheet. If the tubes are not in the correction position, they may be rearranged to match the worksheet. The operational quality of the assays contained within the tubes can be validated at the supplier's factory.)

In some configurations, an automated method can be used by a user of the assays to validate each tube position in the rack plate. This method includes scanning the plate and tubes using a 2-D bar code reader, and executing a plate validation spreadsheet macro (for example, a Microsoft® Excel® macro). In some configurations, to scan the plate and tubes, the plate rack can be placed on the 2-D bar code reader in a standard orientation. For example, tube position "A1" can be placed in the top left corner of the reader. The 1-D bar code on the plate rack can be then scanned. The bar code reader can be then configured, if necessary, to read positions in one column and to read bar codes in a column next to the positions column. Next, the plate rack can be scanned and the results can be saved to a directory that can be accessed from the computer containing the electronic file. In some configurations, the scanning results can be saved as a tab-delimited file.

To validate, the "shipped" worksheet can be opened in the spreadsheet, macros can be enabled, and the validation macro can be run. In some configurations utilizing software that can generate a text file, the validation can be performed by opening the electronic workbook, clicking a mouse on a "shipped" tab to view the worksheet containing the validation macro, clicking on the "validate" button to start the plate validation macro, and, when an "import plate scan" dialog box is presented, selecting "browse" to locate the file from the 2-D bar code scan. After "browse" is selected, the file that resulted from the 2-D bar code scan can be selected and imported into a new worksheet, which, in some configurations, can be called "received". The macro then compares each bar code and its position in the plate rack with the corresponding bar code in the "shipped" worksheet (i.e., the value in the "Vial ID" column). The macro then enters the result in a "validation" column in the "shipped" worksheet. The results for each entry may either be "OK" (or any entry understood as indicating a match) or "ERROR" (or any other entry understood as indicating a non-match). Next, a "shipment validation" dialog box alerts that the validation is complete, and the user clicks "OK" to dismiss the dialog box.

Plate validation errors indicate that the tubes may not in the same position as they were shipped by the supplier to the requestor. The user can resolve plate validation errors by rearranging the tubes to match the "shipped" worksheet. The user can then rescan the plate and execute the validation macro again to validate the plate.

Laboratory Information Management System

In various configurations of the present invention, oligo sets may be supplied in one tube, or in 96 well microtiter plates that can be already barcoded, as described above, to facilitate use of a laboratory information management system employed by the user of the oligo sets. In various configurations, supplied oligos can be scanned into the database, inventory can be tracked, and a nightly report can be generated to notify lab managers of sets ready to be run the following day.

In some configurations of the present invention, the samples supplied to the requestor can be arrayed in 96 or 384 well plates and a map of the plate entered into the database. To conserve clinical DNA, various configurations of the present invention supply only SNPs that pass validation and meet the required population frequencies on the clinical samples.

In various configurations of the present invention, an assay can be prepared for a given run using the probe and primer set and a TaqMan® Universal PCR Master Mix. A robot, such as a Protedyne robot prepares daughter sample plate by adding the assay mixture to the plate wells. The plate can be thermal cycled using, for example, a GeneAmp® 9700. Each step in the assay performance can be logged in the LIMS to allow software to automatically trigger and create a sequence detection system (SDS) binary file that can be used by the 7900HT. This procedure allows laboratory staff to simply place the plate into a stacker of one of the 7900HTs and select a pre-created file in the robot program. In various configurations, an SDS file need not be manually created using SDS software.

In some configurations, the scanned data file from the 7900HT can be recognized by software that passes it to multicomponent analysis software. This analysis software creates a multicomponent file containing the dye intensities of each well and subsequently passes the file to an autocaller program. As discussed in more detail below, the autocaller program identifies the genotype clusters and assigns appropriate calls to the wells. In some configurations, the putative genotypes can be loaded into the database for either manual review or immediate release, depending on the confidence of the autocaller.

In various configurations, the 7900HT and multicomponent analysis software can be controlled by a combination of automated software and triggers which allow the anticipation and detection of the steps in the laboratory performance of assays, thereby allowing continuous scanning by the 7900HT without having to manually create, identify, locate, analyze, call genotypes, or export data files.

In some configurations of the present invention, a laboratory information management system can also be used in the post-manufacturing validation process. Thus, an automated computer system can be provided to support high throughput SNP genotyping that satisfies the increasing demand that disease association studies are placing on current genotyping facilities. This system provides target SNP selection, automated oligo design, in silico assay quality validation, laboratory management of samples, reagents and plates, automated allele calling, optional manual review of autocalls, regular status reports, and linkage disequilibrium analysis. In some configurations, it has been found practical to generate over 2.5 million genotypes from more than 10,000 SNPs, with a target capacity of at least 10,000 genotypes per machine per hour utilizing only limited human intervention and laboratory hardware.

In various configurations, information gathered throughout the genotyping process can be stored in a central database, which can be divided into project management and laboratory schemas.

The project schema facilitates management of abstract entities such as SNP, sample donor, or genotype. For example, projects can be created by indicating an intended customer and loading desired SNP information. The requestor determines what SNP is ordered, scanned, considered validated, possibly discarded or re-designed, and delivered to the requestor. In various configurations, reports can be generated regarding the current progress of a SNP, failure rate of samples, or allele frequencies per population.

The project management component permits fast data analysis, by allowing efficient phenotype relations to both donors and SNPs. In various configurations, the project schema also has the ability to store haplotypes constructed from specific SNP alleles after analysis. The schema may also track literature references for individual SNPs and donors.

In various configurations, a the laboratory component provides tracking details of the process taken by the actual physical aspects of the laboratory performance and this can be mirrored in the project management component. Samples can be received, barcoded, and placed into plates and freezers. Oligos can be received, diluted, assigned into sets, and also placed into freezers. Plates can be arrayed with particular samples and oligos for specific projects. Each well can be scanned (and, in some configurations, re-scanned many times) to provide high accuracy. However, in various configurations, only a 'final' genotype is copied to the project management component where it may eventually be delivered to the customer.

An advantage of having common but separated partitions of the project management and laboratory components is that the laboratory space provides a tracking environment in which experiments can be re-arrayed, rerun, and reviewed multiple times, whereas the project management component remains uncluttered with details as analysis requires a compact schema designed for speed and clarity. This integration of LIMS and data analysis provides for segregated storage to satisfy each schema's different requirements, while keeping the data in one repository for the ability to track an individual genotype's entire history.

The database schema also supports large scale resequencing laboratories by adding relatively few tables, thereby combining SNP discovery, validation, and genotyping into one central repository.

As various changes could be made in the above methods and compositions without departing from the scope of the inventions, it is intended that all matter contained in the above description be interpreted as illustrative and not in a limiting sense. Where examples are recited herein, such examples are intended to be non-limiting. Also as used herein, unless otherwise explicitly stated, the terms "a," "an," "the," "said," and "at least one" are not intended to be limited in number to "one," but rather are intended to be read as encompassing "more than one" (i.e., a plurality) as well.

The description of the invention is merely exemplary in nature and, thus, variations that do not depart from the gist of the invention are intended to be within the scope of the invention. Such variations are not to be regarded as a departure from the spirit and scope of the invention.

All references cited herein are hereby incorporated by reference in their entireties. U.S. application Ser. No. 10/335,707, entitled "Methods of Validating SNPs and Compiling Libraries of Assays", inventors De La Vega, Francisco et al., filed Jan. 2, 2003 and U.S. application Ser. No. 10/335,690, entitled "Single-tube, Ready to Use Assay Kits, and Methods Using Same", inventors De La Vega, Francisco et al., filed Jan. 2, 2003 are both hereby incorporated by reference in their entireties.

What is claimed is:

1. A system for providing to a consumer, an assay configured to detect a presence or an expression of genetic material, the system comprising:
a computer system configured to:
cause a display of a first web-based user interface configured to receive a first input of a first order for a stock assay,
cause a display of a second web-based user interface configured to receive a second input of a request for design of a custom assay comprising a probe comprising a probe sequence and a primer comprising a primer sequence and a third input for a second order for the custom assay,
generate a submission file comprising the first order, the request, or the second order, or any combination thereof, and
design the custom assay based on the submission file and in accordance with criteria selected from one or more of:
avoiding inclusion of a single nucleotide polymorphism or a repeat sequence in the probe sequence and in the primer sequence,
avoiding inclusion of a region of discrepancy between at least two genomic databases in the probe sequence and in the primer sequence, and
including the probe sequence, the primer sequence, or both on an exon-exon boundary of a multi-exon gene;
a system for delivering to the consumer the custom assay manufactured according to the design, the stock assay, or both.

2. The system of claim 1, wherein the computer system is further configured to perform in silico quality control prior to manufacture of the custom assay, the custom assay is a gene expression assay, and the second web-based user interface is further configured to receive, from the consumer, criteria relating to at least one expressed transcript or portion thereof.

3. The system of claim 1, wherein the computer system is further configured to
output a gene exploration platform configured to provide information to assist the consumer in selecting one or both of the stock assay and the custom assay.

4. The system of claim 3 further configured to provide links between the gene exploration platform and the first web-based user interface, the second web-based user interface, or both.

5. The system of claim 3, wherein the gene exploration platform is further configured to provide the consumer with at least one of a computational tool to view and analyze gene structure and function, a genome structure map; and a protein classified by at least one of a family, a function, a process, and a cellular location.

6. The system of claim 3, wherein the gene exploration platform is further configured to provide the consumer with at least one of a chromosome map report, a scaffold report, a sequence report, a gene list, a chromosome map display, a biomolecule report, and a human gene mutation database report.

7. The system of claim 3, wherein the gene exploration platform is further configured to provide a genome navigation facility whereby the consumer can navigate a genome by at least one of searching a genome map and searching a genome assembly.

8. The system of claim 3, wherein the gene exploration platform is further configured to provide a genome navigation facility whereby the consumer can navigate a genome by searching by a gene ID, a gene symbol, and a RefSeq ID.

9. The system of claim 3, wherein the gene exploration platform is further configured to provide a genome navigation facility whereby the consumer can navigate a genome by searching by at least one of a cytogenetic band, by a position on a chromosome, for a STS marker, and for a region between two BACs.

10. A method for providing to a consumer, an assay configured to detect a presence or an expression of genetic material, the method comprising:
causing a display of a web-based user interface configured to receive from a consumer an input of a request for design of a custom assay comprising a probe comprising a probe sequence and a primer comprising a primer sequence, and configured to receive from the consumer an input of an order for the custom assay;
generating a submission file comprising the request, the order, or both;
designing the custom assay based on the submission file and in accordance with criteria selected from one or more of:
avoiding inclusion of a single nucleotide polymorphism or a repeat sequence in the probe sequence and in the primer sequence,
avoiding inclusion of a region of discrepancy between at least two genomic databases in the probe sequence and in the primer sequence, and including the probe sequence, the primer sequence, or both on an exon-exon boundary of a multi-exon gene;

manufacturing the custom assay from the designing; and delivering to the consumer the custom assay.

11. The method of claim 10, wherein the manufacturing comprises high-throughput manufacturing.

12. The method of claim 10 further comprising performing in silico quality control prior to the manufacturing, wherein the custom assay is a gene expression assay and the web-based user interface is further configured to receive, from the consumer, criteria relating to at least one expressed transcript or portion thereof.

13. The method of claim 10, wherein the designing further comprises utilizing specifications comprising at least one of $T_m$, GC content, buffer and salt conditions, oligonucleotide concentration, low oligonucleotide secondary structure, amplicon size, and low incidence of primer-dimer formation.

14. The method of claim 10 further comprising performing quality control testing of the manufactured assays according to pre-selected quality control criteria, wherein the quality control testing comprises at least one of synthesis yield testing, analytical quality control testing, functional testing, and validation testing.

15. The method of claim 14 wherein the synthesis yield testing comprises testing the manufactured custom assay using PAGE or HPLC, and the pre-selected quality control criteria for the synthesis yield testing is about 90% (w/w) product yield.

16. The method of claim 14, wherein the analytical quality control testing comprises testing the manufactured custom assay using mass spectrometry, and the pre-selected quality control criteria for synthesis yield testing is such that determined mass is not more than 5% greater or lesser than calculated mass.

17. The method of claim 14, wherein the manufactured assay is a multi-exon gene expression assay, the functional testing comprises performing designed assay RT-PCR, and the pre-selected quality control criteria for the functional testing comprises detectable amplification of a transcript in accordance with assay design in absence of detectable amplification of genomic DNA.

18. The method of claim 14 wherein the manufactured custom assay is a gene expression assay and the validation testing comprises performing designed assay PCR against a pool of at least about 10 human cDNA samples.

19. The method of claim 18 wherein the pre-selected quality control criteria for the validation testing comprises detection of an amplified transcript at a threshold of less than 35 PCR cycles.

* * * * *